US009725490B2

(12) United States Patent
Katagiri et al.

(10) Patent No.: US 9,725,490 B2
(45) Date of Patent: Aug. 8, 2017

(54) ERAP1-DERIVED PEPTIDE AND USE THEREOF

(75) Inventors: Toyomasa Katagiri, Tokushima (JP); Takuya Tsunoda, Kanagawa (JP)

(73) Assignees: TOKUSHIMA UNIVERSITY, Tokushima (JP); ONCOTHERAPY SCIENCE, INC., Kanagawa (JP)

( * ) Notice: Subject to any disclaimer, the term of this patent is extended or adjusted under 35 U.S.C. 154(b) by 22 days.

(21) Appl. No.: 14/235,666

(22) PCT Filed: Jul. 27, 2012

(86) PCT No.: PCT/JP2012/069131
§ 371 (c)(1),
(2), (4) Date: Jan. 28, 2014

(87) PCT Pub. No.: WO2013/018690
PCT Pub. Date: Feb. 7, 2013

(65) Prior Publication Data

US 2014/0162952 A1 Jun. 12, 2014

(30) Foreign Application Priority Data

Jul. 29, 2011 (JP) ................................ 2011-167171

(51) Int. Cl.

| | |
|---|---|
| ***C07K 7/06*** | (2006.01) |
| ***C07K 7/04*** | (2006.01) |
| ***C07K 14/47*** | (2006.01) |
| ***G01N 33/50*** | (2006.01) |
| ***G01N 33/574*** | (2006.01) |
| ***C12N 9/48*** | (2006.01) |
| ***A61K 31/138*** | (2006.01) |
| ***A61K 38/17*** | (2006.01) |
| *A61K 38/00* | (2006.01) |

(52) U.S. Cl.
CPC ........ *C07K 14/4705* (2013.01); *A61K 31/138* (2013.01); *A61K 38/1709* (2013.01); *C12N 9/485* (2013.01); *G01N 33/5011* (2013.01); *G01N 33/57484* (2013.01); *A61K 38/00* (2013.01); *G01N 2333/4704* (2013.01); *G01N 2333/95* (2013.01); *G01N 2500/02* (2013.01)

(58) Field of Classification Search
None
See application file for complete search history.

(56) References Cited

U.S. PATENT DOCUMENTS

2008/0107668 A1* 5/2008 Philip et al. ............... 424/185.1
2009/0175844 A1 7/2009 Nakamura et al.
2011/0135647 A1 6/2011 Nakamura et al.

FOREIGN PATENT DOCUMENTS

JP 2010-500003 1/2010
WO 2006/085684 8/2006
WO 2008/018642 2/2008

OTHER PUBLICATIONS

Kim, J.W. et al. "Identification and characterization of ERAP1 as a novel molecular target for breast cancer therapy," Proceedings of the Japanese Cancer Association, Sep. 30, 2008, vol. 67th, p. 309.; English summary; Cited in International Search Report.
Kim, J.W. et al. "Activation of an estrogen/estrogen receptor signaling by BIG3 through its inhibitory effect on nuclear transport of PHB2/REA in breast cancer," Cancer Sci., Aug. 2009, vol. 100, No. 8, pp. 1468-1478.; Cited in International Search Report.
C. Kent Osborne and Rachel Schiff, "Estrogen-Receptor Biology: Continuing Progress and Therapeutic Implications," Journal of Clinical Oncology, Mar. 10, 2005, vol. 23, No. 8, pp. 1616-1622.
James D. Yager, Ph.D., and Nancy E. Davidson, M.D., "Estrogen Carcinogenesis in Breast Cancer," the New England Journal of Medicine, Jan. 19, 2006, 354(3), pp. 270-282.
Stephen R.D. Johnson. "New Strategies in Estrogen Receptor-Positive Breast Cancer," Clinical Cancer Research, Mar. 23, 2010; DOI: 10.1158/1078-0432.CCR-09-1823, Clin Cancer Res 2010;16: pp. 1979-1987.
International Search Report dated Oct. 9, 2012 filed in PCT/JP2012/069131.

* cited by examiner

*Primary Examiner* — Michael Pak
(74) *Attorney, Agent, or Firm* — Rankin, Hill & Clark LLP

(57) ABSTRACT

Provided is a novel cancer-treating agent which can be used as a novel choice for the treatment of cancer. Specifically provided are: a peptide that inhibits binding of ERAP1 polypeptide to PHB2 polypeptide, which comprises a binding site of the ERAP1 polypeptide to the PHB2 polypeptide, and a pharmaceutical composition comprising the peptide. In addition, provided is a method for screening a drug candidate for treating and/or preventing cancer using inhibition of the binding of the ERAP1 polypeptide to PP1α polypeptide, PKA polypeptide or PKB polypeptide as an index.

3 Claims, 67 Drawing Sheets

C 1 434

ERAP1 $_{1\text{-}434}$

ERAP1 $_{1\text{-}250}$

ERAP1 $_{1\text{-}100}$

D

FIG. 1-3
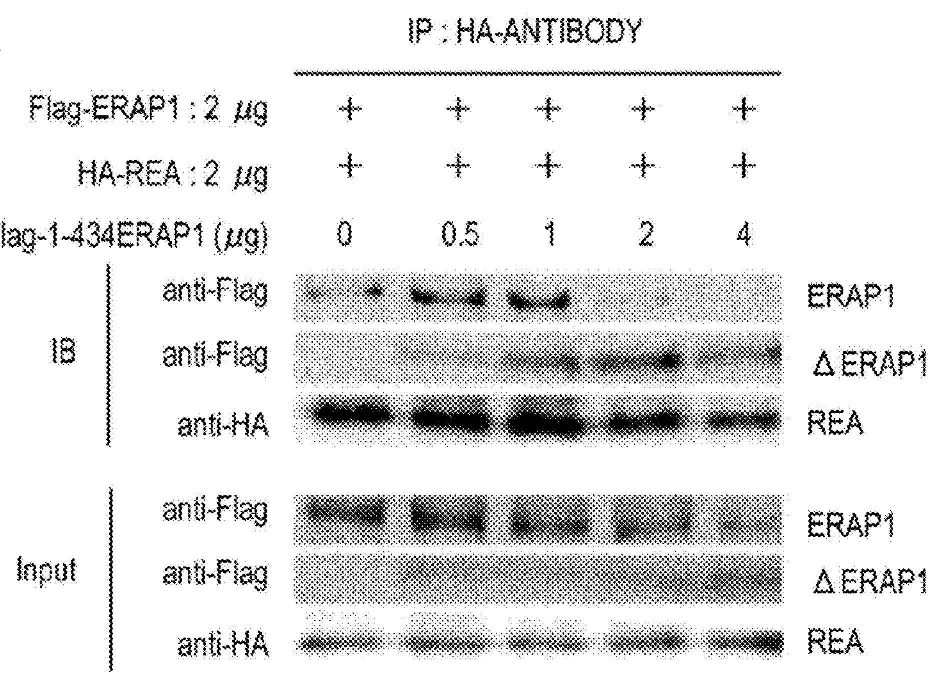
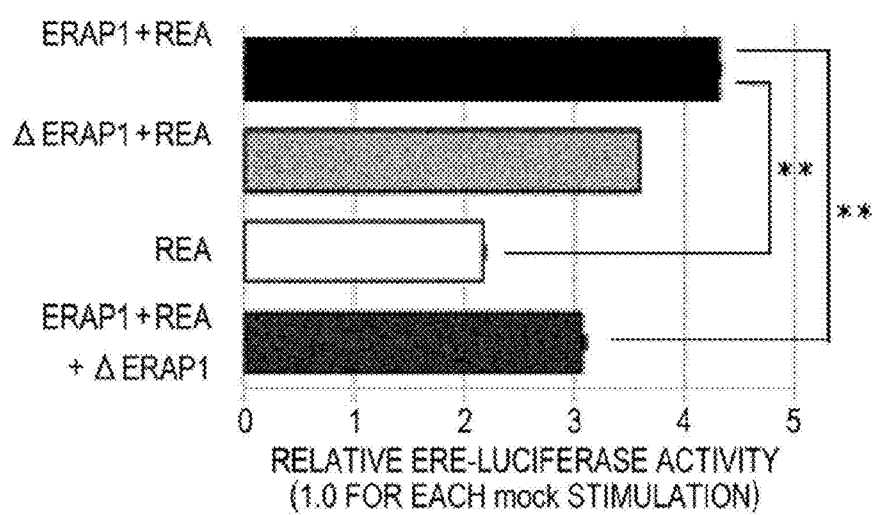

FIG. 1-4
G
| | 157 | 165 | 169 | 173 |
|---|---|---|---|---|
PSIVER SOFTWARE - - - + + - + + + - + + + - + + + - + + - - - - - -
ERAP1$_{1-434}$ -S-I-N-T-A-V-R-A-T-L-S-Q-M-L-S-D-L-T-L-Q-L-R-Q-R-Q-E-
ERAP1 mutant -S-I-N-T-A-V-R-A-T-L-S-A-M-L-S-A-L-T-L-A-L-R-Q-R-Q-E-
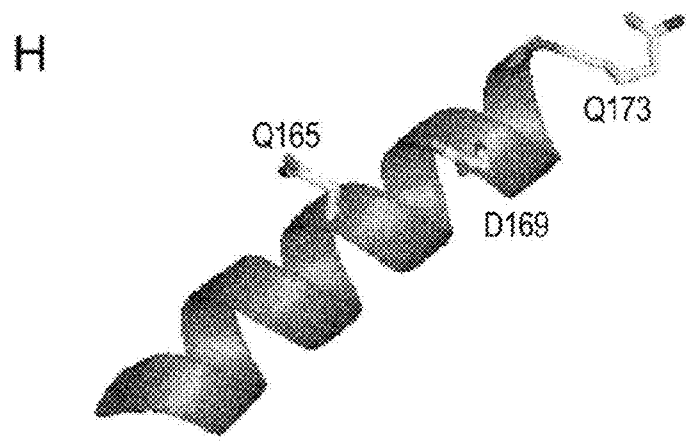
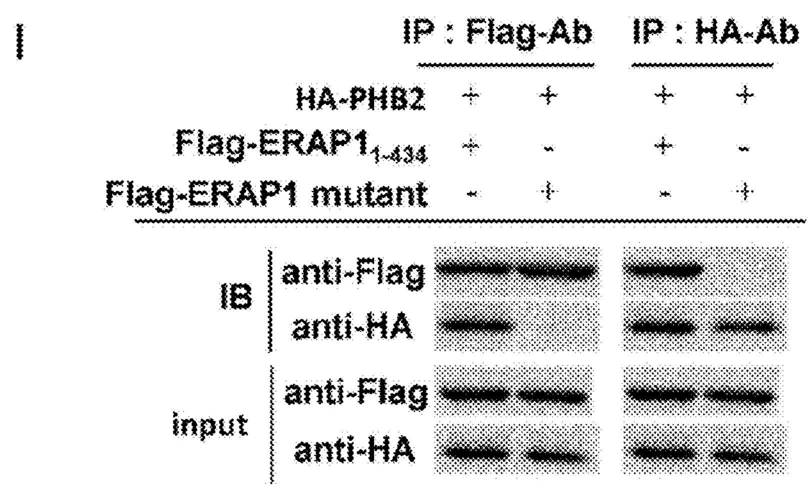

*FIG. 1-5*
J
| | |
|---|---|
| ERAP1-peptide | 11R-GGG-**Q**MLS**D**LTL**Q**LRQR (SEQ ID NO : 27) |
| ERAP1-Scramble peptide | 11R-GGG-DRQLQLSTLQRML (SEQ ID NO : 28) |
| ERAP1-mutant peptide | 11R-GGG-**A**MLS**A**LTL**A**LRQR (SEQ ID NO : 29) |
K
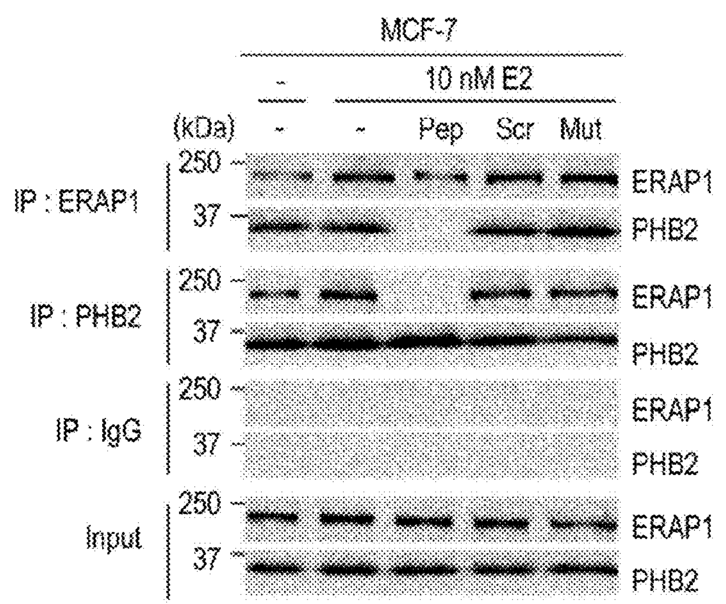
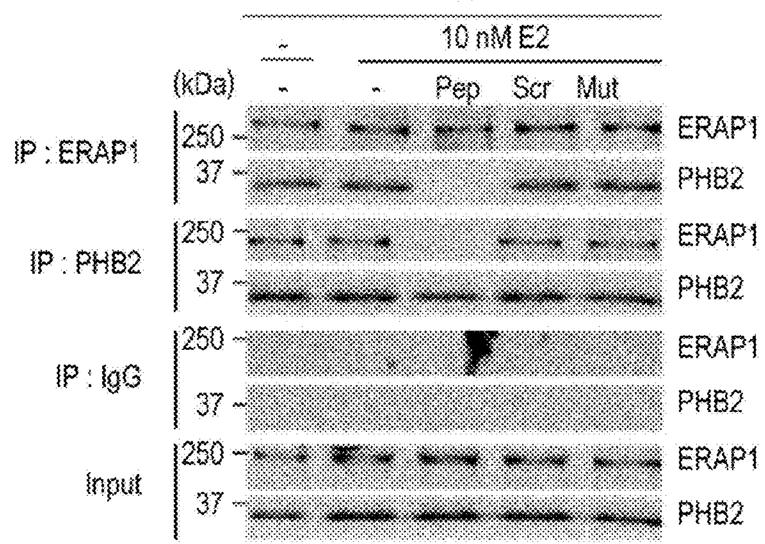

MCF-7

CYTOPLASM NUCLEUS

| | | | | | | | | |
|---|---|---|---|---|---|---|---|---|
| 10 nM E2 | - | + | + | + | - | + | + | + |
| 10 $\mu$M Peptide | - | - | + | - | - | - | + | - |
| 10 $\mu$M Scramble | - | - | - | + | - | - | - | + |

1 hr

IP : ER$\alpha$ — ERAP1, ER$\alpha$, PHB2

IP : ERAP1 — ERAP1, ER$\alpha$, PHB2

IP : PHB2 — ERAP1, ER$\alpha$, PHB2

Input — ERAP1, ER$\alpha$, PHB2, Tubulin, Lamin B 24 hr

IP : ER$\alpha$ — ERAP1, ER$\alpha$, PHB2

IP : ERAP1 — ERAP1, ER$\alpha$, PHB2

IP : PHB2 — ERAP1, ER$\alpha$, PHB2

Input — ERAP1, ER$\alpha$, PHB2, Tubulin, Lamin B

FIG. 6-1
A
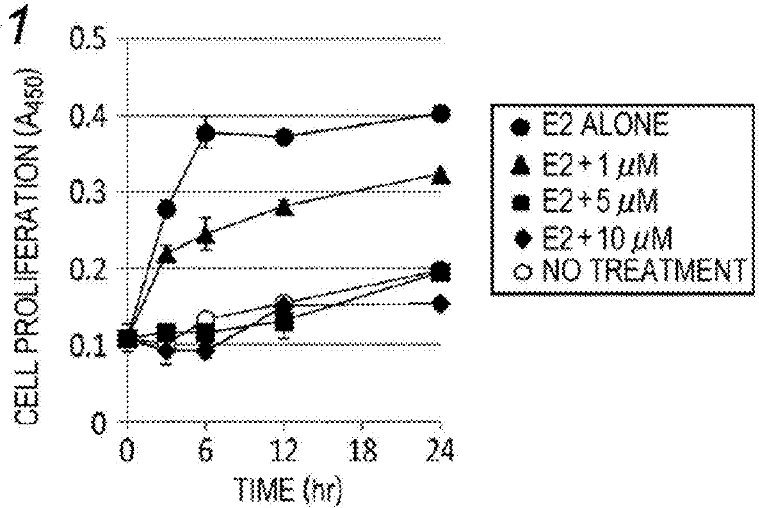
B
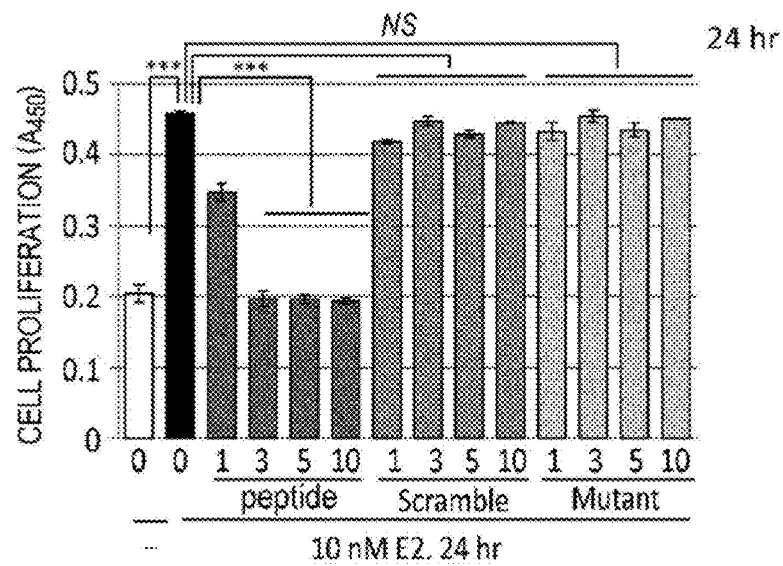
C
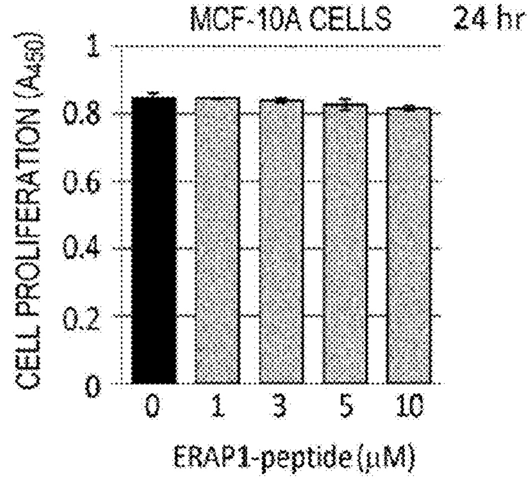

| | pS2 | Cyclin D1 | C-Myc | SP-1 | E2F1 | PgR |
|---|---|---|---|---|---|---|
| Peptide INHIBITION RATE | **95** | **93** | **80** | **81** | **69** | **93** |

| | pS2 | Cyclin D1 | C-Myc | SP-1 | E2F1 | PgR |
|---|---|---|---|---|---|---|
| Peptide INHIBITION RATE | **95** | **93** | **80** | **81** | **69** | **93** |

*FIG. 9–2*
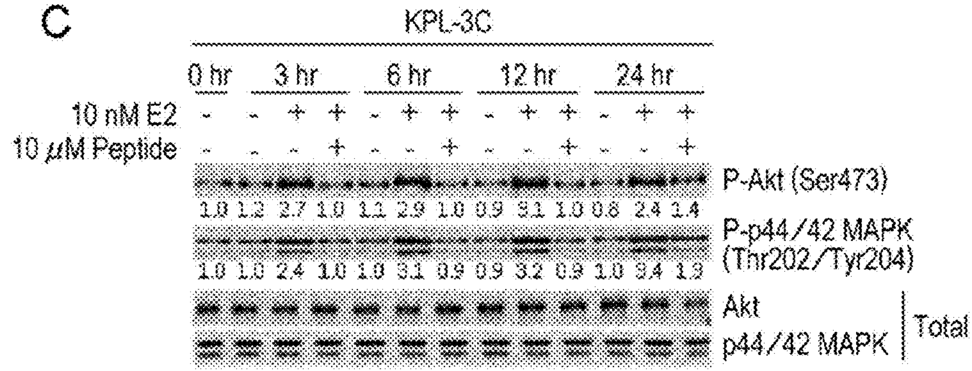
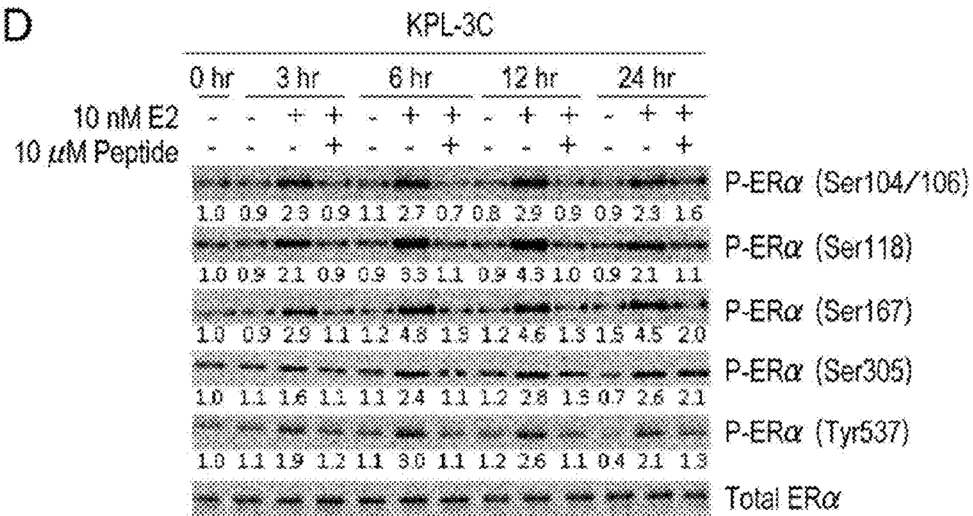
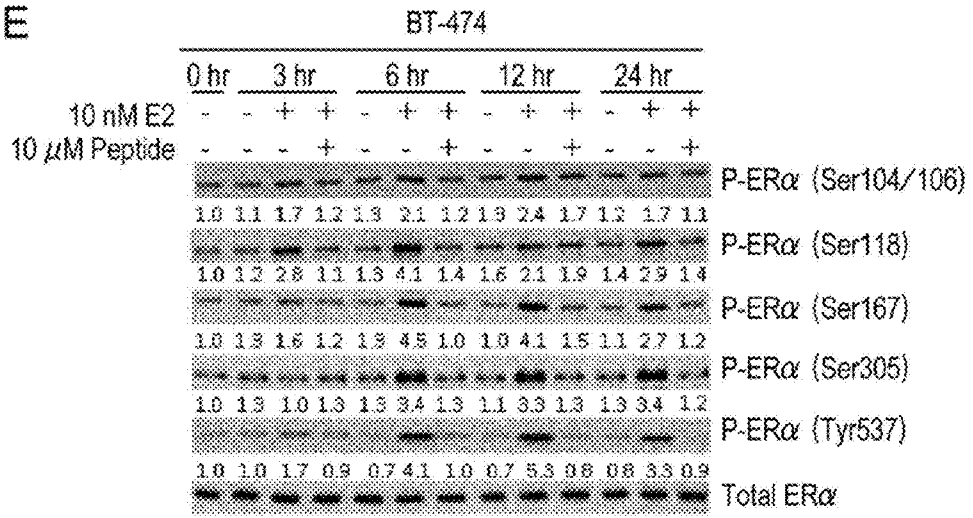

FIG. 10-2
C
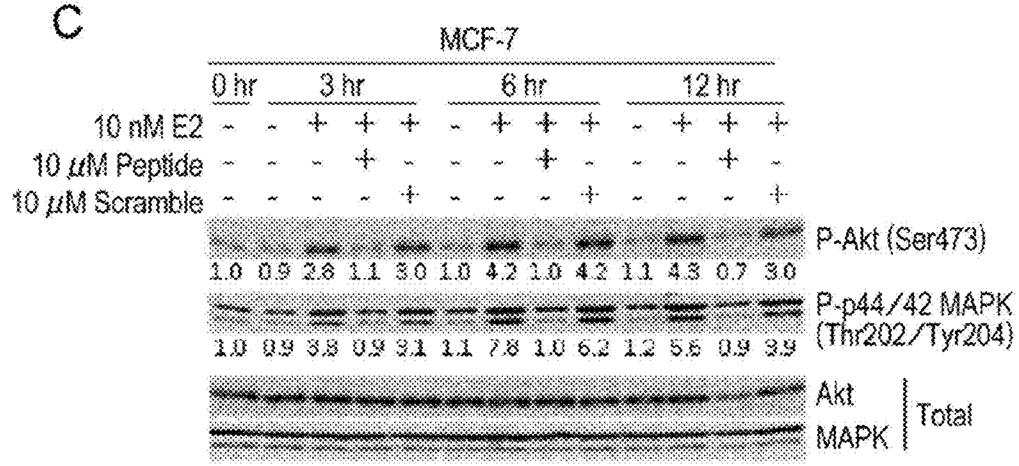
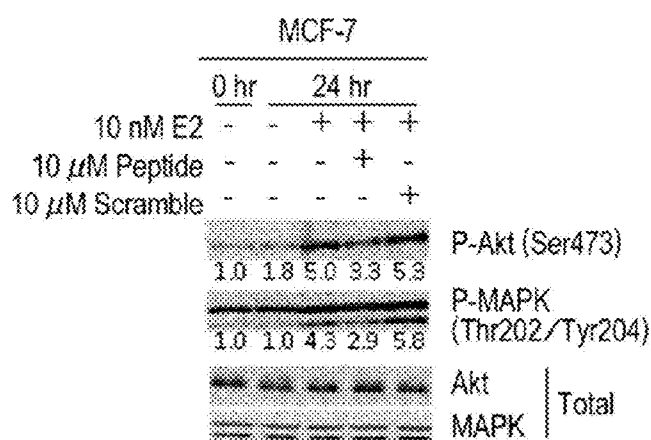
D
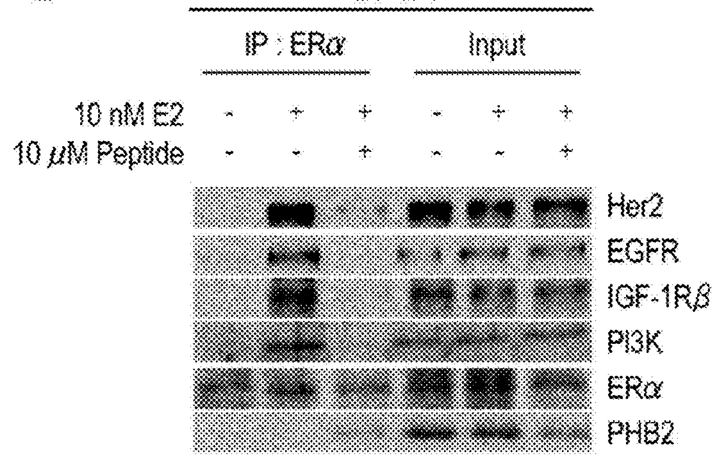

C
*FIG. 11–2*
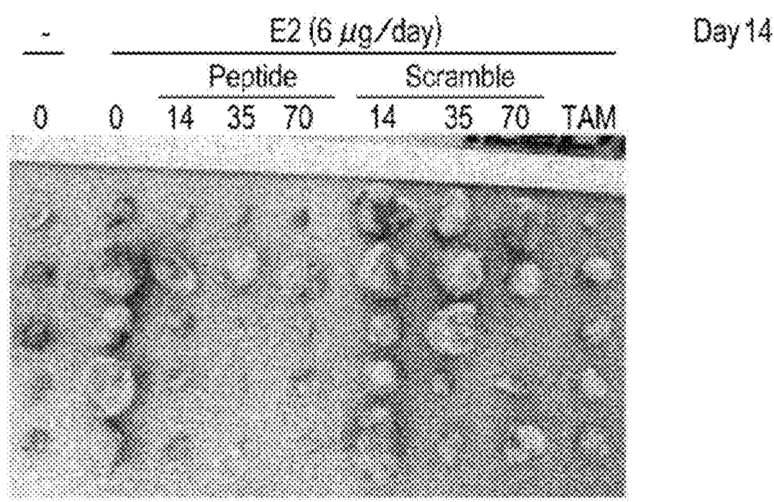
NO TREATMENT
Day 14
E2 (6 μg/day)
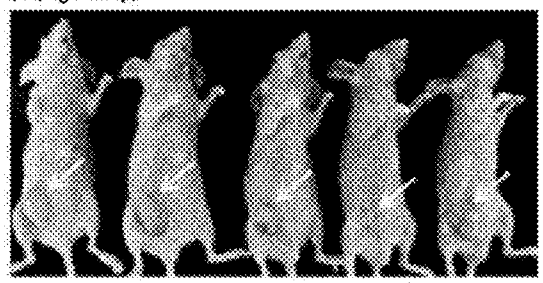
Day 14
E2 + 14 mg/kg Peptide
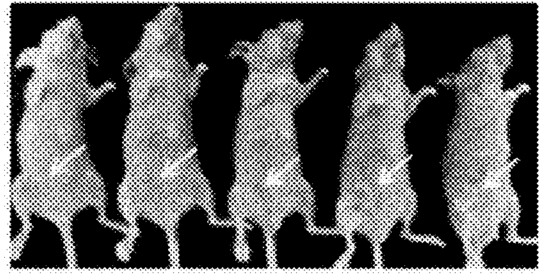
Day 14

| | pS2 | Cyclin D1 | C-Myc | SP-1 |
|---|---|---|---|---|
| Peptide INHIBITION RATE | **82** | **86** | **58** | **58** |
| tamoxifen INHIBITION RATE | **69** | **76** | **71** | **83** |

A

B

FIG. 13-2
C
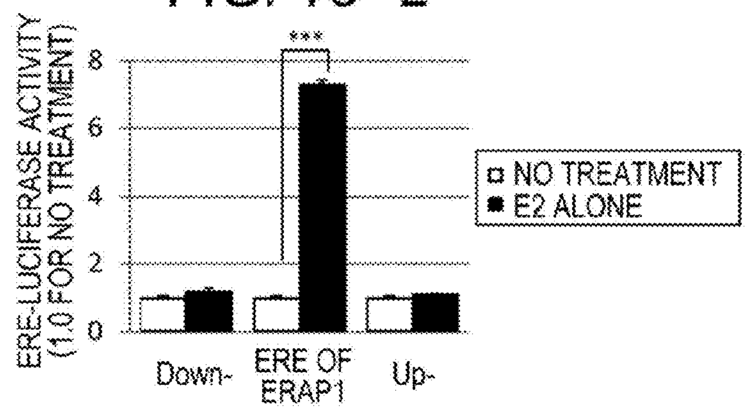
ERE CONSENSUS SEQUENCE IN INTRON 1 OF ERAP1 GENOME
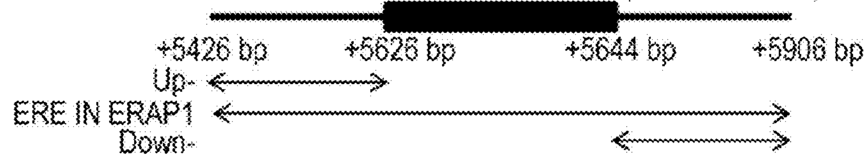
D
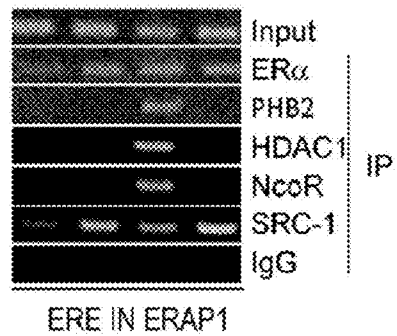
E
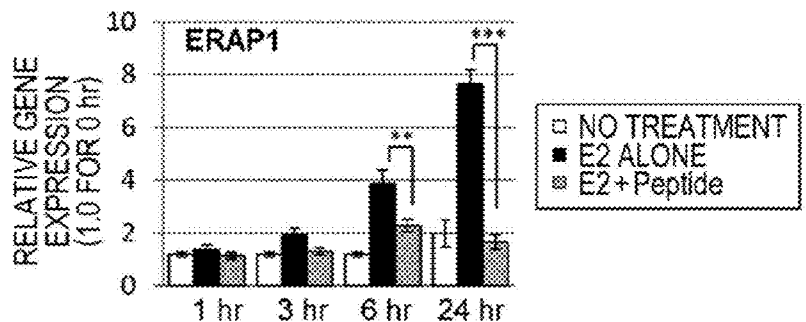

A

B

A

B

C

A

B

C

*FIG. 26–1*
A
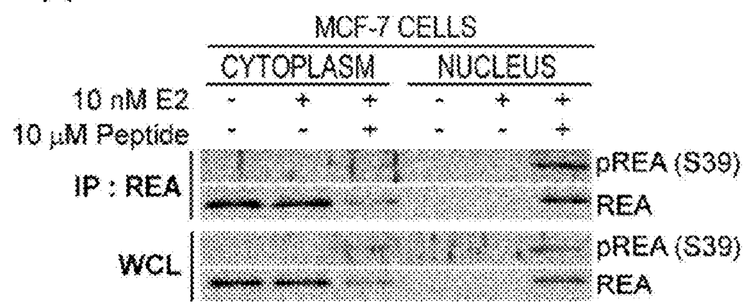
B
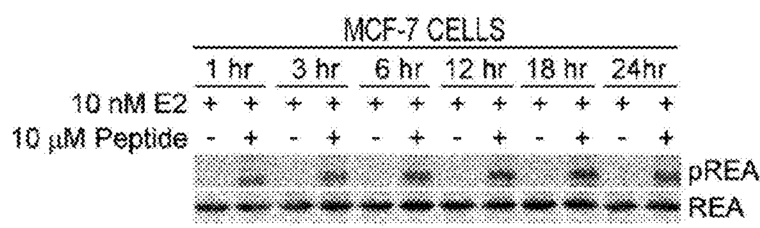
C
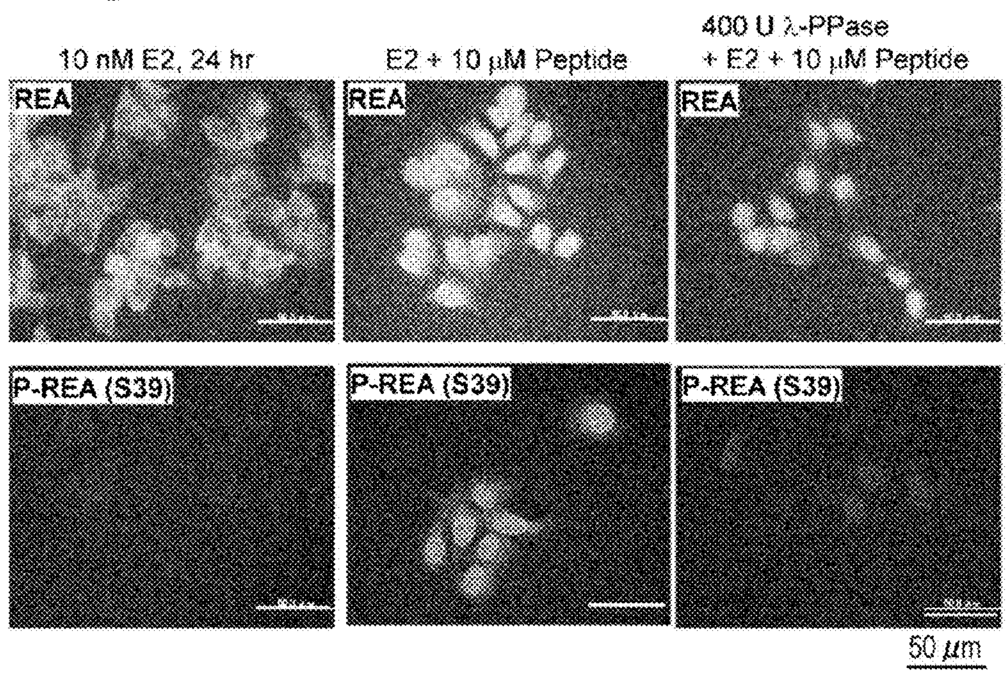

D

E

A

B

A

B

PP1α BINDING MOTIF : RVxF

ESTIMATED PP1α BINDING REGION IN ERAP1 :

1228aa – 1232aa (-RHVSQKAVSFIHDIL-) (SEQ ID NO:67)
(SEQ ID NO:66)

A

B

C

FIG. 30-2
C
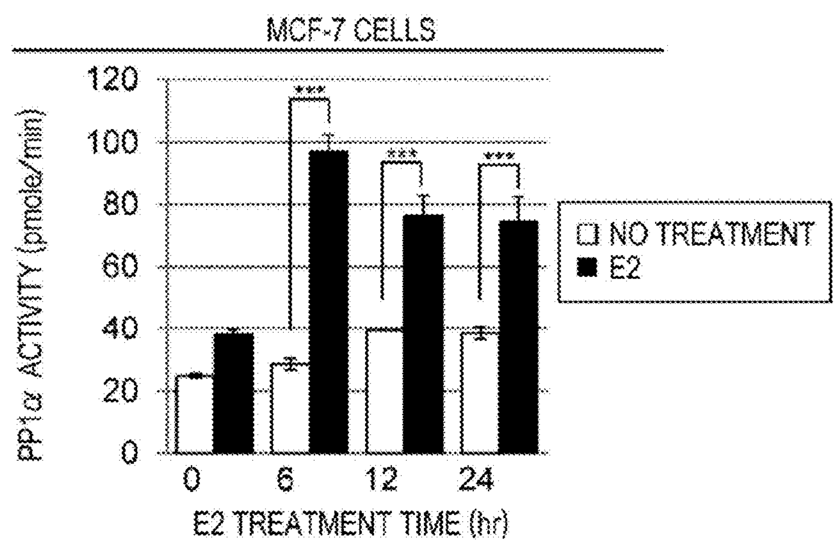
D
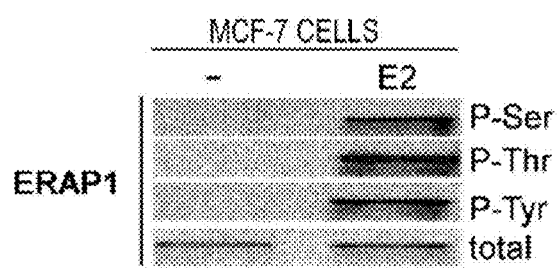
E
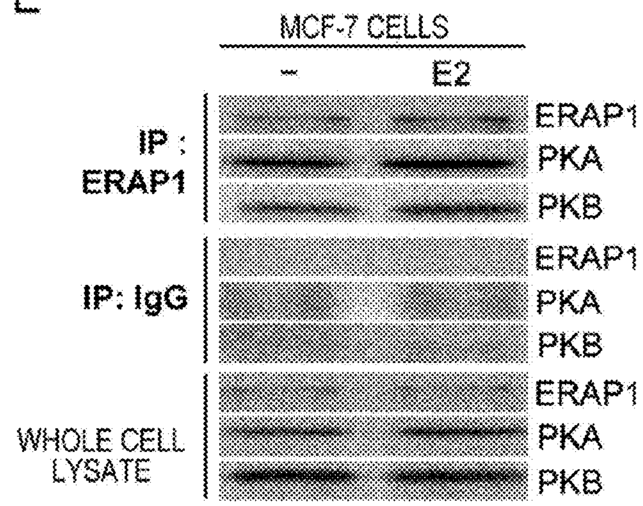

FIG. 31–1
A
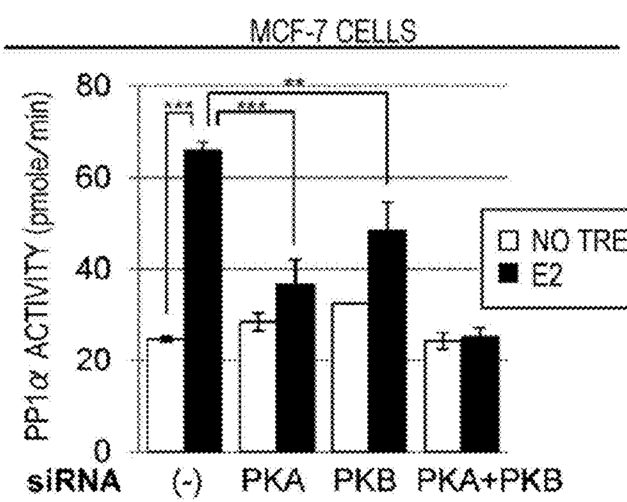
B
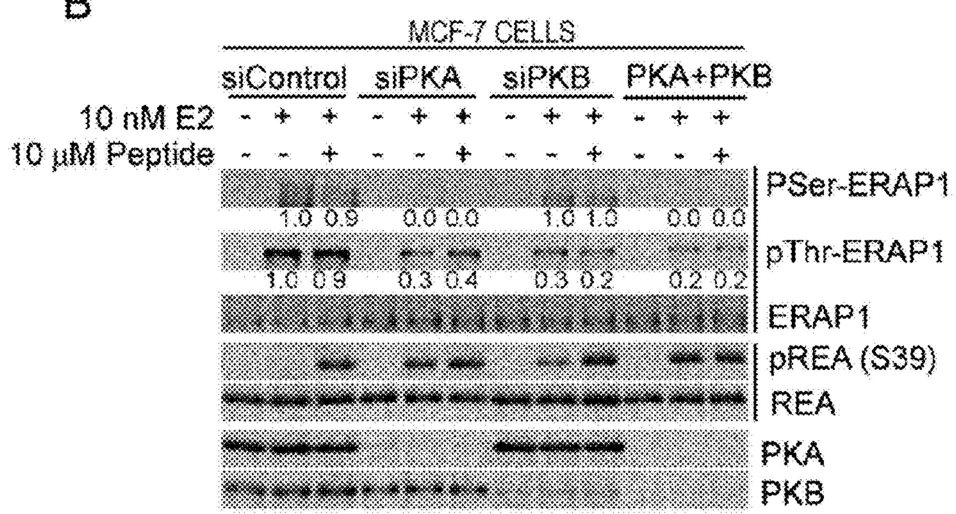
C
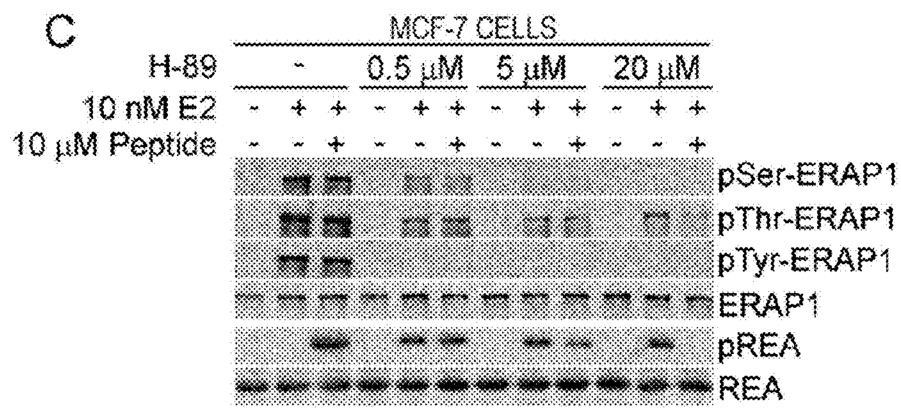

*FIG. 31-2*
D
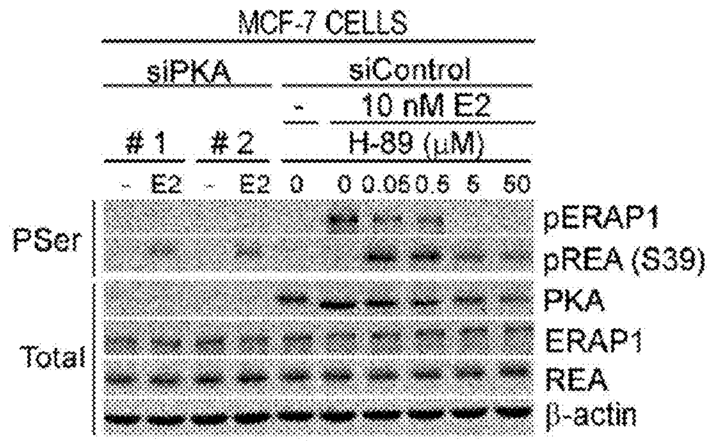
E
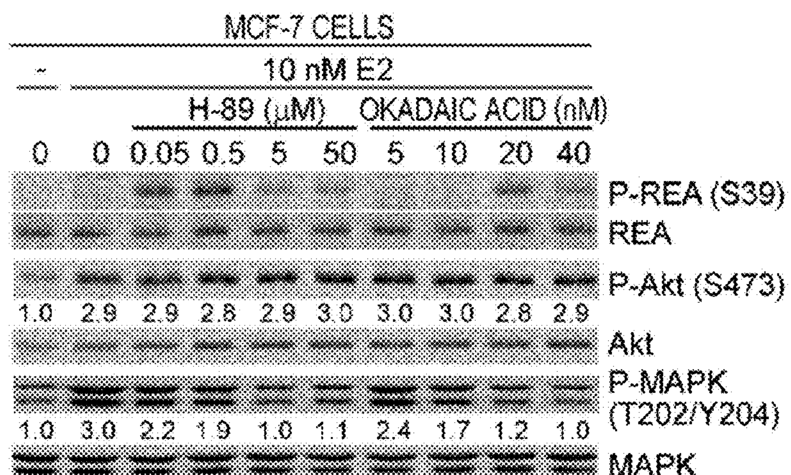
H-89 ; SPECIFIC PKA INHIBITOR : $IC_{50}$ = 10 μM
OKADAIC ACID : PP1α INHIBITOR : $IC_{50}$ = 20 nM
F
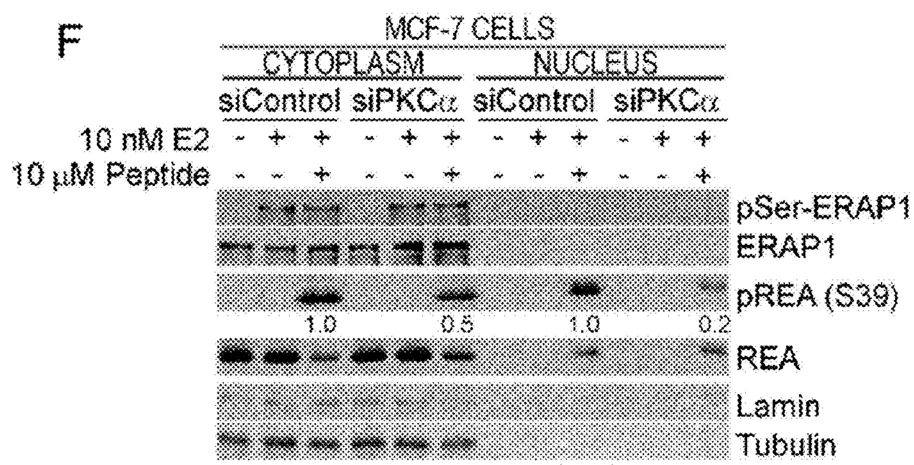

A

B

C

| From | To | | SCORE | SEQUENCE |
|---|---|---|---|---|
| -726 | -704 | 5' UPSTREAM | 0.925 | gttcaaGGCCAcctGGCCAacat (SEQ ID NO : 68) |
| +1851 | +1873 | INTRON 2 | 0.838 | cccaGGTCCcctTGCCTtcctaa (SEQ ID NO : 69) |
| +1936 | +1959 | INTRON 2 | 0.890 | ggGTTCAggtctAGACCttgcatc (SEQ ID NO : 70) |

D

E

5'-ERE CONSTRUCT

TANDEM CONSTRUCT OF 5'- and INTRON 2-ERE

A

B

A

BIACORE

Kd OF Peptide = 18.9 μM

B

FLUORESCENCE SPECTROSCOPY

Kd OF REA = 0.48 mg/mL (14.4 μM)

A

B

A

B

C

A

SEQUENCE LISTING

```
<160> NUMBER OF SEQ ID NOS: 86

<210> SEQ ID NO 1
<211> LENGTH: 21
<212> TYPE: DNA
<213> ORGANISM: Artificial Sequence
<220> FEATURE:
<223> OTHER INFORMATION: A primer for RT-PCR

<400> SEQUENCE: 1

gcagggagag gagtttgtgt g                                              21


<210> SEQ ID NO 2
<211> LENGTH: 20
<212> TYPE: DNA
<213> ORGANISM: Artificial Sequence
<220> FEATURE:
<223> OTHER INFORMATION: A primer for RT-PCR

<400> SEQUENCE: 2

tgggagagga tgaggaggag                                                20


<210> SEQ ID NO 3
<211> LENGTH: 21
<212> TYPE: DNA
<213> ORGANISM: Artificial Sequence
<220> FEATURE:
<223> OTHER INFORMATION: A primer for RT-PCR

<400> SEQUENCE: 3

gaggtgatag cattgctttc g                                              21
```

<210> SEQ ID NO 4
<211> LENGTH: 21
<212> TYPE: DNA
<213> ORGANISM: Artificial Sequence
<220> FEATURE:
<223> OTHER INFORMATION: A primer for RT-PCR

<400> SEQUENCE: 4
caagtcagtg tacaggtaag c 21

<210> SEQ ID NO 5
<211> LENGTH: 20
<212> TYPE: DNA
<213> ORGANISM: Artificial Sequence
<220> FEATURE:
<223> OTHER INFORMATION: A primer for real-time PCR

<400> SEQUENCE: 5
ggcctcctta ggcaaatgtt 20

<210> SEQ ID NO 6
<211> LENGTH: 20
<212> TYPE: DNA
<213> ORGANISM: Artificial Sequence
<220> FEATURE:
<223> OTHER INFORMATION: A primer for real-time PCR

<400> SEQUENCE: 6
cctcctctct gctccaaagg 20

<210> SEQ ID NO 7
<211> LENGTH: 20
<212> TYPE: DNA
<213> ORGANISM: Artificial Sequence
<220> FEATURE:
<223> OTHER INFORMATION: A primer for real-time PCR

<400> SEQUENCE: 7
cagaagtgcg aggaggaggt 20

<210> SEQ ID NO 8
<211> LENGTH: 19
<212> TYPE: DNA
<213> ORGANISM: Artificial Sequence
<220> FEATURE:
<223> OTHER INFORMATION: A primer for real-time PCR

<400> SEQUENCE: 8
cggatggagt tgtcggtgt 19

<210> SEQ ID NO 9
<211> LENGTH: 20
<212> TYPE: DNA
<213> ORGANISM: Artificial Sequence
<220> FEATURE:
<223> OTHER INFORMATION: A primer for real-time PCR

<400> SEQUENCE: 9
cgtctccaca catcagcaca 20

<210> SEQ ID NO 10
<211> LENGTH: 20
<212> TYPE: DNA
<213> ORGANISM: Artificial Sequence
<220> FEATURE:

<223> OTHER INFORMATION: A primer for real-time PCR

<400> SEQUENCE: 10
gctccgtttt agctcgttcc 20

<210> SEQ ID NO 11
<211> LENGTH: 20
<212> TYPE: DNA
<213> ORGANISM: Artificial Sequence
<220> FEATURE:
<223> OTHER INFORMATION: A primer for real-time PCR

<400> SEQUENCE: 11
tgctgctcaa ctctcctcca 20

<210> SEQ ID NO 12
<211> LENGTH: 20
<212> TYPE: DNA
<213> ORGANISM: Artificial Sequence
<220> FEATURE:
<223> OTHER INFORMATION: A primer for real-time PCR

<400> SEQUENCE: 12
gcatctgggc tgttttctcc 20

<210> SEQ ID NO 13
<211> LENGTH: 20
<212> TYPE: DNA
<213> ORGANISM: Artificial Sequence
<220> FEATURE:
<223> OTHER INFORMATION: A primer for real-time PCR

<400> SEQUENCE: 13
taccccaact ccctctaccc 20

<210> SEQ ID NO 14
<211> LENGTH: 20
<212> TYPE: DNA
<213> ORGANISM: Artificial Sequence
<220> FEATURE:
<223> OTHER INFORMATION: A primer for real-time PCR

<400> SEQUENCE: 14
cccactcacc tctcccatct 20

<210> SEQ ID NO 15
<211> LENGTH: 20
<212> TYPE: DNA
<213> ORGANISM: Artificial Sequence
<220> FEATURE:
<223> OTHER INFORMATION: A primer for real-time PCR

<400> SEQUENCE: 15
ccccgagtta ggagacgaga 20

<210> SEQ ID NO 16
<211> LENGTH: 20
<212> TYPE: DNA
<213> ORGANISM: Artificial Sequence
<220> FEATURE:
<223> OTHER INFORMATION: A primer for real-time PCR

<400> SEQUENCE: 16
gcagagggag gagaaagtgg 20

<210> SEQ ID NO 17
<211> LENGTH: 20
<212> TYPE: DNA
<213> ORGANISM: Artificial Sequence
<220> FEATURE:
<223> OTHER INFORMATION: A primer for real-time PCR

<400> SEQUENCE: 17
cttgacaagg cctttggagt 20

<210> SEQ ID NO 18
<211> LENGTH: 20
<212> TYPE: DNA
<213> ORGANISM: Artificial Sequence
<220> FEATURE:
<223> OTHER INFORMATION: A primer for real-time PCR

<400> SEQUENCE: 18
caatatgctt ttcccgcttt 20

<210> SEQ ID NO 19
<211> LENGTH: 20
<212> TYPE: DNA
<213> ORGANISM: Artificial Sequence
<220> FEATURE:
<223> OTHER INFORMATION: A primer for real-time PCR

<400> SEQUENCE: 19
ggatctgctt ctccagtttt 20

<210> SEQ ID NO 20
<211> LENGTH: 20
<212> TYPE: DNA
<213> ORGANISM: Artificial Sequence
<220> FEATURE:
<223> OTHER INFORMATION: A primer for real-time PCR

<400> SEQUENCE: 20
actgagaaat cacgcactgt 20

<210> SEQ ID NO 21
<211> LENGTH: 20
<212> TYPE: DNA
<213> ORGANISM: Artificial Sequence
<220> FEATURE:
<223> OTHER INFORMATION: A primer for real-time PCR

<400> SEQUENCE: 21
aacttagagg tggggagcag 20

<210> SEQ ID NO 22
<211> LENGTH: 22
<212> TYPE: DNA
<213> ORGANISM: Artificial Sequence
<220> FEATURE:
<223> OTHER INFORMATION: A primer for real-time PCR

<400> SEQUENCE: 22
cacaaccatg ccttacttta tc 22

<210> SEQ ID NO 23
<211> LENGTH: 26
<212> TYPE: DNA
<213> ORGANISM: Artificial Sequence
<220> FEATURE:
<223> OTHER INFORMATION: A primer for PCR

<400> SEQUENCE: 23
ggggtacctt atatcactag tcgaca 26

<210> SEQ ID NO 24
<211> LENGTH: 26
<212> TYPE: DNA
<213> ORGANISM: Artificial Sequence
<220> FEATURE:
<223> OTHER INFORMATION: A primer for PCR

<400> SEQUENCE: 24
ccgctcgaga gaactagagc agacaa 26

<210> SEQ ID NO 25
<211> LENGTH: 15
<212> TYPE: DNA
<213> ORGANISM: Homo sapiens
<220> FEATURE:
<221> NAME/KEY: misc_feature
<222> LOCATION: (7)..(9)
<223> OTHER INFORMATION: n is a, c, g, or t

<400> SEQUENCE: 25
aggtcannnt gacct 15

<210> SEQ ID NO 26
<211> LENGTH: 17
<212> TYPE: DNA
<213> ORGANISM: Homo sapiens

<400> SEQUENCE: 26
tccagttgca ttgacct 17

<210> SEQ ID NO 27
<211> LENGTH: 13
<212> TYPE: PRT
<213> ORGANISM: Artificial Sequence
<220> FEATURE:
<223> OTHER INFORMATION: ERAP1 dominant negative peptide

<400> SEQUENCE: 27

Gln Met Leu Ser Asp Leu Thr Leu Gln Leu Arg Gln Arg
1 5 10

<210> SEQ ID NO 28
<211> LENGTH: 13
<212> TYPE: PRT
<213> ORGANISM: Artificial Sequence
<220> FEATURE:
<223> OTHER INFORMATION: ERAP1-scramble peptide

<400> SEQUENCE: 28

Asp Arg Gln Leu Gln Leu Ser Thr Leu Gln Arg Met Leu
1 5 10

<210> SEQ ID NO 29
<211> LENGTH: 13
<212> TYPE: PRT
<213> ORGANISM: Artificial Sequence
<220> FEATURE:
<223> OTHER INFORMATION: ERAP1-mutant peptide

<400> SEQUENCE: 29

Ala Met Leu Ser Ala Leu Thr Leu Ala Leu Arg Gln Arg
1 5 10

<210> SEQ ID NO 30
<211> LENGTH: 13
<212> TYPE: PRT
<213> ORGANISM: Artificial Sequence
<220> FEATURE:
<223> OTHER INFORMATION: ERAP1 dominant negative peptide

<400> SEQUENCE: 30

Ala Thr Leu Ser Gln Met Leu Ser Asp Leu Thr Leu Gln
1 5 10

<210> SEQ ID NO 31
<211> LENGTH: 9
<212> TYPE: PRT
<213> ORGANISM: Artificial Sequence
<220> FEATURE:
<223> OTHER INFORMATION: ERAP1 dominant negative peptide

<400> SEQUENCE: 31

Gln Met Leu Ser Asp Leu Thr Leu Gln
1 5

<210> SEQ ID NO 32
<211> LENGTH: 1302
<212> TYPE: DNA
<213> ORGANISM: Artificial Sequence
<220> FEATURE:
<223> OTHER INFORMATION: Polynucleotide encoding ERAP1 N-terminal fragment

<400> SEQUENCE: 32
atggaagaaa tcctgaggaa gctgcagaag gaggcgtccg ggagcaagta caaagccatc 60
aaggagagct gcacctgggc cctggaaact ctaggtggtc tggataccat tgtcaagatc 120
cctccacatg tactgaggga gaaatgcctg ctgcctctcc agttggcttt ggaatccaag 180
aatgtgaagc tggcccaaca tgctttggca gggatgcaga agcttctgtc ggaagagagg 240
tttgtatcca tggaaacaga ttctgatgag aagcagctgc tcaatcagat actgaatgcc 300
gtgaaagtga cgccttcgct caacgaggac ctgcaggtgg aagtgatgaa ggttttacta 360
tgcatcacct acacgccaac atttgatctg aatgggagtg ccgtgctgaa gatcgcggag 420
gtgtgcattg agacgtacat aagcagctgt caccagcgta gcataaacac tgctgtgcgg 480
gcaactctca gtcaaatgct gagtgacttg actttacagt tacgacagag gcaggagaat 540
acgataattg aaaacccaga tgtcccacag gatttcggga atcaagggtc aacagtagag 600
tccctctgtg atgatgttgt ctctgtactc accgtcctgt gtgagaagct gcaagccgcc 660
ataaatgaca gccagcagct gcagcttctc tacctggagt gcatcctgtc tgtgctcagc 720
agctcctcct cctccatgca cctgcacagg cgcttcacgg acctgatctg gaaaaacctc 780
tgccctgctc tcatcgtgat cttgggggaat ccaattcatg acaaaaccat cacctctgct 840
cacaccagca gcaccagtac cagcctggag tcggactctg cgtctccggg agtgtctgac 900
cacggccgag gatcaggctg ctcctgcact gcgccggccc tgagcggacc tgtggctcgg 960
actatctatt acatcgcagc cgagctggtc cggctggtgg ggtctgtgga ctccatgaag 1020
cccgtgctcc agtccctcta ccaccgagtg ctgctctacc ccccacccca gcaccgggtg 1080
gaagccatca aaataatgaa agagatactt gggagcccac agcgtctctg tgacttggca 1140
ggacccagct ccactgaatc agagtccaga aaaagatcaa tttcaaaaag aaagtctcat 1200
ctggatctcc tcaaactcat catggatggc atgaccgaag catgcatcaa gggtggcatc 1260

```
gaagcttgct atgcagccgt gtcctgtgtc tgcaccttgc tg                    1302


<210> SEQ ID NO 33
<211> LENGTH: 434
<212> TYPE: PRT
<213> ORGANISM: Artificial Sequence
<220> FEATURE:
<223> OTHER INFORMATION: ERAP1 N-terminal fragment

<400> SEQUENCE: 33

Met Glu Glu Ile Leu Arg Lys Leu Gln Lys Glu Ala Ser Gly Ser Lys
1               5                   10                  15

Tyr Lys Ala Ile Lys Glu Ser Cys Thr Trp Ala Leu Glu Thr Leu Gly
            20                  25                  30

Gly Leu Asp Thr Ile Val Lys Ile Pro Pro His Val Leu Arg Glu Lys
        35                  40                  45

Cys Leu Leu Pro Leu Gln Leu Ala Leu Glu Ser Lys Asn Val Lys Leu
    50                  55                  60

Ala Gln His Ala Leu Ala Gly Met Gln Lys Leu Leu Ser Glu Glu Arg
65                  70                  75                  80

Phe Val Ser Met Glu Thr Asp Ser Asp Glu Lys Gln Leu Leu Asn Gln
                85                  90                  95

Ile Leu Asn Ala Val Lys Val Thr Pro Ser Leu Asn Glu Asp Leu Gln
            100                 105                 110

Val Glu Val Met Lys Val Leu Leu Cys Ile Thr Tyr Thr Pro Thr Phe
        115                 120                 125

Asp Leu Asn Gly Ser Ala Val Leu Lys Ile Ala Glu Val Cys Ile Glu
    130                 135                 140

Thr Tyr Ile Ser Ser Cys His Gln Arg Ser Ile Asn Thr Ala Val Arg
145                 150                 155                 160

Ala Thr Leu Ser Gln Met Leu Ser Asp Leu Thr Leu Gln Leu Arg Gln
                165                 170                 175

Arg Gln Glu Asn Thr Ile Ile Glu Asn Pro Asp Val Pro Gln Asp Phe
            180                 185                 190

Gly Asn Gln Gly Ser Thr Val Glu Ser Leu Cys Asp Asp Val Val Ser
        195                 200                 205

Val Leu Thr Val Leu Cys Glu Lys Leu Gln Ala Ala Ile Asn Asp Ser
    210                 215                 220

Gln Gln Leu Gln Leu Leu Tyr Leu Glu Cys Ile Leu Ser Val Leu Ser
225                 230                 235                 240

Ser Ser Ser Ser Ser Met His Leu His Arg Arg Phe Thr Asp Leu Ile
                245                 250                 255

Trp Lys Asn Leu Cys Pro Ala Leu Ile Val Ile Leu Gly Asn Pro Ile
            260                 265                 270

His Asp Lys Thr Ile Thr Ser Ala His Thr Ser Ser Thr Ser Thr Ser
        275                 280                 285

Leu Glu Ser Asp Ser Ala Ser Pro Gly Val Ser Asp His Gly Arg Gly
    290                 295                 300

Ser Gly Cys Ser Cys Thr Ala Pro Ala Leu Ser Gly Pro Val Ala Arg
305                 310                 315                 320

Thr Ile Tyr Tyr Ile Ala Ala Glu Leu Val Arg Leu Val Gly Ser Val
                325                 330                 335

Asp Ser Met Lys Pro Val Leu Gln Ser Leu Tyr His Arg Val Leu Leu
            340                 345                 350

Tyr Pro Pro Pro Gln His Arg Val Glu Ala Ile Lys Ile Met Lys Glu
```

```
        355                 360                 365

Ile Leu Gly Ser Pro Gln Arg Leu Cys Asp Leu Ala Gly Pro Ser Ser
    370                 375                 380

Thr Glu Ser Glu Ser Arg Lys Arg Ser Ile Ser Lys Arg Lys Ser His
385                 390                 395                 400

Leu Asp Leu Leu Lys Leu Ile Met Asp Gly Met Thr Glu Ala Cys Ile
                405                 410                 415

Lys Gly Gly Ile Glu Ala Cys Tyr Ala Ala Val Ser Cys Val Cys Thr
            420                 425                 430

Leu Leu


<210> SEQ ID NO 34
<211> LENGTH: 14852
<212> TYPE: DNA
<213> ORGANISM: Homo sapiens
<220> FEATURE:
<221> NAME/KEY: CDS
<222> LOCATION: (172)..(6705)

<400> SEQUENCE: 34

gtggcccgcg gcatggagcg ggcgtgattc atcagcatcc gcgccggggc ggcatggggg      60

cgcgcgcggc ggccgcctag gcgcccaggg ccaggcagcg gcggcttccc cggcccggct     120

cgcccgcgct tctctccctg tgggcggcgg cccggcgcct ggaaggtcaa g atg gaa      177
                                                         Met Glu
                                                         1

gaa atc ctg agg aag ctg cag aag gag gcg tcc ggg agc aag tac aaa       225
Glu Ile Leu Arg Lys Leu Gln Lys Glu Ala Ser Gly Ser Lys Tyr Lys
        5                   10                  15

gcc atc aag gag agc tgc acc tgg gcc ctg gaa act cta ggt ggt ctg       273
Ala Ile Lys Glu Ser Cys Thr Trp Ala Leu Glu Thr Leu Gly Gly Leu
    20                  25                  30

gat acc att gtc aag atc cct cca cat gta ctg agg gag aaa tgc ctg       321
Asp Thr Ile Val Lys Ile Pro Pro His Val Leu Arg Glu Lys Cys Leu
35                  40                  45                  50

ctg cct ctc cag ttg gct ttg gaa tcc aag aat gtg aag ctg gcc caa       369
Leu Pro Leu Gln Leu Ala Leu Glu Ser Lys Asn Val Lys Leu Ala Gln
                55                  60                  65

cat gct ttg gca ggg atg cag aag ctt ctg tcg gaa gag agg ttt gta       417
His Ala Leu Ala Gly Met Gln Lys Leu Leu Ser Glu Glu Arg Phe Val
            70                  75                  80

tcc atg gaa aca gat tct gat gag aag cag ctg ctc aat cag ata ctg       465
Ser Met Glu Thr Asp Ser Asp Glu Lys Gln Leu Leu Asn Gln Ile Leu
        85                  90                  95

aat gcc gtg aaa gtg acg cct tcg ctc aac gag gac ctg cag gtg gaa       513
Asn Ala Val Lys Val Thr Pro Ser Leu Asn Glu Asp Leu Gln Val Glu
    100                 105                 110

gtg atg aag gtt tta cta tgc atc acc tac acg cca aca ttt gat ctg       561
Val Met Lys Val Leu Leu Cys Ile Thr Tyr Thr Pro Thr Phe Asp Leu
115                 120                 125                 130

aat ggg agt gcc gtg ctg aag atc gcg gag gtg tgc att gag acg tac       609
Asn Gly Ser Ala Val Leu Lys Ile Ala Glu Val Cys Ile Glu Thr Tyr
                135                 140                 145

ata agc agc tgt cac cag cgt agc ata aac act gct gtg cgg gca act       657
Ile Ser Ser Cys His Gln Arg Ser Ile Asn Thr Ala Val Arg Ala Thr
            150                 155                 160

ctc agt caa atg ctg agt gac ttg act tta cag tta cga cag agg cag       705
Leu Ser Gln Met Leu Ser Asp Leu Thr Leu Gln Leu Arg Gln Arg Gln
        165                 170                 175
```

```
gag aat acg ata att gaa aac cca gat gtc cca cag gat ttc ggg aat      753
Glu Asn Thr Ile Ile Glu Asn Pro Asp Val Pro Gln Asp Phe Gly Asn
    180                 185                 190

caa ggg tca aca gta gag tcc ctc tgt gat gat gtt gtc tct gta ctc      801
Gln Gly Ser Thr Val Glu Ser Leu Cys Asp Asp Val Val Ser Val Leu
195                 200                 205                 210

acc gtc ctg tgt gag aag ctg caa gcc gcc ata aat gac agc cag cag      849
Thr Val Leu Cys Glu Lys Leu Gln Ala Ala Ile Asn Asp Ser Gln Gln
                215                 220                 225

ctg cag ctt ctc tac ctg gag tgc atc ctg tct gtg ctc agc agc tcc      897
Leu Gln Leu Leu Tyr Leu Glu Cys Ile Leu Ser Val Leu Ser Ser Ser
            230                 235                 240

tcc tcc tcc atg cac ctg cac agg cgc ttc acg gac ctg atc tgg aaa      945
Ser Ser Ser Met His Leu His Arg Arg Phe Thr Asp Leu Ile Trp Lys
        245                 250                 255

aac ctc tgc cct gct ctc atc gtg atc ttg ggg aat cca att cat gac      993
Asn Leu Cys Pro Ala Leu Ile Val Ile Leu Gly Asn Pro Ile His Asp
    260                 265                 270

aaa acc atc acc tct gct cac acc agc agc acc agt acc agc ctg gag     1041
Lys Thr Ile Thr Ser Ala His Thr Ser Ser Thr Ser Thr Ser Leu Glu
275                 280                 285                 290

tcg gac tct gcg tct ccg gga gtg tct gac cac ggc cga gga tca ggc     1089
Ser Asp Ser Ala Ser Pro Gly Val Ser Asp His Gly Arg Gly Ser Gly
                295                 300                 305

tgc tcc tgc act gcg ccg gcc ctg agc gga cct gtg gct cgg act atc     1137
Cys Ser Cys Thr Ala Pro Ala Leu Ser Gly Pro Val Ala Arg Thr Ile
            310                 315                 320

tat tac atc gca gcc gag ctg gtc cgg ctg gtg ggg tct gtg gac tcc     1185
Tyr Tyr Ile Ala Ala Glu Leu Val Arg Leu Val Gly Ser Val Asp Ser
        325                 330                 335

atg aag ccc gtg ctc cag tcc ctc tac cac cga gtg ctg ctc tac ccc     1233
Met Lys Pro Val Leu Gln Ser Leu Tyr His Arg Val Leu Leu Tyr Pro
    340                 345                 350

cca ccc cag cac cgg gtg gaa gcc atc aaa ata atg aaa gag ata ctt     1281
Pro Pro Gln His Arg Val Glu Ala Ile Lys Ile Met Lys Glu Ile Leu
355                 360                 365                 370

ggg agc cca cag cgt ctc tgt gac ttg gca gga ccc agc tcc act gaa     1329
Gly Ser Pro Gln Arg Leu Cys Asp Leu Ala Gly Pro Ser Ser Thr Glu
                375                 380                 385

tca gag tcc aga aaa aga tca att tca aaa aga aag tct cat ctg gat     1377
Ser Glu Ser Arg Lys Arg Ser Ile Ser Lys Arg Lys Ser His Leu Asp
            390                 395                 400

ctc ctc aaa ctc atc atg gat ggc atg acc gaa gca tgc atc aag ggt     1425
Leu Leu Lys Leu Ile Met Asp Gly Met Thr Glu Ala Cys Ile Lys Gly
        405                 410                 415

ggc atc gaa gct tgc tat gca gcc gtg tcc tgt gtc tgc acc ttg ctg     1473
Gly Ile Glu Ala Cys Tyr Ala Ala Val Ser Cys Val Cys Thr Leu Leu
    420                 425                 430

ggt gcc ctg gat gag ctc agc cag ggg aag ggc ttg agc gaa ggt cag     1521
Gly Ala Leu Asp Glu Leu Ser Gln Gly Lys Gly Leu Ser Glu Gly Gln
435                 440                 445                 450

gtg caa ctg ctg ctt ctg cgc ctt gag gag ctg aag gat ggg gct gag     1569
Val Gln Leu Leu Leu Leu Arg Leu Glu Glu Leu Lys Asp Gly Ala Glu
                455                 460                 465

tgg agc cga gat tcc atg gag atc aat gag gct gac ttc cgc tgg cag     1617
Trp Ser Arg Asp Ser Met Glu Ile Asn Glu Ala Asp Phe Arg Trp Gln
            470                 475                 480

cgg cga gtg ctg tcc tca gaa cac acg ccg tgg gag tca ggg aac gag     1665
Arg Arg Val Leu Ser Ser Glu His Thr Pro Trp Glu Ser Gly Asn Glu
        485                 490                 495
```

```
agg agc ctt gac atc agc atc agt gtc acc aca gac aca ggc cag acc     1713
Arg Ser Leu Asp Ile Ser Ile Ser Val Thr Thr Asp Thr Gly Gln Thr
    500                 505                 510

act ctc gag gga gag ttg ggt cag act aca ccc gag gac cat tcg gga     1761
Thr Leu Glu Gly Glu Leu Gly Gln Thr Thr Pro Glu Asp His Ser Gly
515                 520                 525                 530

aac cac aag aac agt ctc aag tcg cca gcc atc cca gag ggt aag gag     1809
Asn His Lys Asn Ser Leu Lys Ser Pro Ala Ile Pro Glu Gly Lys Glu
                535                 540                 545

acg ctg agc aaa gta ttg gaa aca gag gcg gta gac cag cca gat gtc     1857
Thr Leu Ser Lys Val Leu Glu Thr Glu Ala Val Asp Gln Pro Asp Val
            550                 555                 560

gtg cag aga agc cac acg gtc cct tac cct gac ata act aac ttc ctg     1905
Val Gln Arg Ser His Thr Val Pro Tyr Pro Asp Ile Thr Asn Phe Leu
        565                 570                 575

tca gta gac tgc agg aca agg tcc tat gga tct agg tat agt gag agc     1953
Ser Val Asp Cys Arg Thr Arg Ser Tyr Gly Ser Arg Tyr Ser Glu Ser
    580                 585                 590

aat ttt agc gtt gat gac caa gac ctt tct agg aca gag ttt gat tcc     2001
Asn Phe Ser Val Asp Asp Gln Asp Leu Ser Arg Thr Glu Phe Asp Ser
595                 600                 605                 610

tgt gat cag tac tct atg gca gca gaa aag gac tcg ggc agg tcc gac     2049
Cys Asp Gln Tyr Ser Met Ala Ala Glu Lys Asp Ser Gly Arg Ser Asp
                615                 620                 625

gtg tca gac att ggg tcg gac aac tgt tca cta gcc gat gaa gag cag     2097
Val Ser Asp Ile Gly Ser Asp Asn Cys Ser Leu Ala Asp Glu Glu Gln
            630                 635                 640

aca ccc cgg gac tgc cta ggc cac cgg tcc ctg cga act gcc gcc ctg     2145
Thr Pro Arg Asp Cys Leu Gly His Arg Ser Leu Arg Thr Ala Ala Leu
        645                 650                 655

tct cta aaa ctg ctg aag aac cag gag gcg gat cag cac agc gcc agg     2193
Ser Leu Lys Leu Leu Lys Asn Gln Glu Ala Asp Gln His Ser Ala Arg
    660                 665                 670

ctg ttc ata cag tcc ctg gaa ggc ctc ctc cct cgg ctc ctg tct ctc     2241
Leu Phe Ile Gln Ser Leu Glu Gly Leu Leu Pro Arg Leu Leu Ser Leu
675                 680                 685                 690

tcc aat gta gag gag gtg gac acc gct ctg cag aac ttt gcc tct act     2289
Ser Asn Val Glu Glu Val Asp Thr Ala Leu Gln Asn Phe Ala Ser Thr
                695                 700                 705

ttc tgc tca ggc atg atg cac tct cct ggc ttt gac ggg aat agc agc     2337
Phe Cys Ser Gly Met Met His Ser Pro Gly Phe Asp Gly Asn Ser Ser
            710                 715                 720

ctc agc ttc cag atg ctg atg aac gca gac agc ctc tac aca gct gca     2385
Leu Ser Phe Gln Met Leu Met Asn Ala Asp Ser Leu Tyr Thr Ala Ala
        725                 730                 735

cac tgc gcc ctg ctc ctc aac ctg aag ctc tcc cac ggt gac tac tac     2433
His Cys Ala Leu Leu Leu Asn Leu Lys Leu Ser His Gly Asp Tyr Tyr
    740                 745                 750

agg aag cgg ccg acc ctg gcg cca ggc gtg atg aag gac ttc atg aag     2481
Arg Lys Arg Pro Thr Leu Ala Pro Gly Val Met Lys Asp Phe Met Lys
755                 760                 765                 770

cag gtg cag acc agc ggc gtg ctg atg gtc ttc tct cag gcc tgg att     2529
Gln Val Gln Thr Ser Gly Val Leu Met Val Phe Ser Gln Ala Trp Ile
                775                 780                 785

gag gag ctc tac cat cag gtg ctc gac agg aac atg ctt gga gag gct     2577
Glu Glu Leu Tyr His Gln Val Leu Asp Arg Asn Met Leu Gly Glu Ala
            790                 795                 800

ggc tat tgg ggc agc cca gaa gat aac agc ctt ccc ctc atc aca atg     2625
Gly Tyr Trp Gly Ser Pro Glu Asp Asn Ser Leu Pro Leu Ile Thr Met
```

```
        805                 810                 815

ctg acc gat att gac ggc tta gag agc agt gcc att ggt ggc cag ctg     2673
Leu Thr Asp Ile Asp Gly Leu Glu Ser Ser Ala Ile Gly Gly Gln Leu
    820                 825                 830

atg gcc tcg gct gct aca gag tct cct ttc gcc cag agc agg aga att     2721
Met Ala Ser Ala Ala Thr Glu Ser Pro Phe Ala Gln Ser Arg Arg Ile
835                 840                 845                 850

gat gac tcc aca gtg gca ggc gtg gca ttt gct cgc tat att ctg gtg     2769
Asp Asp Ser Thr Val Ala Gly Val Ala Phe Ala Arg Tyr Ile Leu Val
                855                 860                 865

ggc tgc tgg aag aac ttg atc gat act tta tca acc cca ctg act ggt     2817
Gly Cys Trp Lys Asn Leu Ile Asp Thr Leu Ser Thr Pro Leu Thr Gly
            870                 875                 880

cga atg gcg ggg agc tcc aaa ggg ctg gcc ttc att ctg gga gct gaa     2865
Arg Met Ala Gly Ser Ser Lys Gly Leu Ala Phe Ile Leu Gly Ala Glu
        885                 890                 895

ggc atc aaa gag cag aac cag aag gag cgg gac gcc atc tgc atg agc     2913
Gly Ile Lys Glu Gln Asn Gln Lys Glu Arg Asp Ala Ile Cys Met Ser
    900                 905                 910

ctc gac ggg ctg cgg aaa gcc gca cgg ctg agc tgc gct cta ggc gtt     2961
Leu Asp Gly Leu Arg Lys Ala Ala Arg Leu Ser Cys Ala Leu Gly Val
915                 920                 925                 930

gct gct aac tgc gcc tca gcc ctt gcc cag atg gca gct gcc tcc tgt     3009
Ala Ala Asn Cys Ala Ser Ala Leu Ala Gln Met Ala Ala Ala Ser Cys
                935                 940                 945

gtc caa gaa gaa aaa gaa gag agg gag gcc caa gaa ccc agt gat gcc     3057
Val Gln Glu Glu Lys Glu Glu Arg Glu Ala Gln Glu Pro Ser Asp Ala
            950                 955                 960

atc aca caa gtg aaa cta aaa gtg gag cag aaa ctg gag cag att ggg     3105
Ile Thr Gln Val Lys Leu Lys Val Glu Gln Lys Leu Glu Gln Ile Gly
        965                 970                 975

aag gtg cag ggg gtg tgg ctg cac act gcc cac gtc ttg tgc atg gag     3153
Lys Val Gln Gly Val Trp Leu His Thr Ala His Val Leu Cys Met Glu
    980                 985                 990

gcc atc ctc agc gta ggc  ctg gag atg gga agc  cac aac ccg gac      3198
Ala Ile Leu Ser Val Gly  Leu Glu Met Gly Ser  His Asn Pro Asp
995                 1000                1005

tgc  tgg cca cac gtg ttc  agg gtg tgt gaa tac  gtg ggc acc ctg     3243
Cys  Trp Pro His Val Phe  Arg Val Cys Glu Tyr  Val Gly Thr Leu
1010                 1015                 1020

gag  cac aac cac ttc agc  gat ggt gcc tcg cag  ccc cct ctg acc     3288
Glu  His Asn His Phe Ser  Asp Gly Ala Ser Gln  Pro Pro Leu Thr
1025                 1030                 1035

atc  agc cag ccc cag aag  gcc act gga agc gct  ggc ctc ctt ggg     3333
Ile  Ser Gln Pro Gln Lys  Ala Thr Gly Ser Ala  Gly Leu Leu Gly
1040                 1045                 1050

gac  ccc gag tgt gag ggc  tcg ccc ccc gag cac  agc ccg gag cag     3378
Asp  Pro Glu Cys Glu Gly  Ser Pro Pro Glu His  Ser Pro Glu Gln
1055                 1060                 1065

ggg  cgc tcc ctg agc acg  gcc cct gtc gtc cag  ccc ctg tcc atc     3423
Gly  Arg Ser Leu Ser Thr  Ala Pro Val Val Gln  Pro Leu Ser Ile
1070                 1075                 1080

cag  gac ctc gtc cgg gaa  ggc agc cgg ggt cgg  gcc tcc gac ttc     3468
Gln  Asp Leu Val Arg Glu  Gly Ser Arg Gly Arg  Ala Ser Asp Phe
1085                 1090                 1095

cgc  ggc ggg agc ctc atg  agc ggg agc agc gcg  gcc aag gtg gtg     3513
Arg  Gly Gly Ser Leu Met  Ser Gly Ser Ser Ala  Ala Lys Val Val
1100                 1105                 1110

ctc  acc ctc tcc acg caa  gcc gac agg ctc ttt  gaa gat gct acg     3558
```

```
Leu Thr Leu Ser Thr Gln Ala Asp Arg Leu Phe Glu Asp Ala Thr
1115                1120                1125

gat aag ttg aac ctc atg gcc ttg gga ggt ttt ctt tac cag ctg      3603
Asp Lys Leu Asn Leu Met Ala Leu Gly Gly Phe Leu Tyr Gln Leu
1130                1135                1140

aag aaa gca tcg cag tct cag ctt ttc cat tct gtt aca gat aca      3648
Lys Lys Ala Ser Gln Ser Gln Leu Phe His Ser Val Thr Asp Thr
1145                1150                1155

gtt gat tac tct ctg gca atg cca gga gaa gtt aaa tcc act caa      3693
Val Asp Tyr Ser Leu Ala Met Pro Gly Glu Val Lys Ser Thr Gln
1160                1165                1170

gac cga aaa agc gcc ctc cac ctg ttc cgc ctg ggg aat gcc atg      3738
Asp Arg Lys Ser Ala Leu His Leu Phe Arg Leu Gly Asn Ala Met
1175                1180                1185

ctg agg att gtg cgg agc aaa gca cgg ccc ctg ctc cac gtg atg      3783
Leu Arg Ile Val Arg Ser Lys Ala Arg Pro Leu Leu His Val Met
1190                1195                1200

cgc tgc tgg agc ctt gtg gcc cca cac ctg gtg gag gct gct tgc      3828
Arg Cys Trp Ser Leu Val Ala Pro His Leu Val Glu Ala Ala Cys
1205                1210                1215

cat aag gaa aga cat gtg tct cag aag gct gtt tcc ttc atc cat      3873
His Lys Glu Arg His Val Ser Gln Lys Ala Val Ser Phe Ile His
1220                1225                1230

gac ata ctg aca gaa gtc ctc act gac tgg aat gag cca cct cat      3918
Asp Ile Leu Thr Glu Val Leu Thr Asp Trp Asn Glu Pro Pro His
1235                1240                1245

ttt cac ttc aat gaa gca ctc ttc cga cct ttc gag cgc att atg      3963
Phe His Phe Asn Glu Ala Leu Phe Arg Pro Phe Glu Arg Ile Met
1250                1255                1260

cag ctg gaa ttg tgt gat gag gac gtc caa gac cag gtt gtc aca      4008
Gln Leu Glu Leu Cys Asp Glu Asp Val Gln Asp Gln Val Val Thr
1265                1270                1275

tcc att ggt gag ctg gtt gaa gtg tgt tcc acg cag atc cag tcg      4053
Ser Ile Gly Glu Leu Val Glu Val Cys Ser Thr Gln Ile Gln Ser
1280                1285                1290

gga tgg aga ccc ttg ttc agt gcc ctg gaa aca gtg cat ggc ggg      4098
Gly Trp Arg Pro Leu Phe Ser Ala Leu Glu Thr Val His Gly Gly
1295                1300                1305

aac aag tca gag atg aag gag tac ctg gtt ggt gac tac tcc atg      4143
Asn Lys Ser Glu Met Lys Glu Tyr Leu Val Gly Asp Tyr Ser Met
1310                1315                1320

gga aaa ggc caa gct cca gtg ttt gat gta ttt gaa gct ttt ctc      4188
Gly Lys Gly Gln Ala Pro Val Phe Asp Val Phe Glu Ala Phe Leu
1325                1330                1335

aat act gac aac atc cag gtc ttt gct aat gca gcc act agc tac      4233
Asn Thr Asp Asn Ile Gln Val Phe Ala Asn Ala Ala Thr Ser Tyr
1340                1345                1350

atc atg tgc ctt atg aag ttt gtc aaa gga ctg ggg gag gtg gac      4278
Ile Met Cys Leu Met Lys Phe Val Lys Gly Leu Gly Glu Val Asp
1355                1360                1365

tgt aaa gag att gga gac tgt gcc cca gca ccc gga gcc ccg tcc      4323
Cys Lys Glu Ile Gly Asp Cys Ala Pro Ala Pro Gly Ala Pro Ser
1370                1375                1380

aca gac ctg tgc ctc ccg gcc ctg gat tac ctc agg cgc tgc tct      4368
Thr Asp Leu Cys Leu Pro Ala Leu Asp Tyr Leu Arg Arg Cys Ser
1385                1390                1395

cag tta ttg gcc aaa atc tac aaa atg ccc ttg aag cca ata ttc      4413
Gln Leu Leu Ala Lys Ile Tyr Lys Met Pro Leu Lys Pro Ile Phe
1400                1405                1410
```

```
ctt  agt ggg aga ctt gcc  ggc ttg cct cga aga  ctt cag gaa cag      4458
Leu  Ser Gly Arg Leu Ala  Gly Leu Pro Arg Arg  Leu Gln Glu Gln
1415                1420                1425

tca  gcc agc agt gag gat  gga att gaa tca gtc  ctg tct gat ttt      4503
Ser  Ala Ser Ser Glu Asp  Gly Ile Glu Ser Val  Leu Ser Asp Phe
1430                1435                1440

gat  gat gac acc ggt ctg  ata gaa gtc tgg ata  atc ctg ctg gag      4548
Asp  Asp Asp Thr Gly Leu  Ile Glu Val Trp Ile  Ile Leu Leu Glu
1445                1450                1455

cag  ctg aca gcg gct gtg  tcc aat tgt cca cgg  cag cac caa cca      4593
Gln  Leu Thr Ala Ala Val  Ser Asn Cys Pro Arg  Gln His Gln Pro
1460                1465                1470

cca  act ctg gat tta ctc  ttt gag ctg ttg aga  gat gtg acg aaa      4638
Pro  Thr Leu Asp Leu Leu  Phe Glu Leu Leu Arg  Asp Val Thr Lys
1475                1480                1485

aca  cca gga cca ggg ttt  ggt atc tat gca gtg  gtt cac ctc ctc      4683
Thr  Pro Gly Pro Gly Phe  Gly Ile Tyr Ala Val  Val His Leu Leu
1490                1495                1500

ctt  cct gtg atg tcc gtt  tgg ctc cgc cgg agc  cat aaa gac cat      4728
Leu  Pro Val Met Ser Val  Trp Leu Arg Arg Ser  His Lys Asp His
1505                1510                1515

tcc  tac tgg gat atg gcc  tct gcc aat ttc aag  cac gct att ggt      4773
Ser  Tyr Trp Asp Met Ala  Ser Ala Asn Phe Lys  His Ala Ile Gly
1520                1525                1530

ctg  tcc tgt gag ctg gtg  gtg gag cac att caa  agc ttt cta cat      4818
Leu  Ser Cys Glu Leu Val  Val Glu His Ile Gln  Ser Phe Leu His
1535                1540                1545

tca  gat atc agg tac gag  agc atg atc aat acc  atg ctg aag gac      4863
Ser  Asp Ile Arg Tyr Glu  Ser Met Ile Asn Thr  Met Leu Lys Asp
1550                1555                1560

ctc  ttt gag ttg ctg gtc  gcc tgt gtg gcc aag  ccc act gaa acc      4908
Leu  Phe Glu Leu Leu Val  Ala Cys Val Ala Lys  Pro Thr Glu Thr
1565                1570                1575

atc  tcc aga gtg ggc tgc  tcc tgt att aga tac  gtc ctt gtg aca      4953
Ile  Ser Arg Val Gly Cys  Ser Cys Ile Arg Tyr  Val Leu Val Thr
1580                1585                1590

gcg  ggc cct gtg ttc act  gag gag atg tgg agg  ctt gcc tgc tgt      4998
Ala  Gly Pro Val Phe Thr  Glu Glu Met Trp Arg  Leu Ala Cys Cys
1595                1600                1605

gcc  ctg caa gat gcg ttc  tct gcc aca ctc aag  cca gtg aag gac      5043
Ala  Leu Gln Asp Ala Phe  Ser Ala Thr Leu Lys  Pro Val Lys Asp
1610                1615                1620

ctg  ctg ggc tgc ttc cac  agc ggc acg gag agc  ttc agc ggg gaa      5088
Leu  Leu Gly Cys Phe His  Ser Gly Thr Glu Ser  Phe Ser Gly Glu
1625                1630                1635

ggc  tgc cag gtg cga gtg  gcg gcc ccg tcc tcc  tcc cca agt gcc      5133
Gly  Cys Gln Val Arg Val  Ala Ala Pro Ser Ser  Ser Pro Ser Ala
1640                1645                1650

gag  gcc gag tac tgg cgc  atc cga gcc atg gcc  cag cag gtg ttt      5178
Glu  Ala Glu Tyr Trp Arg  Ile Arg Ala Met Ala  Gln Gln Val Phe
1655                1660                1665

atg  ctg gac acc cag tgc  tca cca aag aca cca  aac aac ttt gac      5223
Met  Leu Asp Thr Gln Cys  Ser Pro Lys Thr Pro  Asn Asn Phe Asp
1670                1675                1680

cac  gct cag tcc tgc cag  ctc att att gag ctg  cct cct gat gaa      5268
His  Ala Gln Ser Cys Gln  Leu Ile Ile Glu Leu  Pro Pro Asp Glu
1685                1690                1695

aaa  cca aat gga cac acc  aag aaa agc gtg tct  ttc agg gaa att      5313
Lys  Pro Asn Gly His Thr  Lys Lys Ser Val Ser  Phe Arg Glu Ile
1700                1705                1710
```

```
gtg  gtg agc ctg ctg tct  cat cag gtg tta ctc  cag aac tta tat      5358
Val  Val Ser Leu Leu Ser  His Gln Val Leu Leu  Gln Asn Leu Tyr
1715                1720                1725

gac  atc ttg tta gaa gag  ttt gtc aaa ggc ccc  tct cct gga gag      5403
Asp  Ile Leu Leu Glu Glu  Phe Val Lys Gly Pro  Ser Pro Gly Glu
1730                1735                1740

gaa  aag acg ata caa gtg  cca gaa gcc aag ctg  gct ggc ttc ctc      5448
Glu  Lys Thr Ile Gln Val  Pro Glu Ala Lys Leu  Ala Gly Phe Leu
1745                1750                1755

aga  tac atc tct atg cag  aac ttg gca gtc ata  ttc gac ctg ctg      5493
Arg  Tyr Ile Ser Met Gln  Asn Leu Ala Val Ile  Phe Asp Leu Leu
1760                1765                1770

ctg  gac tct tat agg act  gcc agg gag ttt gac  acc agc ccc ggg      5538
Leu  Asp Ser Tyr Arg Thr  Ala Arg Glu Phe Asp  Thr Ser Pro Gly
1775                1780                1785

ctg  aag tgc ctg ctg aag  aaa gtg tct ggc atc  ggg ggc gcc gcc      5583
Leu  Lys Cys Leu Leu Lys  Lys Val Ser Gly Ile  Gly Gly Ala Ala
1790                1795                1800

aac  ctc tac cgc cag tct  gcg atg agc ttt aac  att tat ttc cac      5628
Asn  Leu Tyr Arg Gln Ser  Ala Met Ser Phe Asn  Ile Tyr Phe His
1805                1810                1815

gcc  ctg gtg tgt gct gtt  ctc acc aat caa gaa  acc atc acg gcc      5673
Ala  Leu Val Cys Ala Val  Leu Thr Asn Gln Glu  Thr Ile Thr Ala
1820                1825                1830

gag  caa gtg aag aag gtc  ctt ttt gag gac gac  gag aga agc acg      5718
Glu  Gln Val Lys Lys Val  Leu Phe Glu Asp Asp  Glu Arg Ser Thr
1835                1840                1845

gat  tct tcc cag cag tgt  tca tct gag gat gaa  gac atc ttt gag      5763
Asp  Ser Ser Gln Gln Cys  Ser Ser Glu Asp Glu  Asp Ile Phe Glu
1850                1855                1860

gaa  acc gcc cag gtc agc  ccc ccg aga ggc aag  gag aag aga cag      5808
Glu  Thr Ala Gln Val Ser  Pro Pro Arg Gly Lys  Glu Lys Arg Gln
1865                1870                1875

tgg  cgg gca cgg atg ccc  ttg ctc agc gtc cag  cct gtc agc aac      5853
Trp  Arg Ala Arg Met Pro  Leu Leu Ser Val Gln  Pro Val Ser Asn
1880                1885                1890

gca  gat tgg gtg tgg ctg  gtc aag agg ctg cac  aag ctg tgc atg      5898
Ala  Asp Trp Val Trp Leu  Val Lys Arg Leu His  Lys Leu Cys Met
1895                1900                1905

gaa  ctg tgc aac aac tac  atc cag atg cac ttg  gac ctg gag aac      5943
Glu  Leu Cys Asn Asn Tyr  Ile Gln Met His Leu  Asp Leu Glu Asn
1910                1915                1920

tgt  atg gag gag cct ccc  atc ttc aag ggc gac  ccg ttc ttc atc      5988
Cys  Met Glu Glu Pro Pro  Ile Phe Lys Gly Asp  Pro Phe Phe Ile
1925                1930                1935

ctg  ccc tcc ttc cag tcc  gag tca tcc acc cca  tcc acc ggg ggc      6033
Leu  Pro Ser Phe Gln Ser  Glu Ser Ser Thr Pro  Ser Thr Gly Gly
1940                1945                1950

ttc  tct ggg aaa gaa acc  cct tcc gag gat gac  aga agc cag tcc      6078
Phe  Ser Gly Lys Glu Thr  Pro Ser Glu Asp Asp  Arg Ser Gln Ser
1955                1960                1965

cgg  gag cac atg ggc gag  tcc ctg agc ctg aag  gcc ggt ggt ggg      6123
Arg  Glu His Met Gly Glu  Ser Leu Ser Leu Lys  Ala Gly Gly Gly
1970                1975                1980

gac  ctg ctg ctg ccc ccc  agc ccc aaa gtg gag  aag aag gat ccc      6168
Asp  Leu Leu Leu Pro Pro  Ser Pro Lys Val Glu  Lys Lys Asp Pro
1985                1990                1995

agc  cgg aag aag gag tgg  tgg gag aat gcg ggg  aac aaa atc tac      6213
Ser  Arg Lys Lys Glu Trp  Trp Glu Asn Ala Gly  Asn Lys Ile Tyr
```

```
2000                2005                2010

acc  atg gca gcc gac aag  acc att tca aag ttg  atg acc gaa tac      6258
Thr  Met Ala Ala Asp Lys  Thr Ile Ser Lys Leu  Met Thr Glu Tyr
2015                2020                2025

aaa  aag agg aaa cag cag  cac aac ctg tcc gcg  ttc ccc aaa gag      6303
Lys  Lys Arg Lys Gln Gln  His Asn Leu Ser Ala  Phe Pro Lys Glu
2030                2035                2040

gtc  aaa gtg gag aag aaa  gga gag cca ctg ggt  ccc agg ggc cag      6348
Val  Lys Val Glu Lys Lys  Gly Glu Pro Leu Gly  Pro Arg Gly Gln
2045                2050                2055

gac  tcc ccg ctg ctt cag  cgt ccc cag cac ttg  atg gac caa ggg      6393
Asp  Ser Pro Leu Leu Gln  Arg Pro Gln His Leu  Met Asp Gln Gly
2060                2065                2070

caa  atg cgg cat tcc ttc  agc gca ggc ccc gag  ctg ctg cga cag      6438
Gln  Met Arg His Ser Phe  Ser Ala Gly Pro Glu  Leu Leu Arg Gln
2075                2080                2085

gac  aag agg ccc cgc tca  ggc tcc acc ggg agc  tcc ctc agt gtc      6483
Asp  Lys Arg Pro Arg Ser  Gly Ser Thr Gly Ser  Ser Leu Ser Val
2090                2095                2100

tcg  gtg aga gac gca gaa  gca cag atc cag gca  tgg acc aac atg      6528
Ser  Val Arg Asp Ala Glu  Ala Gln Ile Gln Ala  Trp Thr Asn Met
2105                2110                2115

gtg  cta aca gtt ctc aat  cag att cag att ctc  cca gac cag acc      6573
Val  Leu Thr Val Leu Asn  Gln Ile Gln Ile Leu  Pro Asp Gln Thr
2120                2125                2130

ttc  acg gcc ctc cag ccc  gca gtg ttc ccg tgc  atc agt cag ctg      6618
Phe  Thr Ala Leu Gln Pro  Ala Val Phe Pro Cys  Ile Ser Gln Leu
2135                2140                2145

acc  tgt cac gtg acc gac  atc aga gtt cgc cag  gct gtg agg gag      6663
Thr  Cys His Val Thr Asp  Ile Arg Val Arg Gln  Ala Val Arg Glu
2150                2155                2160

tgg  ctg ggc agg gtg ggc  cgt gtc tat gac atc  att gtg tag          6705
Trp  Leu Gly Arg Val Gly  Arg Val Tyr Asp Ile  Ile Val
2165                2170                2175

ccgactcctg ttctactctc ccaccaaata acagtagtga gggttagagt cctgccaata   6765

cagctgttgc attttcccca ccactagccc cacttaaact actactactg tctcagagaa   6825

cagtgtttcc taatgtaaaa agcctttcca accactgatc agcattgggg ccatactaag   6885

gtttgtatct agatgacaca aacgatattc tgattttgca cattattata gaagaatcta   6945

taatccttga tatgtttcta actcttgaag tatatttccc agtgcttttg cttacagtgt   7005

tgtccccaaa tgggtcattt tcaaggatta ctcatttgaa aacactatat tgatccattt   7065

gatccatcat ttaaaaaata aatacaattc ctaaggcaat atctgctggt aagtcaagct   7125

gataaacact cagacatcta gtaccaggga ttattaattg gaggaagatt tatggttatg   7185

ggtctggctg ggaagaagac aactataaat acatattctt gggtgtcata atcaagaaag   7245

aggtgacttc tgttgtaaaa taatccagaa cacttcaaaa ttattcctaa atcattaaga   7305

ttttcaggta ttcaccaatt tccccatgta aggtactgtg ttgtaccttt atttctgtat   7365

ttctaaaaga agaaagttct ttcctagcag ggtttgaagt ctgtggctta tcagcctgtg   7425

acacagagta cccagtgaaa gtggctggta cgtagattgt caagagacat aagaccgacc   7485

agccaccctg gctgttcttg tggtgtttgt ttccatcccc aaggcaaaca aggaaaggaa   7545

aggaaagaag aaaaggtgcc ttagtccttt gttgcacttc catttccatg ccccacaatt   7605

gtctgaacat aaggtatagc atttggtttt taagaaaaca aaacattaag acgcaactca   7665

ttttatatca acacgcttgg aggaaaggga ctcagggaag ggagcaggga gtgtggggtg   7725
```

```
gggatggatt atgatgaaat cattttcaat cttaaaatat aatacaacaa tcttgcaaaa   7785
ttatggtgtc agttacacaa gctctagtct caaaatgaaa gtaatggaga aagacactga   7845
aatttagaaa attttgtcga tttaaaatat ttctcctatc taccaagtaa agttacccta   7905
tgtttgatgt ctttgcattc agaccaatat ttcaggtgga tatttctaag tattactaga   7965
aaatacgttt gaaagcttta tcttattatt tacagtattt ttatatttct tacattatcc   8025
taatgattga aaactcctca atcaagctta cttacacaca ttctacagag ttatttaagg   8085
catacattat aatctcccag ccccattcat aatgaataag tcaccccttta aatataagac   8145
acaaattcta cagtattgaa ataaggattt aaaggggtat ttgtaaactt tgccctcctt   8205
gagaaatatg gaactacctt agaggttaag aggaaggcag tgttctgact tctttaggtg   8265
atctgaaaaa aacaccctta tcatccagtg taccatctag agatcaccac agaatccatt   8325
tttttcccag ttccacaaaa cactctgttt gccttcagtt tttactcact agacaataat   8385
tcaagtttag aaacaggtaa tcagctattt gatcttaaaa ggcaatgaat tgttgggata   8445
tcagtgaact atgttgtata cttttgaatt tttacatttt ataaatggaa ttgaaagttg   8505
gataactgct ttttttaaat tttccaacag aagtaacacc acagttgctt tgtttctttt   8565
tatagcttac ctgaggttca gttcttcttt gtgaacctgt gagtactcca cagtttactg   8625
ggggaaaagg cttcagtaaa gcagaggcta gaattacagt atttatacat agcaactttt   8685
cataaagtag aaaaattcaa aggaagctgt ctcaatttga gaataccagc tgggcacggt   8745
ggctcacgcc tgtaatccca gcacttactt tgggaggcca aggtgggcag ataacctgcg   8805
gtcaggagtt tgagaccagg ctggacaaca tggtgaaacc tcgtctctac taaaaataca   8865
aaaattagcc aggtgtggta ggatgcacct gtaatcccag ctacttagga ggccgagaca   8925
ggagaatcgc tcgaacccag gaggcggacg ttgcagtgag ccaagattgc accattgcac   8985
tccagactgg gtgacaagag tgaaactcca tctaaaaaaa aaaaaaaaaa aaagtgaata   9045
ctgtatccca aagtatgtta gttgtttgtt tggaaatcag cattctcccc gatgctctat   9105
tatgggatcc aaaattcttg aacataagtt taccctgtac tgtgtccaaa cactgttcta   9165
gttctagcct gattatgggt cccaagaata aaaggatgag taggtgtaca gagctcttga   9225
cctacaattt tttaagagtg ttttggtacc ttcccattgt cttctctata actcagtcct   9285
aacatactct gcactcgagt taccagccat ccacactgac atcagatttc aaccagaacc   9345
atcactgagt gacagcagta cttctcagag gtatttgcag cttgatgcaa agtagtctct   9405
aatgagtagg cattcaggtg gttcttccca gcaggtggag aagaaaggga ggagatgaag   9465
aacactgaga ggggagtggc accttcccag gctgcccagc tcagtctctt gccctgttcc   9525
tgtgactcag ctgcccactc ccccaacttt gtttccctcc ctcccagtct ctgaaagtgt   9585
caggtgtttc tctcctcaca gtctcttttg cagcaacagt aagacaaaat tcaaggcagc   9645
cttttaaagt tacgaacagt tattagcatg tatttacaga cctaagcaga atgagagttt   9705
atacattgtt tttagttgcc tgtatttata gccaaaagta tattacctta aagttgagat   9765
ctttctcttc ttttcctaaa ttttggtaaa gtgtgcttca tgaaacaaac atctggaaaa   9825
ctccaagtat aagagaccct ggactgatga tggcccagcc aagtatatgg agggacagag   9885
ttctctctgt cattaatgag gacatcggtt ttcacaattg aacctcatgc actgtccaca   9945
gcatctcacc tagctcctgt atctcctgat ctgcttttaa aaatagttag ttaggctgcc  10005
tttttacacc accttctctc tctccccttg tggtaatttt ccagccttcc ccatagatat  10065
```

```
aaaactagaa cacctttatg atttggggtc tatgtaatga ctgaccgata agaacccagg  10125
cagatgctaa catacttaac agctcgcatt aaaatacttt aaatcaggcg tgatggctca  10185
ttcctgtaat ctcaagcact ttgggaggct aaggtgggtg gatctcttga ggtcaggagt  10245
tcgagaccaa cctggccaac gtggtgaaac cccgtctcta ctaaaaatac aaaattagcc  10305
gggcatggtg gcagctgcct gtaatcccag ctactcggga agctgaggca ggagaattgc  10365
ttgaacctgg gaggtgggga ttgcagtcag ccaagattgt tctgcagcat gggtgacaaa  10425
gtgagacttc gtctcaagta aataaaacta aaatttttaa atcaaacatg acaaaaatgt  10485
taatataatt cagaagtacc ttgaaattga aacatatttg tgcaatgatc attaggcttt  10545
ttgtccttgt tgttttaaaa tgaggcttat acagagtgag ttgagagtca agtagccttc  10605
gctgtgagac ggtaatgcag ttatataata gatacccttg actttgccag attcatcaca  10665
atactgctta tacaggaaag ttttctcaga aaggaaaatc cattagtatc agtcccatca  10725
agccaaacag aatgaagacc tttgatagta atagcaagag gttacaaata gcagggagga  10785
ggcgagtagt gaatgtcact gtgattgcaa acccttacct gtattatcac acgtagtcct  10845
cacaacaacc ttgtgagaca agtgttgtgt tcctcatttt ttcagagggg aacacagacc  10905
cagagaggtt aagaaatttg cccaagataa caagtaaaag gcaaagttgg ttgcaaaaga  10965
ggtgtttctg aattcaaggg ccatactctc tctctgacaa catgctctaa gtccatagag  11025
taagcactct agtatgaaaa aaagtttcaa ggaacgaggc catgaaaatg agactatttg  11085
acatctcaga tctgtctggg atgttatgga ggtttttaaa aataaagttg aaaaaagaaa  11145
atgaatcatg tttatacata aaaaaatcac atgtaacaca tttcaagtgt ttgaaaataa  11205
aaccaaaatc taaactttag tcttcaagca gacattcagt gttactttag aaaactcact  11265
gaattaggtg gaaatgatgg aataatacta ttcatggcca gctattaaca cagaagaaca  11325
tggcagtgtg tgtctggaac ggcatgcaca atttgtaaac ctttttcaaa tatcatttaa  11385
tcaactcaga ataaagtgcc ctgtagccaa cagtgcctct ttacttgctt ctctgggaaa  11445
tacatggtac taaattagta gcacaaagtt tgggaatatg caaaataatg gataaccatt  11505
tttcaaaatg tacattctct gaagaggaag cagctggttg gacaggattt cttgaagagc  11565
caggtgctaa gggcatcagg tcgacatcca tagtaaccat gtgccataac atctacacat  11625
ttccacttgt tttacagaca aggtaacagg cagaaggaaa atccagagtc ttgcagtaag  11685
cagatgacaa aacttcaata tgcttgggca ccacttaggt gaccccaggg agatttagtg  11745
tggccttagg aaagcaaaag agcacttttt attggaaata tgagcttgtc actgggaaag  11805
atttgtaaaa ttgatcaaga acttgattta taattatgcc tcaaaaaaaa aagttctcat  11865
ttagtagtgg agcaatctag aaaacatacc ttttttgttt gtttggaaga tcctctttcc  11925
ctggctgtat tgtagtgttt gctatttgat gtggaaataa ctaataactt aagattttgg  11985
aacagaacac cctttagatt tccaaaacac aattcttatt tcagggaaga cagaccaaaa  12045
atatctcctg agatcattgg tttctttata aattgtggta ccactccatc attgaagaga  12105
aaccactacc acaccactag caccatacag aaccttttct ctgtatcttt gtacaatact  12165
acaaaggggt accagggagg agagagtggc tgaccacttt agtgacaaaa cagcactcca  12225
ctgctggtga atcccatcta attatggtcc ttccaccctt ttcaaccacc aacaactgtt  12285
cgtactgtta attcctatcc tgaaggttta accagtggtt gtctagtatc ttctgtcttt  12345
agaacagtgg ttctcaaact ttagtacaca tcagcatcac ctggagggcc tttttttaaa  12405
ataagacaca gattgctggg ctcatggtca gagttcccag ttaagtaaat caggaaattt  12465
```

```
gtatttctaa caagtttata ggtgaggcca atactgctgt tttgggaact atgctttgag  12525
aaccactgcc ttgaaaaaat ttccaacttc tacctttaag atcagcctga cttatcaaac  12585
gctagagaaa aactgaatct acccttgggc agatgacttg ggattggatt ctatacagca  12645
gtcttgctca atcttcccag tttccagttt tattatacca acaattggtt tttacaagct  12705
agaagacaat gaatgtataa gttctatgga acagtgagat aaatctaagc ttcttgtctt  12765
tgtatttaga aacattgatt ctatggatga tcatttgtat catgttgacc ctttgacttg  12825
tactgaaggt gattttaaat ttaagtatgt agtgtttgaa tttcttccat ccatgtcgtt  12885
ttaatgagat gtttccatgt cagctccttt acagccttgg ctcctggctt acagattttt  12945
gaatagttgt ttgcttgcca gttgttttac atctttcatt ggccaccaaa atattagcca  13005
tttgagatga gatgagacta cttgttgtac cttcatcttt catttaattt tctggcgtaa  13065
attaacattt taatttcata tatatctgta aagagtctac ccaaaggctt cacggaaatt  13125
tgcaaaatga actaattccc ttttaagcag caggtgtgcc tgtttttgac ttttcagtaa  13185
atatgttgtt tgtgcacata tctacatggt ggagaccata ttcattattt catcttccaa  13245
ataatgggaa aaatataaaa gtgaatcagt gtgctttggg aattcagtga aatcatgtta  13305
actcatatag agggggcctt agtttatctc ttctttactg aattaattag ttttggaaat  13365
tcttttacca ttaaaaaaaa ttaaggacca tacagagaat gatttaagaa aaaacaagtc  13425
acttaaaaat catcacctat ttataaactg tattaattac acataatgct tattgattca  13485
atgaggtttc tctaaagact tctgcttaat aaatatgctg acttcattta aattagttta  13545
gactattgta ggaatggaag gaaatgatta tatttactag aattagtgag atcagaaagc  13605
atatcagaat gttgatgata tcaaggagac aatctacaga gtttttgcct ctgtggatgg  13665
aaataagggt gttttttttt ggtttttttt ttactttagt ttcccataat ttttggaaat  13725
tatgtgtgca tttagttctt ttagtaacac tgattttaaa attaaatttc aaaagtcaat  13785
ctctaagagt aatttatttt tgttttacca accagtgcca aaaaggagag gagggaatcc  13845
aaaagccaat cttttgaacc aatgtgtaaa agattatgtt ttttcttaaa gttagggagg  13905
ctcgggccct gacactgcca gccccagtga gcatccctgg ctacctcggg attatgtgca  13965
agctgctttg tcctacattt ctttcatctg gttcttattg ggagtgcttc tctctaataa  14025
aaattgattt cccacaaaat aggcaaagct gaacaaagat gaatgctttt gataagttgg  14085
gtttcacttc agttgaaaca atgtgataga atatccaggt gtggcatgat ggggcaggag  14145
gaggtgccta gagggaaaag ttatttttgt ttcttagtgt tgtgttgtgg ggatgggaca  14205
gataagaata agatgtttat tgccctaatc atgctaagag actattattc aatatgcttt  14265
tcccgctttt ctaagaggaa taaacttaga caaattacat tataaacagt tcccctacta  14325
ctatctccca ctctagataa agccagtggg tggtatgggt ccttttattc cttatagtat  14385
tatgccaaag aatcaactta ttttcattga agattataaa taaatgaagc ttgttatagc  14445
cataatgatt tgagtcagta taccatttta cctataaaat gcaaaattca tccttgcaac  14505
cccattcacc aggagccttg aagcattttg tttactccaa aggccttgtc aaggaagcat  14565
aattttttgt tttgccttct tatttagtca gtttggtcat atttacttaa aaaaacaaac  14625
tgaaaatcac actcctttat atgttgatat aactgatttt atagaatctg tctgttcttt  14685
gtttaacagg tctctgtaag caagcttgca agtgtatttt gtgtacattt tatctgaggt  14745
ggaaatgaaa attctaaaga gaaaatattt taaaagatat tgtatttatg ttgcttgtgt  14805
```

```
tgtagaataa agattcaaat gcattaaaaa tctggtacat gaaacaa          14852


<210> SEQ ID NO 35
<211> LENGTH: 2177
<212> TYPE: PRT
<213> ORGANISM: Homo sapiens

<400> SEQUENCE: 35

Met Glu Glu Ile Leu Arg Lys Leu Gln Lys Glu Ala Ser Gly Ser Lys
1               5                   10                  15

Tyr Lys Ala Ile Lys Glu Ser Cys Thr Trp Ala Leu Glu Thr Leu Gly
            20                  25                  30

Gly Leu Asp Thr Ile Val Lys Ile Pro Pro His Val Leu Arg Glu Lys
        35                  40                  45

Cys Leu Leu Pro Leu Gln Leu Ala Leu Glu Ser Lys Asn Val Lys Leu
    50                  55                  60

Ala Gln His Ala Leu Ala Gly Met Gln Lys Leu Leu Ser Glu Glu Arg
65                  70                  75                  80

Phe Val Ser Met Glu Thr Asp Ser Asp Glu Lys Gln Leu Leu Asn Gln
                85                  90                  95

Ile Leu Asn Ala Val Lys Val Thr Pro Ser Leu Asn Glu Asp Leu Gln
            100                 105                 110

Val Glu Val Met Lys Val Leu Leu Cys Ile Thr Tyr Thr Pro Thr Phe
        115                 120                 125

Asp Leu Asn Gly Ser Ala Val Leu Lys Ile Ala Glu Val Cys Ile Glu
    130                 135                 140

Thr Tyr Ile Ser Ser Cys His Gln Arg Ser Ile Asn Thr Ala Val Arg
145                 150                 155                 160

Ala Thr Leu Ser Gln Met Leu Ser Asp Leu Thr Leu Gln Leu Arg Gln
                165                 170                 175

Arg Gln Glu Asn Thr Ile Ile Glu Asn Pro Asp Val Pro Gln Asp Phe
            180                 185                 190

Gly Asn Gln Gly Ser Thr Val Glu Ser Leu Cys Asp Asp Val Val Ser
        195                 200                 205

Val Leu Thr Val Leu Cys Glu Lys Leu Gln Ala Ala Ile Asn Asp Ser
    210                 215                 220

Gln Gln Leu Gln Leu Leu Tyr Leu Glu Cys Ile Leu Ser Val Leu Ser
225                 230                 235                 240

Ser Ser Ser Ser Ser Met His Leu His Arg Arg Phe Thr Asp Leu Ile
                245                 250                 255

Trp Lys Asn Leu Cys Pro Ala Leu Ile Val Ile Leu Gly Asn Pro Ile
            260                 265                 270

His Asp Lys Thr Ile Thr Ser Ala His Thr Ser Ser Thr Ser Thr Ser
        275                 280                 285

Leu Glu Ser Asp Ser Ala Ser Pro Gly Val Ser Asp His Gly Arg Gly
    290                 295                 300

Ser Gly Cys Ser Cys Thr Ala Pro Ala Leu Ser Gly Pro Val Ala Arg
305                 310                 315                 320

Thr Ile Tyr Tyr Ile Ala Ala Glu Leu Val Arg Leu Val Gly Ser Val
                325                 330                 335

Asp Ser Met Lys Pro Val Leu Gln Ser Leu Tyr His Arg Val Leu Leu
            340                 345                 350

Tyr Pro Pro Pro Gln His Arg Val Glu Ala Ile Lys Ile Met Lys Glu
        355                 360                 365
```

```
Ile Leu Gly Ser Pro Gln Arg Leu Cys Asp Leu Ala Gly Pro Ser Ser
    370                 375                 380

Thr Glu Ser Glu Ser Arg Lys Arg Ser Ile Ser Lys Arg Lys Ser His
385                 390                 395                 400

Leu Asp Leu Leu Lys Leu Ile Met Asp Gly Met Thr Glu Ala Cys Ile
                405                 410                 415

Lys Gly Gly Ile Glu Ala Cys Tyr Ala Ala Val Ser Cys Val Cys Thr
            420                 425                 430

Leu Leu Gly Ala Leu Asp Glu Leu Ser Gln Gly Lys Gly Leu Ser Glu
        435                 440                 445

Gly Gln Val Gln Leu Leu Leu Leu Arg Leu Glu Glu Leu Lys Asp Gly
    450                 455                 460

Ala Glu Trp Ser Arg Asp Ser Met Glu Ile Asn Glu Ala Asp Phe Arg
465                 470                 475                 480

Trp Gln Arg Arg Val Leu Ser Ser Glu His Thr Pro Trp Glu Ser Gly
                485                 490                 495

Asn Glu Arg Ser Leu Asp Ile Ser Ile Ser Val Thr Thr Asp Thr Gly
            500                 505                 510

Gln Thr Thr Leu Glu Gly Glu Leu Gly Gln Thr Thr Pro Glu Asp His
        515                 520                 525

Ser Gly Asn His Lys Asn Ser Leu Lys Ser Pro Ala Ile Pro Glu Gly
    530                 535                 540

Lys Glu Thr Leu Ser Lys Val Leu Glu Thr Glu Ala Val Asp Gln Pro
545                 550                 555                 560

Asp Val Val Gln Arg Ser His Thr Val Pro Tyr Pro Asp Ile Thr Asn
                565                 570                 575

Phe Leu Ser Val Asp Cys Arg Thr Arg Ser Tyr Gly Ser Arg Tyr Ser
            580                 585                 590

Glu Ser Asn Phe Ser Val Asp Asp Gln Asp Leu Ser Arg Thr Glu Phe
        595                 600                 605

Asp Ser Cys Asp Gln Tyr Ser Met Ala Ala Glu Lys Asp Ser Gly Arg
    610                 615                 620

Ser Asp Val Ser Asp Ile Gly Ser Asp Asn Cys Ser Leu Ala Asp Glu
625                 630                 635                 640

Glu Gln Thr Pro Arg Asp Cys Leu Gly His Arg Ser Leu Arg Thr Ala
                645                 650                 655

Ala Leu Ser Leu Lys Leu Leu Lys Asn Gln Glu Ala Asp Gln His Ser
            660                 665                 670

Ala Arg Leu Phe Ile Gln Ser Leu Glu Gly Leu Leu Pro Arg Leu Leu
        675                 680                 685

Ser Leu Ser Asn Val Glu Glu Val Asp Thr Ala Leu Gln Asn Phe Ala
    690                 695                 700

Ser Thr Phe Cys Ser Gly Met Met His Ser Pro Gly Phe Asp Gly Asn
705                 710                 715                 720

Ser Ser Leu Ser Phe Gln Met Leu Met Asn Ala Asp Ser Leu Tyr Thr
                725                 730                 735

Ala Ala His Cys Ala Leu Leu Leu Asn Leu Lys Leu Ser His Gly Asp
            740                 745                 750

Tyr Tyr Arg Lys Arg Pro Thr Leu Ala Pro Gly Val Met Lys Asp Phe
        755                 760                 765

Met Lys Gln Val Gln Thr Ser Gly Val Leu Met Val Phe Ser Gln Ala
    770                 775                 780

Trp Ile Glu Glu Leu Tyr His Gln Val Leu Asp Arg Asn Met Leu Gly
```

```
785                 790                 795                 800

Glu Ala Gly Tyr Trp Gly Ser Pro Glu Asp Asn Ser Leu Pro Leu Ile
                805                 810                 815

Thr Met Leu Thr Asp Ile Asp Gly Leu Glu Ser Ser Ala Ile Gly Gly
            820                 825                 830

Gln Leu Met Ala Ser Ala Ala Thr Glu Ser Pro Phe Ala Gln Ser Arg
        835                 840                 845

Arg Ile Asp Asp Ser Thr Val Ala Gly Val Ala Phe Ala Arg Tyr Ile
    850                 855                 860

Leu Val Gly Cys Trp Lys Asn Leu Ile Asp Thr Leu Ser Thr Pro Leu
865                 870                 875                 880

Thr Gly Arg Met Ala Gly Ser Ser Lys Gly Leu Ala Phe Ile Leu Gly
                885                 890                 895

Ala Glu Gly Ile Lys Glu Gln Asn Gln Lys Glu Arg Asp Ala Ile Cys
            900                 905                 910

Met Ser Leu Asp Gly Leu Arg Lys Ala Ala Arg Leu Ser Cys Ala Leu
        915                 920                 925

Gly Val Ala Ala Asn Cys Ala Ser Ala Leu Ala Gln Met Ala Ala Ala
    930                 935                 940

Ser Cys Val Gln Glu Glu Lys Glu Glu Arg Glu Ala Gln Glu Pro Ser
945                 950                 955                 960

Asp Ala Ile Thr Gln Val Lys Leu Lys Val Glu Gln Lys Leu Glu Gln
                965                 970                 975

Ile Gly Lys Val Gln Gly Val Trp Leu His Thr Ala His Val Leu Cys
            980                 985                 990

Met Glu Ala Ile Leu Ser Val Gly  Leu Glu Met Gly Ser  His Asn Pro
        995                 1000                1005

Asp Cys  Trp Pro His Val Phe  Arg Val Cys Glu Tyr  Val Gly Thr
    1010                1015                1020

Leu Glu  His Asn His Phe Ser  Asp Gly Ala Ser Gln  Pro Pro Leu
    1025                1030                1035

Thr Ile  Ser Gln Pro Gln Lys  Ala Thr Gly Ser Ala  Gly Leu Leu
    1040                1045                1050

Gly Asp  Pro Glu Cys Glu Gly  Ser Pro Pro Glu His  Ser Pro Glu
    1055                1060                1065

Gln Gly  Arg Ser Leu Ser Thr  Ala Pro Val Val Gln  Pro Leu Ser
    1070                1075                1080

Ile Gln  Asp Leu Val Arg Glu  Gly Ser Arg Gly Arg  Ala Ser Asp
    1085                1090                1095

Phe Arg  Gly Gly Ser Leu Met  Ser Gly Ser Ser Ala  Ala Lys Val
    1100                1105                1110

Val Leu  Thr Leu Ser Thr Gln  Ala Asp Arg Leu Phe  Glu Asp Ala
    1115                1120                1125

Thr Asp  Lys Leu Asn Leu Met  Ala Leu Gly Gly Phe  Leu Tyr Gln
    1130                1135                1140

Leu Lys  Lys Ala Ser Gln Ser  Gln Leu Phe His Ser  Val Thr Asp
    1145                1150                1155

Thr Val  Asp Tyr Ser Leu Ala  Met Pro Gly Glu Val  Lys Ser Thr
    1160                1165                1170

Gln Asp  Arg Lys Ser Ala Leu  His Leu Phe Arg Leu  Gly Asn Ala
    1175                1180                1185

Met Leu  Arg Ile Val Arg Ser  Lys Ala Arg Pro Leu  Leu His Val
    1190                1195                1200
```

```
Met Arg  Cys Trp Ser Leu Val  Ala Pro His Leu Val  Glu Ala Ala
    1205                 1210                 1215

Cys His  Lys Glu Arg His Val  Ser Gln Lys Ala Val  Ser Phe Ile
    1220                 1225                 1230

His Asp  Ile Leu Thr Glu Val  Leu Thr Asp Trp Asn  Glu Pro Pro
    1235                 1240                 1245

His Phe  His Phe Asn Glu Ala  Leu Phe Arg Pro Phe  Glu Arg Ile
    1250                 1255                 1260

Met Gln  Leu Glu Leu Cys Asp  Glu Asp Val Gln Asp  Gln Val Val
    1265                 1270                 1275

Thr Ser  Ile Gly Glu Leu Val  Glu Val Cys Ser Thr  Gln Ile Gln
    1280                 1285                 1290

Ser Gly  Trp Arg Pro Leu Phe  Ser Ala Leu Glu Thr  Val His Gly
    1295                 1300                 1305

Gly Asn  Lys Ser Glu Met Lys  Glu Tyr Leu Val Gly  Asp Tyr Ser
    1310                 1315                 1320

Met Gly  Lys Gly Gln Ala Pro  Val Phe Asp Val Phe  Glu Ala Phe
    1325                 1330                 1335

Leu Asn  Thr Asp Asn Ile Gln  Val Phe Ala Asn Ala  Ala Thr Ser
    1340                 1345                 1350

Tyr Ile  Met Cys Leu Met Lys  Phe Val Lys Gly Leu  Gly Glu Val
    1355                 1360                 1365

Asp Cys  Lys Glu Ile Gly Asp  Cys Ala Pro Ala Pro  Gly Ala Pro
    1370                 1375                 1380

Ser Thr  Asp Leu Cys Leu Pro  Ala Leu Asp Tyr Leu  Arg Arg Cys
    1385                 1390                 1395

Ser Gln  Leu Leu Ala Lys Ile  Tyr Lys Met Pro Leu  Lys Pro Ile
    1400                 1405                 1410

Phe Leu  Ser Gly Arg Leu Ala  Gly Leu Pro Arg Arg  Leu Gln Glu
    1415                 1420                 1425

Gln Ser  Ala Ser Ser Glu Asp  Gly Ile Glu Ser Val  Leu Ser Asp
    1430                 1435                 1440

Phe Asp  Asp Asp Thr Gly Leu  Ile Glu Val Trp Ile  Ile Leu Leu
    1445                 1450                 1455

Glu Gln  Leu Thr Ala Ala Val  Ser Asn Cys Pro Arg  Gln His Gln
    1460                 1465                 1470

Pro Pro  Thr Leu Asp Leu Leu  Phe Glu Leu Leu Arg  Asp Val Thr
    1475                 1480                 1485

Lys Thr  Pro Gly Pro Gly Phe  Gly Ile Tyr Ala Val  Val His Leu
    1490                 1495                 1500

Leu Leu  Pro Val Met Ser Val  Trp Leu Arg Arg Ser  His Lys Asp
    1505                 1510                 1515

His Ser  Tyr Trp Asp Met Ala  Ser Ala Asn Phe Lys  His Ala Ile
    1520                 1525                 1530

Gly Leu  Ser Cys Glu Leu Val  Val Glu His Ile Gln  Ser Phe Leu
    1535                 1540                 1545

His Ser  Asp Ile Arg Tyr Glu  Ser Met Ile Asn Thr  Met Leu Lys
    1550                 1555                 1560

Asp Leu  Phe Glu Leu Leu Val  Ala Cys Val Ala Lys  Pro Thr Glu
    1565                 1570                 1575

Thr Ile  Ser Arg Val Gly Cys  Ser Cys Ile Arg Tyr  Val Leu Val
    1580                 1585                 1590
```

```
Thr Ala  Gly Pro Val Phe Thr  Glu Glu Met Trp Arg  Leu Ala Cys
    1595                 1600                 1605

Cys Ala  Leu Gln Asp Ala Phe  Ser Ala Thr Leu Lys  Pro Val Lys
    1610                 1615                 1620

Asp Leu  Leu Gly Cys Phe His  Ser Gly Thr Glu Ser  Phe Ser Gly
    1625                 1630                 1635

Glu Gly  Cys Gln Val Arg Val  Ala Ala Pro Ser Ser  Ser Pro Ser
    1640                 1645                 1650

Ala Glu  Ala Glu Tyr Trp Arg  Ile Arg Ala Met Ala  Gln Gln Val
    1655                 1660                 1665

Phe Met  Leu Asp Thr Gln Cys  Ser Pro Lys Thr Pro  Asn Asn Phe
    1670                 1675                 1680

Asp His  Ala Gln Ser Cys Gln  Leu Ile Ile Glu Leu  Pro Pro Asp
    1685                 1690                 1695

Glu Lys  Pro Asn Gly His Thr  Lys Lys Ser Val Ser  Phe Arg Glu
    1700                 1705                 1710

Ile Val  Val Ser Leu Leu Ser  His Gln Val Leu Leu  Gln Asn Leu
    1715                 1720                 1725

Tyr Asp  Ile Leu Leu Glu Glu  Phe Val Lys Gly Pro  Ser Pro Gly
    1730                 1735                 1740

Glu Glu  Lys Thr Ile Gln Val  Pro Glu Ala Lys Leu  Ala Gly Phe
    1745                 1750                 1755

Leu Arg  Tyr Ile Ser Met Gln  Asn Leu Ala Val Ile  Phe Asp Leu
    1760                 1765                 1770

Leu Leu  Asp Ser Tyr Arg Thr  Ala Arg Glu Phe Asp  Thr Ser Pro
    1775                 1780                 1785

Gly Leu  Lys Cys Leu Leu Lys  Lys Val Ser Gly Ile  Gly Gly Ala
    1790                 1795                 1800

Ala Asn  Leu Tyr Arg Gln Ser  Ala Met Ser Phe Asn  Ile Tyr Phe
    1805                 1810                 1815

His Ala  Leu Val Cys Ala Val  Leu Thr Asn Gln Glu  Thr Ile Thr
    1820                 1825                 1830

Ala Glu  Gln Val Lys Lys Val  Leu Phe Glu Asp Asp  Glu Arg Ser
    1835                 1840                 1845

Thr Asp  Ser Ser Gln Gln Cys  Ser Ser Glu Asp Glu  Asp Ile Phe
    1850                 1855                 1860

Glu Glu  Thr Ala Gln Val Ser  Pro Pro Arg Gly Lys  Glu Lys Arg
    1865                 1870                 1875

Gln Trp  Arg Ala Arg Met Pro  Leu Leu Ser Val Gln  Pro Val Ser
    1880                 1885                 1890

Asn Ala  Asp Trp Val Trp Leu  Val Lys Arg Leu His  Lys Leu Cys
    1895                 1900                 1905

Met Glu  Leu Cys Asn Asn Tyr  Ile Gln Met His Leu  Asp Leu Glu
    1910                 1915                 1920

Asn Cys  Met Glu Glu Pro Pro  Ile Phe Lys Gly Asp  Pro Phe Phe
    1925                 1930                 1935

Ile Leu  Pro Ser Phe Gln Ser  Glu Ser Ser Thr Pro  Ser Thr Gly
    1940                 1945                 1950

Gly Phe  Ser Gly Lys Glu Thr  Pro Ser Glu Asp Asp  Arg Ser Gln
    1955                 1960                 1965

Ser Arg  Glu His Met Gly Glu  Ser Leu Ser Leu Lys  Ala Gly Gly
    1970                 1975                 1980

Gly Asp  Leu Leu Leu Pro Pro  Ser Pro Lys Val Glu  Lys Lys Asp
```

```
    1985                1990                1995

Pro Ser  Arg Lys Lys Glu Trp  Trp Glu Asn Ala Gly  Asn Lys Ile
    2000                2005                2010

Tyr Thr  Met Ala Ala Asp Lys  Thr Ile Ser Lys Leu  Met Thr Glu
    2015                2020                2025

Tyr Lys  Lys Arg Lys Gln Gln  His Asn Leu Ser Ala  Phe Pro Lys
    2030                2035                2040

Glu Val  Lys Val Glu Lys Lys  Gly Glu Pro Leu Gly  Pro Arg Gly
    2045                2050                2055

Gln Asp  Ser Pro Leu Leu Gln  Arg Pro Gln His Leu  Met Asp Gln
    2060                2065                2070

Gly Gln  Met Arg His Ser Phe  Ser Ala Gly Pro Glu  Leu Leu Arg
    2075                2080                2085

Gln Asp  Lys Arg Pro Arg Ser  Gly Ser Thr Gly Ser  Ser Leu Ser
    2090                2095                2100

Val Ser  Val Arg Asp Ala Glu  Ala Gln Ile Gln Ala  Trp Thr Asn
    2105                2110                2115

Met Val  Leu Thr Val Leu Asn  Gln Ile Gln Ile Leu  Pro Asp Gln
    2120                2125                2130

Thr Phe  Thr Ala Leu Gln Pro  Ala Val Phe Pro Cys  Ile Ser Gln
    2135                2140                2145

Leu Thr  Cys His Val Thr Asp  Ile Arg Val Arg Gln  Ala Val Arg
    2150                2155                2160

Glu Trp  Leu Gly Arg Val Gly  Arg Val Tyr Asp Ile  Ile Val
    2165                2170                2175


<210> SEQ ID NO 36
<211> LENGTH: 1457
<212> TYPE: DNA
<213> ORGANISM: Homo sapiens
<220> FEATURE:
<221> NAME/KEY: CDS
<222> LOCATION: (211)..(1110)

<400> SEQUENCE: 36

tccgtatgcg cgattcctgt gcgcgaagtt cgggtccgta gtgggctaag gggagggtt     60

tcaaagggag cgcacttccg ctgccctttc tttcgccagc cttacgggcc cgaaccctcg    120

tgtgaagggt gcagtaccta agccggagcg gggtagaggc gggccggcac cccttctga     180

cctccagtgc cgccggcctc aagatcagac atg gcc cag aac ttg aag gac ttg     234
                                 Met Ala Gln Asn Leu Lys Asp Leu
                                 1               5

gcg gga cgg ctg ccc gcc ggg ccc cgg ggc atg ggc acg gcc ctg aag      282
Ala Gly Arg Leu Pro Ala Gly Pro Arg Gly Met Gly Thr Ala Leu Lys
    10                  15                  20

ctg ttg ctg ggg gcc ggc gcc gtg gcc tac ggt gtg cgc gaa tct gtg      330
Leu Leu Leu Gly Ala Gly Ala Val Ala Tyr Gly Val Arg Glu Ser Val
25                  30                  35                  40

ttc acc gtg gaa ggc ggg cac aga gcc atc ttc ttc aat cgg atc ggt      378
Phe Thr Val Glu Gly Gly His Arg Ala Ile Phe Phe Asn Arg Ile Gly
                45                  50                  55

gga gtg cag cag gac act atc ctg gcc gag ggc ctt cac ttc agg atc      426
Gly Val Gln Gln Asp Thr Ile Leu Ala Glu Gly Leu His Phe Arg Ile
            60                  65                  70

cct tgg ttc cag tac ccc att atc tat gac att cgg gcc aga cct cga      474
Pro Trp Phe Gln Tyr Pro Ile Ile Tyr Asp Ile Arg Ala Arg Pro Arg
        75                  80                  85
```

```
aaa atc tcc tcc cct aca ggc tcc aaa gac cta cag atg gtg aat atc      522
Lys Ile Ser Ser Pro Thr Gly Ser Lys Asp Leu Gln Met Val Asn Ile
    90                  95                  100

tcc ctg cga gtg ttg tct cga ccc aat gct cag gag ctt cct agc atg      570
Ser Leu Arg Val Leu Ser Arg Pro Asn Ala Gln Glu Leu Pro Ser Met
105                 110                 115                 120

tac cag cgc cta ggg ctg gac tac gag gaa cga gtg ttg ccg tcc att      618
Tyr Gln Arg Leu Gly Leu Asp Tyr Glu Glu Arg Val Leu Pro Ser Ile
                125                 130                 135

gtc aac gag gtg ctc aag agt gtg gtg gcc aag ttc aat gcc tca cag      666
Val Asn Glu Val Leu Lys Ser Val Val Ala Lys Phe Asn Ala Ser Gln
            140                 145                 150

ctg atc acc cag cgg gcc cag gta tcc ctg ttg atc cgc cgg gag ctg      714
Leu Ile Thr Gln Arg Ala Gln Val Ser Leu Leu Ile Arg Arg Glu Leu
        155                 160                 165

aca gag agg gcc aag gac ttc agc ctc atc ctg gat gat gtg gcc atc      762
Thr Glu Arg Ala Lys Asp Phe Ser Leu Ile Leu Asp Asp Val Ala Ile
    170                 175                 180

aca gag ctg agc ttt agc cga gag tac aca gct gct gta gaa gcc aaa      810
Thr Glu Leu Ser Phe Ser Arg Glu Tyr Thr Ala Ala Val Glu Ala Lys
185                 190                 195                 200

caa gtg gcc cag cag gag gcc cag cgg gcc caa ttc ttg gta gaa aaa      858
Gln Val Ala Gln Gln Glu Ala Gln Arg Ala Gln Phe Leu Val Glu Lys
                205                 210                 215

gca aag cag gaa cag cgg cag aaa att gtg cag gcc gag ggt gag gcc      906
Ala Lys Gln Glu Gln Arg Gln Lys Ile Val Gln Ala Glu Gly Glu Ala
            220                 225                 230

gag gct gcc aag atg ctt gga gaa gca ctg agc aag aac cct ggc tac      954
Glu Ala Ala Lys Met Leu Gly Glu Ala Leu Ser Lys Asn Pro Gly Tyr
        235                 240                 245

atc aaa ctt cgc aag att cga gca gcc cag aat atc tcc aag acg atc     1002
Ile Lys Leu Arg Lys Ile Arg Ala Ala Gln Asn Ile Ser Lys Thr Ile
    250                 255                 260

gcc aca tca cag aat cgt atc tat ctc aca gct gac aac ctt gtg ctg     1050
Ala Thr Ser Gln Asn Arg Ile Tyr Leu Thr Ala Asp Asn Leu Val Leu
265                 270                 275                 280

aac cta cag gat gaa agt ttc acc agg gga agt gac agc ctc atc aag     1098
Asn Leu Gln Asp Glu Ser Phe Thr Arg Gly Ser Asp Ser Leu Ile Lys
                285                 290                 295

ggt aag aaa tga gcctagtcac caagaactcc acccccagag gaagtggatc         1150
Gly Lys Lys

tgcttctcca gtttttgagg agccagccag ggtccagca cagccctacc ccgccccagt    1210

atcatgcgat ggtcccccac accggttccc tgaacccctc ttggattaag gaagactgaa   1270

gactagcccc ttttctgggg aattactttc ctcctccctg tgttaactgg ggctgttggg   1330

gacagtgcgt gatttctcag tgatttccta cagtgttgtt ccctccctca aggctgggag   1390

gagataaaca ccaacccagg aattctcaat aaatttttat tacttaacct gaaaaaaaaa   1450

aaaaaaa                                                             1457


<210> SEQ ID NO 37
<211> LENGTH: 299
<212> TYPE: PRT
<213> ORGANISM: Homo sapiens

<400> SEQUENCE: 37

Met Ala Gln Asn Leu Lys Asp Leu Ala Gly Arg Leu Pro Ala Gly Pro
1               5                   10                  15

Arg Gly Met Gly Thr Ala Leu Lys Leu Leu Leu Gly Ala Gly Ala Val
```

```
            20                  25                  30

Ala Tyr Gly Val Arg Glu Ser Val Phe Thr Val Glu Gly Gly His Arg
        35                  40                  45

Ala Ile Phe Phe Asn Arg Ile Gly Gly Val Gln Gln Asp Thr Ile Leu
    50                  55                  60

Ala Glu Gly Leu His Phe Arg Ile Pro Trp Phe Gln Tyr Pro Ile Ile
65                  70                  75                  80

Tyr Asp Ile Arg Ala Arg Pro Arg Lys Ile Ser Ser Pro Thr Gly Ser
                85                  90                  95

Lys Asp Leu Gln Met Val Asn Ile Ser Leu Arg Val Leu Ser Arg Pro
            100                 105                 110

Asn Ala Gln Glu Leu Pro Ser Met Tyr Gln Arg Leu Gly Leu Asp Tyr
        115                 120                 125

Glu Glu Arg Val Leu Pro Ser Ile Val Asn Glu Val Leu Lys Ser Val
    130                 135                 140

Val Ala Lys Phe Asn Ala Ser Gln Leu Ile Thr Gln Arg Ala Gln Val
145                 150                 155                 160

Ser Leu Leu Ile Arg Arg Glu Leu Thr Glu Arg Ala Lys Asp Phe Ser
                165                 170                 175

Leu Ile Leu Asp Asp Val Ala Ile Thr Glu Leu Ser Phe Ser Arg Glu
            180                 185                 190

Tyr Thr Ala Ala Val Glu Ala Lys Gln Val Ala Gln Gln Glu Ala Gln
        195                 200                 205

Arg Ala Gln Phe Leu Val Glu Lys Ala Lys Gln Glu Gln Arg Gln Lys
    210                 215                 220

Ile Val Gln Ala Glu Gly Glu Ala Glu Ala Ala Lys Met Leu Gly Glu
225                 230                 235                 240

Ala Leu Ser Lys Asn Pro Gly Tyr Ile Lys Leu Arg Lys Ile Arg Ala
                245                 250                 255

Ala Gln Asn Ile Ser Lys Thr Ile Ala Thr Ser Gln Asn Arg Ile Tyr
            260                 265                 270

Leu Thr Ala Asp Asn Leu Val Leu Asn Leu Gln Asp Glu Ser Phe Thr
        275                 280                 285

Arg Gly Ser Asp Ser Leu Ile Lys Gly Lys Lys
    290                 295


<210> SEQ ID NO 38
<211> LENGTH: 6330
<212> TYPE: DNA
<213> ORGANISM: Homo sapiens
<220> FEATURE:
<221> NAME/KEY: CDS
<222> LOCATION: (235)..(2022)

<400> SEQUENCE: 38

aggagctggc ggagggcgtt cgtcctggga ctgcacttgc tcccgtcggg tcgcccggct      60

tcaccggacc cgcaggctcc cggggcaggg ccggggccag agctcgcgtg tcggcgggac     120

atgcgctgcg tcgcctctaa cctcgggctg tgctcttttt ccaggtggcc cgccggtttc     180

tgagccttct gccctgcggg gacacggtct gcaccctgcc cgcggccacg gacc atg       237
                                                            Met
                                                            1

acc atg acc ctc cac acc aaa gca tct ggg atg gcc cta ctg cat cag       285
Thr Met Thr Leu His Thr Lys Ala Ser Gly Met Ala Leu Leu His Gln
            5                   10                  15

atc caa ggg aac gag ctg gag ccc ctg aac cgt ccg cag ctc aag atc       333
```

```
Ile Gln Gly Asn Glu Leu Glu Pro Leu Asn Arg Pro Gln Leu Lys Ile
        20                  25                  30

ccc ctg gag cgg ccc ctg ggc gag gtg tac ctg gac agc agc aag ccc      381
Pro Leu Glu Arg Pro Leu Gly Glu Val Tyr Leu Asp Ser Ser Lys Pro
    35                  40                  45

gcc gtg tac aac tac ccc gag ggc gcc gcc tac gag ttc aac gcc gcg      429
Ala Val Tyr Asn Tyr Pro Glu Gly Ala Ala Tyr Glu Phe Asn Ala Ala
50                  55                  60                  65

gcc gcc gcc aac gcg cag gtc tac ggt cag acc ggc ctc ccc tac ggc      477
Ala Ala Ala Asn Ala Gln Val Tyr Gly Gln Thr Gly Leu Pro Tyr Gly
                70                  75                  80

ccc ggg tct gag gct gcg gcg ttc ggc tcc aac ggc ctg ggg ggt ttc      525
Pro Gly Ser Glu Ala Ala Ala Phe Gly Ser Asn Gly Leu Gly Gly Phe
            85                  90                  95

ccc cca ctc aac agc gtg tct ccg agc ccg ctg atg cta ctg cac ccg      573
Pro Pro Leu Asn Ser Val Ser Pro Ser Pro Leu Met Leu Leu His Pro
        100                 105                 110

ccg ccg cag ctg tcg cct ttc ctg cag ccc cac ggc cag cag gtg ccc      621
Pro Pro Gln Leu Ser Pro Phe Leu Gln Pro His Gly Gln Gln Val Pro
    115                 120                 125

tac tac ctg gag aac gag ccc agc ggc tac acg gtg cgc gag gcc ggc      669
Tyr Tyr Leu Glu Asn Glu Pro Ser Gly Tyr Thr Val Arg Glu Ala Gly
130                 135                 140                 145

ccg ccg gca ttc tac agg cca aat tca gat aat cga cgc cag ggt ggc      717
Pro Pro Ala Phe Tyr Arg Pro Asn Ser Asp Asn Arg Arg Gln Gly Gly
                150                 155                 160

aga gaa aga ttg gcc agt acc aat gac aag gga agt atg gct atg gaa      765
Arg Glu Arg Leu Ala Ser Thr Asn Asp Lys Gly Ser Met Ala Met Glu
            165                 170                 175

tct gcc aag gag act cgc tac tgt gca gtg tgc aat gac tat gct tca      813
Ser Ala Lys Glu Thr Arg Tyr Cys Ala Val Cys Asn Asp Tyr Ala Ser
        180                 185                 190

ggc tac cat tat gga gtc tgg tcc tgt gag ggc tgc aag gcc ttc ttc      861
Gly Tyr His Tyr Gly Val Trp Ser Cys Glu Gly Cys Lys Ala Phe Phe
    195                 200                 205

aag aga agt att caa gga cat aac gac tat atg tgt cca gcc acc aac      909
Lys Arg Ser Ile Gln Gly His Asn Asp Tyr Met Cys Pro Ala Thr Asn
210                 215                 220                 225

cag tgc acc att gat aaa aac agg agg aag agc tgc cag gcc tgc cgg      957
Gln Cys Thr Ile Asp Lys Asn Arg Arg Lys Ser Cys Gln Ala Cys Arg
                230                 235                 240

ctc cgc aaa tgc tac gaa gtg gga atg atg aaa ggt ggg ata cga aaa     1005
Leu Arg Lys Cys Tyr Glu Val Gly Met Met Lys Gly Gly Ile Arg Lys
            245                 250                 255

gac cga aga gga ggg aga atg ttg aaa cac aag cgc cag aga gat gat     1053
Asp Arg Arg Gly Gly Arg Met Leu Lys His Lys Arg Gln Arg Asp Asp
        260                 265                 270

ggg gag ggc agg ggt gaa gtg ggg tct gct gga gac atg aga gct gcc     1101
Gly Glu Gly Arg Gly Glu Val Gly Ser Ala Gly Asp Met Arg Ala Ala
    275                 280                 285

aac ctt tgg cca agc ccg ctc atg atc aaa cgc tct aag aag aac agc     1149
Asn Leu Trp Pro Ser Pro Leu Met Ile Lys Arg Ser Lys Lys Asn Ser
290                 295                 300                 305

ctg gcc ttg tcc ctg acg gcc gac cag atg gtc agt gcc ttg ttg gat     1197
Leu Ala Leu Ser Leu Thr Ala Asp Gln Met Val Ser Ala Leu Leu Asp
                310                 315                 320

gct gag ccc ccc ata ctc tat tcc gag tat gat cct acc aga ccc ttc     1245
Ala Glu Pro Pro Ile Leu Tyr Ser Glu Tyr Asp Pro Thr Arg Pro Phe
            325                 330                 335
```

-continued

```
agt gaa gct tcg atg atg ggc tta ctg acc aac ctg gca gac agg gag     1293
Ser Glu Ala Ser Met Met Gly Leu Leu Thr Asn Leu Ala Asp Arg Glu
        340                 345                 350

ctg gtt cac atg atc aac tgg gcg aag agg gtg cca ggc ttt gtg gat     1341
Leu Val His Met Ile Asn Trp Ala Lys Arg Val Pro Gly Phe Val Asp
    355                 360                 365

ttg acc ctc cat gat cag gtc cac ctt cta gaa tgt gcc tgg cta gag     1389
Leu Thr Leu His Asp Gln Val His Leu Leu Glu Cys Ala Trp Leu Glu
370                 375                 380                 385

atc ctg atg att ggt ctc gtc tgg cgc tcc atg gag cac cca ggg aag     1437
Ile Leu Met Ile Gly Leu Val Trp Arg Ser Met Glu His Pro Gly Lys
                390                 395                 400

cta ctg ttt gct cct aac ttg ctc ttg gac agg aac cag gga aaa tgt     1485
Leu Leu Phe Ala Pro Asn Leu Leu Leu Asp Arg Asn Gln Gly Lys Cys
            405                 410                 415

gta gag ggc atg gtg gag atc ttc gac atg ctg ctg gct aca tca tct     1533
Val Glu Gly Met Val Glu Ile Phe Asp Met Leu Leu Ala Thr Ser Ser
        420                 425                 430

cgg ttc cgc atg atg aat ctg cag gga gag gag ttt gtg tgc ctc aaa     1581
Arg Phe Arg Met Met Asn Leu Gln Gly Glu Glu Phe Val Cys Leu Lys
    435                 440                 445

tct att att ttg ctt aat tct gga gtg tac aca ttt ctg tcc agc acc     1629
Ser Ile Ile Leu Leu Asn Ser Gly Val Tyr Thr Phe Leu Ser Ser Thr
450                 455                 460                 465

ctg aag tct ctg gaa gag aag gac cat atc cac cga gtc ctg gac aag     1677
Leu Lys Ser Leu Glu Glu Lys Asp His Ile His Arg Val Leu Asp Lys
                470                 475                 480

atc aca gac act ttg atc cac ctg atg gcc aag gca ggc ctg acc ctg     1725
Ile Thr Asp Thr Leu Ile His Leu Met Ala Lys Ala Gly Leu Thr Leu
            485                 490                 495

cag cag cag cac cag cgg ctg gcc cag ctc ctc ctc atc ctc tcc cac     1773
Gln Gln Gln His Gln Arg Leu Ala Gln Leu Leu Leu Ile Leu Ser His
        500                 505                 510

atc agg cac atg agt aac aaa ggc atg gag cat ctg tac agc atg aag     1821
Ile Arg His Met Ser Asn Lys Gly Met Glu His Leu Tyr Ser Met Lys
    515                 520                 525

tgc aag aac gtg gtg ccc ctc tat gac ctg ctg ctg gag atg ctg gac     1869
Cys Lys Asn Val Val Pro Leu Tyr Asp Leu Leu Leu Glu Met Leu Asp
530                 535                 540                 545

gcc cac cgc cta cat gcg ccc act agc cgt gga ggg gca tcc gtg gag     1917
Ala His Arg Leu His Ala Pro Thr Ser Arg Gly Gly Ala Ser Val Glu
                550                 555                 560

gag acg gac caa agc cac ttg gcc act gcg ggc tct act tca tcg cat     1965
Glu Thr Asp Gln Ser His Leu Ala Thr Ala Gly Ser Thr Ser Ser His
            565                 570                 575

tcc ttg caa aag tat tac atc acg ggg gag gca gag ggt ttc cct gcc     2013
Ser Leu Gln Lys Tyr Tyr Ile Thr Gly Glu Ala Glu Gly Phe Pro Ala
        580                 585                 590

acg gtc tga gagctccctg gctcccacac ggttcagata atccctgctg             2062
Thr Val
    595

cattttaccc tcatcatgca ccactttagc caaattctgt ctcctgcata cactccggca   2122

tgcatccaac accaatggct ttctagatga gtggccattc atttgcttgc tcagttctta   2182

gtggcacatc ttctgtcttc tgttgggaac agccaaaggg attccaaggc taaatctttg   2242

taacagctct ctttcccccct tgctatgtta ctaagcgtga ggattcccgt agctcttcac   2302

agctgaactc agtctatggg ttggggctca gataactctg tgcatttaag ctacttgtag   2362

agacccaggc ctggagagta gacattttgc ctctgataag cactttttaa atggctctaa   2422
```

```
gaataagcca cagcaaagaa tttaaagtgg ctcctttaat tggtgacttg gagaaagcta   2482
ggtcaagggt ttattatagc accctcttgt attcctatgg caatgcatcc ttttatgaaa   2542
gtggtacacc ttaaagcttt tatatgactg tagcagagta tctggtgatt gtcaattcat   2602
tccccctata ggaatacaag ggcacacag ggaaggcaga tcccctagtt ggcaagacta    2662
ttttaacttg atacactgca gattcagatg tgctgaaagc tctgcctctg gctttccggt   2722
catgggttcc agttaattca tgcctcccat ggacctatgg agagcagcaa gttgatctta   2782
gttaagtctc cctatatgag ggataagttc ctgatttttg tttttatttt tgtgttacaa   2842
aagaaagccc tccctccctg aacttgcagt aaggtcagct tcaggacctg ttccagtggg   2902
cactgtactt ggatcttccc ggcgtgtgtg tgccttacac aggggtgaac tgttcactgt   2962
ggtgatgcat gatgagggta aatggtagtt gaaaggagca ggggccctgg tgttgcattt   3022
agccctgggg catggagctg aacagtactt gtgcaggatt gttgtggcta ctagagaaca   3082
agagggaaag tagggcagaa actggataca gttctgaggc acagccagac ttgctcaggg   3142
tggccctgcc acaggctgca gctacctagg aacattcctt gcagaccccg cattgccctt   3202
tgggggtgcc ctgggatccc tggggtagtc cagctcttct tcatttccca gcgtggccct   3262
ggttggaaga agcagctgtc acagctgctg tagacagctg tgttcctaca attggcccag   3322
caccctgggg cacgggagaa gggtggggac cgttgctgtc actactcagg ctgactgggg   3382
cctggtcaga ttacgtatgc ccttggtggt ttagagataa tccaaaatca gggtttggtt   3442
tggggaagaa aatcctcccc cttcctcccc cgccccgttc cctaccgcct ccactcctgc   3502
cagctcattt ccttcaattt cctttgacct ataggctaaa aaagaaaggc tcattccagc   3562
cacagggcag ccttccctgg gcctttgctt ctctagcaca attatgggtt acttcctttt   3622
tcttaacaaa aaagaatgtt tgatttcctc tgggtgacct tattgtctgt aattgaaacc   3682
ctattgagag gtgatgtctg tgttagccaa tgacccaggt gagctgctcg ggcttctctt   3742
ggtatgtctt gtttggaaaa gtggatttca ttcatttctg attgtccagt taagtgatca   3802
ccaaaggact gagaatctgg gagggcaaaa aaaaaaaaaa agtttttatg tgcacttaaa   3862
tttggggaca attttatgta tctgtgttaa ggatatgttt aagaacataa ttcttttgtt   3922
gctgtttgtt taagaagcac cttagtttgt ttaagaagca ccttatatag tataatatat   3982
atttttttga aattacattg cttgtttatc agacaattga atgtagtaat tctgttctgg   4042
atttaatttg actgggttaa catgcaaaaa ccaaggaaaa atatttagtt tttttttttt   4102
tttttgtata cttttcaagc taccttgtca tgtatacagt catttatgcc taaagcctgg   4162
tgattattca tttaaatgaa gatcacattt catatcaact tttgtatcca cagtagacaa   4222
aatagcacta atccagatgc ctattgttgg atactgaatg acagacaatc ttatgtagca   4282
aagattatgc ctgaaaagga aaattattca gggcagctaa ttttgctttt accaaaatat   4342
cagtagtaat atttttggac agtagctaat gggtcagtgg gttcttttta atgtttatac   4402
ttagattttc ttttaaaaaa attaaaataa aacaaaaaaa aatttctagg actagacgat   4462
gtaataccag ctaaagccaa acaattatac agtggaaggt tttacattat tcatccaatg   4522
tgtttctatt catgttaaga tactactaca tttgaagtgg gcagagaaca tcagatgatt   4582
gaaatgttcg cccaggggtc tccagcaact ttggaaatct ctttgtattt ttacttgaag   4642
tgccactaat ggacagcaga tattttctgg ctgatgttgg tattgggtgt aggaacatga   4702
tttaaaaaaa aactcttgcc tctgctttcc cccactctga ggcaagttaa aatgtaaaag   4762
```

```
atgtgattta tctggggggc tcaggtatgg tggggaagtg gattcaggaa tctggggaat   4822

ggcaaatata ttaagaagag tattgaaagt atttggagga aaatggttaa ttctgggtgt   4882

gcaccagggt tcagtagagt ccacttctgc cctggagacc acaaatcaac tagctccatt   4942

tacagccatt tctaaaatgg cagcttcagt tctagagaag aaagaacaac atcagcagta   5002

aagtccatgg aatagctagt ggtctgtgtt tcttttcgcc attgcctagc ttgccgtaat   5062

gattctataa tgccatcatg cagcaattat gagaggctag gtcatccaaa gagaagaccc   5122

tatcaatgta ggttgcaaaa tctaacccct aaggaagtgc agtctttgat ttgatttccc   5182

tagtaacctt gcagatatgt ttaaccaagc catagcccat gccttttgag ggctgaacaa   5242

ataagggact tactgataat ttacttttga tcacattaag gtgttctcac cttgaaatct   5302

tatacactga aatggccatt gatttaggcc actggcttag agtactcctt cccctgcatg   5362

acactgatta caaatacttt cctattcata ctttccaatt atgagatgga ctgtgggtac   5422

tgggagtgat cactaacacc atagtaatgt ctaatattca caggcagatc tgcttgggga   5482

agctagttat gtgaaaggca aatagagtca tacagtagct caaaaggcaa ccataattct   5542

ctttggtgca ggtcttggga gcgtgatcta gattacactg caccattccc aagttaatcc   5602

cctgaaaact tactctcaac tggagcaaat gaactttggt cccaaatatc catcttttca   5662

gtagcgttaa ttatgctctg tttccaactg catttccttt ccaattgaat taaagtgtgg   5722

cctcgttttt agtcatttaa aattgtttc taagtaattg ctgcctctat tatggcactt   5782

caattttgca ctgtcttttg agattcaaga aaaatttcta ttcttttttt tgcatccaat   5842

tgtgcctgaa cttttaaaat atgtaaatgc tgccatgttc caaacccatc gtcagtgtgt   5902

gtgtttagag ctgtgcaccc tagaaacaac atattgtccc atgagcaggt gcctgagaca   5962

cagacccctt tgcattcaca gagaggtcat tggttataga gacttgaatt aataagtgac   6022

attatgccag tttctgttct ctcacaggtg ataaacaatg ctttttgtgc actacatact   6082

cttcagtgta gagctcttgt tttatgggaa aaggctcaaa tgccaaattg tgtttgatgg   6142

attaatatgc ccttttgccg atgcatacta ttactgatgt gactcggttt tgtcgcagct   6202

ttgctttgtt taatgaaaca cacttgtaaa cctcttttgc actttgaaaa agaatccagc   6262

gggatgctcg agcacctgta aacaattttc tcaacctatt tgatgttcaa ataaagaatt   6322

aaactaaa                                                              6330

<210> SEQ ID NO 39
<211> LENGTH: 595
<212> TYPE: PRT
<213> ORGANISM: Homo sapiens

<400> SEQUENCE: 39

Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
            20                  25                  30

Ile Pro Leu Glu Arg Pro Leu Gly Glu Val Tyr Leu Asp Ser Ser Lys
        35                  40                  45

Pro Ala Val Tyr Asn Tyr Pro Glu Gly Ala Ala Tyr Glu Phe Asn Ala
    50                  55                  60

Ala Ala Ala Ala Asn Ala Gln Val Tyr Gly Gln Thr Gly Leu Pro Tyr
65                  70                  75                  80

Gly Pro Gly Ser Glu Ala Ala Ala Phe Gly Ser Asn Gly Leu Gly Gly
                85                  90                  95
```

```
Phe Pro Pro Leu Asn Ser Val Ser Pro Ser Pro Leu Met Leu Leu His
            100                 105                 110

Pro Pro Pro Gln Leu Ser Pro Phe Leu Gln Pro His Gly Gln Gln Val
        115                 120                 125

Pro Tyr Tyr Leu Glu Asn Glu Pro Ser Gly Tyr Thr Val Arg Glu Ala
    130                 135                 140

Gly Pro Pro Ala Phe Tyr Arg Pro Asn Ser Asp Asn Arg Arg Gln Gly
145                 150                 155                 160

Gly Arg Glu Arg Leu Ala Ser Thr Asn Asp Lys Gly Ser Met Ala Met
                165                 170                 175

Glu Ser Ala Lys Glu Thr Arg Tyr Cys Ala Val Cys Asn Asp Tyr Ala
            180                 185                 190

Ser Gly Tyr His Tyr Gly Val Trp Ser Cys Glu Gly Cys Lys Ala Phe
        195                 200                 205

Phe Lys Arg Ser Ile Gln Gly His Asn Asp Tyr Met Cys Pro Ala Thr
    210                 215                 220

Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
                245                 250                 255

Lys Asp Arg Arg Gly Gly Arg Met Leu Lys His Lys Arg Gln Arg Asp
            260                 265                 270

Asp Gly Glu Gly Arg Gly Glu Val Gly Ser Ala Gly Asp Met Arg Ala
        275                 280                 285

Ala Asn Leu Trp Pro Ser Pro Leu Met Ile Lys Arg Ser Lys Lys Asn
    290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
            340                 345                 350

Glu Leu Val His Met Ile Asn Trp Ala Lys Arg Val Pro Gly Phe Val
        355                 360                 365

Asp Leu Thr Leu His Asp Gln Val His Leu Leu Glu Cys Ala Trp Leu
    370                 375                 380

Glu Ile Leu Met Ile Gly Leu Val Trp Arg Ser Met Glu His Pro Gly
385                 390                 395                 400

Lys Leu Leu Phe Ala Pro Asn Leu Leu Leu Asp Arg Asn Gln Gly Lys
                405                 410                 415

Cys Val Glu Gly Met Val Glu Ile Phe Asp Met Leu Leu Ala Thr Ser
            420                 425                 430

Ser Arg Phe Arg Met Met Asn Leu Gln Gly Glu Glu Phe Val Cys Leu
        435                 440                 445

Lys Ser Ile Ile Leu Leu Asn Ser Gly Val Tyr Thr Phe Leu Ser Ser
    450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
                485                 490                 495

Leu Gln Gln Gln His Gln Arg Leu Ala Gln Leu Leu Leu Ile Leu Ser
            500                 505                 510
```

```
His Ile Arg His Met Ser Asn Lys Gly Met Glu His Leu Tyr Ser Met
        515                 520                 525

Lys Cys Lys Asn Val Val Pro Leu Tyr Asp Leu Leu Leu Glu Met Leu
    530                 535                 540

Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
                565                 570                 575

His Ser Leu Gln Lys Tyr Tyr Ile Thr Gly Glu Ala Glu Gly Phe Pro
            580                 585                 590

Ala Thr Val
        595


<210> SEQ ID NO 40
<211> LENGTH: 2169
<212> TYPE: DNA
<213> ORGANISM: Homo sapiens
<220> FEATURE:
<221> NAME/KEY: CDS
<222> LOCATION: (469)..(2061)

<400> SEQUENCE: 40

ctcggtcttt aaaaggaaga aggggcttat cgttaagtcg cttgtgatct tttcagtttc      60

tccagctgct ggctttttgg acacccactc ccccgccagg aggcagttgc aagcgcggag     120

gctgcgagaa ataactgcct cttgaaactt gcagggcgaa gagcaggcgg cgagcgctgg     180

gccggggagg gaccacccga gctgcgacgg gctctggggc tgcggggcag ggctggcgcc     240

cggagcctga gctgcaggag gtgcgctcgc tttcctcaac aggtggcggc ggggcgcgcg     300

ccgggagacc ccccctaatg cgggaaaagc acgtgtccgc attttagaga aggcaaggcc     360

ggtgtgttta tctgcaagcc attatacttg cccacgaatc tttgagaaca ttataatgac     420

ctttgtgcct cttcttgcaa ggtgttttct cagctgttat ctcaagac atg gat ata      477
                                                     Met Asp Ile
                                                     1

aaa aac tca cca tct agc ctt aat tct cct tcc tcc tac aac tgc agt       525
Lys Asn Ser Pro Ser Ser Leu Asn Ser Pro Ser Ser Tyr Asn Cys Ser
    5                   10                  15

caa tcc atc tta ccc ctg gag cac ggc tcc ata tac ata cct tcc tcc       573
Gln Ser Ile Leu Pro Leu Glu His Gly Ser Ile Tyr Ile Pro Ser Ser
20                  25                  30                  35

tat gta gac agc cac cat gaa tat cca gcc atg aca ttc tat agc cct       621
Tyr Val Asp Ser His His Glu Tyr Pro Ala Met Thr Phe Tyr Ser Pro
                40                  45                  50

gct gtg atg aat tac agc att ccc agc aat gtc act aac ttg gaa ggt       669
Ala Val Met Asn Tyr Ser Ile Pro Ser Asn Val Thr Asn Leu Glu Gly
            55                  60                  65

ggg cct ggt cgg cag acc aca agc cca aat gtg ttg tgg cca aca cct       717
Gly Pro Gly Arg Gln Thr Thr Ser Pro Asn Val Leu Trp Pro Thr Pro
        70                  75                  80

ggg cac ctt tct cct tta gtg gtc cat cgc cag tta tca cat ctg tat       765
Gly His Leu Ser Pro Leu Val Val His Arg Gln Leu Ser His Leu Tyr
    85                  90                  95

gcg gaa cct caa aag agt ccc tgg tgt gaa gca aga tcg cta gaa cac       813
Ala Glu Pro Gln Lys Ser Pro Trp Cys Glu Ala Arg Ser Leu Glu His
100                 105                 110                 115

acc tta cct gta aac aga gag aca ctg aaa agg aag gtt agt ggg aac       861
Thr Leu Pro Val Asn Arg Glu Thr Leu Lys Arg Lys Val Ser Gly Asn
                120                 125                 130
```

```
cgt tgc gcc agc cct gtt act ggt cca ggt tca aag agg gat gct cac      909
Arg Cys Ala Ser Pro Val Thr Gly Pro Gly Ser Lys Arg Asp Ala His
            135                 140                 145

ttc tgc gct gtc tgc agc gat tac gca tcg gga tat cac tat gga gtc      957
Phe Cys Ala Val Cys Ser Asp Tyr Ala Ser Gly Tyr His Tyr Gly Val
        150                 155                 160

tgg tcg tgt gaa gga tgt aag gcc ttt ttt aaa aga agc att caa gga     1005
Trp Ser Cys Glu Gly Cys Lys Ala Phe Phe Lys Arg Ser Ile Gln Gly
    165                 170                 175

cat aat gat tat att tgt cca gct aca aat cag tgt aca atc gat aaa     1053
His Asn Asp Tyr Ile Cys Pro Ala Thr Asn Gln Cys Thr Ile Asp Lys
180                 185                 190                 195

aac cgg cgc aag agc tgc cag gcc tgc cga ctt cgg aag tgt tac gaa     1101
Asn Arg Arg Lys Ser Cys Gln Ala Cys Arg Leu Arg Lys Cys Tyr Glu
                200                 205                 210

gtg gga atg gtg aag tgt ggc tcc cgg aga gag aga tgt ggg tac cgc     1149
Val Gly Met Val Lys Cys Gly Ser Arg Arg Glu Arg Cys Gly Tyr Arg
            215                 220                 225

ctt gtg cgg aga cag aga agt gcc gac gag cag ctg cac tgt gcc ggc     1197
Leu Val Arg Arg Gln Arg Ser Ala Asp Glu Gln Leu His Cys Ala Gly
        230                 235                 240

aag gcc aag aga agt ggc ggc cac gcg ccc cga gtg cgg gag ctg ctg     1245
Lys Ala Lys Arg Ser Gly Gly His Ala Pro Arg Val Arg Glu Leu Leu
    245                 250                 255

ctg gac gcc ctg agc ccc gag cag cta gtg ctc acc ctc ctg gag gct     1293
Leu Asp Ala Leu Ser Pro Glu Gln Leu Val Leu Thr Leu Leu Glu Ala
260                 265                 270                 275

gag ccg ccc cat gtg ctg atc agc cgc ccc agt gcg ccc ttc acc gag     1341
Glu Pro Pro His Val Leu Ile Ser Arg Pro Ser Ala Pro Phe Thr Glu
                280                 285                 290

gcc tcc atg atg atg tcc ctg acc aag ttg gcc gac aag gag ttg gta     1389
Ala Ser Met Met Met Ser Leu Thr Lys Leu Ala Asp Lys Glu Leu Val
            295                 300                 305

cac atg atc agc tgg gcc aag aag att ccc ggc ttt gtg gag ctc agc     1437
His Met Ile Ser Trp Ala Lys Lys Ile Pro Gly Phe Val Glu Leu Ser
        310                 315                 320

ctg ttc gac caa gtg cgg ctc ttg gag agc tgt tgg atg gag gtg tta     1485
Leu Phe Asp Gln Val Arg Leu Leu Glu Ser Cys Trp Met Glu Val Leu
    325                 330                 335

atg atg ggg ctg atg tgg cgc tca att gac cac ccc ggc aag ctc atc     1533
Met Met Gly Leu Met Trp Arg Ser Ile Asp His Pro Gly Lys Leu Ile
340                 345                 350                 355

ttt gct cca gat ctt gtt ctg gac agg gat gag ggg aaa tgc gta gaa     1581
Phe Ala Pro Asp Leu Val Leu Asp Arg Asp Glu Gly Lys Cys Val Glu
                360                 365                 370

gga att ctg gaa atc ttt gac atg ctc ctg gca act act tca agg ttt     1629
Gly Ile Leu Glu Ile Phe Asp Met Leu Leu Ala Thr Thr Ser Arg Phe
            375                 380                 385

cga gag tta aaa ctc caa cac aaa gaa tat ctc tgt gtc aag gcc atg     1677
Arg Glu Leu Lys Leu Gln His Lys Glu Tyr Leu Cys Val Lys Ala Met
        390                 395                 400

atc ctg ctc aat tcc agt atg tac cct ctg gtc aca gcg acc cag gat     1725
Ile Leu Leu Asn Ser Ser Met Tyr Pro Leu Val Thr Ala Thr Gln Asp
    405                 410                 415

gct gac agc agc cgg aag ctg gct cac ttg ctg aac gcc gtg acc gat     1773
Ala Asp Ser Ser Arg Lys Leu Ala His Leu Leu Asn Ala Val Thr Asp
420                 425                 430                 435

gct ttg gtt tgg gtg att gcc aag agc ggc atc tcc tcc cag cag caa     1821
Ala Leu Val Trp Val Ile Ala Lys Ser Gly Ile Ser Ser Gln Gln Gln
                440                 445                 450
```

```
tcc atg cgc ctg gct aac ctc ctg atg ctc ctg tcc cac gtc agg cat     1869
Ser Met Arg Leu Ala Asn Leu Leu Met Leu Leu Ser His Val Arg His
            455                 460                 465

gcg agt aac aag ggc atg gaa cat ctg ctc aac atg aag tgc aaa aat     1917
Ala Ser Asn Lys Gly Met Glu His Leu Leu Asn Met Lys Cys Lys Asn
        470                 475                 480

gtg gtc cca gtg tat gac ctg ctg ctg gag atg ctg aat gcc cac gtg     1965
Val Val Pro Val Tyr Asp Leu Leu Leu Glu Met Leu Asn Ala His Val
    485                 490                 495

ctt cgc ggg tgc aag tcc tcc atc acg ggg tcc gag tgc agc ccg gca     2013
Leu Arg Gly Cys Lys Ser Ser Ile Thr Gly Ser Glu Cys Ser Pro Ala
500                 505                 510                 515

gag gac agt aaa agc aaa gag ggc tcc cag aac cca cag tct cag tga     2061
Glu Asp Ser Lys Ser Lys Glu Gly Ser Gln Asn Pro Gln Ser Gln
                520                 525                 530

cgcctggccc tgaggtgaac tggcccacag aggtcacagg ctgaagcgtg aactccagtg   2121

tgtcaggagc ctgggcttca tctttctgct gtgtggtccc tcatttgg                2169


<210> SEQ ID NO 41
<211> LENGTH: 530
<212> TYPE: PRT
<213> ORGANISM: Homo sapiens

<400> SEQUENCE: 41

Met Asp Ile Lys Asn Ser Pro Ser Ser Leu Asn Ser Pro Ser Ser Tyr
1               5                   10                  15

Asn Cys Ser Gln Ser Ile Leu Pro Leu Glu His Gly Ser Ile Tyr Ile
            20                  25                  30

Pro Ser Ser Tyr Val Asp Ser His His Glu Tyr Pro Ala Met Thr Phe
        35                  40                  45

Tyr Ser Pro Ala Val Met Asn Tyr Ser Ile Pro Ser Asn Val Thr Asn
    50                  55                  60

Leu Glu Gly Gly Pro Gly Arg Gln Thr Thr Ser Pro Asn Val Leu Trp
65                  70                  75                  80

Pro Thr Pro Gly His Leu Ser Pro Leu Val Val His Arg Gln Leu Ser
                85                  90                  95

His Leu Tyr Ala Glu Pro Gln Lys Ser Pro Trp Cys Glu Ala Arg Ser
            100                 105                 110

Leu Glu His Thr Leu Pro Val Asn Arg Glu Thr Leu Lys Arg Lys Val
        115                 120                 125

Ser Gly Asn Arg Cys Ala Ser Pro Val Thr Gly Pro Gly Ser Lys Arg
    130                 135                 140

Asp Ala His Phe Cys Ala Val Cys Ser Asp Tyr Ala Ser Gly Tyr His
145                 150                 155                 160

Tyr Gly Val Trp Ser Cys Glu Gly Cys Lys Ala Phe Phe Lys Arg Ser
                165                 170                 175

Ile Gln Gly His Asn Asp Tyr Ile Cys Pro Ala Thr Asn Gln Cys Thr
            180                 185                 190

Ile Asp Lys Asn Arg Arg Lys Ser Cys Gln Ala Cys Arg Leu Arg Lys
        195                 200                 205

Cys Tyr Glu Val Gly Met Val Lys Cys Gly Ser Arg Arg Glu Arg Cys
    210                 215                 220

Gly Tyr Arg Leu Val Arg Arg Gln Arg Ser Ala Asp Glu Gln Leu His
225                 230                 235                 240

Cys Ala Gly Lys Ala Lys Arg Ser Gly Gly His Ala Pro Arg Val Arg
```

```
                245                 250                 255

Glu Leu Leu Leu Asp Ala Leu Ser Pro Glu Gln Leu Val Leu Thr Leu
            260                 265                 270

Leu Glu Ala Glu Pro Pro His Val Leu Ile Ser Arg Pro Ser Ala Pro
        275                 280                 285

Phe Thr Glu Ala Ser Met Met Met Ser Leu Thr Lys Leu Ala Asp Lys
    290                 295                 300

Glu Leu Val His Met Ile Ser Trp Ala Lys Lys Ile Pro Gly Phe Val
305                 310                 315                 320

Glu Leu Ser Leu Phe Asp Gln Val Arg Leu Leu Glu Ser Cys Trp Met
                325                 330                 335

Glu Val Leu Met Met Gly Leu Met Trp Arg Ser Ile Asp His Pro Gly
            340                 345                 350

Lys Leu Ile Phe Ala Pro Asp Leu Val Leu Asp Arg Asp Glu Gly Lys
        355                 360                 365

Cys Val Glu Gly Ile Leu Glu Ile Phe Asp Met Leu Leu Ala Thr Thr
    370                 375                 380

Ser Arg Phe Arg Glu Leu Lys Leu Gln His Lys Glu Tyr Leu Cys Val
385                 390                 395                 400

Lys Ala Met Ile Leu Leu Asn Ser Ser Met Tyr Pro Leu Val Thr Ala
                405                 410                 415

Thr Gln Asp Ala Asp Ser Ser Arg Lys Leu Ala His Leu Leu Asn Ala
            420                 425                 430

Val Thr Asp Ala Leu Val Trp Val Ile Ala Lys Ser Gly Ile Ser Ser
        435                 440                 445

Gln Gln Gln Ser Met Arg Leu Ala Asn Leu Leu Met Leu Leu Ser His
    450                 455                 460

Val Arg His Ala Ser Asn Lys Gly Met Glu His Leu Leu Asn Met Lys
465                 470                 475                 480

Cys Lys Asn Val Val Pro Val Tyr Asp Leu Leu Leu Glu Met Leu Asn
                485                 490                 495

Ala His Val Leu Arg Gly Cys Lys Ser Ser Ile Thr Gly Ser Glu Cys
            500                 505                 510

Ser Pro Ala Glu Asp Ser Lys Ser Lys Glu Gly Ser Gln Asn Pro Gln
        515                 520                 525

Ser Gln
    530


<210> SEQ ID NO 42
<211> LENGTH: 9
<212> TYPE: PRT
<213> ORGANISM: Artificial Sequence
<220> FEATURE:
<223> OTHER INFORMATION: A cell membrane permeable peptide

<400> SEQUENCE: 42

Arg Lys Lys Arg Arg Gln Arg Arg Arg
1               5


<210> SEQ ID NO 43
<211> LENGTH: 21
<212> TYPE: PRT
<213> ORGANISM: Artificial Sequence
<220> FEATURE:
<223> OTHER INFORMATION: A cell membrane permeable peptide

<400> SEQUENCE: 43
```

```
Thr Arg Ser Ser Arg Ala Gly Leu Gln Phe Pro Val Gly Arg Val His
1               5                   10                  15

Arg Leu Leu Arg Lys
            20


<210> SEQ ID NO 44
<211> LENGTH: 27
<212> TYPE: PRT
<213> ORGANISM: Artificial Sequence
<220> FEATURE:
<223> OTHER INFORMATION: A cell membrane permeable peptide

<400> SEQUENCE: 44

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25


<210> SEQ ID NO 45
<211> LENGTH: 18
<212> TYPE: PRT
<213> ORGANISM: Artificial Sequence
<220> FEATURE:
<223> OTHER INFORMATION: A cell membrane permeable peptide

<400> SEQUENCE: 45

Lys Leu Ala Leu Lys Leu Ala Leu Lys Ala Leu Lys Ala Ala Leu Lys
1               5                   10                  15

Leu Ala


<210> SEQ ID NO 46
<211> LENGTH: 16
<212> TYPE: PRT
<213> ORGANISM: Artificial Sequence
<220> FEATURE:
<223> OTHER INFORMATION: A cell membrane permeable peptide

<400> SEQUENCE: 46

Ala Ala Val Ala Leu Leu Pro Ala Val Leu Leu Ala Leu Leu Ala Pro
1               5                   10                  15


<210> SEQ ID NO 47
<211> LENGTH: 5
<212> TYPE: PRT
<213> ORGANISM: Artificial Sequence
<220> FEATURE:
<223> OTHER INFORMATION: A cell membrane permeable peptide

<400> SEQUENCE: 47

Val Pro Met Leu Lys
1               5


<210> SEQ ID NO 48
<211> LENGTH: 5
<212> TYPE: PRT
<213> ORGANISM: Artificial Sequence
<220> FEATURE:
<223> OTHER INFORMATION: A cell membrane permeable peptide

<400> SEQUENCE: 48

Pro Met Leu Lys Glu
1               5


<210> SEQ ID NO 49
<211> LENGTH: 28
```

<212> TYPE: PRT
<213> ORGANISM: Artificial Sequence
<220> FEATURE:
<223> OTHER INFORMATION: A cell membrane permeable peptide

<400> SEQUENCE: 49

Met Ala Asn Leu Gly Tyr Trp Leu Leu Ala Leu Phe Val Thr Met Trp
1 5 10 15

Thr Asp Val Gly Leu Cys Lys Lys Arg Pro Lys Pro
20 25

<210> SEQ ID NO 50
<211> LENGTH: 18
<212> TYPE: PRT
<213> ORGANISM: Artificial Sequence
<220> FEATURE:
<223> OTHER INFORMATION: A cell membrane permeable peptide

<400> SEQUENCE: 50

Leu Leu Ile Ile Leu Arg Arg Arg Ile Arg Lys Gln Ala His Ala His
1 5 10 15

Ser Lys

<210> SEQ ID NO 51
<211> LENGTH: 21
<212> TYPE: PRT
<213> ORGANISM: Artificial Sequence
<220> FEATURE:
<223> OTHER INFORMATION: A cell membrane permeable peptide

<400> SEQUENCE: 51

Lys Glu Thr Trp Trp Glu Thr Trp Trp Thr Glu Trp Ser Gln Pro Lys
1 5 10 15

Lys Lys Arg Lys Val
20

<210> SEQ ID NO 52
<211> LENGTH: 18
<212> TYPE: PRT
<213> ORGANISM: Artificial Sequence
<220> FEATURE:
<223> OTHER INFORMATION: A cell membrane permeable peptide

<400> SEQUENCE: 52

Arg Gly Gly Arg Leu Ser Tyr Ser Arg Arg Arg Phe Ser Thr Ser Thr
1 5 10 15

Gly Arg

<210> SEQ ID NO 53
<211> LENGTH: 15
<212> TYPE: PRT
<213> ORGANISM: Artificial Sequence
<220> FEATURE:
<223> OTHER INFORMATION: A cell membrane permeable peptide

<400> SEQUENCE: 53

Ser Asp Leu Trp Glu Met Met Met Val Ser Leu Ala Cys Gln Tyr
1 5 10 15

<210> SEQ ID NO 54
<211> LENGTH: 12
<212> TYPE: PRT
<213> ORGANISM: Artificial Sequence
<220> FEATURE:
<223> OTHER INFORMATION: A cell membrane permeable peptide

<400> SEQUENCE: 54

Thr Ser Pro Leu Asn Ile His Asn Gly Gln Lys Leu
1 5 10

<210> SEQ ID NO 55
<211> LENGTH: 11
<212> TYPE: PRT
<213> ORGANISM: Artificial Sequence
<220> FEATURE:
<223> OTHER INFORMATION: A cell membrane permeable peptide

<400> SEQUENCE: 55

Arg Arg Arg Arg Arg Arg Arg Arg Arg Arg Arg
1 5 10

<210> SEQ ID NO 56
<211> LENGTH: 19
<212> TYPE: DNA
<213> ORGANISM: Artificial Sequence
<220> FEATURE:
<223> OTHER INFORMATION: ERE consensus sequence

<400> SEQUENCE: 56
tccagttgca ttgacctga 19

<210> SEQ ID NO 57
<211> LENGTH: 16
<212> TYPE: PRT
<213> ORGANISM: Artificial Sequence
<220> FEATURE:
<223> OTHER INFORMATION: A cell membrane permeable peptide

<400> SEQUENCE: 57

Arg Gln Ile Lys Ile Trp Phe Gln Asn Arg Arg Met Lys Trp Lys Lys
1 5 10 15

<210> SEQ ID NO 58
<211> LENGTH: 20
<212> TYPE: DNA
<213> ORGANISM: Artificial Sequence
<220> FEATURE:
<223> OTHER INFORMATION: A primer for real-time PCR

<400> SEQUENCE: 58
actatgtgga caggggcaag 20

<210> SEQ ID NO 59
<211> LENGTH: 20
<212> TYPE: DNA
<213> ORGANISM: Artificial Sequence
<220> FEATURE:
<223> OTHER INFORMATION: A primer for real-time PCR

<400> SEQUENCE: 59
caggcagttg aagcagtcag 20

<210> SEQ ID NO 60
<211> LENGTH: 20
<212> TYPE: DNA
<213> ORGANISM: Artificial Sequence
<220> FEATURE:
<223> OTHER INFORMATION: A primer for PCR

<400> SEQUENCE: 60
tcaaaagcta attatggggc 20

<210> SEQ ID NO 61
<211> LENGTH: 21
<212> TYPE: DNA
<213> ORGANISM: Artificial Sequence
<220> FEATURE:
<223> OTHER INFORMATION: A primer for PCR

<400> SEQUENCE: 61
tcaagcgatt ctcctgcctc a 21

<210> SEQ ID NO 62
<211> LENGTH: 21
<212> TYPE: DNA
<213> ORGANISM: Artificial Sequence
<220> FEATURE:
<223> OTHER INFORMATION: A primer for PCR

<400> SEQUENCE: 62
gagatccgcg gtctgtgcct g 21

<210> SEQ ID NO 63
<211> LENGTH: 21
<212> TYPE: DNA
<213> ORGANISM: Artificial Sequence
<220> FEATURE:
<223> OTHER INFORMATION: A primer for PCR

<400> SEQUENCE: 63
caggactgcg ctcaagggag g 21

<210> SEQ ID NO 64
<211> LENGTH: 21
<212> TYPE: DNA
<213> ORGANISM: Artificial Sequence
<220> FEATURE:
<223> OTHER INFORMATION: A primer for PCR

<400> SEQUENCE: 64
cactggaccc cacagagttc c 21

<210> SEQ ID NO 65
<211> LENGTH: 21
<212> TYPE: DNA
<213> ORGANISM: Artificial Sequence
<220> FEATURE:
<223> OTHER INFORMATION: A primer for PCR

<400> SEQUENCE: 65
tagttgctct cgggagggaa a 21

<210> SEQ ID NO 66
<211> LENGTH: 5
<212> TYPE: PRT
<213> ORGANISM: Homo sapiens

<400> SEQUENCE: 66

Lys Ala Val Ser Phe
1               5

<210> SEQ ID NO 67
<211> LENGTH: 15
<212> TYPE: PRT
<213> ORGANISM: Homo sapiens

<400> SEQUENCE: 67

```
Arg His Val Ser Gln Lys Ala Val Ser Phe Ile His Asp Ile Leu
1               5                   10                  15


<210> SEQ ID NO 68
<211> LENGTH: 23
<212> TYPE: DNA
<213> ORGANISM: Artificial Sequence
<220> FEATURE:
<223> OTHER INFORMATION: Estrogen responsible element

<400> SEQUENCE: 68

gttcaaggcc acctggccaa cat                                             23


<210> SEQ ID NO 69
<211> LENGTH: 23
<212> TYPE: DNA
<213> ORGANISM: Artificial Sequence
<220> FEATURE:
<223> OTHER INFORMATION: Estrogen responsible element

<400> SEQUENCE: 69

cccaggtccc cttgccttcc taa                                             23


<210> SEQ ID NO 70
<211> LENGTH: 24
<212> TYPE: DNA
<213> ORGANISM: Artificial Sequence
<220> FEATURE:
<223> OTHER INFORMATION: Estrogen responsible element

<400> SEQUENCE: 70

gggttcaggt ctagaccttg catc                                            24


<210> SEQ ID NO 71
<211> LENGTH: 1521
<212> TYPE: DNA
<213> ORGANISM: Homo sapiens
<220> FEATURE:
<221> NAME/KEY: CDS
<222> LOCATION: (124)..(1149)

<400> SEQUENCE: 71

gcggggccgc gggccggggg cggactgggg cgggcggaag gagagccagg ccggaaggag      60

gctgccggag ggcgggaggc aggagcgggc caggagctgc tgggctggag cggcggcgcc     120

gcc atg tcc gac agc gag aag ctc aac ctg gac tcg atc atc ggg cgc       168
    Met Ser Asp Ser Glu Lys Leu Asn Leu Asp Ser Ile Ile Gly Arg
    1               5                   10                  15

ctg ctg gaa ggg tcc agg gtc ctg aca ccc cat tgc gcc cca gtg cag       216
Leu Leu Glu Gly Ser Arg Val Leu Thr Pro His Cys Ala Pro Val Gln
                20                  25                  30

ggc tcg cgg cct ggc aag aat gta cag ctg aca gag aac gag atc cgc       264
Gly Ser Arg Pro Gly Lys Asn Val Gln Leu Thr Glu Asn Glu Ile Arg
            35                  40                  45

ggt ctg tgc ctg aaa tcc cgg gag att ttt ctg agc cag ccc att ctt       312
Gly Leu Cys Leu Lys Ser Arg Glu Ile Phe Leu Ser Gln Pro Ile Leu
        50                  55                  60

ctg gag ctg gag gca ccc ctc aag atc tgc ggt gac ata cac ggc cag       360
Leu Glu Leu Glu Ala Pro Leu Lys Ile Cys Gly Asp Ile His Gly Gln
    65                  70                  75

tac tac gac ctt ctg cga cta ttt gag tat ggc ggt ttc cct ccc gag       408
Tyr Tyr Asp Leu Leu Arg Leu Phe Glu Tyr Gly Gly Phe Pro Pro Glu
80                  85                  90                  95
```

```
agc aac tac ctc ttt ctg ggg gac tat gtg gac agg ggc aag cag tcc      456
Ser Asn Tyr Leu Phe Leu Gly Asp Tyr Val Asp Arg Gly Lys Gln Ser
                100                 105                 110

ttg gag acc atc tgc ctg ctg ctg gcc tat aag atc aag tac ccc gag      504
Leu Glu Thr Ile Cys Leu Leu Leu Ala Tyr Lys Ile Lys Tyr Pro Glu
            115                 120                 125

aac ttc ttc ctg ctc cgt ggg aac cac gag tgt gcc agc atc aac cgc      552
Asn Phe Phe Leu Leu Arg Gly Asn His Glu Cys Ala Ser Ile Asn Arg
        130                 135                 140

atc tat ggt ttc tac gat gag tgc aag aga cgc tac aac atc aaa ctg      600
Ile Tyr Gly Phe Tyr Asp Glu Cys Lys Arg Arg Tyr Asn Ile Lys Leu
    145                 150                 155

tgg aaa acc ttc act gac tgc ttc aac tgc ctg ccc atc gcg gcc ata      648
Trp Lys Thr Phe Thr Asp Cys Phe Asn Cys Leu Pro Ile Ala Ala Ile
160                 165                 170                 175

gtg gac gaa aag atc ttc tgc tgc cac gga ggc ctg tcc ccg gac ctg      696
Val Asp Glu Lys Ile Phe Cys Cys His Gly Gly Leu Ser Pro Asp Leu
                180                 185                 190

cag tct atg gag cag att cgg cgg atc atg cgg ccc aca gat gtg cct      744
Gln Ser Met Glu Gln Ile Arg Arg Ile Met Arg Pro Thr Asp Val Pro
            195                 200                 205

gac cag ggc ctg ctg tgt gac ctg ctg tgg tct gac cct gac aag gac      792
Asp Gln Gly Leu Leu Cys Asp Leu Leu Trp Ser Asp Pro Asp Lys Asp
        210                 215                 220

gtg cag ggc tgg ggc gag aac gac cgt ggc gtc tct ttt acc ttt gga      840
Val Gln Gly Trp Gly Glu Asn Asp Arg Gly Val Ser Phe Thr Phe Gly
    225                 230                 235

gcc gag gtg gtg gcc aag ttc ctc cac aag cac gac ttg gac ctc atc      888
Ala Glu Val Val Ala Lys Phe Leu His Lys His Asp Leu Asp Leu Ile
240                 245                 250                 255

tgc cga gca cac cag gtg gta gaa gac ggc tac gag ttc ttt gcc aag      936
Cys Arg Ala His Gln Val Val Glu Asp Gly Tyr Glu Phe Phe Ala Lys
                260                 265                 270

cgg cag ctg gtg aca ctt ttc tca gct ccc aac tac tgt ggc gag ttt      984
Arg Gln Leu Val Thr Leu Phe Ser Ala Pro Asn Tyr Cys Gly Glu Phe
            275                 280                 285

gac aat gct ggc gcc atg atg agt gtg gac gag acc ctc atg tgc tct     1032
Asp Asn Ala Gly Ala Met Met Ser Val Asp Glu Thr Leu Met Cys Ser
        290                 295                 300

ttc cag atc ctc aag ccc gcc gac aag aac aag ggg aag tac ggg cag     1080
Phe Gln Ile Leu Lys Pro Ala Asp Lys Asn Lys Gly Lys Tyr Gly Gln
    305                 310                 315

ttc agt ggc ctg aac cct gga ggc cga ccc atc acc cca ccc cgc aat     1128
Phe Ser Gly Leu Asn Pro Gly Gly Arg Pro Ile Thr Pro Pro Arg Asn
320                 325                 330                 335

tcc gcc aaa gcc aag aaa tag cccccgcaca ccaccctgtg ccccagatga        1179
Ser Ala Lys Ala Lys Lys
                340

tggattgatt gtacagaaat catgctgcca tgctgggggg gggtcacccc gacccctcag   1239

gcccacctgt cacggggaac atggagcctt ggtgtatttt tcttttcttt ttttaatgaa   1299

tcaatagcag cgtccagtcc cccagggctg cttcctgcct gcacctgcgg tgactgtgag   1359

caggatcctg gggccgaggc tgcagctcag ggcaacggca ggccaggtcg tgggtctcca   1419

gccgtgcttg gcctcagggc tggcagccgg atcctggggc aacccatctg gtctcttgaa   1479

taaaggtcaa agctggattc tcgcaaaaaa aaaaaaaaaa aa                      1521
```

```
<210> SEQ ID NO 72
<211> LENGTH: 341
```

```
<212> TYPE: PRT
<213> ORGANISM: Homo sapiens

<400> SEQUENCE: 72

Met Ser Asp Ser Glu Lys Leu Asn Leu Asp Ser Ile Ile Gly Arg Leu
1               5                   10                  15

Leu Glu Gly Ser Arg Val Leu Thr Pro His Cys Ala Pro Val Gln Gly
            20                  25                  30

Ser Arg Pro Gly Lys Asn Val Gln Leu Thr Glu Asn Glu Ile Arg Gly
        35                  40                  45

Leu Cys Leu Lys Ser Arg Glu Ile Phe Leu Ser Gln Pro Ile Leu Leu
    50                  55                  60

Glu Leu Glu Ala Pro Leu Lys Ile Cys Gly Asp Ile His Gly Gln Tyr
65                  70                  75                  80

Tyr Asp Leu Leu Arg Leu Phe Glu Tyr Gly Gly Phe Pro Pro Glu Ser
                85                  90                  95

Asn Tyr Leu Phe Leu Gly Asp Tyr Val Asp Arg Gly Lys Gln Ser Leu
            100                 105                 110

Glu Thr Ile Cys Leu Leu Leu Ala Tyr Lys Ile Lys Tyr Pro Glu Asn
        115                 120                 125

Phe Phe Leu Leu Arg Gly Asn His Glu Cys Ala Ser Ile Asn Arg Ile
    130                 135                 140

Tyr Gly Phe Tyr Asp Glu Cys Lys Arg Arg Tyr Asn Ile Lys Leu Trp
145                 150                 155                 160

Lys Thr Phe Thr Asp Cys Phe Asn Cys Leu Pro Ile Ala Ala Ile Val
                165                 170                 175

Asp Glu Lys Ile Phe Cys Cys His Gly Gly Leu Ser Pro Asp Leu Gln
            180                 185                 190

Ser Met Glu Gln Ile Arg Arg Ile Met Arg Pro Thr Asp Val Pro Asp
        195                 200                 205

Gln Gly Leu Leu Cys Asp Leu Leu Trp Ser Asp Pro Asp Lys Asp Val
    210                 215                 220

Gln Gly Trp Gly Glu Asn Asp Arg Gly Val Ser Phe Thr Phe Gly Ala
225                 230                 235                 240

Glu Val Val Ala Lys Phe Leu His Lys His Asp Leu Asp Leu Ile Cys
                245                 250                 255

Arg Ala His Gln Val Val Glu Asp Gly Tyr Glu Phe Phe Ala Lys Arg
            260                 265                 270

Gln Leu Val Thr Leu Phe Ser Ala Pro Asn Tyr Cys Gly Glu Phe Asp
        275                 280                 285

Asn Ala Gly Ala Met Met Ser Val Asp Glu Thr Leu Met Cys Ser Phe
    290                 295                 300

Gln Ile Leu Lys Pro Ala Asp Lys Asn Lys Gly Lys Tyr Gly Gln Phe
305                 310                 315                 320

Ser Gly Leu Asn Pro Gly Gly Arg Pro Ile Thr Pro Pro Arg Asn Ser
                325                 330                 335

Ala Lys Ala Lys Lys
            340


<210> SEQ ID NO 73
<211> LENGTH: 1488
<212> TYPE: DNA
<213> ORGANISM: Homo sapiens
<220> FEATURE:
<221> NAME/KEY: CDS
<222> LOCATION: (124)..(1116)
```

```
<400> SEQUENCE: 73

gcggggccgc gggccggggg cggactgggg cgggcggaag gagagccagg ccggaaggag      60

gctgccggag ggcgggaggc aggagcgggc caggagctgc tgggctggag cggcggcgcc     120

gcc atg tcc gac agc gag aag ctc aac ctg gac tcg atc atc ggg cgc       168
    Met Ser Asp Ser Glu Lys Leu Asn Leu Asp Ser Ile Ile Gly Arg
    1               5                   10                  15

ctg ctg gaa gtg cag ggc tcg cgg cct ggc aag aat gta cag ctg aca       216
Leu Leu Glu Val Gln Gly Ser Arg Pro Gly Lys Asn Val Gln Leu Thr
                20                  25                  30

gag aac gag atc cgc ggt ctg tgc ctg aaa tcc cgg gag att ttt ctg       264
Glu Asn Glu Ile Arg Gly Leu Cys Leu Lys Ser Arg Glu Ile Phe Leu
            35                  40                  45

agc cag ccc att ctt ctg gag ctg gag gca ccc ctc aag atc tgc ggt       312
Ser Gln Pro Ile Leu Leu Glu Leu Glu Ala Pro Leu Lys Ile Cys Gly
        50                  55                  60

gac ata cac ggc cag tac tac gac ctt ctg cga cta ttt gag tat ggc       360
Asp Ile His Gly Gln Tyr Tyr Asp Leu Leu Arg Leu Phe Glu Tyr Gly
    65                  70                  75

ggt ttc cct ccc gag agc aac tac ctc ttt ctg ggg gac tat gtg gac       408
Gly Phe Pro Pro Glu Ser Asn Tyr Leu Phe Leu Gly Asp Tyr Val Asp
80                  85                  90                  95

agg ggc aag cag tcc ttg gag acc atc tgc ctg ctg ctg gcc tat aag       456
Arg Gly Lys Gln Ser Leu Glu Thr Ile Cys Leu Leu Leu Ala Tyr Lys
                100                 105                 110

atc aag tac ccc gag aac ttc ttc ctg ctc cgt ggg aac cac gag tgt       504
Ile Lys Tyr Pro Glu Asn Phe Phe Leu Leu Arg Gly Asn His Glu Cys
            115                 120                 125

gcc agc atc aac cgc atc tat ggt ttc tac gat gag tgc aag aga cgc       552
Ala Ser Ile Asn Arg Ile Tyr Gly Phe Tyr Asp Glu Cys Lys Arg Arg
        130                 135                 140

tac aac atc aaa ctg tgg aaa acc ttc act gac tgc ttc aac tgc ctg       600
Tyr Asn Ile Lys Leu Trp Lys Thr Phe Thr Asp Cys Phe Asn Cys Leu
    145                 150                 155

ccc atc gcg gcc ata gtg gac gaa aag atc ttc tgc tgc cac gga ggc       648
Pro Ile Ala Ala Ile Val Asp Glu Lys Ile Phe Cys Cys His Gly Gly
160                 165                 170                 175

ctg tcc ccg gac ctg cag tct atg gag cag att cgg cgg atc atg cgg       696
Leu Ser Pro Asp Leu Gln Ser Met Glu Gln Ile Arg Arg Ile Met Arg
                180                 185                 190

ccc aca gat gtg cct gac cag ggc ctg ctg tgt gac ctg ctg tgg tct       744
Pro Thr Asp Val Pro Asp Gln Gly Leu Leu Cys Asp Leu Leu Trp Ser
            195                 200                 205

gac cct gac aag gac gtg cag ggc tgg ggc gag aac gac cgt ggc gtc       792
Asp Pro Asp Lys Asp Val Gln Gly Trp Gly Glu Asn Asp Arg Gly Val
        210                 215                 220

tct ttt acc ttt gga gcc gag gtg gtg gcc aag ttc ctc cac aag cac       840
Ser Phe Thr Phe Gly Ala Glu Val Val Ala Lys Phe Leu His Lys His
    225                 230                 235

gac ttg gac ctc atc tgc cga gca cac cag gtg gta gaa gac ggc tac       888
Asp Leu Asp Leu Ile Cys Arg Ala His Gln Val Val Glu Asp Gly Tyr
240                 245                 250                 255

gag ttc ttt gcc aag cgg cag ctg gtg aca ctt ttc tca gct ccc aac       936
Glu Phe Phe Ala Lys Arg Gln Leu Val Thr Leu Phe Ser Ala Pro Asn
                260                 265                 270

tac tgt ggc gag ttt gac aat gct ggc gcc atg atg agt gtg gac gag       984
Tyr Cys Gly Glu Phe Asp Asn Ala Gly Ala Met Met Ser Val Asp Glu
            275                 280                 285
```

```
acc ctc atg tgc tct ttc cag atc ctc aag ccc gcc gac aag aac aag     1032
Thr Leu Met Cys Ser Phe Gln Ile Leu Lys Pro Ala Asp Lys Asn Lys
        290                 295                 300

ggg aag tac ggg cag ttc agt ggc ctg aac cct gga ggc cga ccc atc     1080
Gly Lys Tyr Gly Gln Phe Ser Gly Leu Asn Pro Gly Gly Arg Pro Ile
    305                 310                 315

acc cca ccc cgc aat tcc gcc aaa gcc aag aaa tag cccccgcaca          1126
Thr Pro Pro Arg Asn Ser Ala Lys Ala Lys Lys
320                 325                 330

ccaccctgtg ccccagatga tggattgatt gtacagaaat catgctgcca tgctgggggg   1186

gggtcacccc gacccctcag gcccacctgt cacggggaac atggagcctt ggtgtatttt   1246

tcttttcttt ttttaatgaa tcaatagcag cgtccagtcc cccagggctg cttcctgcct   1306

gcacctgcgg tgactgtgag caggatcctg gggccgaggc tgcagctcag ggcaacggca   1366

ggccaggtcg tgggtctcca gccgtgcttg gcctcagggc tggcagccgg atcctggggc   1426

aacccatctg gtctcttgaa taaaggtcaa agctggattc tcgcaaaaaa aaaaaaaaaa   1486

aa                                                                  1488


<210> SEQ ID NO 74
<211> LENGTH: 330
<212> TYPE: PRT
<213> ORGANISM: Homo sapiens

<400> SEQUENCE: 74

Met Ser Asp Ser Glu Lys Leu Asn Leu Asp Ser Ile Ile Gly Arg Leu
1               5                   10                  15

Leu Glu Val Gln Gly Ser Arg Pro Gly Lys Asn Val Gln Leu Thr Glu
            20                  25                  30

Asn Glu Ile Arg Gly Leu Cys Leu Lys Ser Arg Glu Ile Phe Leu Ser
        35                  40                  45

Gln Pro Ile Leu Leu Glu Leu Glu Ala Pro Leu Lys Ile Cys Gly Asp
    50                  55                  60

Ile His Gly Gln Tyr Tyr Asp Leu Leu Arg Leu Phe Glu Tyr Gly Gly
65                  70                  75                  80

Phe Pro Pro Glu Ser Asn Tyr Leu Phe Leu Gly Asp Tyr Val Asp Arg
                85                  90                  95

Gly Lys Gln Ser Leu Glu Thr Ile Cys Leu Leu Leu Ala Tyr Lys Ile
            100                 105                 110

Lys Tyr Pro Glu Asn Phe Phe Leu Leu Arg Gly Asn His Glu Cys Ala
        115                 120                 125

Ser Ile Asn Arg Ile Tyr Gly Phe Tyr Asp Glu Cys Lys Arg Arg Tyr
    130                 135                 140

Asn Ile Lys Leu Trp Lys Thr Phe Thr Asp Cys Phe Asn Cys Leu Pro
145                 150                 155                 160

Ile Ala Ala Ile Val Asp Glu Lys Ile Phe Cys Cys His Gly Gly Leu
                165                 170                 175

Ser Pro Asp Leu Gln Ser Met Glu Gln Ile Arg Arg Ile Met Arg Pro
            180                 185                 190

Thr Asp Val Pro Asp Gln Gly Leu Leu Cys Asp Leu Leu Trp Ser Asp
        195                 200                 205

Pro Asp Lys Asp Val Gln Gly Trp Gly Glu Asn Asp Arg Gly Val Ser
    210                 215                 220

Phe Thr Phe Gly Ala Glu Val Val Ala Lys Phe Leu His Lys His Asp
225                 230                 235                 240
```

```
Leu Asp Leu Ile Cys Arg Ala His Gln Val Val Glu Asp Gly Tyr Glu
            245                 250                 255

Phe Phe Ala Lys Arg Gln Leu Val Thr Leu Phe Ser Ala Pro Asn Tyr
            260                 265                 270

Cys Gly Glu Phe Asp Asn Ala Gly Ala Met Met Ser Val Asp Glu Thr
        275                 280                 285

Leu Met Cys Ser Phe Gln Ile Leu Lys Pro Ala Asp Lys Asn Lys Gly
    290                 295                 300

Lys Tyr Gly Gln Phe Ser Gly Leu Asn Pro Gly Gly Arg Pro Ile Thr
305                 310                 315                 320

Pro Pro Arg Asn Ser Ala Lys Ala Lys Lys
            325                 330


<210> SEQ ID NO 75
<211> LENGTH: 1356
<212> TYPE: DNA
<213> ORGANISM: Homo sapiens
<220> FEATURE:
<221> NAME/KEY: CDS
<222> LOCATION: (124)..(984)

<400> SEQUENCE: 75

gcggggccgc gggccggggg cggactgggg cgggcggaag gagagccagg ccggaaggag      60

gctgccggag ggcgggaggc aggagcgggc caggagctgc tgggctggag cggcggcgcc     120

gcc atg tcc gac agc gag aag ctc aac ctg gac tcg atc atc ggg cgc       168
    Met Ser Asp Ser Glu Lys Leu Asn Leu Asp Ser Ile Ile Gly Arg
    1               5                   10                  15

ctg ctg gaa ggt gac ata cac ggc cag tac tac gac ctt ctg cga cta       216
Leu Leu Glu Gly Asp Ile His Gly Gln Tyr Tyr Asp Leu Leu Arg Leu
            20                  25                  30

ttt gag tat ggc ggt ttc cct ccc gag agc aac tac ctc ttt ctg ggg       264
Phe Glu Tyr Gly Gly Phe Pro Pro Glu Ser Asn Tyr Leu Phe Leu Gly
            35                  40                  45

gac tat gtg gac agg ggc aag cag tcc ttg gag acc atc tgc ctg ctg       312
Asp Tyr Val Asp Arg Gly Lys Gln Ser Leu Glu Thr Ile Cys Leu Leu
        50                  55                  60

ctg gcc tat aag atc aag tac ccc gag aac ttc ttc ctg ctc cgt ggg       360
Leu Ala Tyr Lys Ile Lys Tyr Pro Glu Asn Phe Phe Leu Leu Arg Gly
    65                  70                  75

aac cac gag tgt gcc agc atc aac cgc atc tat ggt ttc tac gat gag       408
Asn His Glu Cys Ala Ser Ile Asn Arg Ile Tyr Gly Phe Tyr Asp Glu
80                  85                  90                  95

tgc aag aga cgc tac aac atc aaa ctg tgg aaa acc ttc act gac tgc       456
Cys Lys Arg Arg Tyr Asn Ile Lys Leu Trp Lys Thr Phe Thr Asp Cys
            100                 105                 110

ttc aac tgc ctg ccc atc gcg gcc ata gtg gac gaa aag atc ttc tgc       504
Phe Asn Cys Leu Pro Ile Ala Ala Ile Val Asp Glu Lys Ile Phe Cys
            115                 120                 125

tgc cac gga ggc ctg tcc ccg gac ctg cag tct atg gag cag att cgg       552
Cys His Gly Gly Leu Ser Pro Asp Leu Gln Ser Met Glu Gln Ile Arg
        130                 135                 140

cgg atc atg cgg ccc aca gat gtg cct gac cag ggc ctg ctg tgt gac       600
Arg Ile Met Arg Pro Thr Asp Val Pro Asp Gln Gly Leu Leu Cys Asp
    145                 150                 155

ctg ctg tgg tct gac cct gac aag gac gtg cag ggc tgg ggc gag aac       648
Leu Leu Trp Ser Asp Pro Asp Lys Asp Val Gln Gly Trp Gly Glu Asn
160                 165                 170                 175

gac cgt ggc gtc tct ttt acc ttt gga gcc gag gtg gtg gcc aag ttc       696
Asp Arg Gly Val Ser Phe Thr Phe Gly Ala Glu Val Val Ala Lys Phe
```

```
                180                 185                 190

ctc cac aag cac gac ttg gac ctc atc tgc cga gca cac cag gtg gta      744
Leu His Lys His Asp Leu Asp Leu Ile Cys Arg Ala His Gln Val Val
            195                 200                 205

gaa gac ggc tac gag ttc ttt gcc aag cgg cag ctg gtg aca ctt ttc      792
Glu Asp Gly Tyr Glu Phe Phe Ala Lys Arg Gln Leu Val Thr Leu Phe
        210                 215                 220

tca gct ccc aac tac tgt ggc gag ttt gac aat gct ggc gcc atg atg      840
Ser Ala Pro Asn Tyr Cys Gly Glu Phe Asp Asn Ala Gly Ala Met Met
    225                 230                 235

agt gtg gac gag acc ctc atg tgc tct ttc cag atc ctc aag ccc gcc      888
Ser Val Asp Glu Thr Leu Met Cys Ser Phe Gln Ile Leu Lys Pro Ala
240                 245                 250                 255

gac aag aac aag ggg aag tac ggg cag ttc agt ggc ctg aac cct gga      936
Asp Lys Asn Lys Gly Lys Tyr Gly Gln Phe Ser Gly Leu Asn Pro Gly
                260                 265                 270

ggc cga ccc atc acc cca ccc cgc aat tcc gcc aaa gcc aag aaa tag      984
Gly Arg Pro Ile Thr Pro Pro Arg Asn Ser Ala Lys Ala Lys Lys
            275                 280                 285

cccccgcaca ccaccctgtg ccccagatga tggattgatt gtacagaaat catgctgcca   1044

tgctgggggg gggtcacccc gacccctcag gcccacctgt cacggggaac atggagcctt   1104

ggtgtatttt tcttttcttt ttttaatgaa tcaatagcag cgtccagtcc cccagggctg   1164

cttcctgcct gcacctgcgg tgactgtgag caggatcctg gggccgaggc tgcagctcag   1224

ggcaacggca ggccaggtcg tgggtctcca gccgtgcttg gcctcagggc tggcagccgg   1284

atcctggggc aacccatctg gtctcttgaa taaaggtcaa agctggattc tcgcaaaaaa   1344

aaaaaaaaaa aa                                                        1356


<210> SEQ ID NO 76
<211> LENGTH: 286
<212> TYPE: PRT
<213> ORGANISM: Homo sapiens

<400> SEQUENCE: 76

Met Ser Asp Ser Glu Lys Leu Asn Leu Asp Ser Ile Ile Gly Arg Leu
1               5                   10                  15

Leu Glu Gly Asp Ile His Gly Gln Tyr Tyr Asp Leu Leu Arg Leu Phe
            20                  25                  30

Glu Tyr Gly Gly Phe Pro Pro Glu Ser Asn Tyr Leu Phe Leu Gly Asp
        35                  40                  45

Tyr Val Asp Arg Gly Lys Gln Ser Leu Glu Thr Ile Cys Leu Leu Leu
    50                  55                  60

Ala Tyr Lys Ile Lys Tyr Pro Glu Asn Phe Phe Leu Leu Arg Gly Asn
65                  70                  75                  80

His Glu Cys Ala Ser Ile Asn Arg Ile Tyr Gly Phe Tyr Asp Glu Cys
                85                  90                  95

Lys Arg Arg Tyr Asn Ile Lys Leu Trp Lys Thr Phe Thr Asp Cys Phe
            100                 105                 110

Asn Cys Leu Pro Ile Ala Ala Ile Val Asp Glu Lys Ile Phe Cys Cys
        115                 120                 125

His Gly Gly Leu Ser Pro Asp Leu Gln Ser Met Glu Gln Ile Arg Arg
    130                 135                 140

Ile Met Arg Pro Thr Asp Val Pro Asp Gln Gly Leu Leu Cys Asp Leu
145                 150                 155                 160

Leu Trp Ser Asp Pro Asp Lys Asp Val Gln Gly Trp Gly Glu Asn Asp
```

```
                165                 170                 175

Arg Gly Val Ser Phe Thr Phe Gly Ala Glu Val Val Ala Lys Phe Leu
            180                 185                 190

His Lys His Asp Leu Asp Leu Ile Cys Arg Ala His Gln Val Val Glu
        195                 200                 205

Asp Gly Tyr Glu Phe Phe Ala Lys Arg Gln Leu Val Thr Leu Phe Ser
    210                 215                 220

Ala Pro Asn Tyr Cys Gly Glu Phe Asp Asn Ala Gly Ala Met Met Ser
225                 230                 235                 240

Val Asp Glu Thr Leu Met Cys Ser Phe Gln Ile Leu Lys Pro Ala Asp
                245                 250                 255

Lys Asn Lys Gly Lys Tyr Gly Gln Phe Ser Gly Leu Asn Pro Gly Gly
            260                 265                 270

Arg Pro Ile Thr Pro Pro Arg Asn Ser Ala Lys Ala Lys Lys
        275                 280                 285


<210> SEQ ID NO 77
<211> LENGTH: 2689
<212> TYPE: DNA
<213> ORGANISM: Homo sapiens
<220> FEATURE:
<221> NAME/KEY: CDS
<222> LOCATION: (201)..(1256)

<400> SEQUENCE: 77

gatcttgggc tgaggttccc gggcgggcgg gcgcggagag acgcgggaag caggggctgg      60

gcgggggtcg cggcgccgca gctagcgcag ccagcccgag ggccgccgcc gccgccgccc     120

agcgcgctcc ggggccgccg gccgcagcca gcacccgccg cgccgcagct ccgggaccgg     180

ccccggccgc cgccgccgcg atg ggc aac gcc gcc gcc gcc aag aag ggc agc     233
                      Met Gly Asn Ala Ala Ala Ala Lys Lys Gly Ser
                      1               5                   10

gag cag gag agc gtg aaa gaa ttc tta gcc aaa gcc aaa gaa gat ttt       281
Glu Gln Glu Ser Val Lys Glu Phe Leu Ala Lys Ala Lys Glu Asp Phe
            15                  20                  25

ctt aaa aaa tgg gaa agt ccc gct cag aac aca gcc cac ttg gat cag       329
Leu Lys Lys Trp Glu Ser Pro Ala Gln Asn Thr Ala His Leu Asp Gln
        30                  35                  40

ttt gaa cga atc aag acc ctc ggc acg ggc tcc ttc ggg cgg gtg atg       377
Phe Glu Arg Ile Lys Thr Leu Gly Thr Gly Ser Phe Gly Arg Val Met
    45                  50                  55

ctg gtg aaa cac aag gag acc ggg aac cac tat gcc atg aag atc ctc       425
Leu Val Lys His Lys Glu Thr Gly Asn His Tyr Ala Met Lys Ile Leu
60                  65                  70                  75

gac aaa cag aag gtg gtg aaa ctg aaa cag atc gaa cac acc ctg aat       473
Asp Lys Gln Lys Val Val Lys Leu Lys Gln Ile Glu His Thr Leu Asn
                80                  85                  90

gaa aag cgc atc ctg caa gct gtc aac ttt ccg ttc ctc gtc aaa ctc       521
Glu Lys Arg Ile Leu Gln Ala Val Asn Phe Pro Phe Leu Val Lys Leu
            95                  100                 105

gag ttc tcc ttc aag gac aac tca aac tta tac atg gtc atg gag tac       569
Glu Phe Ser Phe Lys Asp Asn Ser Asn Leu Tyr Met Val Met Glu Tyr
        110                 115                 120

gtg ccc ggc ggg gag atg ttc tca cac cta cgg cgg atc gga agg ttc       617
Val Pro Gly Gly Glu Met Phe Ser His Leu Arg Arg Ile Gly Arg Phe
    125                 130                 135

agt gag ccc cat gcc cgt ttc tac gcg gcc cag atc gtc ctg acc ttt       665
Ser Glu Pro His Ala Arg Phe Tyr Ala Ala Gln Ile Val Leu Thr Phe
140                 145                 150                 155
```

```
gag tat ctg cac tcg ctg gat ctc atc tac agg gac ctg aag ccg gag      713
Glu Tyr Leu His Ser Leu Asp Leu Ile Tyr Arg Asp Leu Lys Pro Glu
                160                 165                 170

aat ctg ctc att gac cag cag ggc tac att cag gtg aca gac ttc ggt      761
Asn Leu Leu Ile Asp Gln Gln Gly Tyr Ile Gln Val Thr Asp Phe Gly
            175                 180                 185

ttc gcc aag cgc gtg aag ggc cgc act tgg acc ttg tgc ggc acc cct      809
Phe Ala Lys Arg Val Lys Gly Arg Thr Trp Thr Leu Cys Gly Thr Pro
        190                 195                 200

gag tac ctg gcc cct gag att atc ctg agc aaa ggc tac aac aag gcc      857
Glu Tyr Leu Ala Pro Glu Ile Ile Leu Ser Lys Gly Tyr Asn Lys Ala
    205                 210                 215

gtg gac tgg tgg gcc ctg ggg gtt ctt atc tat gaa atg gcc gct ggc      905
Val Asp Trp Trp Ala Leu Gly Val Leu Ile Tyr Glu Met Ala Ala Gly
220                 225                 230                 235

tac ccg ccc ttc ttc gca gac cag ccc atc cag atc tat gag aag atc      953
Tyr Pro Pro Phe Phe Ala Asp Gln Pro Ile Gln Ile Tyr Glu Lys Ile
                240                 245                 250

gtc tct ggg aag gtg cgc ttc cct tcc cac ttc agc tct gac ttg aag     1001
Val Ser Gly Lys Val Arg Phe Pro Ser His Phe Ser Ser Asp Leu Lys
            255                 260                 265

gac ctg ctg cgg aac ctc ctg cag gta gat ctc acc aag cgc ttt ggg     1049
Asp Leu Leu Arg Asn Leu Leu Gln Val Asp Leu Thr Lys Arg Phe Gly
        270                 275                 280

aac ctc aag aat ggg gtc aac gat atc aag aac cac aag tgg ttt gcc     1097
Asn Leu Lys Asn Gly Val Asn Asp Ile Lys Asn His Lys Trp Phe Ala
    285                 290                 295

aca act gac tgg att gcc atc tac cag agg aag gtg gaa gct ccc ttc     1145
Thr Thr Asp Trp Ile Ala Ile Tyr Gln Arg Lys Val Glu Ala Pro Phe
300                 305                 310                 315

ata cca aag ttt aaa ggc cct ggg gat acg agt aac ttt gac gac tat     1193
Ile Pro Lys Phe Lys Gly Pro Gly Asp Thr Ser Asn Phe Asp Asp Tyr
                320                 325                 330

gag gaa gaa gaa atc cgg gtc tcc atc aat gag aag tgt ggc aag gag     1241
Glu Glu Glu Glu Ile Arg Val Ser Ile Asn Glu Lys Cys Gly Lys Glu
            335                 340                 345

ttt tct gag ttt tag gggcatgcct gtgcccccat gggttttctt ttttcttttt     1296
Phe Ser Glu Phe
        350

tcttttttt ggtcgggggg gtgggagggt tggattgaac agccagaggg ccccagagtt   1356

ccttgcatct aatttcaccc ccaccccacc ctccagggtt agggggagca ggaagcccag   1416

ataatcagag ggacagaaac accagctgct ccccctcatc cccttcaccc tcctgccccc   1476

tctcccactt ttcccttcct ctttccccac agccccccag cccctcagcc ctcccagccc   1536

acttctgcct gttttaaacg agtttctcaa ctccagtcag accaggtctt gctggtgtat   1596

ccagggacag ggtatggaaa gaggggctca cgcttaactc cagcccccac ccacaccccc   1656

atcccaccca accacaggcc ccacttgcta agggcaaatg aacgaagcgc caaccttcct   1716

ttcggagtaa tcctgcctgg gaaggagaga tttttagtga catgttcagt gggttgcttg   1776

ctagaatttt tttaaaaaaa caacaattta aaatcttatt taagttccac cagtgcctcc   1836

ctccctcctt cctctactcc caccccctccc atgtcccccc attcctcaaa tccattttaa   1896

agagaagcag actgactttg gaaagggagg cgctggggtt tgaacctccc cgctgctaat   1956

ctcccctggg cccctccccg gggaatcctc tctgccaatc ctgcgagggt ctaggcccct   2016

ttaggaagcc tccgctctct ttttccccaa cagacctgtc ttcacccttg ggctttgaaa   2076
```

```
gccagacaaa gcagctgccc ctctccctgc caaagaggag tcatccccca aaaagacaga   2136

gggggagccc caagcccaag tctttcctcc cagcagcgtt tccccccaac tccttaattt   2196

tattctccgc tagattttaa cgtccagcct tccctcagct gagtggggag ggcatccctg   2256

caaaagggaa cagaagaggc caagtccccc caagccacgg cccggggttc aaggctagag   2316

ctgctgggga ggggctgcct gttttactca cccaccagct tccgcctccc ccatcctggg   2376

cgcccctcct ccagcttagc tgtcagctgt ccatcacctc tcccccactt tctcatttgt   2436

gctttttttct ctcgtaatag aaaagtgggg agccgctggg gagccacccc attcatcccc   2496

gtatttcccc ctctcataac ttctccccat cccaggagga gttctcaggc ctggggtggg   2556

gccccgggtg ggtgcggggg cgattcaacc tgtgtgctgc gaaggacgag acttcctctt   2616

gaacagtgtg ctgttgtaaa catatttgaa aactattacc aataaagttt tgtttaaaaa   2676

aaaaaaaaaa aaa                                                     2689
```

<210> SEQ ID NO 78
<211> LENGTH: 351
<212> TYPE: PRT
<213> ORGANISM: Homo sapiens

<400> SEQUENCE: 78

```
Met Gly Asn Ala Ala Ala Ala Lys Lys Gly Ser Glu Gln Glu Ser Val
1               5                   10                  15

Lys Glu Phe Leu Ala Lys Ala Lys Glu Asp Phe Leu Lys Lys Trp Glu
            20                  25                  30

Ser Pro Ala Gln Asn Thr Ala His Leu Asp Gln Phe Glu Arg Ile Lys
        35                  40                  45

Thr Leu Gly Thr Gly Ser Phe Gly Arg Val Met Leu Val Lys His Lys
    50                  55                  60

Glu Thr Gly Asn His Tyr Ala Met Lys Ile Leu Asp Lys Gln Lys Val
65                  70                  75                  80

Val Lys Leu Lys Gln Ile Glu His Thr Leu Asn Glu Lys Arg Ile Leu
                85                  90                  95

Gln Ala Val Asn Phe Pro Phe Leu Val Lys Leu Glu Phe Ser Phe Lys
            100                 105                 110

Asp Asn Ser Asn Leu Tyr Met Val Met Glu Tyr Val Pro Gly Gly Glu
        115                 120                 125

Met Phe Ser His Leu Arg Arg Ile Gly Arg Phe Ser Glu Pro His Ala
    130                 135                 140

Arg Phe Tyr Ala Ala Gln Ile Val Leu Thr Phe Glu Tyr Leu His Ser
145                 150                 155                 160

Leu Asp Leu Ile Tyr Arg Asp Leu Lys Pro Glu Asn Leu Leu Ile Asp
                165                 170                 175

Gln Gln Gly Tyr Ile Gln Val Thr Asp Phe Gly Phe Ala Lys Arg Val
            180                 185                 190

Lys Gly Arg Thr Trp Thr Leu Cys Gly Thr Pro Glu Tyr Leu Ala Pro
        195                 200                 205

Glu Ile Ile Leu Ser Lys Gly Tyr Asn Lys Ala Val Asp Trp Trp Ala
    210                 215                 220

Leu Gly Val Leu Ile Tyr Glu Met Ala Ala Gly Tyr Pro Pro Phe Phe
225                 230                 235                 240

Ala Asp Gln Pro Ile Gln Ile Tyr Glu Lys Ile Val Ser Gly Lys Val
                245                 250                 255

Arg Phe Pro Ser His Phe Ser Ser Asp Leu Lys Asp Leu Leu Arg Asn
```

```
            260                 265                 270

Leu Leu Gln Val Asp Leu Thr Lys Arg Phe Gly Asn Leu Lys Asn Gly
        275                 280                 285

Val Asn Asp Ile Lys Asn His Lys Trp Phe Ala Thr Thr Asp Trp Ile
    290                 295                 300

Ala Ile Tyr Gln Arg Lys Val Glu Ala Pro Phe Ile Pro Lys Phe Lys
305                 310                 315                 320

Gly Pro Gly Asp Thr Ser Asn Phe Asp Asp Tyr Glu Glu Glu Glu Ile
                325                 330                 335

Arg Val Ser Ile Asn Glu Lys Cys Gly Lys Glu Phe Ser Glu Phe
            340                 345                 350


<210> SEQ ID NO 79
<211> LENGTH: 2490
<212> TYPE: DNA
<213> ORGANISM: Homo sapiens
<220> FEATURE:
<221> NAME/KEY: CDS
<222> LOCATION: (26)..(1057)

<400> SEQUENCE: 79

ggtgccctga gaacaggact gagtg atg gct tcc aac tcc agc gat gtg aaa       52
                            Met Ala Ser Asn Ser Ser Asp Val Lys
                            1               5

gaa ttc tta gcc aaa gcc aaa gaa gat ttt ctt aaa aaa tgg gaa agt      100
Glu Phe Leu Ala Lys Ala Lys Glu Asp Phe Leu Lys Lys Trp Glu Ser
10                  15                  20                  25

ccc gct cag aac aca gcc cac ttg gat cag ttt gaa cga atc aag acc      148
Pro Ala Gln Asn Thr Ala His Leu Asp Gln Phe Glu Arg Ile Lys Thr
                30                  35                  40

ctc ggc acg ggc tcc ttc ggg cgg gtg atg ctg gtg aaa cac aag gag      196
Leu Gly Thr Gly Ser Phe Gly Arg Val Met Leu Val Lys His Lys Glu
            45                  50                  55

acc ggg aac cac tat gcc atg aag atc ctc gac aaa cag aag gtg gtg      244
Thr Gly Asn His Tyr Ala Met Lys Ile Leu Asp Lys Gln Lys Val Val
        60                  65                  70

aaa ctg aaa cag atc gaa cac acc ctg aat gaa aag cgc atc ctg caa      292
Lys Leu Lys Gln Ile Glu His Thr Leu Asn Glu Lys Arg Ile Leu Gln
    75                  80                  85

gct gtc aac ttt ccg ttc ctc gtc aaa ctc gag ttc tcc ttc aag gac      340
Ala Val Asn Phe Pro Phe Leu Val Lys Leu Glu Phe Ser Phe Lys Asp
90                  95                  100                 105

aac tca aac tta tac atg gtc atg gag tac gtg ccc ggc ggg gag atg      388
Asn Ser Asn Leu Tyr Met Val Met Glu Tyr Val Pro Gly Gly Glu Met
                110                 115                 120

ttc tca cac cta cgg cgg atc gga agg ttc agt gag ccc cat gcc cgt      436
Phe Ser His Leu Arg Arg Ile Gly Arg Phe Ser Glu Pro His Ala Arg
            125                 130                 135

ttc tac gcg gcc cag atc gtc ctg acc ttt gag tat ctg cac tcg ctg      484
Phe Tyr Ala Ala Gln Ile Val Leu Thr Phe Glu Tyr Leu His Ser Leu
        140                 145                 150

gat ctc atc tac agg gac ctg aag ccg gag aat ctg ctc att gac cag      532
Asp Leu Ile Tyr Arg Asp Leu Lys Pro Glu Asn Leu Leu Ile Asp Gln
    155                 160                 165

cag ggc tac att cag gtg aca gac ttc ggt ttc gcc aag cgc gtg aag      580
Gln Gly Tyr Ile Gln Val Thr Asp Phe Gly Phe Ala Lys Arg Val Lys
170                 175                 180                 185

ggc cgc act tgg acc ttg tgc ggc acc cct gag tac ctg gcc cct gag      628
Gly Arg Thr Trp Thr Leu Cys Gly Thr Pro Glu Tyr Leu Ala Pro Glu
                190                 195                 200
```

```
att atc ctg agc aaa ggc tac aac aag gcc gtg gac tgg tgg gcc ctg      676
Ile Ile Leu Ser Lys Gly Tyr Asn Lys Ala Val Asp Trp Trp Ala Leu
            205                 210                 215

ggg gtt ctt atc tat gaa atg gcc gct ggc tac ccg ccc ttc ttc gca      724
Gly Val Leu Ile Tyr Glu Met Ala Ala Gly Tyr Pro Pro Phe Phe Ala
        220                 225                 230

gac cag ccc atc cag atc tat gag aag atc gtc tct ggg aag gtg cgc      772
Asp Gln Pro Ile Gln Ile Tyr Glu Lys Ile Val Ser Gly Lys Val Arg
    235                 240                 245

ttc cct tcc cac ttc agc tct gac ttg aag gac ctg ctg cgg aac ctc      820
Phe Pro Ser His Phe Ser Ser Asp Leu Lys Asp Leu Leu Arg Asn Leu
250                 255                 260                 265

ctg cag gta gat ctc acc aag cgc ttt ggg aac ctc aag aat ggg gtc      868
Leu Gln Val Asp Leu Thr Lys Arg Phe Gly Asn Leu Lys Asn Gly Val
                270                 275                 280

aac gat atc aag aac cac aag tgg ttt gcc aca act gac tgg att gcc      916
Asn Asp Ile Lys Asn His Lys Trp Phe Ala Thr Thr Asp Trp Ile Ala
            285                 290                 295

atc tac cag agg aag gtg gaa gct ccc ttc ata cca aag ttt aaa ggc      964
Ile Tyr Gln Arg Lys Val Glu Ala Pro Phe Ile Pro Lys Phe Lys Gly
        300                 305                 310

cct ggg gat acg agt aac ttt gac gac tat gag gaa gaa gaa atc cgg     1012
Pro Gly Asp Thr Ser Asn Phe Asp Asp Tyr Glu Glu Glu Glu Ile Arg
    315                 320                 325

gtc tcc atc aat gag aag tgt ggc aag gag ttt tct gag ttt tag         1057
Val Ser Ile Asn Glu Lys Cys Gly Lys Glu Phe Ser Glu Phe
330                 335                 340

gggcatgcct gtgcccccat gggtttcttt ttttcttttt tctttttttt ggtcgggggg   1117

gtgggagggt tggattgaac agccagaggg ccccagagtt ccttgcatct aatttcaccc   1177

ccaccccacc ctccagggtt agggggagca ggaagcccag ataatcagag ggacagaaac   1237

accagctgct ccccctcatc cccttcaccc tcctgccccc tctcccactt ttcccttcct   1297

ctttccccac agccccccag cccctcagcc ctcccagccc acttctgcct gttttaaacg   1357

agtttctcaa ctccagtcag accaggtctt gctggtgtat ccagggacag ggtatggaaa   1417

gaggggctca cgcttaactc cagcccccac ccacaccccc atcccaccca accacaggcc   1477

ccacttgcta agggcaaatg aacgaagcgc caaccttcct ttcggagtaa tcctgcctgg   1537

gaaggagaga tttttagtga catgttcagt gggttgcttg ctagaatttt tttaaaaaaa   1597

caacaattta aaatcttatt taagttccac cagtgcctcc ctccctcctt cctctactcc   1657

cacccctccc atgtcccccc attcctcaaa tccattttaa agagaagcag actgactttg   1717

gaaagggagg cgctggggtt tgaacctccc cgctgctaat ctcccctggg cccctccccg   1777

gggaatcctc tctgccaatc ctgcgagggt ctaggcccct ttaggaagcc tccgctctct   1837

ttttccccaa cagacctgtc ttcacccttg ggctttgaaa gccagacaaa gcagctgccc   1897

ctctccctgc caaagaggag tcatccccca aaaagacaga gggggagccc caagcccaag   1957

tctttcctcc cagcagcgtt tccccccaac tccttaattt tattctccgc tagattttaa   2017

cgtccagcct tccctcagct gagtggggag ggcatccctg caaaagggaa cagaagaggc   2077

caagtccccc caagccacgg cccggggttc aaggctagag ctgctgggga ggggctgcct   2137

gttttactca cccaccagct tccgcctccc ccatcctggg cgcccctcct ccagcttagc   2197

tgtcagctgt ccatcacctc tcccccactt tctcatttgt gctttttttct ctcgtaatag  2257

aaaagtgggg agccgctggg gagccacccc attcatcccc gtatttcccc ctctcataac   2317
```

```
ttctccccat cccaggagga gttctcaggc ctggggtggg gccccgggtg ggtgcggggg   2377

cgattcaacc tgtgtgctgc gaaggacgag acttcctctt gaacagtgtg ctgttgtaaa   2437

catatttgaa aactattacc aataaagttt tgtttaaaaa aaaaaaaaaa aaa          2490


<210> SEQ ID NO 80
<211> LENGTH: 343
<212> TYPE: PRT
<213> ORGANISM: Homo sapiens

<400> SEQUENCE: 80

Met Ala Ser Asn Ser Ser Asp Val Lys Glu Phe Leu Ala Lys Ala Lys
1               5                   10                  15

Glu Asp Phe Leu Lys Lys Trp Glu Ser Pro Ala Gln Asn Thr Ala His
            20                  25                  30

Leu Asp Gln Phe Glu Arg Ile Lys Thr Leu Gly Thr Gly Ser Phe Gly
        35                  40                  45

Arg Val Met Leu Val Lys His Lys Glu Thr Gly Asn His Tyr Ala Met
    50                  55                  60

Lys Ile Leu Asp Lys Gln Lys Val Val Lys Leu Lys Gln Ile Glu His
65                  70                  75                  80

Thr Leu Asn Glu Lys Arg Ile Leu Gln Ala Val Asn Phe Pro Phe Leu
                85                  90                  95

Val Lys Leu Glu Phe Ser Phe Lys Asp Asn Ser Asn Leu Tyr Met Val
            100                 105                 110

Met Glu Tyr Val Pro Gly Gly Glu Met Phe Ser His Leu Arg Arg Ile
        115                 120                 125

Gly Arg Phe Ser Glu Pro His Ala Arg Phe Tyr Ala Ala Gln Ile Val
    130                 135                 140

Leu Thr Phe Glu Tyr Leu His Ser Leu Asp Leu Ile Tyr Arg Asp Leu
145                 150                 155                 160

Lys Pro Glu Asn Leu Leu Ile Asp Gln Gln Gly Tyr Ile Gln Val Thr
                165                 170                 175

Asp Phe Gly Phe Ala Lys Arg Val Lys Gly Arg Thr Trp Thr Leu Cys
            180                 185                 190

Gly Thr Pro Glu Tyr Leu Ala Pro Glu Ile Ile Leu Ser Lys Gly Tyr
        195                 200                 205

Asn Lys Ala Val Asp Trp Trp Ala Leu Gly Val Leu Ile Tyr Glu Met
    210                 215                 220

Ala Ala Gly Tyr Pro Pro Phe Phe Ala Asp Gln Pro Ile Gln Ile Tyr
225                 230                 235                 240

Glu Lys Ile Val Ser Gly Lys Val Arg Phe Pro Ser His Phe Ser Ser
                245                 250                 255

Asp Leu Lys Asp Leu Leu Arg Asn Leu Leu Gln Val Asp Leu Thr Lys
            260                 265                 270

Arg Phe Gly Asn Leu Lys Asn Gly Val Asn Asp Ile Lys Asn His Lys
        275                 280                 285

Trp Phe Ala Thr Thr Asp Trp Ile Ala Ile Tyr Gln Arg Lys Val Glu
    290                 295                 300

Ala Pro Phe Ile Pro Lys Phe Lys Gly Pro Gly Asp Thr Ser Asn Phe
305                 310                 315                 320

Asp Asp Tyr Glu Glu Glu Glu Ile Arg Val Ser Ile Asn Glu Lys Cys
                325                 330                 335

Gly Lys Glu Phe Ser Glu Phe
            340
```

<210> SEQ ID NO 81
<211> LENGTH: 2794
<212> TYPE: DNA
<213> ORGANISM: Homo sapiens
<220> FEATURE:
<221> NAME/KEY: CDS
<222> LOCATION: (341)..(1783)

<400> SEQUENCE: 81
cggcaggacc gagcgcggca ggcggctggc ccagcgcagc cagcgcggcc cgaaggacgg 60
gagcaggcgg ccgagcaccg agcgctgggc accgggcacc gagcggcggc ggcacgcgag 120
gcccggcccc gagcagcgcc cccgcccgcc gcggcctcca gcccggcccc gcccagcgcc 180
ggcccgcggg gatgcggagc ggcgggcgcc ggaggccgcg gcccggctag gcccgcgctc 240
gcgcccggac gcggcggccc gaggctgtgg ccaggccagc tgggctcggg gagcgccagc 300
ctgagaggag cgcgtgagcg tcgcgggagc ctcgggcacc atg agc gac gtg gct 355
Met Ser Asp Val Ala
1 5 att gtg aag gag ggt tgg ctg cac aaa cga ggg gag tac atc aag acc 403
Ile Val Lys Glu Gly Trp Leu His Lys Arg Gly Glu Tyr Ile Lys Thr
10 15 20 tgg cgg cca cgc tac ttc ctc ctc aag aat gat ggc acc ttc att ggc 451
Trp Arg Pro Arg Tyr Phe Leu Leu Lys Asn Asp Gly Thr Phe Ile Gly
25 30 35 tac aag gag cgg ccg cag gat gtg gac caa cgt gag gct ccc ctc aac 499
Tyr Lys Glu Arg Pro Gln Asp Val Asp Gln Arg Glu Ala Pro Leu Asn
40 45 50 aac ttc tct gtg gcg cag tgc cag ctg atg aag acg gag cgg ccc cgg 547
Asn Phe Ser Val Ala Gln Cys Gln Leu Met Lys Thr Glu Arg Pro Arg
55 60 65 ccc aac acc ttc atc atc cgc tgc ctg cag tgg acc act gtc atc gaa 595
Pro Asn Thr Phe Ile Ile Arg Cys Leu Gln Trp Thr Thr Val Ile Glu
70 75 80 85 cgc acc ttc cat gtg gag act cct gag gag cgg gag gag tgg aca acc 643
Arg Thr Phe His Val Glu Thr Pro Glu Glu Arg Glu Glu Trp Thr Thr
90 95 100 gcc atc cag act gtg gct gac ggc ctc aag aag cag gag gag gag gag 691
Ala Ile Gln Thr Val Ala Asp Gly Leu Lys Lys Gln Glu Glu Glu Glu
105 110 115 atg gac ttc cgg tcg ggc tca ccc agt gac aac tca ggg gct gaa gag 739
Met Asp Phe Arg Ser Gly Ser Pro Ser Asp Asn Ser Gly Ala Glu Glu
120 125 130 atg gag gtg tcc ctg gcc aag ccc aag cac cgc gtg acc atg aac gag 787
Met Glu Val Ser Leu Ala Lys Pro Lys His Arg Val Thr Met Asn Glu
135 140 145 ttt gag tac ctg aag ctg ctg ggc aag ggc act ttc ggc aag gtg atc 835
Phe Glu Tyr Leu Lys Leu Leu Gly Lys Gly Thr Phe Gly Lys Val Ile
150 155 160 165 ctg gtg aag gag aag gcc aca ggc cgc tac tac gcc atg aag atc ctc 883
Leu Val Lys Glu Lys Ala Thr Gly Arg Tyr Tyr Ala Met Lys Ile Leu
170 175 180 aag aag gaa gtc atc gtg gcc aag gac gag gtg gcc cac aca ctc acc 931
Lys Lys Glu Val Ile Val Ala Lys Asp Glu Val Ala His Thr Leu Thr
185 190 195 gag aac cgc gtc ctg cag aac tcc agg cac ccc ttc ctc aca gcc ctg 979
Glu Asn Arg Val Leu Gln Asn Ser Arg His Pro Phe Leu Thr Ala Leu
200 205 210 aag tac tct ttc cag acc cac gac cgc ctc tgc ttt gtc atg gag tac 1027

```
Lys Tyr Ser Phe Gln Thr His Asp Arg Leu Cys Phe Val Met Glu Tyr
    215                 220                 225

gcc aac ggg ggc gag ctg ttc ttc cac ctg tcc cgg gag cgt gtg ttc      1075
Ala Asn Gly Gly Glu Leu Phe Phe His Leu Ser Arg Glu Arg Val Phe
230                 235                 240                 245

tcc gag gac cgg gcc cgc ttc tat ggc gct gag att gtg tca gcc ctg      1123
Ser Glu Asp Arg Ala Arg Phe Tyr Gly Ala Glu Ile Val Ser Ala Leu
                250                 255                 260

gac tac ctg cac tcg gag aag aac gtg gtg tac cgg gac ctc aag ctg      1171
Asp Tyr Leu His Ser Glu Lys Asn Val Val Tyr Arg Asp Leu Lys Leu
            265                 270                 275

gag aac ctc atg ctg gac aag gac ggg cac att aag atc aca gac ttc      1219
Glu Asn Leu Met Leu Asp Lys Asp Gly His Ile Lys Ile Thr Asp Phe
        280                 285                 290

ggg ctg tgc aag gag ggg atc aag gac ggt gcc acc atg aag acc ttt      1267
Gly Leu Cys Lys Glu Gly Ile Lys Asp Gly Ala Thr Met Lys Thr Phe
    295                 300                 305

tgc ggc aca cct gag tac ctg gcc ccc gag gtg ctg gag gac aat gac      1315
Cys Gly Thr Pro Glu Tyr Leu Ala Pro Glu Val Leu Glu Asp Asn Asp
310                 315                 320                 325

tac ggc cgt gca gtg gac tgg tgg ggg ctg ggc gtg gtc atg tac gag      1363
Tyr Gly Arg Ala Val Asp Trp Trp Gly Leu Gly Val Val Met Tyr Glu
                330                 335                 340

atg atg tgc ggt cgc ctg ccc ttc tac aac cag gac cat gag aag ctt      1411
Met Met Cys Gly Arg Leu Pro Phe Tyr Asn Gln Asp His Glu Lys Leu
            345                 350                 355

ttt gag ctc atc ctc atg gag gag atc cgc ttc ccg cgc acg ctt ggt      1459
Phe Glu Leu Ile Leu Met Glu Glu Ile Arg Phe Pro Arg Thr Leu Gly
        360                 365                 370

ccc gag gcc aag tcc ttg ctt tca ggg ctg ctc aag aag gac ccc aag      1507
Pro Glu Ala Lys Ser Leu Leu Ser Gly Leu Leu Lys Lys Asp Pro Lys
    375                 380                 385

cag agg ctt ggc ggg ggc tcc gag gac gcc aag gag atc atg cag cat      1555
Gln Arg Leu Gly Gly Gly Ser Glu Asp Ala Lys Glu Ile Met Gln His
390                 395                 400                 405

cgc ttc ttt gcc ggt atc gtg tgg cag cac gtg tac gag aag aag ctc      1603
Arg Phe Phe Ala Gly Ile Val Trp Gln His Val Tyr Glu Lys Lys Leu
                410                 415                 420

agc cca ccc ttc aag ccc cag gtc acg tcg gag act gac acc agg tat      1651
Ser Pro Pro Phe Lys Pro Gln Val Thr Ser Glu Thr Asp Thr Arg Tyr
            425                 430                 435

ttt gat gag gag ttc acg gcc cag atg atc acc atc aca cca cct gac      1699
Phe Asp Glu Glu Phe Thr Ala Gln Met Ile Thr Ile Thr Pro Pro Asp
        440                 445                 450

caa gat gac agc atg gag tgt gtg gac agc gag cgc agg ccc cac ttc      1747
Gln Asp Asp Ser Met Glu Cys Val Asp Ser Glu Arg Arg Pro His Phe
    455                 460                 465

ccc cag ttc tcc tac tcg gcc agc ggc acg gcc tga ggcggcggtg          1793
Pro Gln Phe Ser Tyr Ser Ala Ser Gly Thr Ala
470                 475                 480

gactgcgctg gacgatagct tggagggatg gagaggcggc ctcgtgccat gatctgtatt    1853

taatggtttt tatttctcgg gtgcatttga gagaagccac gctgtcctct cgagcccaga    1913

tggaaagacg tttttgtgct gtgggcagca ccctcccccg cagcggggta gggaagaaaa    1973

ctatcctgcg ggttttaatt tatttcatcc agtttgttct ccgggtgtgg cctcagccct    2033

cagaacaatc cgattcacgt agggaaatgt taaggacttc tgcagctatg cgcaatgtgg    2093

cattgggggg ccgggcaggt cctgcccatg tgtcccctca ctctgtcagc cagccgccct    2153
```

```
gggctgtctg tcaccagcta tctgtcatct ctctggggcc ctgggcctca gttcaacctg   2213

gtggcaccag atgcaacctc actatggtat gctggccagc accctctcct gggggtggca   2273

ggcacacagc agcccccag cactaaggcc gtgtctctga ggacgtcatc ggaggctggg   2333

cccctgggat gggaccaggg atgggggatg ggccagggtt tacccagtgg gacagaggag   2393

caaggtttaa atttgttatt gtgtattatg ttgttcaaat gcattttggg ggtttttaat   2453

ctttgtgaca ggaaagccct cccccttccc cttctgtgtc acagttcttg gtgactgtcc   2513

caccgggagc ctccccctca gatgatctct ccacggtagc acttgacctt ttcgacgctt   2573

aacctttccg ctgtcgcccc aggccctccc tgactccctg tgggggtggc catccctggg   2633

cccctccacg cctcctggcc agacgctgcc gctgccgctg caccacggcg tttttttaca   2693

acattcaact ttagtatttt tactattata atataatatg gaaccttccc tccaaattct   2753

tcaataaaag ttgcttttca aaaaaaaaaa aaaaaaaaaa a                        2794
```

<210> SEQ ID NO 82
<211> LENGTH: 480
<212> TYPE: PRT
<213> ORGANISM: Homo sapiens

<400> SEQUENCE: 82

```
Met Ser Asp Val Ala Ile Val Lys Glu Gly Trp Leu His Lys Arg Gly
1               5                   10                  15

Glu Tyr Ile Lys Thr Trp Arg Pro Arg Tyr Phe Leu Leu Lys Asn Asp
            20                  25                  30

Gly Thr Phe Ile Gly Tyr Lys Glu Arg Pro Gln Asp Val Asp Gln Arg
        35                  40                  45

Glu Ala Pro Leu Asn Asn Phe Ser Val Ala Gln Cys Gln Leu Met Lys
    50                  55                  60

Thr Glu Arg Pro Arg Pro Asn Thr Phe Ile Ile Arg Cys Leu Gln Trp
65                  70                  75                  80

Thr Thr Val Ile Glu Arg Thr Phe His Val Glu Thr Pro Glu Glu Arg
                85                  90                  95

Glu Glu Trp Thr Thr Ala Ile Gln Thr Val Ala Asp Gly Leu Lys Lys
            100                 105                 110

Gln Glu Glu Glu Glu Met Asp Phe Arg Ser Gly Ser Pro Ser Asp Asn
        115                 120                 125

Ser Gly Ala Glu Glu Met Glu Val Ser Leu Ala Lys Pro Lys His Arg
    130                 135                 140

Val Thr Met Asn Glu Phe Glu Tyr Leu Lys Leu Leu Gly Lys Gly Thr
145                 150                 155                 160

Phe Gly Lys Val Ile Leu Val Lys Glu Lys Ala Thr Gly Arg Tyr Tyr
                165                 170                 175

Ala Met Lys Ile Leu Lys Lys Glu Val Ile Val Ala Lys Asp Glu Val
            180                 185                 190

Ala His Thr Leu Thr Glu Asn Arg Val Leu Gln Asn Ser Arg His Pro
        195                 200                 205

Phe Leu Thr Ala Leu Lys Tyr Ser Phe Gln Thr His Asp Arg Leu Cys
    210                 215                 220

Phe Val Met Glu Tyr Ala Asn Gly Gly Glu Leu Phe Phe His Leu Ser
225                 230                 235                 240

Arg Glu Arg Val Phe Ser Glu Asp Arg Ala Arg Phe Tyr Gly Ala Glu
                245                 250                 255

Ile Val Ser Ala Leu Asp Tyr Leu His Ser Glu Lys Asn Val Val Tyr
```

```
            260                 265                 270

Arg Asp Leu Lys Leu Glu Asn Leu Met Leu Asp Lys Asp Gly His Ile
        275                 280                 285

Lys Ile Thr Asp Phe Gly Leu Cys Lys Glu Gly Ile Lys Asp Gly Ala
    290                 295                 300

Thr Met Lys Thr Phe Cys Gly Thr Pro Glu Tyr Leu Ala Pro Glu Val
305                 310                 315                 320

Leu Glu Asp Asn Asp Tyr Gly Arg Ala Val Asp Trp Trp Gly Leu Gly
                325                 330                 335

Val Val Met Tyr Glu Met Met Cys Gly Arg Leu Pro Phe Tyr Asn Gln
            340                 345                 350

Asp His Glu Lys Leu Phe Glu Leu Ile Leu Met Glu Glu Ile Arg Phe
        355                 360                 365

Pro Arg Thr Leu Gly Pro Glu Ala Lys Ser Leu Leu Ser Gly Leu Leu
    370                 375                 380

Lys Lys Asp Pro Lys Gln Arg Leu Gly Gly Gly Ser Glu Asp Ala Lys
385                 390                 395                 400

Glu Ile Met Gln His Arg Phe Phe Ala Gly Ile Val Trp Gln His Val
                405                 410                 415

Tyr Glu Lys Lys Leu Ser Pro Pro Phe Lys Pro Gln Val Thr Ser Glu
            420                 425                 430

Thr Asp Thr Arg Tyr Phe Asp Glu Glu Phe Thr Ala Gln Met Ile Thr
        435                 440                 445

Ile Thr Pro Pro Asp Gln Asp Asp Ser Met Glu Cys Val Asp Ser Glu
    450                 455                 460

Arg Arg Pro His Phe Pro Gln Phe Ser Tyr Ser Ala Ser Gly Thr Ala
465                 470                 475                 480
```

<210> SEQ ID NO 83
<211> LENGTH: 2878
<212> TYPE: DNA
<213> ORGANISM: Homo sapiens
<220> FEATURE:
<221> NAME/KEY: CDS
<222> LOCATION: (425)..(1867)

<400> SEQUENCE: 83

```
cggcaggacc gagcgcggca ggcggctggc ccagcgcagc cagcgcggcc cgaaggacgg      60

gagcaggcgg ccgagcaccg agcgctgggc accgggcacc gagcggcggc ggcacgcgag     120

gcccggcccc gagcagcgcc cccgcccgcc gcggcctcca gcccggcccc gcccagcgcc     180

ggcccgcggg gatgcggagc ggcgggcgcc ggaggccgcg gcccggctag gcccgcgctc     240

gcgcccggac gcggcggccc ggggcttagg gaaggccgag ccagcctggg tcaaagaagt     300

caaaggggct gcctggagga ggcagcctgt cagctggtgc atcagaggct gtggccaggc     360

cagctgggct cggggagcgc cagcctgaga ggagcgcgtg agcgtcgcgg gagcctcggg     420

cacc atg agc gac gtg gct att gtg aag gag ggt tgg ctg cac aaa cga      469
     Met Ser Asp Val Ala Ile Val Lys Glu Gly Trp Leu His Lys Arg
     1               5                   10                  15

ggg gag tac atc aag acc tgg cgg cca cgc tac ttc ctc ctc aag aat      517
Gly Glu Tyr Ile Lys Thr Trp Arg Pro Arg Tyr Phe Leu Leu Lys Asn
                20                  25                  30

gat ggc acc ttc att ggc tac aag gag cgg ccg cag gat gtg gac caa      565
Asp Gly Thr Phe Ile Gly Tyr Lys Glu Arg Pro Gln Asp Val Asp Gln
            35                  40                  45

cgt gag gct ccc ctc aac aac ttc tct gtg gcg cag tgc cag ctg atg      613
```

```
Arg Glu Ala Pro Leu Asn Asn Phe Ser Val Ala Gln Cys Gln Leu Met
        50                  55                  60

aag acg gag cgg ccc cgg ccc aac acc ttc atc atc cgc tgc ctg cag      661
Lys Thr Glu Arg Pro Arg Pro Asn Thr Phe Ile Ile Arg Cys Leu Gln
    65                  70                  75

tgg acc act gtc atc gaa cgc acc ttc cat gtg gag act cct gag gag      709
Trp Thr Thr Val Ile Glu Arg Thr Phe His Val Glu Thr Pro Glu Glu
80                  85                  90                  95

cgg gag gag tgg aca acc gcc atc cag act gtg gct gac ggc ctc aag      757
Arg Glu Glu Trp Thr Thr Ala Ile Gln Thr Val Ala Asp Gly Leu Lys
                100                 105                 110

aag cag gag gag gag gag atg gac ttc cgg tcg ggc tca ccc agt gac      805
Lys Gln Glu Glu Glu Glu Met Asp Phe Arg Ser Gly Ser Pro Ser Asp
            115                 120                 125

aac tca ggg gct gaa gag atg gag gtg tcc ctg gcc aag ccc aag cac      853
Asn Ser Gly Ala Glu Glu Met Glu Val Ser Leu Ala Lys Pro Lys His
        130                 135                 140

cgc gtg acc atg aac gag ttt gag tac ctg aag ctg ctg ggc aag ggc      901
Arg Val Thr Met Asn Glu Phe Glu Tyr Leu Lys Leu Leu Gly Lys Gly
    145                 150                 155

act ttc ggc aag gtg atc ctg gtg aag gag aag gcc aca ggc cgc tac      949
Thr Phe Gly Lys Val Ile Leu Val Lys Glu Lys Ala Thr Gly Arg Tyr
160                 165                 170                 175

tac gcc atg aag atc ctc aag aag gaa gtc atc gtg gcc aag gac gag      997
Tyr Ala Met Lys Ile Leu Lys Lys Glu Val Ile Val Ala Lys Asp Glu
                180                 185                 190

gtg gcc cac aca ctc acc gag aac cgc gtc ctg cag aac tcc agg cac     1045
Val Ala His Thr Leu Thr Glu Asn Arg Val Leu Gln Asn Ser Arg His
            195                 200                 205

ccc ttc ctc aca gcc ctg aag tac tct ttc cag acc cac gac cgc ctc     1093
Pro Phe Leu Thr Ala Leu Lys Tyr Ser Phe Gln Thr His Asp Arg Leu
        210                 215                 220

tgc ttt gtc atg gag tac gcc aac ggg ggc gag ctg ttc ttc cac ctg     1141
Cys Phe Val Met Glu Tyr Ala Asn Gly Gly Glu Leu Phe Phe His Leu
    225                 230                 235

tcc cgg gag cgt gtg ttc tcc gag gac cgg gcc cgc ttc tat ggc gct     1189
Ser Arg Glu Arg Val Phe Ser Glu Asp Arg Ala Arg Phe Tyr Gly Ala
240                 245                 250                 255

gag att gtg tca gcc ctg gac tac ctg cac tcg gag aag aac gtg gtg     1237
Glu Ile Val Ser Ala Leu Asp Tyr Leu His Ser Glu Lys Asn Val Val
                260                 265                 270

tac cgg gac ctc aag ctg gag aac ctc atg ctg gac aag gac ggg cac     1285
Tyr Arg Asp Leu Lys Leu Glu Asn Leu Met Leu Asp Lys Asp Gly His
            275                 280                 285

att aag atc aca gac ttc ggg ctg tgc aag gag ggg atc aag gac ggt     1333
Ile Lys Ile Thr Asp Phe Gly Leu Cys Lys Glu Gly Ile Lys Asp Gly
        290                 295                 300

gcc acc atg aag acc ttt tgc ggc aca cct gag tac ctg gcc ccc gag     1381
Ala Thr Met Lys Thr Phe Cys Gly Thr Pro Glu Tyr Leu Ala Pro Glu
    305                 310                 315

gtg ctg gag gac aat gac tac ggc cgt gca gtg gac tgg tgg ggg ctg     1429
Val Leu Glu Asp Asn Asp Tyr Gly Arg Ala Val Asp Trp Trp Gly Leu
320                 325                 330                 335

ggc gtg gtc atg tac gag atg atg tgc ggt cgc ctg ccc ttc tac aac     1477
Gly Val Val Met Tyr Glu Met Met Cys Gly Arg Leu Pro Phe Tyr Asn
                340                 345                 350

cag gac cat gag aag ctt ttt gag ctc atc ctc atg gag gag atc cgc     1525
Gln Asp His Glu Lys Leu Phe Glu Leu Ile Leu Met Glu Glu Ile Arg
            355                 360                 365
```

```
ttc ccg cgc acg ctt ggt ccc gag gcc aag tcc ttg ctt tca ggg ctg     1573
Phe Pro Arg Thr Leu Gly Pro Glu Ala Lys Ser Leu Leu Ser Gly Leu
        370                 375                 380

ctc aag aag gac ccc aag cag agg ctt ggc ggg ggc tcc gag gac gcc     1621
Leu Lys Lys Asp Pro Lys Gln Arg Leu Gly Gly Gly Ser Glu Asp Ala
    385                 390                 395

aag gag atc atg cag cat cgc ttc ttt gcc ggt atc gtg tgg cag cac     1669
Lys Glu Ile Met Gln His Arg Phe Phe Ala Gly Ile Val Trp Gln His
400                 405                 410                 415

gtg tac gag aag aag ctc agc cca ccc ttc aag ccc cag gtc acg tcg     1717
Val Tyr Glu Lys Lys Leu Ser Pro Pro Phe Lys Pro Gln Val Thr Ser
                420                 425                 430

gag act gac acc agg tat ttt gat gag gag ttc acg gcc cag atg atc     1765
Glu Thr Asp Thr Arg Tyr Phe Asp Glu Glu Phe Thr Ala Gln Met Ile
            435                 440                 445

acc atc aca cca cct gac caa gat gac agc atg gag tgt gtg gac agc     1813
Thr Ile Thr Pro Pro Asp Gln Asp Asp Ser Met Glu Cys Val Asp Ser
        450                 455                 460

gag cgc agg ccc cac ttc ccc cag ttc tcc tac tcg gcc agc ggc acg     1861
Glu Arg Arg Pro His Phe Pro Gln Phe Ser Tyr Ser Ala Ser Gly Thr
    465                 470                 475

gcc tga ggcggcggtg gactgcgctg gacgatagct tggagggatg gagaggcggc      1917
Ala
480

ctcgtgccat gatctgtatt taatggtttt tatttctcgg gtgcatttga gagaagccac   1977

gctgtcctct cgagcccaga tggaaagacg tttttgtgct gtgggcagca ccctcccccg   2037

cagcggggta gggaagaaaa ctatcctgcg ggttttaatt tatttcatcc agtttgttct   2097

ccgggtgtgg cctcagccct cagaacaatc cgattcacgt agggaaatgt taaggacttc   2157

tgcagctatg cgcaatgtgg cattgggggg ccgggcaggt cctgcccatg tgtcccctca   2217

ctctgtcagc cagccgccct gggctgtctg tcaccagcta tctgtcatct ctctggggcc   2277

ctgggcctca gttcaacctg gtggcaccag atgcaacctc actatggtat gctggccagc   2337

accctctcct gggggtggca ggcacacagc agccccccag cactaaggcc gtgtctctga   2397

ggacgtcatc ggaggctggg cccctgggat gggaccaggg atgggggatg ggccagggtt   2457

tacccagtgg gacagaggag caaggtttaa atttgttatt gtgtattatg ttgttcaaat   2517

gcattttggg ggtttttaat ctttgtgaca ggaaagccct ccccccttccc cttctgtgtc  2577

acagttcttg gtgactgtcc caccgggagc ctccccctca gatgatctct ccacggtagc   2637

acttgacctt ttcgacgctt aacctttccg ctgtcgcccc aggccctccc tgactccctg   2697

tgggggtggc catccctggg cccctccacg cctcctggcc agacgctgcc gctgccgctg   2757

caccacggcg ttttttttaca acattcaact ttagtatttt tactattata atataatatg  2817

gaaccttccc tccaaattct tcaataaaag ttgcttttca aaaaaaaaaa aaaaaaaaaa   2877

a                                                                   2878


<210> SEQ ID NO 84
<211> LENGTH: 480
<212> TYPE: PRT
<213> ORGANISM: Homo sapiens

<400> SEQUENCE: 84

Met Ser Asp Val Ala Ile Val Lys Glu Gly Trp Leu His Lys Arg Gly
1               5                   10                  15

Glu Tyr Ile Lys Thr Trp Arg Pro Arg Tyr Phe Leu Leu Lys Asn Asp
            20                  25                  30
```

```
Gly Thr Phe Ile Gly Tyr Lys Glu Arg Pro Gln Asp Val Asp Gln Arg
        35                  40                  45

Glu Ala Pro Leu Asn Asn Phe Ser Val Ala Gln Cys Gln Leu Met Lys
    50                  55                  60

Thr Glu Arg Pro Arg Pro Asn Thr Phe Ile Ile Arg Cys Leu Gln Trp
65                  70                  75                  80

Thr Thr Val Ile Glu Arg Thr Phe His Val Glu Thr Pro Glu Glu Arg
                85                  90                  95

Glu Glu Trp Thr Thr Ala Ile Gln Thr Val Ala Asp Gly Leu Lys Lys
            100                 105                 110

Gln Glu Glu Glu Glu Met Asp Phe Arg Ser Gly Ser Pro Ser Asp Asn
        115                 120                 125

Ser Gly Ala Glu Glu Met Glu Val Ser Leu Ala Lys Pro Lys His Arg
    130                 135                 140

Val Thr Met Asn Glu Phe Glu Tyr Leu Lys Leu Leu Gly Lys Gly Thr
145                 150                 155                 160

Phe Gly Lys Val Ile Leu Val Lys Glu Lys Ala Thr Gly Arg Tyr Tyr
                165                 170                 175

Ala Met Lys Ile Leu Lys Lys Glu Val Ile Val Ala Lys Asp Glu Val
            180                 185                 190

Ala His Thr Leu Thr Glu Asn Arg Val Leu Gln Asn Ser Arg His Pro
        195                 200                 205

Phe Leu Thr Ala Leu Lys Tyr Ser Phe Gln Thr His Asp Arg Leu Cys
    210                 215                 220

Phe Val Met Glu Tyr Ala Asn Gly Gly Glu Leu Phe Phe His Leu Ser
225                 230                 235                 240

Arg Glu Arg Val Phe Ser Glu Asp Arg Ala Arg Phe Tyr Gly Ala Glu
                245                 250                 255

Ile Val Ser Ala Leu Asp Tyr Leu His Ser Glu Lys Asn Val Val Tyr
            260                 265                 270

Arg Asp Leu Lys Leu Glu Asn Leu Met Leu Asp Lys Asp Gly His Ile
        275                 280                 285

Lys Ile Thr Asp Phe Gly Leu Cys Lys Glu Gly Ile Lys Asp Gly Ala
    290                 295                 300

Thr Met Lys Thr Phe Cys Gly Thr Pro Glu Tyr Leu Ala Pro Glu Val
305                 310                 315                 320

Leu Glu Asp Asn Asp Tyr Gly Arg Ala Val Asp Trp Trp Gly Leu Gly
                325                 330                 335

Val Val Met Tyr Glu Met Met Cys Gly Arg Leu Pro Phe Tyr Asn Gln
            340                 345                 350

Asp His Glu Lys Leu Phe Glu Leu Ile Leu Met Glu Glu Ile Arg Phe
        355                 360                 365

Pro Arg Thr Leu Gly Pro Glu Ala Lys Ser Leu Leu Ser Gly Leu Leu
    370                 375                 380

Lys Lys Asp Pro Lys Gln Arg Leu Gly Gly Gly Ser Glu Asp Ala Lys
385                 390                 395                 400

Glu Ile Met Gln His Arg Phe Phe Ala Gly Ile Val Trp Gln His Val
                405                 410                 415

Tyr Glu Lys Lys Leu Ser Pro Pro Phe Lys Pro Gln Val Thr Ser Glu
            420                 425                 430

Thr Asp Thr Arg Tyr Phe Asp Glu Glu Phe Thr Ala Gln Met Ile Thr
        435                 440                 445
```

```
Ile Thr Pro Pro Asp Gln Asp Asp Ser Met Glu Cys Val Asp Ser Glu
    450                 455                 460

Arg Arg Pro His Phe Pro Gln Phe Ser Tyr Ser Ala Ser Gly Thr Ala
465                 470                 475                 480


<210> SEQ ID NO 85
<211> LENGTH: 3008
<212> TYPE: DNA
<213> ORGANISM: Homo sapiens
<220> FEATURE:
<221> NAME/KEY: CDS
<222> LOCATION: (555)..(1997)

<400> SEQUENCE: 85

taattatggg tctgtaacca ccctggactg ggtgctcctc actgacggac ttgtctgaac     60

ctctctttgt ctccagcgcc cagcactggg cctggcaaaa cctgagacgc ccggtacatg    120

ttggccaaat gaatgaacca gattcagacc ggcaggggcg ctgtggttta ggaggggcct    180

ggggtttctc ccaggaggtt tttgggcttg cgctggaggg ctctggactc ccgtttgcgc    240

cagtggcctg catcctggtc ctgtcttcct catgtttgaa tttctttgct ttcctagtct    300

ggggagcagg gaggagccct gtgccctgtc ccaggatcca tgggtaggaa caccatggac    360

agggagagca aacggggcca tctgtcacca ggggcttagg gaaggccgag ccagcctggg    420

tcaaagaagt caaaggggct gcctggagga ggcagcctgt cagctggtgc atcagaggct    480

gtggccaggc cagctgggct cggggagcgc cagcctgaga ggagcgcgtg agcgtcgcgg    540

gagcctcggg cacc atg agc gac gtg gct att gtg aag gag ggt tgg ctg      590
                Met Ser Asp Val Ala Ile Val Lys Glu Gly Trp Leu
                1               5                   10

cac aaa cga ggg gag tac atc aag acc tgg cgg cca cgc tac ttc ctc      638
His Lys Arg Gly Glu Tyr Ile Lys Thr Trp Arg Pro Arg Tyr Phe Leu
        15                  20                  25

ctc aag aat gat ggc acc ttc att ggc tac aag gag cgg ccg cag gat      686
Leu Lys Asn Asp Gly Thr Phe Ile Gly Tyr Lys Glu Arg Pro Gln Asp
    30                  35                  40

gtg gac caa cgt gag gct ccc ctc aac aac ttc tct gtg gcg cag tgc      734
Val Asp Gln Arg Glu Ala Pro Leu Asn Asn Phe Ser Val Ala Gln Cys
45                  50                  55                  60

cag ctg atg aag acg gag cgg ccc cgg ccc aac acc ttc atc atc cgc      782
Gln Leu Met Lys Thr Glu Arg Pro Arg Pro Asn Thr Phe Ile Ile Arg
                65                  70                  75

tgc ctg cag tgg acc act gtc atc gaa cgc acc ttc cat gtg gag act      830
Cys Leu Gln Trp Thr Thr Val Ile Glu Arg Thr Phe His Val Glu Thr
            80                  85                  90

cct gag gag cgg gag gag tgg aca acc gcc atc cag act gtg gct gac      878
Pro Glu Glu Arg Glu Glu Trp Thr Thr Ala Ile Gln Thr Val Ala Asp
        95                  100                 105

ggc ctc aag aag cag gag gag gag gag atg gac ttc cgg tcg ggc tca      926
Gly Leu Lys Lys Gln Glu Glu Glu Glu Met Asp Phe Arg Ser Gly Ser
    110                 115                 120

ccc agt gac aac tca ggg gct gaa gag atg gag gtg tcc ctg gcc aag      974
Pro Ser Asp Asn Ser Gly Ala Glu Glu Met Glu Val Ser Leu Ala Lys
125                 130                 135                 140

ccc aag cac cgc gtg acc atg aac gag ttt gag tac ctg aag ctg ctg     1022
Pro Lys His Arg Val Thr Met Asn Glu Phe Glu Tyr Leu Lys Leu Leu
                145                 150                 155

ggc aag ggc act ttc ggc aag gtg atc ctg gtg aag gag aag gcc aca     1070
Gly Lys Gly Thr Phe Gly Lys Val Ile Leu Val Lys Glu Lys Ala Thr
            160                 165                 170
```

```
ggc cgc tac tac gcc atg aag atc ctc aag aag gaa gtc atc gtg gcc      1118
Gly Arg Tyr Tyr Ala Met Lys Ile Leu Lys Lys Glu Val Ile Val Ala
        175                 180                 185

aag gac gag gtg gcc cac aca ctc acc gag aac cgc gtc ctg cag aac      1166
Lys Asp Glu Val Ala His Thr Leu Thr Glu Asn Arg Val Leu Gln Asn
    190                 195                 200

tcc agg cac ccc ttc ctc aca gcc ctg aag tac tct ttc cag acc cac      1214
Ser Arg His Pro Phe Leu Thr Ala Leu Lys Tyr Ser Phe Gln Thr His
205                 210                 215                 220

gac cgc ctc tgc ttt gtc atg gag tac gcc aac ggg ggc gag ctg ttc      1262
Asp Arg Leu Cys Phe Val Met Glu Tyr Ala Asn Gly Gly Glu Leu Phe
                225                 230                 235

ttc cac ctg tcc cgg gag cgt gtg ttc tcc gag gac cgg gcc cgc ttc      1310
Phe His Leu Ser Arg Glu Arg Val Phe Ser Glu Asp Arg Ala Arg Phe
            240                 245                 250

tat ggc gct gag att gtg tca gcc ctg gac tac ctg cac tcg gag aag      1358
Tyr Gly Ala Glu Ile Val Ser Ala Leu Asp Tyr Leu His Ser Glu Lys
        255                 260                 265

aac gtg gtg tac cgg gac ctc aag ctg gag aac ctc atg ctg gac aag      1406
Asn Val Val Tyr Arg Asp Leu Lys Leu Glu Asn Leu Met Leu Asp Lys
    270                 275                 280

gac ggg cac att aag atc aca gac ttc ggg ctg tgc aag gag ggg atc      1454
Asp Gly His Ile Lys Ile Thr Asp Phe Gly Leu Cys Lys Glu Gly Ile
285                 290                 295                 300

aag gac ggt gcc acc atg aag acc ttt tgc ggc aca cct gag tac ctg      1502
Lys Asp Gly Ala Thr Met Lys Thr Phe Cys Gly Thr Pro Glu Tyr Leu
                305                 310                 315

gcc ccc gag gtg ctg gag gac aat gac tac ggc cgt gca gtg gac tgg      1550
Ala Pro Glu Val Leu Glu Asp Asn Asp Tyr Gly Arg Ala Val Asp Trp
            320                 325                 330

tgg ggg ctg ggc gtg gtc atg tac gag atg atg tgc ggt cgc ctg ccc      1598
Trp Gly Leu Gly Val Val Met Tyr Glu Met Met Cys Gly Arg Leu Pro
        335                 340                 345

ttc tac aac cag gac cat gag aag ctt ttt gag ctc atc ctc atg gag      1646
Phe Tyr Asn Gln Asp His Glu Lys Leu Phe Glu Leu Ile Leu Met Glu
    350                 355                 360

gag atc cgc ttc ccg cgc acg ctt ggt ccc gag gcc aag tcc ttg ctt      1694
Glu Ile Arg Phe Pro Arg Thr Leu Gly Pro Glu Ala Lys Ser Leu Leu
365                 370                 375                 380

tca ggg ctg ctc aag aag gac ccc aag cag agg ctt ggc ggg ggc tcc      1742
Ser Gly Leu Leu Lys Lys Asp Pro Lys Gln Arg Leu Gly Gly Gly Ser
                385                 390                 395

gag gac gcc aag gag atc atg cag cat cgc ttc ttt gcc ggt atc gtg      1790
Glu Asp Ala Lys Glu Ile Met Gln His Arg Phe Phe Ala Gly Ile Val
            400                 405                 410

tgg cag cac gtg tac gag aag aag ctc agc cca ccc ttc aag ccc cag      1838
Trp Gln His Val Tyr Glu Lys Lys Leu Ser Pro Pro Phe Lys Pro Gln
        415                 420                 425

gtc acg tcg gag act gac acc agg tat ttt gat gag gag ttc acg gcc      1886
Val Thr Ser Glu Thr Asp Thr Arg Tyr Phe Asp Glu Glu Phe Thr Ala
    430                 435                 440

cag atg atc acc atc aca cca cct gac caa gat gac agc atg gag tgt      1934
Gln Met Ile Thr Ile Thr Pro Pro Asp Gln Asp Asp Ser Met Glu Cys
445                 450                 455                 460

gtg gac agc gag cgc agg ccc cac ttc ccc cag ttc tcc tac tcg gcc      1982
Val Asp Ser Glu Arg Arg Pro His Phe Pro Gln Phe Ser Tyr Ser Ala
                465                 470                 475

agc ggc acg gcc tga ggcggcggtg gactgcgctg gacgatagct tggagggatg      2037
Ser Gly Thr Ala
            480
```

```
gagaggcggc ctcgtgccat gatctgtatt taatggtttt tatttctcgg gtgcatttga   2097

gagaagccac gctgtcctct cgagcccaga tggaaagacg tttttgtgct gtgggcagca   2157

ccctcccccg cagcggggta gggaagaaaa ctatcctgcg ggttttaatt tatttcatcc   2217

agtttgttct ccgggtgtgg cctcagccct cagaacaatc cgattcacgt agggaaatgt   2277

taaggacttc tgcagctatg cgcaatgtgg cattgggggg ccgggcaggt cctgcccatg   2337

tgtcccctca ctctgtcagc cagccgccct gggctgtctg tcaccagcta tctgtcatct   2397

ctctggggcc ctgggcctca gttcaacctg gtggcaccag atgcaacctc actatggtat   2457

gctggccagc accctctcct gggggtggca ggcacacagc agcccccag cactaaggcc   2517

gtgtctctga ggacgtcatc ggaggctggg cccctgggat gggaccaggg atgggggatg   2577

ggccagggtt tacccagtgg gacagaggag caaggtttaa atttgttatt gtgtattatg   2637

ttgttcaaat gcattttggg ggtttttaat ctttgtgaca ggaaagccct ccccccttccc   2697

cttctgtgtc acagttcttg gtgactgtcc caccgggagc ctccccctca gatgatctct   2757

ccacggtagc acttgacctt ttcgacgctt aacctttccg ctgtcgcccc aggccctccc   2817

tgactccctg tgggggtggc catccctggg cccctccacg cctcctggcc agacgctgcc   2877

gctgccgctg caccacggcg ttttttttaca acattcaact ttagtatttt tactattata   2937

atataatatg gaaccttccc tccaaattct tcaataaaag ttgcttttca aaaaaaaaaa   2997

aaaaaaaaaa a                                                        3008
```

```
<210> SEQ ID NO 86
<211> LENGTH: 480
<212> TYPE: PRT
<213> ORGANISM: Homo sapiens

<400> SEQUENCE: 86

Met Ser Asp Val Ala Ile Val Lys Glu Gly Trp Leu His Lys Arg Gly
1               5                   10                  15

Glu Tyr Ile Lys Thr Trp Arg Pro Arg Tyr Phe Leu Leu Lys Asn Asp
            20                  25                  30

Gly Thr Phe Ile Gly Tyr Lys Glu Arg Pro Gln Asp Val Asp Gln Arg
        35                  40                  45

Glu Ala Pro Leu Asn Asn Phe Ser Val Ala Gln Cys Gln Leu Met Lys
    50                  55                  60

Thr Glu Arg Pro Arg Pro Asn Thr Phe Ile Ile Arg Cys Leu Gln Trp
65                  70                  75                  80

Thr Thr Val Ile Glu Arg Thr Phe His Val Glu Thr Pro Glu Glu Arg
                85                  90                  95

Glu Glu Trp Thr Thr Ala Ile Gln Thr Val Ala Asp Gly Leu Lys Lys
            100                 105                 110

Gln Glu Glu Glu Glu Met Asp Phe Arg Ser Gly Ser Pro Ser Asp Asn
        115                 120                 125

Ser Gly Ala Glu Glu Met Glu Val Ser Leu Ala Lys Pro Lys His Arg
    130                 135                 140

Val Thr Met Asn Glu Phe Glu Tyr Leu Lys Leu Leu Gly Lys Gly Thr
145                 150                 155                 160

Phe Gly Lys Val Ile Leu Val Lys Glu Lys Ala Thr Gly Arg Tyr Tyr
                165                 170                 175

Ala Met Lys Ile Leu Lys Lys Glu Val Ile Val Ala Lys Asp Glu Val
            180                 185                 190
```

-continued

```
Ala His Thr Leu Thr Glu Asn Arg Val Leu Gln Asn Ser Arg His Pro
        195                 200                 205

Phe Leu Thr Ala Leu Lys Tyr Ser Phe Gln Thr His Asp Arg Leu Cys
    210                 215                 220

Phe Val Met Glu Tyr Ala Asn Gly Gly Glu Leu Phe Phe His Leu Ser
225                 230                 235                 240

Arg Glu Arg Val Phe Ser Glu Asp Arg Ala Arg Phe Tyr Gly Ala Glu
                245                 250                 255

Ile Val Ser Ala Leu Asp Tyr Leu His Ser Glu Lys Asn Val Val Tyr
            260                 265                 270

Arg Asp Leu Lys Leu Glu Asn Leu Met Leu Asp Lys Asp Gly His Ile
        275                 280                 285

Lys Ile Thr Asp Phe Gly Leu Cys Lys Glu Gly Ile Lys Asp Gly Ala
    290                 295                 300

Thr Met Lys Thr Phe Cys Gly Thr Pro Glu Tyr Leu Ala Pro Glu Val
305                 310                 315                 320

Leu Glu Asp Asn Asp Tyr Gly Arg Ala Val Asp Trp Trp Gly Leu Gly
                325                 330                 335

Val Val Met Tyr Glu Met Met Cys Gly Arg Leu Pro Phe Tyr Asn Gln
            340                 345                 350

Asp His Glu Lys Leu Phe Glu Leu Ile Leu Met Glu Glu Ile Arg Phe
        355                 360                 365

Pro Arg Thr Leu Gly Pro Glu Ala Lys Ser Leu Leu Ser Gly Leu Leu
    370                 375                 380

Lys Lys Asp Pro Lys Gln Arg Leu Gly Gly Gly Ser Glu Asp Ala Lys
385                 390                 395                 400

Glu Ile Met Gln His Arg Phe Phe Ala Gly Ile Val Trp Gln His Val
                405                 410                 415

Tyr Glu Lys Lys Leu Ser Pro Pro Phe Lys Pro Gln Val Thr Ser Glu
            420                 425                 430

Thr Asp Thr Arg Tyr Phe Asp Glu Glu Phe Thr Ala Gln Met Ile Thr
        435                 440                 445

Ile Thr Pro Pro Asp Gln Asp Asp Ser Met Glu Cys Val Asp Ser Glu
    450                 455                 460

Arg Arg Pro His Phe Pro Gln Phe Ser Tyr Ser Ala Ser Gly Thr Ala
465                 470                 475                 480
```

ERAP1-DERIVED PEPTIDE AND USE THEREOF

TECHNICAL FIELD

The present invention relates to an ERAP1-derived peptide and therapeutic use thereof.

BACKGROUND ART

Breast cancer is the highest incident cancer for Japanese females. Breast cancer often depends on hormone (estrogen: E2). Proliferation of breast cancer is promoted through activation of a receptor of the hormone (estrogen receptor: ER). As a mechanism for breast cancer proliferation by ER activation, two different mechanisms are reported: a mechanism in which ER functions as a transcriptional regulator (genomic activation); and a mechanism in which ER participates in the activation of intracellular phosphorylation cascade as a membrane-type ER localized on a cell membrane (non-genomic activation) (Non-Patent Documents 1 to 3). However, there are still many unclear points for the molecular mechanism of the ER activation itself.

In addition, the survival rate of breast cancer patients is remarkably improved by using tamoxifen (TAM) as an antiestrogen in postoperative adjuvant therapy or in standard treatment of advanced or relapsed breast cancer. However, about 30% of ER-positive breast cancer is refractory to TAM. In addition, according to a standard treatment, TAM is administered for 5 years in a postoperative adjuvant therapy. Thus, there is a serious problem in that prolonged use of TAM makes breast cancer cells resistant to TAM (Non-Patent Documents 1 to 3). As a mechanism of this TAM-refractoriness or resistance, there are several mechanisms reported such as accelerated estrogen sensitiveness, and crosstalk of a membrane receptor such as EGER, HER2 and IGFR with a signal route of a growth factor (Non-Patent Documents 1 to 3). However, there are still many unclear points about the mechanism of refractory or resistance to TAM. In addition, in recent years, aromatase inhibitors or LH-RH agonist preparations are also used in treatment for breast cancer. However, these medicines suppress estrogen production. Thus, side effects are reported, such as a decrease in bone density due to a decrease in estrogen level. As described above, urgent problems are elucidation of the ER activity-regulated mechanism of the E2-dependent breast cancer and development of a novel therapeutic agent TIN the E2-dependent breast cancer.

The present inventors have identified so far to novel Estrogen Receptor Activity-regulated Protein 1 (ERAP1) (also known as BIG3) observed to be highly expressed specifically in breast cancer at high frequency, through a comprehensive analysis of gene expression in breast cancer using cDNA microarray (Patent Document 1 and Non-Patent Document 4). The findings as described below are obtained by a detailed analysis of functions of ERAP1. Namely ERAP1 binds to PHB2/REA protein (prohibition 2/Repressor of Estrogen Activity), a repressor of ER activation in the cytoplasm, to block E2-dependent nuclear translocation of PHB2/REA. Therefore, ERAP1 may lead to constitutive activation of ER in breast cancer cells by inhibiting ERα activity-suppression function of PFB2/REA (Patent Document 1 and Non-Patent Document 4).

RELATED ART DOCUMENTS

Patent Document

Patent Document 1: WO 2008/018642

NON PATENT DOCUMENTS

Non-Patent Document 1: Osborne C K, Schiff R. J Clin Oncol. 2005; 23: 1616-22.

Non-Patent Document 2: Yager J D, Davidson N E, N Engl J Med. 2006; 354: 70-82.

Non-Patent Document 3: Johnston S R, Clin Cancer Res. 2010; 16: 1979-87.

Non-Patent Document 4: Kim J W, Akiyama M. Park J H, et al. Cancer Sci. 2009; 100: 1468-78.

SUMMARY OF THE INVENTION

Problems to be Solved by the Invention

A problem to be solved by the present invention is to provide a peptide useful for treatment of breast cancer and the like, and application of the peptide to breast cancer therapy. In addition, a problem to be solved by the present invention is to provide a method for screening a candidate material for a drug useful for treating and/or presenting cancers such as breast cancer.

Solutions to the Problems

The present inventors have found that a peptide fragment of ERAP1 (ERAP1 peptide) comprising a binding site to PHB2 inhibits binding of ERAP1 to PHB2 to cause nuclear translocation of PHB2, thereby causing suppression of ER transcriptional activation by PHB2. Furthermore, the present inventors have confirmed that PHB2 is dissociated from ERAP1 and binds to ER on the cell membrane, and suppresses Akt route activation, MAPK route activation, and nuclear ER phosphorylation. Therefore, the present inventors have confirmed that the ERAP1 peptide suppresses both of the genomic activation route and the non-genomic activation route of ER. In addition, the present inventors have confirmed that the ERAP1 peptide also suppresses down-regulation by protein degradation of ER by ubiquitin-proteasome pathway, which is essential for the transcriptional activation of ER. Namely, the present inventors have confirmed that the ERAP1 peptide completely suppresses the transcriptional activation of ER. Furthermore, the present inventors have confirmed that the ERAP1 peptide has an antitumor effect on estrogen-dependent breast cancer. Namely, the ERAP1 peptide suppresses estrogen-dependent cell proliferation of the ER-positive breast cancer cells. In addition, the ERAP1 peptide also exhibits antitumor effects in tests with mice orthotopically transplanted with breast cancer cells. In addition, the present inventors have found that the ERAP1 peptide also has a suppression effect on non-estrogen-dependent cell proliferation of the estrogen receptor-positive breast cancer cells. Furthermore, the present inventors have found that the ERAP1 peptide suppresses cell proliferation of the tamoxifen-resistant breast cancer cells. In addition, the present inventors have confirmed that concomitant use of the ERAP1 peptide and tamoxifen has a higher antitumor effect than individual use thereof.

In the present inventors have found that phosphorylation at Ser39 of PHB2 is important for suppressing estrogen-dependent cell proliferation. The present inventors have confirmed that phosphorylation at Ser39 of PHB2 is due to dephosphorylation of PP1α that is indirectly bound via ERAP1. Furthermore, the present inventors have confirmed that the phosphatase activity of PP1α is regulated by phosphorylation of ERAP1 by PKA and PKB. These results show that binding of ERAP1 to PKA, PKB, or PP1α plays an important role in the estrogen-dependent cell proliferation.

Furthermore, the present inventors have confirmed that the ERAP1 peptide also suppresses proliferation of estrogen receptor-negative breast cancer cells.

The present invention is based on the findings described above, and relates to [1] to [26] described below:

[1] a peptide that inhibits binding of ERAP1 polypeptide to PHB2 polypeptide; the peptide including a binding sites of the ERAP1 polypeptide to the PHB2 polypeptide;

[2] the peptide described in [1], wherein the binding sites are glutamine at position 165, aspartic acid at position 169 and glutamine at position 173 of an amino acid sequence described in SEQ ID NO: 35;

[3] the peptide described in [2] including an amino acid sequence described in any one of the following (a) and (b):

(a) an amino acid sequence described in SEQ ID NO: 31, and (b) an amino acid sequence described in SEQ ID NO: 31 in which one two, or several amino acid residues other than glutamine at position 1, aspartic acid it position 5, and glutamine at position 9 are substituted with other amino acid residues;

[4] the peptide described in [3] including an amino acid sequence selected from a group consisting of (a) to (d) described below:

(a) an amino acid sequence described in SEQ ID NO: 27;

(b) an amino acid sequence described in SEQ ID NO: 27 in which one, two or several amino acid residues other than glutamine at position 1, aspartic acid at position 5 and glutamine at position 9 are substituted with other amino acid residues;

(c) an amino acid sequence described in SEQ ID NO: 30; and (d) an amino acid sequence described in SEQ ID NO: 30 in which one, two or several amino acid residues other than glutamine at position 5, aspartic acid at position 9 and glutamine at position 13 are substituted with other amino acid residues besides;

[5] the peptide described in any one of [1] to [4], wherein the amino acid consists of 50 or less amino acid residues:

[6] the peptide described in any one [1] to [5], wherein the peptide is modified by a cell membrane-permeable substance;

[7] the peptide described in any one of [1] to [6], having one or both of properties (i) and (ii) described below;

(i) property of promoting nuclear translocation of PHB2 polypeptide in estrogen receptor-positive cells expressing ERAP1 polypeptide; and (ii) property of promoting binding of estrogen receptors present in the nucleus and/or on the cell membrane to PHB2 polypeptide in estrogen receptor-positive cells expressing ERAP1 polypeptide;

[8] a polynucleotide encoding the peptide described in any one of [1] to [7];

[9] a vector comprising the polynucleotide described in [8];

[10] a pharmaceutical composition including at least one ingredient selected from a group consisting of a peptide described in [1] to [7], a polynucleotide encoding the peptide, and a pharmaceutically acceptable salt of the peptide;

[11] the pharmaceutical composition described in [10] for treating and/or preventing cancer;

[12] the pharmaceutical composition described in [11], wherein the cancer is estrogen receptor-positive;

[13] the pharmaceutical composition described in [12], wherein the cancer is breast cancer;

[14] the pharmaceutical composition described in [12] or [13], wherein the cancer is tamoxifen-resistant;

[15] A pharmaceutical composition for potentiating the therapeutic effects of a hormone therapy agent on cancer, the pharmaceutical composition including the peptide described in any one of [1] to [7] or a polynucleotide encoding the peptide;

[16] a pharmaceutical composition for suppressing activation of estrogen receptor in estrogen receptor-positive cells, the pharmaceutical composition including the peptide described M stun one of [1] to [7] or a polynucleotide encoding the peptide;

[17] a method for treating and/or preventing cancer, the method including administering the peptide described in any one of [1] to [7] or a polynucleotide encoding the peptide to a subject;

[18] the method described in [17] further including administering a hormone therapy agent to a subject;

[19] a method for potentiating the therapeutic effects of a hormone therapy agent on breast cancer in a subject, which includes the following (a) and (b):

(a) administering a hormone therapy agent to a subject; and (b) administering the peptide described in any one of [1] or [7] a polynucleotide encoding the peptide to a subject;

[20] a method for suppressing activation of estrogen receptor, the method including bringing the peptide described in any one of [1] to [7] or a polynucleotide encoding the peptide into contact with estrogen receptor-positive cells;

[21] a method for determining the prognosis of a subject having breast cancer, the method including the following (a) to (c):

(a) detecting the expression level of ERAP1 gene in a biological sample collected from the subject;

(b) comparing the expression level detected in (a) with a control level; and (c) determining the prognosis of the subject on the basis of the comparison of (b);

[22] the method described in [21], wherein the control level is a good prognosis control level, and increase of the expression level with respect to the control level is determined as poor prognosis;

[23] the method described in [21] or [22], wherein the expression level is obtained by any one of the following, (a) and (b):

(a) detecting mRNA encoding ERAP1 polypeptide; and (b) detecting ERAP1 polypeptide;

[24] a method for screening a candidate material for suppressing proliferation of cancer cells, or a candidate material for treating and/or preventing cancer, the method including:

(a) bringing ERAP1 polypeptide or a functional equivalent thereof into contact with PKA polypeptide, PKB polypeptide or PP1α polypeptide, or a functional equivalent thereof in the presence of a test substance;

(b) detecting the binding level between the polypeptides in (a); and (c) selecting, a test substance that decreases the binding level between the above-mentioned polypeptides in comparison to the binding level detected in the absence of the test substance, as a candidate material for suppressing proliferation of cancer cells, or a candidate material for treating and/or preventing cancer;

[25] the method described in [24], wherein the cancer is estrogen receptor-positive; and

[26] the method described in [24] or [25], wherein the cancer is breast cancer.

Effects of the Invention

According to the present invention, provided is an ERAP1 peptide useful for treating and/or preventing cancer, particularly estrogen receptor-positive cancer. According to the ERAP1 peptide of the present invention, provided is a pharmaceutical composition for treating or preventing cancer, more specifically estrogen receptor-positive cancer. Cancers where the ERAP1 peptide of the present invention can exert desired effects include estrogen-dependent breast cancer. The present invention provides a therapeutic technique with a novel mechanism for estrogen-dependent breast cancer for which any novel therapeutic technique has been desired.

In addition, according to the present invention, provided is a method for screening a candidate material for a drug useful for treating and/or preventing cancer, particularly estrogen receptor-positive cancer.

BRIEF DESCRIPTION OF THE DRAWINGS

FIG. 1-2 is a diagram illustrating that the transcellular ERAP1 peptide binds to PHB7, and inhibits the interaction between ERAP1 and PHB2. (C) is a schematic diagram illustrating the Flag-ERAP1 fragment clone of $ERAP1_{1-434}$ and two Flag-ERAP1 fragment clones from which the C terminal region of ERAP1 are deleted. (D) shows the results of immunoblotting analysis by which the binding region to PHB2 in $ERAP1_{1-434}$ was identified. COS-7 cells were transfected with any one of the ERAP1 constructs shown in (C) ($ERAP1_{1-434}$, $ERAP1_{1-250}$, $ERAP1_{1-100}$) together with the PHB2 construct. The cells were lysed after 48 hours from the transfection. Then, Flag-tagged ERAP1 was immunoprecipitated from the cell lysate with anti-Flag antibody. The immunoprecipitated protein and the cell lysate (input) sere subjected to immunoblotting analysis (IB) using the antibodies shown in the figure.

FIG. 1-3 is a diagram illustrating that the transcellular ERAP1 peptide binds to PHB2, and inhibits the interaction between ERAP1 and PHB2. (E) shows the results of immunoblotting analysis showing that the ERAP1-deleted variant inhibits the interaction between ERAP1 and PHB2. COS-7 cells were transfected with Flag-full-length ERAP1, an HA-PHB2 construct, and an ERAP1-deleted variant construct (ΔERAP1: $ERAP1_{1-434}$) in the concentrations shown in the figure. The cells were lysed after 48 hours from the transfection. Then, HA-tagged PHB2 was immunoprecipitated from the cell lysate with anti-HA antibody. The immunoprecipitated protein and the cell lysate (input) were subjected to immunoblotting analysis using the antibodies shown in the figure. (F) shows the results of the luciferase assay by which the inhibition effect of the ERAP1-deleted variant on the transcriptional activity of ERα was evaluated. COS-7 cells were transfected with ΔERAP1, full-length ERAP1, PHB2, ERα and each plasmid of an ERE-luciferase vector. At the same time, the cells were stimulated with 1 μM E2 for 48 hours. The data show the multiples when the value for non-treated cells was designated as 1, and show the mean±SE of three independent experiments. **P<0.01.

FIG. 1-4 is a diagram illustrating that the transcellular ERAP1 peptide binds to PHB2, and inhibits the interaction between ERAP1 and PHB2. (G) shows the interaction site estimated with the PISVER software and the sequence of the mutant ERAP1 construct. (+) on the PISVER software shows an amino acid residues having 0.39 or more of the default threshold, and the bold-faced amino acid residues represent an amino acid residues that showed the highest score (≥0.6) with respect to the interaction between ERAP1 and PHB2. (H) shows the deduced PHB2-binding sites (Q165, D169, Q173) in the estimated three-dimensional structure of ERAP1. (I) shows the results of immunoblotting analysis b which the PHB2-binding region in ERAP1 was evaluated.

FIG. 1-5 is a diagram illustrating that the transcellular ERAP1 peptide binds to PHB2, and inhibits the interaction between ERAP1 and PHB2. (J) shows the sequences of the ERAP-1 peptide, the ERAP1-scramble peptide and the ERAP1-mutant peptide. (K) is a diagram illustrating the inhibition effects of the ERAP1-peptide on the ERAP1-PHB2 interaction in MCF-7 cells (upper panel) and KPL-3C cells (lower panel). MCF-7 cells or KPL-3C cells were treated with 10 μM of the ERAP1-peptide (Pep), the ERAP1-scramble peptide (Scr) or the ERAP1-mutant peptide (Mut). Then, immediately, the cells were stimulated with 10 nM E2 for 24 hours. The cell lysate of these cells was immunoprecipitated with the antibodies or normal rabbit IgG shown in the figure. Then, immunoblotting was performed with an anti-ERAP1 antibody or an anti-PHB2 antibody.

FIG. 2 is a diagram illustrating the results of immunoblotting analysis by which binding of the ERAP1-peptide to PHB2 was evaluated. The cell lysate of the COS-7 cells temporarily transfected with the Flag-tagged ERAP1 plasmid was incubated for 1 hour together with 6×His-tagged recombinant PHB2 protein (10 μg) and the ERAP1-peptide, the ERAP1-scramble peptide, or the ERAP1-mutant peptide in each concentration shown in the figure. Then, His-PHB2 was subjected to pull-down with Ni-NTA agarose (Ni-resin).

FIG. 3-1 is a diagram illustrating that ERAP1-peptide treatment promotes nuclear translocation of PHB2. (A) shows the results of immunoblotting analysis by which the localities of ERAP1 and PHB2 are detected. MCF-7 cells were stimulated for 24 hours with 10 μM ERAP1-peptide and/or 10 nM E2. The cells were fractioned into mitochondria, cytoplasm, and nuclear fractions by specific gravity centrifugation. Then, each fraction was subjected to immunoblotting analysis using an anti-ERAP1 antibody and an anti-PHB2 antibody. PRDX3, α/β-Tublin (Tublin) and lamin B are markers for mitochondria, cytoplasm, and nuclear fractions, respectively (upper panel). The protein content of each fraction was evaluated with Coomassie-stained SDS-PAGE gel (lower panel). (B) shows the results of immunoblotting analysis by which the intracellular localization of PHB2 is detected. KPL-3C cells were treated for 24 hours with 10 μM HA-tagged ERAP1-peptide and/or 10 nM E2. Then, the cells were fractionated into cytoplasm and nuclear fractions by specific gravity centrifugation. Then, which fraction was immunoprecipitated with anti-ERα antibody, an anti-ERAP1 antibody or an anti-PHB2 antibody. Then, immunoblotting was performed with each antibody shown in the figure (an anti-ERAP1 antibody, an anti-ERα antibody, an anti-PHB2 antibody and an anti-HA antibody (Peptide)). α/β-Tubulin (Tubulin) and Lamin B are markers for cytoplasm and nuclear fractions, respectively.

FIG. 3-2 is a diagram illustrating promotion effect of PHB2 nuclear translocation and suppression effect of the transcriptional activation of ER by ERAP1-peptide treatment. (C) illustrates representative images of stained immune cells, showing the localization of the ERAP1-peptide (HA-tagged ERAP1-peptide) and PHB2. MCF-7 cells were treated with 10 μM HA-tagged ERAP1-peptide for 24 hours in the presence or in the absence of 10 nM E2. After the immobilization, the cells were subjected to immunonfluorescent staining using an anti-HA antibody, an anti-PHB2 antibody and DAPI (for discriminating the nucleus). The arrow indicates the nuclear-translocated ERAP1-peptide. (D) shows the results of the luciferase assay by which the inhibition effect of the ERAP1-peptide was evaluated. MCF-7 cells temporarily transfected with an ERE-luciferase reporter vector were treated with an HA-tagged ERAP1-peptide in the concentrations shown in the figure. Then, immediately, the cells were stimulated with 10 nM E2 for 24 hours. TAM indicates the tamoxifen treatment. The data show the ratio bur the value for non-treated cells was designated as 1, and show the mean±SE of three independent experiments. P<001; *P<0.001.

FIG. 3-3 is as diagram illustrating the results of the luciferase assay by which the inhibition effect of the ERAP1-peptide was evaluated. MCF-7 cells temporarily transfected with an ERE-luciferase reporter vector (F) or an AP-1-luciferase reporter vector (F) were treated with the ERAP1-peptide, the scramble peptide or the mutant peptide in the concentrations shown in the future. Then, immediately, the cells were stimulated with 10 nM E2 for 24 hours. TAM indicates the tamoxifen treatment. The data show the ratio when the value for non-treated cells was designated as 1, and show the mean±SE of three independent experiments. ***P<0.001; NS, no significance.

FIG. 3-4 is as diagram illustrating suppression effect of the transcriptional activation of ER by ERAP1-peptide treatment and reconstitution of a chromatin remodeling complex, (G) shows the results of the luciferase assay by which the inhibition effect of the ERAP1-peptide was evaluated. KPL-3C cells temporarily transfected with an ERE-luciferase reporter vector were treated with the ERAP1-peptide in the concentrations shown in the figure. Then, immediately, the cells were stimulated with 10 nM E2 for 24 hours. TAM indicates the tamoxifen treatment. The data show the ratio when the value for non-treated cells was designated as 1, and show the mean±SE of three independent experiments. P<0.01; *P<0.001, (H) shows the results of immunoblotting analysis by which reconstitution of the chromatin remodeling complex by addition of the ERAP1-peptide was examined. KPL-3C cells were treated for 24 hours with the ERAP1-peptide and/or E2. Then, the nuclear fraction was immunoprecipitated with anti-ERα antibody or an anti-PHB2 antibody. Subsequently, the immunoprecipitate was subjected to immunoblotting analysis using the antibodies shown in the figure.

FIG. 4-1 is a diagram illustrating that the ERAP1-peptide promotes nuclear translocation of PHB2. (A) The upper panel illustrates representative images of stained immune cells, showing the intracellular localization of PHB2. MCF-7 cells were treated with 10 μM ERAP1-peptide or ERAP1-scramble peptide. Subsequently, the cells were treated with 10 nM E2. After the immobilization, the cells were subjected to immunofluorescent staining using an anti-PHB2 antibody and DAPI (for discriminating the nucleus). The arrow shows nuclear-translocated PHB2. The lower panel shows statistical analysis data of the PHB2 signal intensity in the nucleus. The data show the ratio when the value for non-treated cells was designated as 1, and show the mean±SE of four independent experiments. *P<0.05; P<0.01; *P<0.001.

FIG. 4-2 is a diagram illustrating that the ERAP1-peptide promotes nuclear translocation of PHB2. (B) is a diagram illustrating the results of immunoblotting analysis by which the intracellular localization of PHB2 was detected, MCF-7 cells were treated with the ERAP1-peptide or the ERAP1-scramble peptide. Subsequently immediately, the cells were treated with 10 nM E2. The cells were fractionated into cytoplasm and nuclear fractions after 1 hour or 24 hours. Each fraction was immunoprecipitated with anti-ERα antibody, an anti-ERAP1 antibody or a PH82 antibody. Furthermore, the immunoblotting was performed with melt antibody shown in the figure with respect to the obtained sample, α/β-Tublin (Tubutin) and Lamin B are markers for cytoplasm and nuclear fractions, respectively.

FIG. 4-3 is a diagram illustrating that the ERAP1-peptide promotes nuclear translocation of PHB2. (C) and (D) are figures that show the results of the luciferase assay by which the inhibition effect of the ERAP1-peptide on the ERα transcriptional activity was evaluated. MCF-7 cells temporarily transfected with an ERE-luciferase reporter vector (C) or an AP-1-luciferase reporter vector (D) were treated with the ERAP1-peptide in the concentrations shown in the figure or 10 nM tamoxifen. Then, immediately, the cells were stimulated with 10 nM E2 thr 24 hours. The data show the ratio when the value for non-treated cells was designated as 1, and show the mean±SE of three independent experiments. P<0.01; *P<0.001.

FIG. 4-4 is a diagram illustrating that the ERAP1-peptide promotes nuclear translocation of PHB2. (E) shows the results of immunoblotting analysis showing conversion of the chromatin remodeling complex by the ERAP1-peptide. MCF-7 cells were treated with the ERAP1-peptide and/or 10 nM E2 for 24 hours. Then, the nuclear fraction was immunoprecipitated with anti-ERα antibody or an anti-PHB2 antibody. Subsequently, the immunoprecipitate was subjected to immunoblotting analysis using the antibodies shown in the figure. (F) shows the results of the deacetylation assay of as chromatin remodeling complex formed by ERAP1-peptide treatment. MCF-7 cells were treated with the ERAP1-peptide and/or E2 for 24 hours. Then, the cell lysate was immunoprecipitated with anti-PHB2 antibody. Subsequently, the HDAC activity in the immunoprecipitate was measured with a commercially available kit. The nuclear extract from the HeLa cells and PBS were used as a positive control (P) and as negative control (N), respectively. The data show the mean±SE of three independent experiments.

FIG. 4-5 is a diagram illustrating that the ERAP1-peptide promotes nuclear translocation of PHB2. (G) shows the inhibition effect of the ERAP1-peptide in down-regulation of E2-dependent ERα. Treatment was performed with the ERAP1-peptide and/or E2 for the various times shown in the figure. Then, the protein level and the mRNA level for the expression of ERα were obtained by Western blotting (the upper panel: Protein) and semi-quantitative RT-PCR (the lower panel: mRNA), respectively. β-actin is a loading control for each. (H) shows the effects of the ERAP1-peptide in polyubiquitination of ERα. MCF-7 cells were treated with the ERAP1-peptide and/or E2 in the presence of 1 μM MG-132 for 1 hour. Then, the cell lysate was immunoprecipitated with anti-ERα antibody. Then, immunoblotting analysis was performed using the antibodies, shown in the figure.

FIG. 5 is a diagram illustrating the results of immunoblotting analysis by which the effects of the ERAP1-peptide in the down-regulation by polyubiquitination of ERα and proteasome decomposition were evaluated. The upper panel and the lower panel show the results obtained by the procedures described below. Namely, KPL-3C cells were treated with the ERAP1-peptide and/or 10 nM E2 for 1 hour. Then, the protein level and the mRNA level of ERα were examined by Western blotting and semi-quantitative RT-PCR. The results thereof are shown in the upper panel. β-actin is a loading control. Then KPL-3C cells were treated with the ERAP1-peptide and/or E2 in the presence of 1 μM MG-132 for 1 hour. Then, the cell lysate was immunoprecipitated with anti-ERα antibody. Subsequently, immunoblotting analysis was performed using the antibodies shown in the figure. The results thereof are shown in the lower panel.

FIG. 6-1 is a diagram illustrating that ERAP1-peptide treatment suppresses ERα-dependent cell proliferation of breast cancer cell lines. (A) and (B) show the results of MTT assay by which the inhibition effect of the ERAP1-peptide in the E2-dependent cell proliferation was evaluated. MCF-7 cells were treated with the ERAP1-peptide (A, B) the ERAP1-scramble peptide (B) or the ERAP1-mutant peptide (B). Then, immediately, the cells were stimulated with 10 nM E2 for the various times shown in the figure (A) or for 24 hours (B). The data show the mean±SE of three independent experiments. ***P<0.001; NS, no significance. (C) shows the results of MTT assay showing that the ERAP1-peptide had no effect on proliferation of ERα/ERAP1-negative mammary epithelial cells, MCF-10A. The cells were treated for 24 hours with the ERAP1-peptide in the concentrations shown in the figure, and the cell proliferation was evaluated.

FIG. 6-2 is a diagram illustrating that ERAP1-peptide treatment suppresses ERα-dependent cell proliferation of breast cancer cell lines. (D) shows the results of FACS analysis showing, the effects of the ERAP1-peptide on the cell cycle. MCF-7 cells were treated with 10 μM ERAP1-peptide or 10 μM tamoxifen. Then, immediately, the cells were stimulated with 10 nM E2 for 24 hours. After the immobilization, the cells were stained with propidium iodide, and analyzed by flow cytometry.

FIG. 6-3 is a diagram illustrating that ERAP1-peptide treatment suppresses ERα-dependent cell proliferation of breast cancer cell lines. (E) shows the results of real time PCR by which the effects of the ERAP1-peptide in the gene expression were evaluated. MCF-7 cells were treated with the ERAP1-peptide and/or E2 as described above. After the RNA extraction and the cDNA synthesis, the gene expression was evaluated. The data show the ratio when the value at 0 hour was designated as 1.0, and show the mean±SE of three independent experiments. P<0.01; *P<0.001.

FIG. 7-1 is a diagram illustrating that ERAP1-peptide treatment suppresses ERα-dependent cell proliferation of breast cancer cell lines. (A) shows the results of MTT assay by which the inhibition effect of the ERAP1-peptide on proliferation of KPL-3C cells was evaluated. KPL-3C cells were treated with the ERAP1-peptide, the scramble peptide or the mutant peptide. Then, immediately, the cells were stimulated with 10 nM E2 for 24 hours. The data show the mean±SE of three independent experiments. ***P<0.001; NS, no significance, (B) shows the results of MTT assay by which long term treatment with the ERAP1-peptide was evaluated. MCF-7 cells were treated with the ERAP1-peptide in the concentrations shown in the figure. Then, immediately, the cells were stimulated with 10 nM E2. Then, the ERAP1-peptide was added every day for low days. The data show the mean±SE of three independent experiments. The arrow indicates addition of the ERAP1-peptide.

FIG. 7-2 is a diagram illustrating that ERAP1-peptide treatment suppresses ERα-dependent cell proliferation of breast cancer cell lines. (C) shows the results of MTT assay by which the inhibition effect of the ERAP1-peptide on the cell proliferation of ERα/ERAP1-positive breast cancer cell lines was evaluated. Various ERα/ERAP1-positive breast cancer cell lines shown in the figure were treated with 10 μM of the ERAP1-peptide or the scramble peptide or 10 nM tamoxifen. Then, immediately, the cells were stimulated with 10 nM E2 for 24 hours. The data show the mean±SE of three independent experiments. P<0.01; *P≥0.001.

FIG. 7-3 is a diagram illustrating that ERAP1-peptide treatment suppresses ERα-dependent cell proliferation of breast cancer cell lines. (D) shows the results of MTT assay and the luciferase assay by which the stability of the ERAP1-peptide was tested. MCF-7 cells were treated with 10 μM ERAP1-peptide. Then, immediately, the cells were stimulated with 10 nM E2 (white square). Then, 10 μM ERAP1-peptide was added every day for four days (black square). The data show the mean±SE of three independent experiments.

FIG. 7-4 is a diagram illustrating that ERAP1-peptide treatment suppresses ERα-dependent cell proliferation of breast cancer cell lines. (E) shows the results of FACS analysis showing the effects of the ERAP1-peptide on the cell cycle. KPL-3C cells were treated with 10 μM ERAP1-peptide or 10 nM tamoxifen. Then, immediately, the cells were stimulated with 10 nM E2 for 24 hours. After the immobilization, the cells were stained with propidium iodide, and analyzed by flow cytometry.

FIG. 8-1 is a diagram illustrating the inhibition effect of the ERAP1-peptide on the gene expression of the ER target gene. (A) shows the results of quantitative RT-PCR by which the inhibition effect of the ERAP1-peptide on the ER target gene was evaluated. MCP-7 cells were treated with 10 μM ERAP1-peptide. Then, immediately, the cells were stimulated with 10 nM E2 for the times shown in the figure. After the RNA extraction and the following cDNA synthesis, expression of the genes shown in the figure was evaluated with quantitative RT-PCR.

FIG. 8-2 is a diagram illustrating the inhibition effect of the ERAP1-peptide on the gene expression of the ER target gene. (B) shows the results of quantitative RT-PCR showing the effects of the ERAP1-peptide on the gene expression. KPL-3C. cells were treated with the ERAP1-peptide and/or E2 for 24 hours. After the RNA extraction and the following cDNA synthesis, the gene expression was evaluated. The data show the mean±SE of three independent experiments. *P<0.05; P>0.01; *P<0.001.

FIG. 9-1 is a diagram illustrating that ERAP1-peptide treatment suppresses the non-genomic activation route. (A) shows the results of immunoblotting analysis showing the expressions of the membrane receptors of the respective growth factors. The cell lysate of the ERα-positive breast cancer cell lines shown in the figure was subjected to immunoblotting analysis using the antibodies shown in the figure. (B) shows the results of immunoblotting analysis by which the effects of the ERAP1-peptide on the interaction between ERα and IGF-1Rβ in KPL-3C cells were evaluated. KPL-3C cells were treated with the ERAP1-peptide and/or E2 for 24 hours. Then the nuclear fraction was immunoprecipitated with anti-ERα antibody. Subsequently, immunoblotting analysis was performed using the antibodies shown in the figure.

FIG. 9-2 is a diagram illustrating that ERAP1-peptide treatment suppresses the non-genomic activation route. (C to E) shows the results of immunoblotting analysis by which the inhibition effect of the ERAP1-peptide on E2-induced phosphorylation was evaluated. The cells (C and D) or BT474 cells (E) Were treated with the ERAP1-peptide. Then, immediately, the cells were treated with 10 nM E2 for the times shown in the figure. Then, the phosphorylation levels of Akt (C). MAPK (C) and ERα (D and E) were evaluated with Western blotting. The relative phosphorylation levels were quantified by densitometry analysis, and the ratio to the value at 0 hour for non-treated cells was calculated. These data described above are representative examples of two independent experiments.

FIG. 10-1 shows that the ERAP1-peptide regulates E2-induced non-genomic activation route via IGF-1Rβ and She. (A) shows the results of immunoblotting analysis by which the inhibition effect of the ERAP1-peptide on the interaction of ERα-IGF-1Rβ was evaluated. MCF-7 cells were treated with the ERAP1-peptide. Then, immediately, the cells were stimulated with 10 nM E2 for 24 hours. Then, the cytoplasm fraction was immunoprecipitated with anti-ERα antibody. Furthermore, with respect to the obtained sample, immunoblotting analysis was performed using the antibodies shown in the figure. (B) shows the results of immunoblotting analysis by which the inhibition effect of the ERAP1-peptide on the interaction of ERα-PI3K was evaluated. MCF-7 cells were treated with the ERAP1-peptide. Then, immediately, the cells were stimulated with 10 nM E2 for 24 hours. Then the cytoplasm fraction was immunoprecipitated with anti-ERα antibody or anti-PHB2 antibody. Furthermore, with respect to the obtained sample, immunoblotting analysis was performed using the antibodies shown in the figure.

FIG. 10-2 is a diagram illustrating that the ERAP1-peptide regulates E2-induced non-genomic activation route via IGF-1Rβ and Shc. (C) shows the results of immunoblotting analysis by which the inhibition effect of the ERAP1-peptide on E2-induced phosphorylation was evaluated. MCF-7 cells were treated with the ERAP1 peptide and/or E2 for the times shown in the figure. Then, the phosphorylation levels of Akt and MAPK were evaluated by Western blotting using the antibodies shown in the figure. (D) shows the results of immunoblotting analysis by which the inhibition effect of the ERAP1-peptide on the interactions of ERα-IGF-1Rβ, ERα-PI3K, ERα-EGFR and ERα-Her2 in BT-474 cells was evaluated. BT-474 cells were treated with the ERAP1-peptide and/or E2 for 24 hours. Then, the cytoplasm fraction was immunoprecipitated with anti-ERα antibody. Furthermore, with respect to the obtained sample, immunoblotting analysis was performed using the antibodies shown in the figure.

FIG. 10-3 is a diagram illustrating that the ERAP1-peptide regulates E2-induced non-genomic activation route via IGF-1Rβ and Shc. (E) shows the results of immunoblotting analysis by which the inhibition effect of the ERAP1-peptide on E2-induced phosphorylation was evaluated. BT-474 cells were treated with the ERAP1-peptide. Then, immediately, the cells were stimulated with 10 nM E2 for the times shown in the figure. Then, the phosphorylation levels of Akt and MAPK were evaluated by Western blotting. (F) shows the results of immunoblotting analysis by which the inhibition effect of the ERAP1-peptide on E2-induced ERα phosphorylation was evaluated. MCF-7 cells were treated with the ERAP1-peptide or the ERAP1-scramble peptide. Then, immediately, the cells were stimulated with 10 nM E2 for the times shown in the figure. Then, the phosphorylation level of ERα was evaluated by Western blotting using the antibodies shown in the figure. The relative phosphorylation levels were quantified by densitometry analysis, and the ratio to the value at 0 hour in the untreated cells was calculated. These data described above are representative examples of three independent experiments.

FIG. 11-1 is a diagram illustrating that the ERAP1-peptide inhibits tumor proliferation in a mouse orthotopically transplanted with human breast cancer. (A) and (B) show the influence of the ERAP1-peptide on the tumor volume. KPL-2 cells were subcutaneously transplanted into the breast fat body of as BALB/c nude mouse. The treatment test (5 individuals/group) was initiated (day 0) when the volume of the tumor in the absence E2 reached about 50-80 $mm^3$. The ERAP1-peptide (14, 35 and 70 mg/kg), the scramble peptide (14, 35 and 70 mg/kg) or tamoxifen (4 mg/kg) was administered every day by intraperitoneal injection to a cancerous mouse orthotopically transplanted with KPL-3C tumor. At the same time, E2 (6 μg/day) was administered subcutaneously every day. (A) shows the results of the tumor size measured for 2 weeks. (B) shows the average tumor volume at day 11 after ERAP1-peptide treatment.

FIG. 11-2 is a diagram illustrating that the ERAP1-peptide inhibits tumor proliferation in a mouse orthotopically transplanted with human breast cancer. (C) shows representative examples of the KPL-3C heterotransplanted tumor (upper panel) and the mouse (lower panel) shown in the figure at day 14 after the treatment.

FIG. 11-3 is a diagram illustrating that the ERAP1-peptide inhibits tumor proliferation in a mouse orthotopically transplanted with human breast cancer. (D) shows the change of the average body weight of the ERAP1-peptide-treated mouse. (E) shows the results of quantitative RT-PCR by which the inhibition effect of the ERAP1-peptide on the expression level of the representative ERα target genes in the tumor was evaluated. The mouse was euthanatized on day 14, and the tumor was removed, and the expression level of the downstream genes in each tumor was obtained by quantitative RT-PCR. The data show the ratio when the gene expression level in the non-treated group was designated as 1, and show the mean±SE of five mice. $*P<0.05$; $P<0.01$; $*P<0.001$.

FIG. 11-4 is a diagram illustrating that the ERAP1-peptide inhibits tumor proliferation in a mouse orthotopically transplanted with human breast cancer. (F) shows the results of immunoblotting analysis by which the effects of the ERAP1-peptide on the phosphorylation levels of various signal proteins in the tumors were evaluated.

FIG. 13-1 is a diagram illustrating positive feedback regulation of the transcriptional activation of ERAP1. (A) shows the results of quantitative RT-PCR by which up-regulation of ERAP1 by E2 stimulation was evaluated. MCF-7 cells were stimulated with 10 nM E2 for the times shown in the figure, and the expression of ERAP1 was evaluated by quantitative RT-PCR at the mRNA level. Each sample was standardized with the mRNA content of β2-MG, and the relative ERAP1 expression level was represented by the ratio when the value at 0 hour for non-treated cells was designated as 1. The data show the mean±SE of three independent experiments. ***P<0.001. (B) shows the results at quantitative RT-PCR and immunoblottings by which the influence of tamoxifen on the ERAP1 expression was evaluated. MCF-7 cells were treated with tamoxifen (TAM) in the concentrations shown in the figure. Then, immediately, the cells were stimulated with 10 nM E2 for 24 hours, and the mRNA level and the protein level of ERAP1 were obtained by quantitative. RT-PCR (left panel) and Western blotting (right panel). In the quantitative RT-PCR, the data were standardized with the β2-MG content, and shown with the ratio when the value for non-treated cells was designated as 1. In the Western blotting analysis β-actin was used as a loading control.

FIG. 13-2 is a diagram illustrating positive feedback regulation of the transcriptional activation of ERAP. (C) shows the results of the luciferase assay by which the transcriptional activation of ERAP1 via the ERE sequence in the intron was evaluated. MCF-7 cells were transfected with a luciferase reporter vector comprising a construct containing ERE-conserved motif (TCCAGTTGCATTGACCTGA) (SEQ ID NO: 56) located in intron 1 of the ERAP1 gene, a construct consisting of the upstream sequence not containing the ERE motif, or a construct consisting of the downstream sequence not containing the ERE motif (lower panel). Then, the cells were stimulated with 10 nM E2 for 24 hours, and the luciferase activity was measured. The data show the mean±SE of three independent experiments. *P<0.001. (D) shows the results of ChIP assay by which the transcriptional activation of ERAP1 via the estimated ERE sequence in intron 1 was evaluated. MCF-7 cells were treated with 10 μM ERAP1-peptide or the scramble peptide. Then, immediately, the cells were stimulated with 10 nM E2 for 24 hours. The chromatin was prepared, and immunoprecipitated with the antibodies shown in the figure. The chromatin immunoprecipitation analysis was performed using primers specific for the ERE region in the intron of ERAP1. (E) shows the results of real time PCR by which the inhibition effect of the ERAP1-peptide on the expression of ERAP1 was evaluated, MCF-7 cells were treated with 10 μM ERAP1-peptide. Then, immediately, the cells were stimulated with 10 nM E2 for the times shown in the figure. After the RNA extraction and the following cDNA synthesis, the expression of ERAP1 was evaluated with real time PCR. The data show the ratio when the value at 0 hour for non-treated cells was designated as 1, and show the mean±SE of three independent experiments. P<0.01; ***P<0.00.

FIG. 16 shows the results of MTT assay by which the inhibition effect of the ERAP1-peptide on proliferation of ERα-positive breast cancer cell lines (MCF-7, KPL-3C, ZR-75-1 and T47D) was evaluated. Each of the cells was treated with 10 μM ERAP1-peptide for 24 hours (MCF-7), for 48 hours (KPL-3C) or for 96 hours (ZR-75-1 and T47D). The data show the mean±SE of three independent experiments. *P<0.05; **P<0.01.

FIG. 26-1 is a diagram illustrating the results of evaluations for the phosphorylation in nuclear-translocated Ser39 of PHB2/REA. (A) shows the results of immunoblotting analysis by which phosphorylation of nuclear-translocated PHB2/REA (Ser39) by the transcellular ERAP1-peptide was evaluated. MCF-7 cells were treated with 10 μM ERAP1-peptide. Then, immediately, the cells were stimulated with 10 nM E2 for 24 hours. The cells were fractionated into cytoplasm and nuclear fractions by specific gravity centrifugation. Then, each fraction was immunoprecipitated with anti-PHB2/REA antibody. Then, the cells were lysed. Then, the immunoprecipitated protein and the cell lysate were subjected to immunoblotting analysis with the antibodies shown in the figure. (B) shows the results of successive immunoblotting analysis by which the serine phosphorylation of PHB2/REA separated by ERAP1-peptide treatment was evaluated MCF-7 cells were treated with 10 μM ERAP1-peptide. Then, immediately, the cells were temporally stimulated with 10 nM E2. Each cell lysate was subjected to immunoblotting analysis with an anti-PHB2/REA antibody and an anti-phosphorylation PHB2/REA (S39) antibody. (C) shows representative cell immunostaining images showing phosphorylation of REA (S39). MCF-7 cells were treated with the ERAP1-peptide and λ-phosphatase (400 U) in the presence of 10 nM E2 for 24 hours. After the immobilization, the cells were subjected to immunofluorescent staring.

FIG. 26-2 is a diagram illustrating the results of evaluations for the phosphorylation in the nuclear-translocated Ser39 of PHB2/REA. (D) shows the results of immunoblotting analysis by which phosphorylation of PHB2/REA (Ser39) nuclear-translocated by suppression for the expression of ERAP1 was evaluated. MCF-7 cells suppressed for expression of ERAP1 by siRNA method were stimulated with 10 nM E2 for 24 hours. Then, the cells were fractionated into the cytoplasm fraction (C) and the nuclear fraction (N) by specific gravity centrifugation. Then, each fraction was subjected to immunoblotting analysis with the antibodies shown in the figure. (E) shows the results of real time PCR by which the expressions of ERα downstream genes by suppression for the expression of ERAP1 were evaluated. MCF-7 cells suppressed for expression of ERAP1 by siRNA method were treated with 10 μM ERAP1-peptide. Then, immediately, the cells were stimulated with 10 nM E2 for 24 hours. After the RNA extraction and the following cDNA synthesis, the expressions of ERα downstream genes (ERAP1, CCND1, TFF1 and c-Myc) were evaluated with real time PCR. The data show the ratio when the value for non-treated cells was designated as 1.0, and show the mean±SE of three independent experiments. P<0.01, *P<0.001.

FIG. 28-1 is a diagram illustrating that ERAP1 and PP1α interact with each other. (A) shows the results of immunoblotting analysis showing the binding of ERAP1 to PP1α. MCF-7 cells were treated with 10 μM ERAP1-peptide. Then, immediately, the cells were stimulated with 10 nM E2 for 24 hours. Then, the cells were lysed. Then, ERAP1 was immunoprecipitated from the cell lysate with anti-ERAP1 antibody. Furthermore, the obtained sample was subjected to immunoblotting analysis with the antibodies shown in the figure. The data are representative examples of three independent experiments. (B) shows the results of immunoblotting analysis by which PP1α binding region was confirmed in ERAP1. HEK293T cells were transfected with an ERAP1 construct (ΔPP1α) in which 1228-1232 aa (KAVSF), i.e., the deduced PP1α binding motif, was deleted, and an ERα construct. After 48 hours, the cells were stimulated with 10 nM E2 for 24 hours. Then, the cells were lysed. Then, FLAG-tagged ERAP1 was immunoprecipitated from the cell lysate with anti-FLAG antibody. Furthermore, the immunoprecipitated protein was subjected to immunoblotting analysis with the antibodies shown in the figure. The data are representative examples of two independent experiments.

FIG. 28-2 is a diagram illustrating that ERAP1 and PP1α interact with each other. (C) shows the results of immunoblotting analysis showing that ERAP1, PHB2/REA and ERα form a complex by suppression for PP1α expression. MCF-7 cells suppressed for expression of PP1α by siRNA method, were treated with 10 μM ERAP1-peptide. Then, immediately, the cells were stimulated with 10 nM E2 for 24 hours. The cells were fractionated into cytoplasm and nuclear fractions by specific gravity centrifugation. Then, each fraction was immunoprecipitated with anti-ERα antibody. Then, the cells were lysed. Then, the immunoprecipitated protein and the cell lysate were subjected to immunoblotting analysis with the antibodies shown in the figure. (D) shows the results of immunoblotting analysis showing that PP1α indirectly binds to PHB2/REA through ERAP1. MCF-7 cells suppressed for expression of ERAP1 by siRNA method, were stimulated with 10 nM E2 for 24 hours. Then, the cells were immunoprecipitated with anti-PHB2/REA antibody and an IgG antibody. Then, the cells were lysed. Then, the immunoprecipitated protein and the cell lysate were subjected to immunoblotting analysis with the antibodies shown in the figure.

FIG. 30-1 is a diagram illustrating that phosphorylation of ERAP1 induces the phosphatase activity of PP1α. (A) shows the results of siRNA test showing that ERAP1 negatively regulates the PP1α activity. MCF-7 cells in which the expression of ERAP1 or PP1α was suppressed by siRNA method were lysed. Then, the phosphatase activity of the obtained cell lysate was calculated. The data show the mean±SE of three independent experiments. *P<0.001. (B) shows the results of phosphatase activity analysis and immunoblotting analysis by which the inhibition effect of ERAP1 on the PP1α activity was evaluated. HEK293T cells were transfected with an ERAP1 construct (0.5, 1.0 and 2.0 μg) or PP1α binding region-deleted ERAP1 construct (ΔPP1α: 2.0 μg), and lysed. Then, the cell lysate was immunoprecipitated with anti-PP1α antibody. Furthermore, with respect to the obtained sample, phosphatase activity analysis (upper panel) and immunoblotting analysis (lower panel) were performed. The phosphatase activity shows the mean±SE of three independent experiments. P<0.01. ***P<0.001.

FIG. 30-2 is a diagram illustrating that phosphorylation of ERAP1 induces the phosphatase activity of PP1α. (C) shows the results of the phosphatase assay showing that estrogen stimulation induces the PP1α activity. MCF-7 cells were stimulated with 10 nM E2 for 6, 12 or 24 hours. Then, the phosphatase activity of the cell lysate was calculated. The data show the mean±SE of three independent experiments, ***P<0.001. (D) shows the results of immunoblotting analysis by which phosphorylation of ERAP1 by estrogen stimulation was evaluated. MCF-7 cells were stimulated with 10 nM E2 for 24 hours. Then, the cell lysate was subjected to immunoblotting analysis with the anti-phosphorylation antibodies shown in the figure. The data are representative examples of three independent experiments. (E) shows the results of immunoblotting analysis showing the binding of ERAP1 to PKA and PKB. MCF-7 cells were stimulated with 10 nM E2 for 24 hours. Then, the cells were lysed. Then, the cell lysate was immunoprecipitated with anti-ERAP1 antibody and an IgG antibody. Furthermore, the obtained sample was subjected to immunoblotting analysis with the antibodies shown in the figure. The data are representative examples of three independent experiments.

FIG. 31-1 is a diagram illustrating that phosphorylation of ERAP1 by PKA and PKB regulates phosphorylation of PHB2/REA (S39) through the PP1α activity. (A) shows the results of the phosphatase assay showing that PKA and PKB cause the PP1α activity, MCF-7 cells suppressed for expression of PKA or PKB, or both of PKA and PKB by siRNA method were stimulated with 10 nM E2 for 24 hours. Then, the cell lysate solution was immunoprecipitated with anti-ERAP1 antibody. Furthermore, the phosphatase activity of the obtained sample was calculated. The data show the mean±SE of three independent experiments. P<0.01, *P<0.001. (B) shows the results of immunoblotting analysis showing that PKA and PKB cause phosphorylation of ERAP1. MCF-7 cells suppressed for expression of PKA or PKB, or both of PKA and PKB by siRNA method, were treated with 10 μM ERAP1 peptide. Then, immediately, the cells were stimulated with 10 nM E2 for 24 hours. Then, the cell lysate was subjected to immunoblotting analysis with the antibodies shown in the figure. The data show the ratio when the value of the phosphorylation by E2 stimulation in siControl-treated cells was designated as 1.0, and are representative examples of three independent experiments. (C) shows the results of immunoblotting analysis showing that inhibition of the PKA activity by H-89 regulates phosphorylation of ERAP1 and PHB2/REA. MCF-7 cells were treated with H-89 for 30 minutes and washed with PBS. Then, the cells were treated with 10 μM ERAP1-PEPTIDE. Then, immediately, the cells were stimulated with 10 nM E2 for 24 hours. Then, the cell lysate was subjected to immunoblotting analysis with the antibodies shown in the figure.

FIG. 31-2 is a diagram illustrating that phosphorylation of ERAP1 by PKA and PKB regulates phosphorylation of PHB2/REA (S39) through the PP1α activity. (D) shows the results of immunoblotting analysis showing that serine phosphorylation of ERAP1 is suppressed by inhibition of the PKA activity and phosphorylation of PHB2/REA. (S39) is caused. MCF-7 cells suppressed for expression of PKA by siRNA method, were stimulated with 10 nM E2 for 24 hours. In addition, MCF-7 cells were treated with H-89 for 30 minutes and washed with PBS. Then, immediately, the cells were stimulated with 10 nM E2 for 24 hours. Then, the cell lysate was subjected to immunoblotting analysis with the antibodies shown in the figure. (E) shows the results of immunoblotting analysis showing that inhibition of the PKA activity causes phosphorylation of PHB2/REA (S39). MCF-7 cells were treated with H-89 and okadaic acid for 30 minutes and washed with PBS. Then, immediately, the cells were stimulated with 10 nM E2 for 24 hours. Then, the cell lysate was subjected to immunoblotting analysis with the antibodies shown in the figure. (F) shows the results of immunoblotting analysis showing that PKCα causes phosphorylation of REA (S39). MCF-7 cells suppressed for expression of PKCα by siRNA method were treated with 10 μM ERAP1 peptide. Then, immediately, the cells were stimulated with 10 nM E2 for 24 hours. The cells were fractionated into cytoplasm and nuclear fractions by specific gravity centrifugation. Then, each fraction was subjected to immunoblotting analysis with the antibodies shown in the figure. The data show the ratio when the value of REA phosphorylation of the siControl-treated and ERAP1 peptide-treated cells was designated as 1.0.

FIG. 41-1 is a diagram illustrating that ROS production in the mitochondria by E2 stimulation is induced through ERAP1. (A) shows the results of immunoblotting analysis showing that ERAP1 was localized in the mitochondria. MCF-7 cells were treated with 10 μM ERAP1-peptide. Then, immediately the cells were stimulated with 10 nM E2 for 24 hours. The cells were fractionated into the mitochondria fraction (M), the cytoplasm fraction (C) and the nuclear fraction (N) by specific gravity centrifugation. Then, each fraction was subjected to immunoblotting analysis with the antibodies shown in the figure. Lamin B, α/β-Tubulin (Tubulin) and PRDX3 are markers for the nuclear fraction, the cytoplasm fraction and the mitochondria fraction, respectively.

FIG. 41-2 is a diagram illustrating that ROS production in the mitochondria by E2 stimulation is induced through ERAP1. (B) shows the results of evaluations for ROS production via ERAP1 in the mitochondria. MCF-7 cells, and MCF-7 cells suppressed for expression of ERAP1, and HCC1395 cells were treated with 10 μM DHR123 for 15 minutes. The cells were washed, and then stimulated with 10 μM ERAP1-peptide and 10 nM E2 for 24 hours, and analyzed by flow cytometry. Cells treated with 1 mM $H_2O_2$ for 24 hours were used as a positive control. The data are representative examples of two independent experiments.

MODES FOR CARRYING OUT THE INVENTION

Definition

Figure 1:
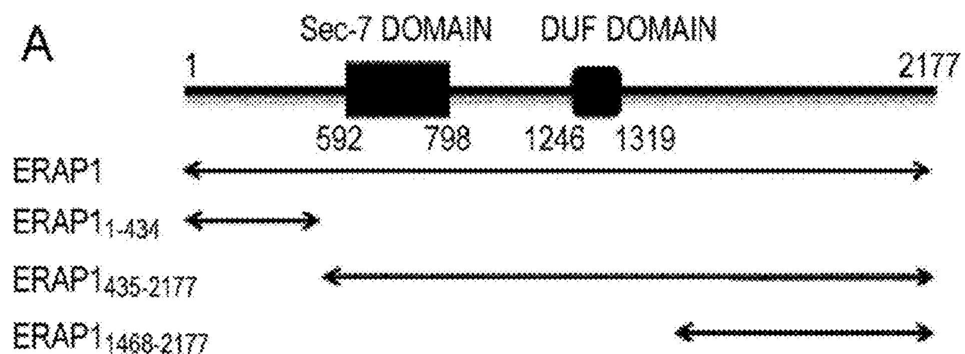
FIG. 1-1 is a diagram illustrating that the transcellular ERAP1 peptide binds to PHB2, and inhibits the interaction between ERAP1 and PHB2. (A) is a schematic diagram illustrating three Flag-ERAP1 fragment clones from which either one of human ERAP1 and a terminal region thereof is deleted. (B) is as diagram illustrating the results of immunoblotting analysis by which the PHB2-binding region a ERAP1 was identified. COS-7 cells were transfected with any one of the ERAP1 constructs shown in the figure (full-length ERAP1, $ERAP1_{1-434}$, $ERAP1_{435-2177}$, and $ERAP1_{1468-2177}$) together with the PHB2 construct. The cells were lysed after 48 hours from the transfection. Then Flag-tagged ERAP1 was immunoprecipitated from the cell lysate with anti-Flag antibody. The immunoprecipitated protein and the cell lysate (input) were subjected to immunoblotting analysis (IB) using the antibodies shown in the figure.
Figure 1:
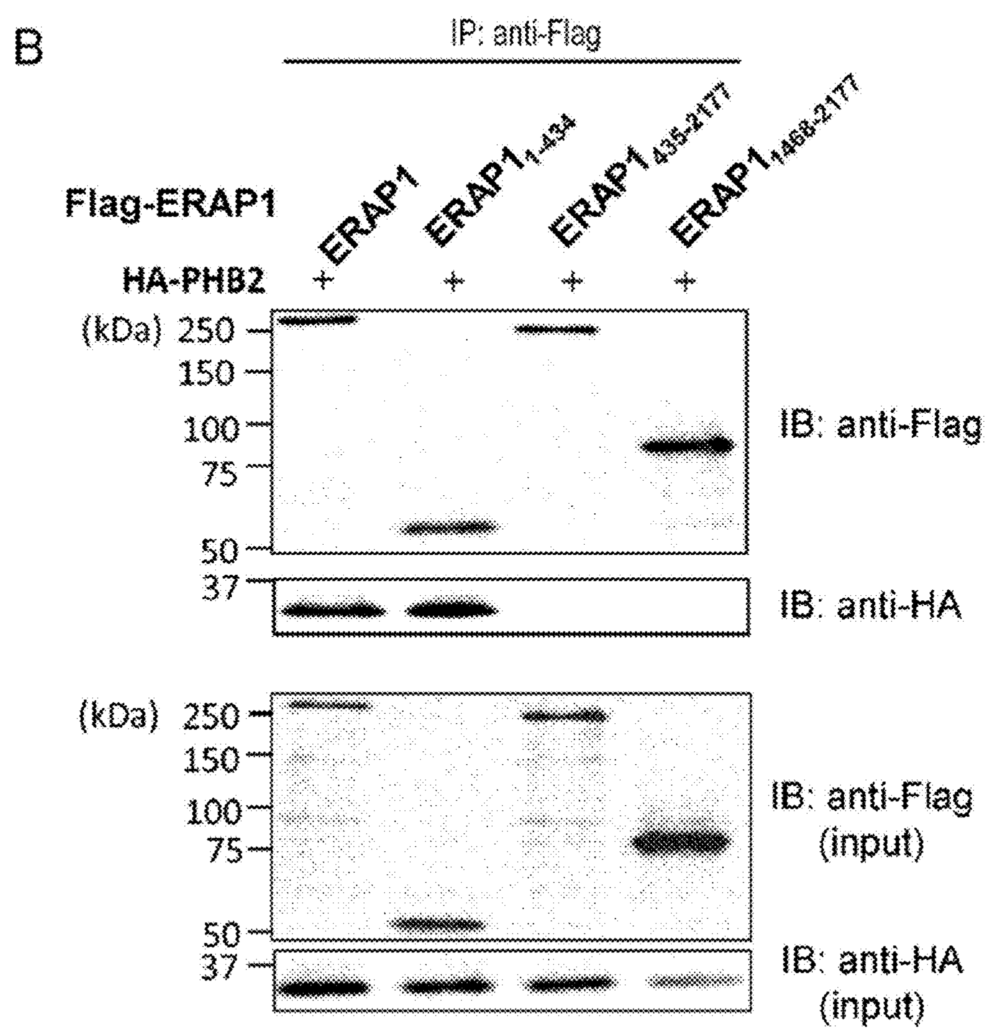

Although any methods and materials similar or equivalent to those described herein can be used in practicing or testing embodiments of the present invention, the preferred methods, devices, and materials are now described. However, before the present materials and methods are described, it is to be understood that the present invention is not limited to the particular sizes, shapes, dimensions, materials, methodologies, protocols, and the like described herein, as these may vary in accordance with routine experimentation and optimization. It is also to be understood that the terminology used in the description is for the purpose of describing the particular versions or embodiments only, and is not intended to limit the scope of the present invention which will be limited only by the appended claims.

The disclosure of each publication, patent or patent application mentioned in this specification is specifically incorporated by reference herein in its entirety. However, nothing herein is to be construed as an admission that the invention is not entitled to antedate such disclosure by virtue of prior invention.

Unless otherwise defined, all technical and scientific terms used herein have the same meaning as commonly understood by one of ordinary skill in the art to which this invention belongs. In case of conflict, the present specification, including definitions, will control.

The words “a”, “an”, and “the” as used herein mean “at least one” unless otherwise specifically indicated.

The terms “isolated” and “purified” used in relation with a substance (e.g., peptide or polynucleotide) indicate that the substance is substantially free from at least one substance that may else be included in the natural source. Thus, an isolated or purified peptide refers to peptides that are substantially free of cellular materials such as carbohydrate, lipid, or other contaminating proteins from the cell or tissue source from which the peptide is obtained or substantially free of chemical precursors or other chemical substances when chemically synthesized. The term “substantially free of cell materials” includes preparations of a peptide in which the peptide is separated from cellular components of the cells from which it isolated or recombinantly produced.

Thus, a peptide that is substantially free of cell materials includes preparations of a peptide having less than about 30%, 20%, 10% or 5% (by dry weight) of heterologous protein. When the peptide is recombinantly produced, the preparation is also substantially free of culture medium, and includes preparations of a polypeptide with contaminating culture medium that is less than about 20%, 10%, or 5% of the volume of the peptide preparation in some embodiments. When the polypeptide is produced by chemical synthesis, the preparation is substantially free of chemical precursors or other chemical substances, and includes preparations of a peptide with chemical precursors or other chemical substances involved in the synthesis of the peptide that is less than about 30%, 20%, 10%, or 5% (by dry weight) of the volume of the peptide preparation in some embodiments. In the preferred embodiments, the peptide of the present invention is isolated or purified.

The terms “polypeptide”, “peptide”, and “protein” are used herein interchangeably to refer to a polymer of amino acid residues. These terms apply to amino acid polymers in which one or more amino acid residues are modified residues or non-naturally occurring residues, for example, artificial chemical mimetics of a corresponding naturally occurring amino acid, as well as to naturally occurring amino acid polymers.

The term “amino acid” is used herein to refer to naturally occurring and synthetic amino acids, as well as amino acid analogs and amino acid mimetics that similarly function to the naturally occurring amino acids. Naturally occurring amino acids may be those encoded by the genetic code, as well as those modified after translation in cells (e.g., hydroxyproline, γ-carboxyglutamic acid, and O-phosphoserine). The term “amino acid analog” is used herein to refer to compounds that have the same basic chemical structure (an α carbon bound to a hydrogen, a carboxy group, an amino group, and an R group) as a naturally occurring amino acid, but have a modified R group or modified backbones (e.g., homoserine, norleucine, methionine, sulfoxide, methionine methyl sulfonium). The term “amino acid mimetic" is used herein to refer to chemical compounds that have different structures from, but similar functions to, general amino acids.

Amino acids may be herein referred to as their commonly known three letter symbols or the one-letter symbols recommended by the IUPAC/IUB Biochemical Nomenclature Commission.

The terms "polynucleotide" and "nucleic acid" are used herein interchangeably to refer to a polymer of nucleotides. These terms include both of naturally occurring nucleic acid polymers and non-naturally occurring nucleic acid polymers. The nucleotides are referred to as their commonly acceptable single-letter codes like the amino acids.

The term "treatment" in the context of the present invention means improvement of at least one symptom generated by a target disease or suppression for the progress of the symptoms. Example of the "treatment of cancer" include inhibition of proliferation of cancer cells, regression of cancer, detectable improvement, alleviation or suppression for the progress of symptoms involved with cancer, and suppression for metastasis.

The term "prevention" in the context of the present invention means avoidance, suppression or delay of generation of a target disease. The prevention can be performed at primary, secondary, and tertiary prevention levels. The primary prevention is avoidance of outbreak of a disease, and the secondary, and tertiary levels of the prevention include activities for the purpose of recovering functions and decreasing complications associated with a disease, thereby to prevent the progress of the disease and appearance of the symptoms, and decrease adverse influences of the disease already established. Examples of the "prevention of cancer" include avoidance or delay of outbreak of cancer, suppression or delay of the progress of the symptoms from an initial step, and suppression for metastasis after surgery.

Herein, the term "ERAP1 polypeptide" refers to a polypeptide encoded by ERAP1 (Estrogen Receptor Activity-regulated Protein 1) gene. More specifically, "ERAP1 polypeptide" refers to a human ERAP1 protein, a polypeptide consisting of the amino acid sequence described in SEQ ID NO: 35 (GeneBank Accession No. BAH83562.1). However, in the present invention, the ERAP1 polypeptide is not limited thereto, but also includes isoforms and mutants thereof. "ERAP1" is also referred to as "BIG3 (Brefeldin A-Inhibited Guanine nucleotide-exchange protein 3)", "A7322", or "KIAA1244". Herein, "ERAP1 polypeptide" is also described as "ERAP1". An example of a representative base sequence of the gene sequence of human ERAP1 is shown in SEQ ID NO: 34 (GeneBank Accession No. AB252196.1).

Herein, the term "PHB2 polypeptide" refers to a polypeptide encoded by PHB2 (prohibitin2) gene. More specifically, "PHB2 polypeptide" refers to a polypeptide consisting of the amino acid sequence described in SEQ ID NO: 37 (GeneBank Accession No. NP_001138303.1), which is human PHB2 protein. However, in the present invention, the PHB2 polypeptide is not limited thereto, but also includes isoforms and mutants thereof. "PHB2" is also referred to as "REA (Repressor of Estrogen Activity)". Herein, "PHB2 polypeptide" is also described as "PHB2" or "PHB2/REA". An example of a representative base sequence of the human PHB2 gene is shown in SEQ ID NO: 36 (GeneBank Accession No. NM_001144831.1).

Herein, the term "PP1α polypeptide" refers to a polypeptide encoded by PPPCA (protein phosphatase 1, catalytic subunit, alpha isozyme) gene. More specifically, "PP1α polypeptide" refers to a polypeptide consisting of the amino acid sequence described in SEQ ID NO: 72, 74 or 76 (GeneBank Accession No. NP_001008709, NP_002699.1 or NP_996756.1), which is human PP1α protein. However, in the present invention, the PP1α polypeptide is not limited thereto, but also includes isoforms and mutants thereof. Herein, "PP1α polypeptide" is also described as "PP1α". Representative examples of the base sequence of the human PP1α gene are shown in SEQ ID NOs: 71, 73 and 75 (GeneBank Accession Nos. NM_001008709, NM_002708.3 and NM_206873.1).

Herein, the term "PKA polypeptide" refers to a polypeptide encoded by PRKACA (protein kinase, cAMP-dependent catalytic, alpha) gene. More specifically, "PKA polypeptide" refers to a polypeptide consisting of the amino acid sequence described in SEQ ID NO: 78 or 80 (GeneBank Accession No. NP_002721.1 or NP_997401.1), which is human PKA (Protein kinase A) protein. However, in the present invention, the PKA polypeptide is not limited thereto, but also includes isoforms and mutants thereof. Herein, "PKA polypeptide" is also described as "PKA". Representative examples of the base sequence of the human PKA gene are shown in SEQ ID NOs: 77 and 79 (GeneBank Accession Nos. NM_002730.3 and NM_207518.1).

Herein, the term "PKB polypeptide" refers to a polypeptide encoded by AKTI (v-akt murine thymoma viral oncogene homolog 1) gene. More specifically, "PKB polypeptide" refers to the amino acid sequence described in SEQ ID NO: 82, 84 or 86 (GeneBank Accession No. NP_001014431, NP_001014432 or NP_005154), which is human PKB (Protein kinase B) protein. However, in the present invention, the PKB polypeptide is not limited thereto, but also includes isoforms and mutants thereof "PKB polypeptide" is also referred to as "PKB". Representative examples of the base sequence of the human PKB gene is shown in SEQ ID NOs: 81, 83 and 85 (GeneBank Accession Nos. NM_001014431, NM_001014432 and NM_005163).

The term "estrogen receptor" used herein includes both of estrogen receptor a (ERα) and estrogen receptor β (ERβ). ERα and ERβ are encoded by ESR1 gene and ESR2 gene, respectively. Representative base sequence of the human ESR1 gene and amino acid sequence of human ERα are shown in SEQ ID NO: 38 (GeneBank Accetion No. NM_000125.3) and SEQ ID NO: 39 (GeneBank Accetion No. NP_000116.2), respectively. In addition, representative base sequence of the human ESR2 gene and amino acid sequence of human ERβ are shown in SEQ ID NO: 40 (GeneBank Accetion No. NM_001437.2) and SEQ ID NO: 41 (GeneBank Accetion No. NP_001428.1), respectively. However, in the present invention, the base sequence and the amino acid sequence of the estrogen receptor are not limited thereto, but include isoforms and mutants thereof. In the preferred embodiments, the estrogen receptor is ERα. It is reported that any of ERα and ERβ is regulated by PHB2 polypeptide with respect to the transcriptional activation (Mnontano M M, et al., Proc Natl Acad Sci USA. 1999; 96: 6947-52.).

Herein, the term "estrogen receptor-positive" used with respect to a cell or cancer means that a cell or a cancer cell that constitutes a cancer expresses an estrogen receptor. Whether a cell or cancer is the estrogen receptor-positive or not can be confirmed by a known method such as ELISA method and immunohistochemical staining method. In addition, herein, the term "estrogen receptor-negative" used with respect to a cell or cancer means that a cell or a cancer cell that constitutes a cancer does not express an estrogen receptor.

1. ERAP1 Peptide

The present invention provides a peptide that inhibits binding of the ERAP1 polypeptide to the PHB2 polypeptide, which comprises a binding site of the ERAP1 polypeptide to the PHB2 polypeptide. The peptide of the present invention herein is also described as "ERAP1 peptide".

The peptide of the present invention has an ability to bind to PHB2 polypeptide by comprising a binding site of the ERAP1 polypeptide to the PHB2 polypeptide. As a result, the peptide of the present invention competitively inhibits binding of the ERAP1 polypeptide to the PHB2 polypeptide. The ERAP1 peptide of the present invention may be a salt as long as it has an action of inhibiting binding of the ERAP1 polypeptide to the PHB2 polypeptide. For example, the ERAP1 peptide of the present invention may be a salt with an acid (e.g., inorganic acid or organic acid) or a base (e.g., alkali metal, alkali earth metal, or amine). Examples of the salt with an acid include salts with an inorganic acid (e.g., hydrochloric acid, phosphoric acid, hydrobromic acid, sulfuric acid, or acetic acid) and salts with an organic acid (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid, or meglumine acid). Examples of the salt with a base include salts with sodium, potassium, calcium, and ammonium. Preferred examples of the salt of the peptide of the present invention include acetic acid salt, hydrochloric acid salt, meglumine acid salt, and ammonium salt.

The binding site to the PHB2 polypeptide in the ERAP1 polypeptide means an amino acid residue that is involved in binding to the PHB2 polypeptide in the amino acid sequence that constitutes the ERAP1 polypeptide. Examples of such amino acid residues include the glutamine at position 165, the aspartic acid at position 169, and the glutamine at position 173 in the amino acid sequence described in SEQ ID NO: 33. Thus, in the preferred embodiments, the peptide of the present invention is a peptide that inhibits binding of the ERAP1 polypeptide to the PHB2 polypeptide, which comprises the glutamine at position 165, the aspartic acid at position 169 and the glutamine at position 173 in the amino acid sequence described in SEQ ID NO: 33. Furthermore, herein, the number of particular amino acid residues in the amino acid sequence represents the number of the amino acid residues counted from the N-terminal.

In the more preferred embodiments, the peptide of the present invention includes the amino acid sequence from the glutamine at position 165 to the glutamine at position 173 in the amino acid sequence described in SEQ ID NO: 33 (QMLSDLTLQ (SEQ ID NO: 31)). Examples of such peptide include the ERAP1-peptide (QMLSDLTLQLRQR (SEQ ID NO: 27)) and the ERAP1-peptide-2 (ATLSQMLSDLTLQ (SEQ ID NO: 30)) described in Examples of the specification. Thus, preferred examples of the peptide of the present invention include peptides comprising an amino acid sequence selected from a group consisting of (a) to (c) described below:

(a) amino acid sequence described in SEQ ID NO: 31/QMLSDLTLQ;

(b) amino acid sequence described in SEQ ID NO: 27/QMLSDLTLQLRQR; and (c) amino acid sequence described in SEQ ID NO: 30/ATLSQMLSDLTLQ.

However, the peptide of the present invention is not limited thereto, and the amino acid sequence that constitutes the peptide is not particularly limited if the amino acid sequence comprises a binding site of the ERAP1 polypeptide to the PHB2 polypeptide, and has an activity of inhibiting binding of the ERAP1 polypeptide to the PHB2 polypeptide.

It is known that alteration of one or more amino acids in a peptide generally has no influence on the functions of the peptide. In practice, it is known that a peptide having an amino acid sequence in which one or more amino acid residues are altered by substitution, deletion, insertion, and/or addition, keeps biological activities of the original peptide (Mark et al., Proc Natl Acad Sci USA 81: 5662-6 (1.984); Zoller and Smith, Nucleic Acids Res 10: 6487-500 (1982); Dalbadie-McFarland et al., Proc Natl. Acad Sci USA 79: 6409-13 (1982)). Thus, the peptide of the present invention includes peptides that comprise the amino acid sequence selected from a group consisting of (a') to (c') described below, and have an activity of inhibiting binding of the ERAP1 polypeptide to the PHB2 polypeptide:

(a') amino acid sequence in which one, two or several amino acid residues besides the glutamine at position 1/Q, the aspartic acid at position 5/D and the glutamine at position 9/Q are substituted with other amino acid residues in the amino acid sequence described in SEQ ID NO: 31;

(b') amino acid sequence in which one, two or several amino acid residues besides the glutamine at position 1/Q, the aspartic acid at position 5/D and the glutamine at position 9/Q are substituted with other amino acid residues in the amino acid sequence described in SEQ ID NO: 27; and (c') amino acid sequence in which one, two or several amino acid residues besides the glutamine at position 5/Q, the aspartic acid at position 9/D and the glutamine at position 13/Q are substituted with other amino acid residues in the amino acid sequence described in SEQ ID NO: 30.

The substituted amino acid residues in the above-mentioned (a') to (c') may be any amino acid residue as long as the ability of inhibiting the binding of the ERAP1 polypeptide to the PHB2 polypeptide is maintained. The substituted amino acid residues can be determined by estimating amino acid residues that are not involved in binding to the PHB2 peptide using a calculation method such as PSIVER. For example, the amino acid residues estimated as "-" in FIG. 1G can be preferably selected as a candidate residue for the substitution. The number of the substituted amino acid residues is not particularly limited as well, as long as the ability of inhibiting the binding of the ERAP1 polypeptide to the PHB2 polypeptide is maintained, and one, two or several amino acid residues can be substituted. The "several" is preferably six, five, four or three.

For example, the ERAP1 peptide defined in (a') is a peptide that has an activity of inhibiting binding of the ERAP1 polypeptide to the PHB2 polypeptide, and comprises an amino acid sequence in which one, two or several amino acid residues are substituted with other amino acid residues besides the glutamine at position 1/Q, the aspartic acid at position 5/D and the glutamine at position 9/Q in the amino acid sequence described in SEQ ID NO: 31. (a') encompasses a peptide that inhibits binding of the ERAP1 polypeptide to the PHB2 polypeptide. This peptide is, for example, a peptide consisting of an amino acid sequence in which all of the three amino acid residues described below are conserved, and amino acid residues in the other positions are substituted in a successive amino acid sequence comprising 165-173 (SEQ ID NO: 31) in the amino acid sequence of SEQ ID NO: 35.

The glutamine at position 165/Q,
the aspartic acid at position 169/D and
the glutamine at position 173/Q of SEQ ID NO: 35

In the preferred embodiments, substitution of amino acid residues acceptable in other positions than the above-mentioned three amino acids, is commonly 10 or less, or 8 or less, for example, 7 or less, preferably 6 or less, more preferably 5 or less, particularly preferably 3 or less. Examples of such ERAP1 peptide include a peptide that is constituted by amino acids of 30 residues or less, or 20 residues or less, typically 19 residues or less, preferably 18 residues or less, and more preferably 17 residues or less.

Generally, it is recognized that substitution for other amino acid residues by which the properties of the amino acid side chain of the original amino acid residues are conserved, tends to have no influence on the functions of the original peptide. Such substitution is often referred to as "conservative substitution" or "conservative alteration". Thus, the substitution in the above-mentioned (a') to (c') is preferably performed by the conservative substitution.

Conservative substitution tables showing functionally similar amino acids are well known in the art. Examples of the property of an amino acid side chain that is desirably conserved include hydrophobic amino acids (A, I, L, M, F, P, W, Y and V), hydrophilic amino acids (R, D, N, C, E, Q, G, H, K, S and T), aliphatic side chains (G, A, V, L, I and P), hydroxyl group-containing side chains (S, T and Y), sulfur atom-containing side chains (C and M); carboxylic acid- and amide-containing side chains (D, N, E and Q), base-containing side chains (R, K and H), and functional groups of aromatic-containing side chains (H, F, Y and W) or side chains having characteristics of the functional group in common. In addition, the 8 groups described below comprise amino acids that are recognized to be mutually conservatively substituted, respectively in the art:

1) alanine (A) and glycine (G):
2) aspartic acid (D) and glutamic acid (E);
3) asparagine (N) and glutamine (Q):
4) arginine (R) and lysine (K);
5) isoleucine (I), leucine (L), methionine (M), and valine (V);
6) phenyl alanine (F), tyrosine (Y), and tryptophan (W);
7) serine (S) and threonine (T); and
8) cysteine (C) and methionine (M) (see, e.g., Creighton, Proteins 1984).

However, the substitution in the above-mentioned (a') to (c') is not limited thereto, and may be non-conservative substitution as long as the activity of inhibiting the binding of the ERAP1 polypeptide to the PHB2 polypeptide is maintained.

The peptide of the present invention may comprise amino acid residues besides the binding site to the PHB2 polypeptide in the ERAP1 polypeptide as long as the activity of inhibiting the binding of the ERAP1 polypeptide to the PHB2 polypeptide is maintained. For example, the fragment of the ERAP1 polypeptide comprising the binding site to the PHB2 polypeptide in the ERAP1 polypeptide is suitable as the peptide of the present invention. Thus, the fragment of the ERAP1 polypeptide (SEQ ID NO: 35) comprising the amino acid sequence from the glutamic acid at position 165 to the glutamic acid at position 173 and the surrounding sequence is a preferable example of the peptide of the present invention.

For example, examples of the ERAP1 peptide of the present invention may include peptides that comprise the amino acid sequence of SEQ ID NO: 31 (9 residues), and is constituted by amino acids of for example, 30 residues or less, or 20 residues or less, typically 19 residues or less, preferably 18 residues or less, more preferably 17 residues or less. Examples of such peptide may include peptides that comprise the amino acid sequence of SEQ ID NO: 31 (9 residues) and the amino acid sequence selected from full-length amino acid sequences constituting the ERAP1 polypeptide, and are constituted by amino acids of 30 residues or less, or 20 residues or less, typically 19 residues or less, preferably 18 residues or less, more preferably 17 residues or less.

In the preferred embodiments of the present invention, the amino acids that are added to the amino acid sequence of SEQ ID NO: 31 may be 0 (namely, the amino acid sequence consisting of SEQ ID NO: 31), or 1, or 2 or more successive amino acid sequences that are selected from full-length amino acid sequences constituting the ERAP1 polypeptide (SEQ ID NO: 35). The amino acid sequence of SEQ ID NO: 31 is an amino acid sequence comprising the glutamine at position 165/Q, the aspartic acid at position 169/D and the glutamine at position 173/Q of the full-length amino acid sequence constituting the ERAP1 polypeptide (SEQ ID NO: 35). Thus, in the preferred embodiments of the present invention, the amino acid residues or amino acid sequences that are added to SEQ ID NO: 31 may be selected from amino acid sequences adjacent to 165-173 in the amino acid sequence of SEQ ID NO: 35. In other words, the ERAP1 peptide of the present invention is preferably a peptide comprising the amino acid sequence described in SEQ ID NO: 31/QMLSDLTLQ, and consisting of a successive amino acid sequence selected from the amino acid sequences consisting of ATLS+QMLSDLTLQ+LRQR (corresponding to a region covered by SEQ ID NO: 27 and SEQ ID NO: 30).

The peptide of the present invention desirably has either one or both of the properties (i) and (ii) described below in addition to the activity of inhibiting the binding of the ERAP1 polypeptide to the PHB2 polypeptide:

(i) property of promoting nuclear translocation of the PHB2 polypeptide in estrogen receptor-positive cells in which the ERAP1 polypeptide is expressed; and (ii) property of promoting the binding of the estrogen receptor present in the nucleus and/or on the cell membrane to the PHB2 polypeptide in estrogen receptor-positive cells in which the ERAP1 polypeptide is expressed.

Figure 3:
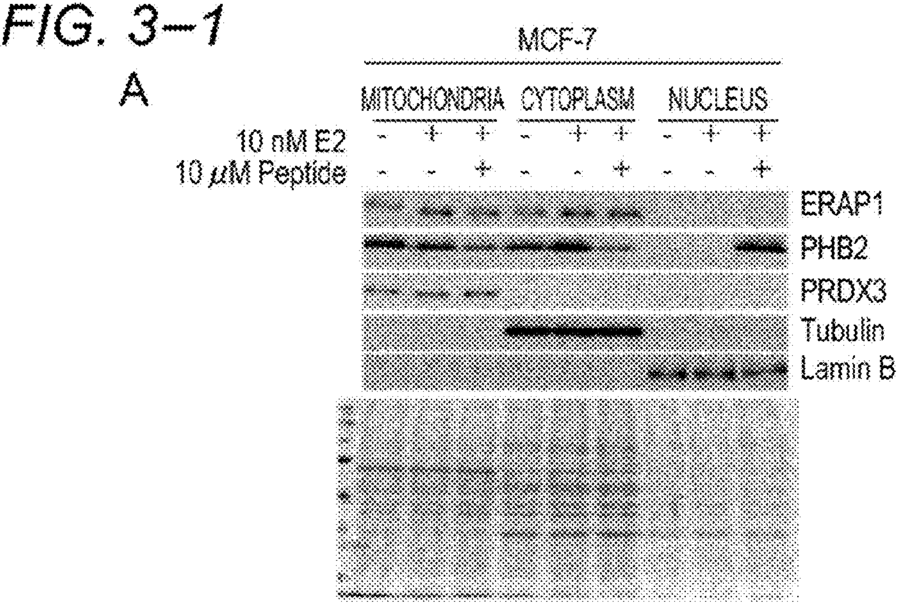
Figure 1:
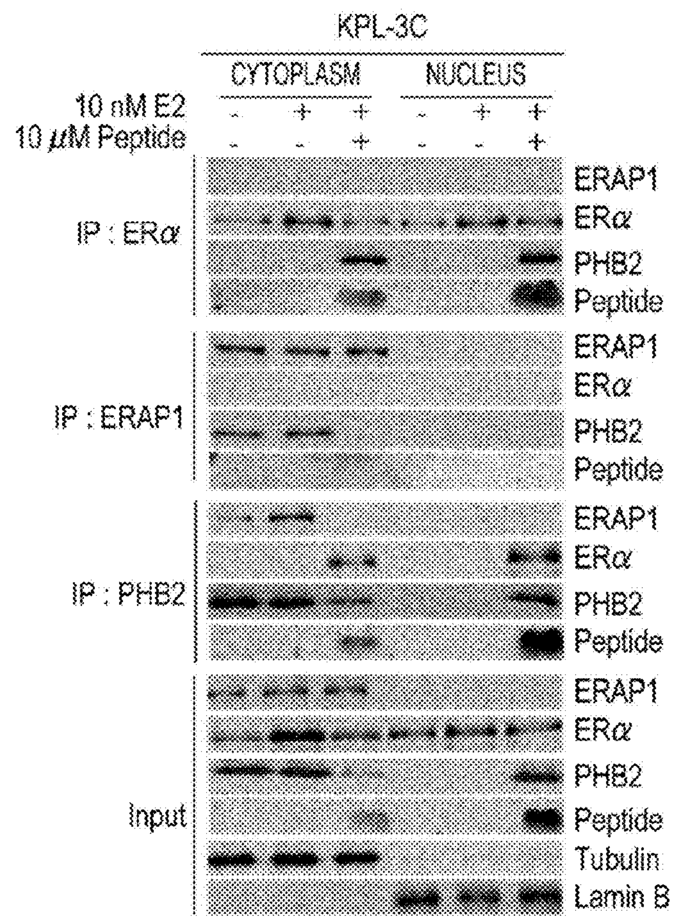
Figure 3:
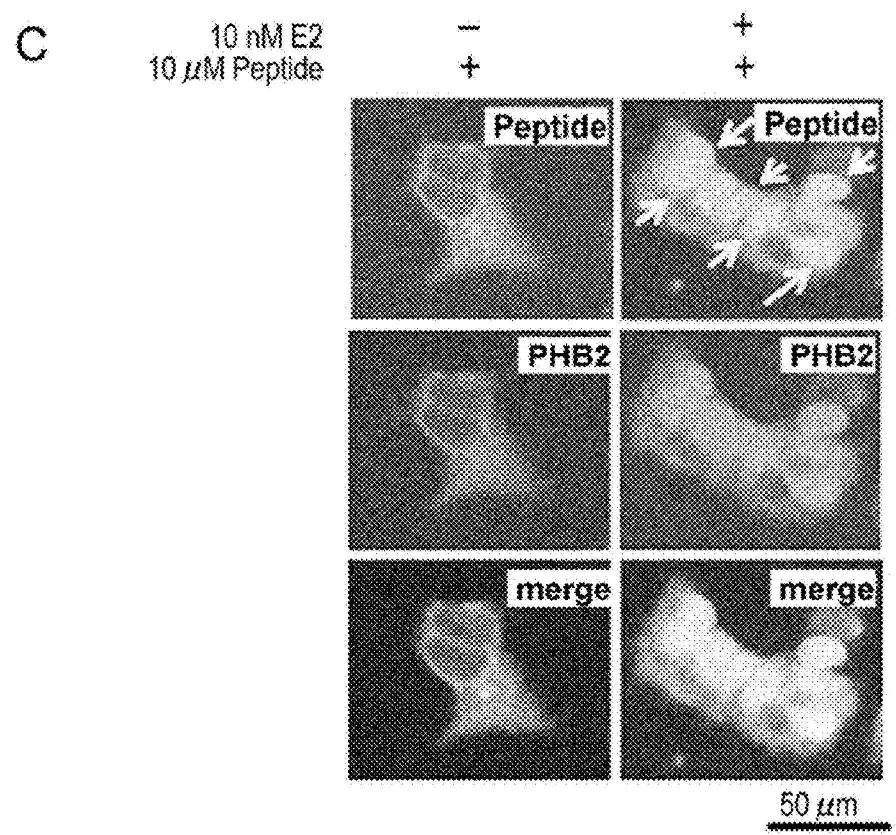
Figure 2:
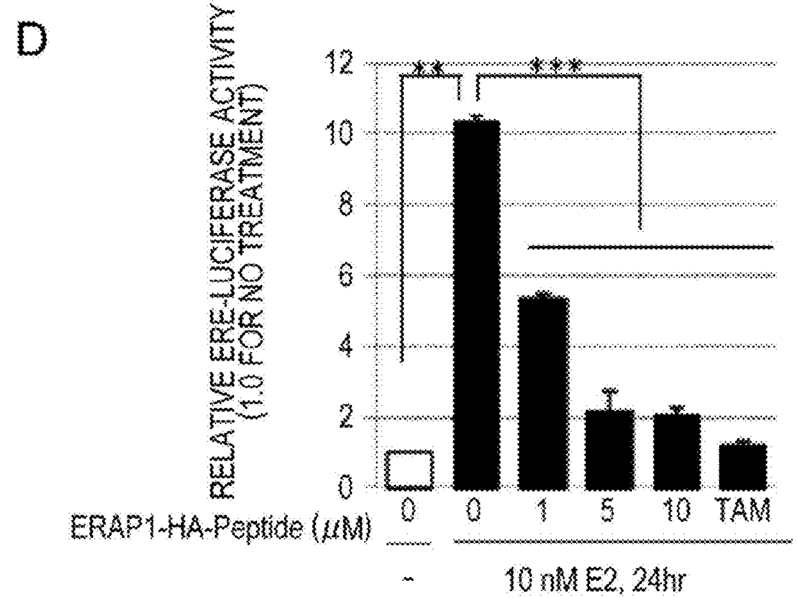
Figure 3:
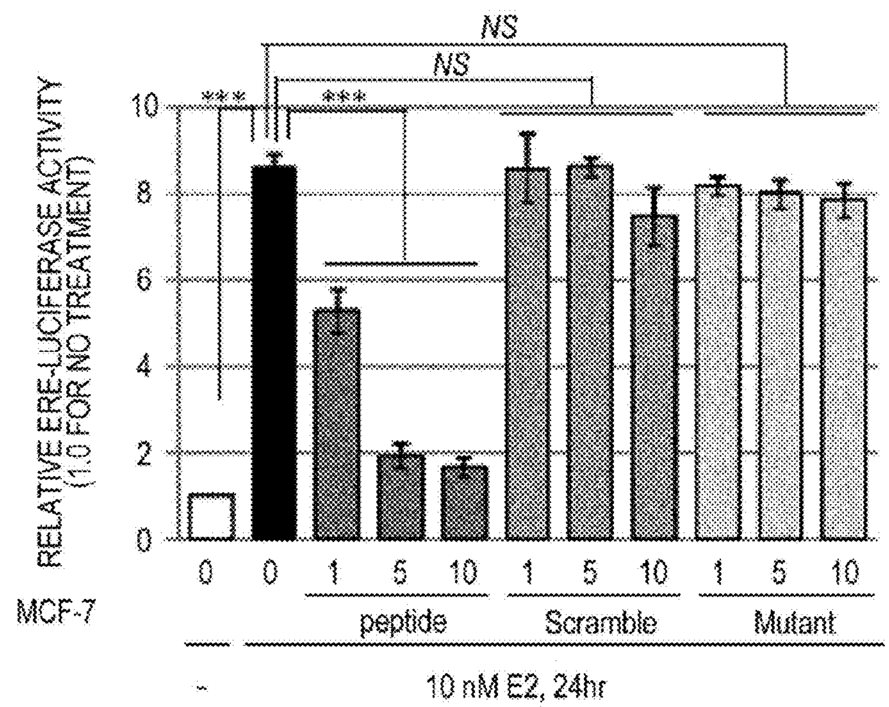
Figure 3:
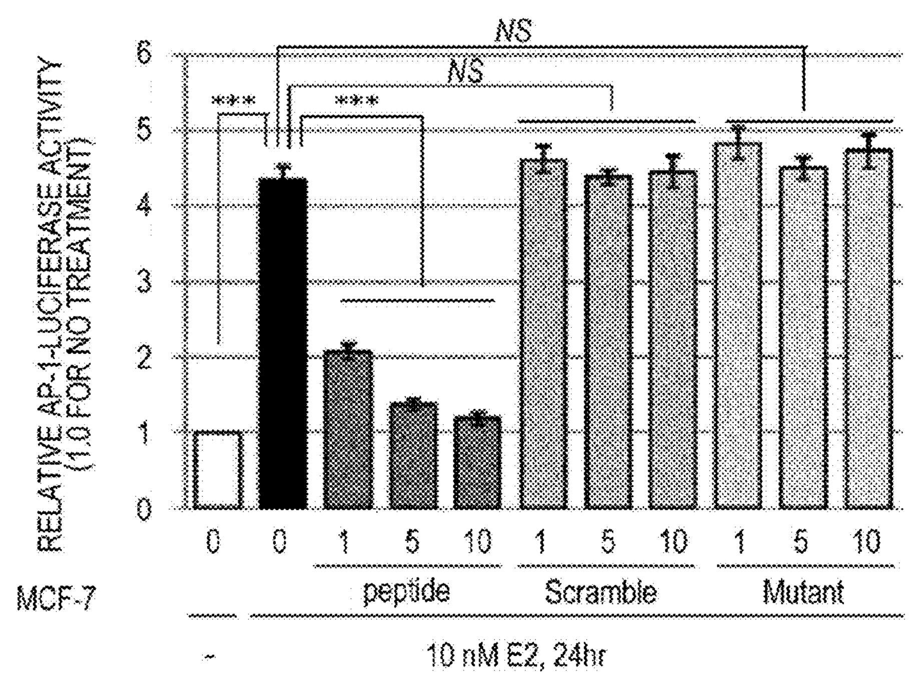
Figure 3:
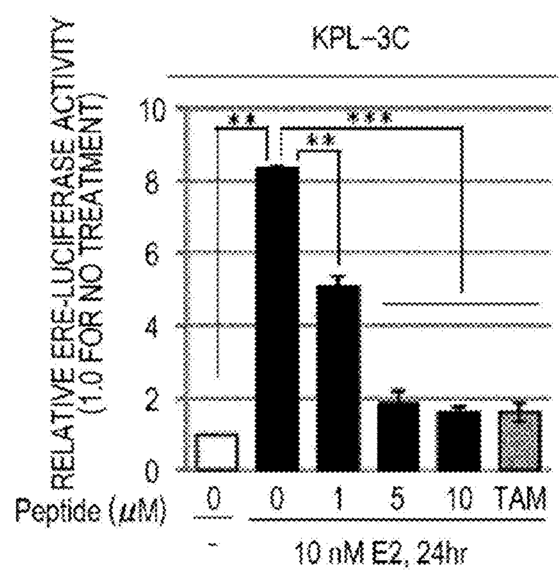
Figure 4:
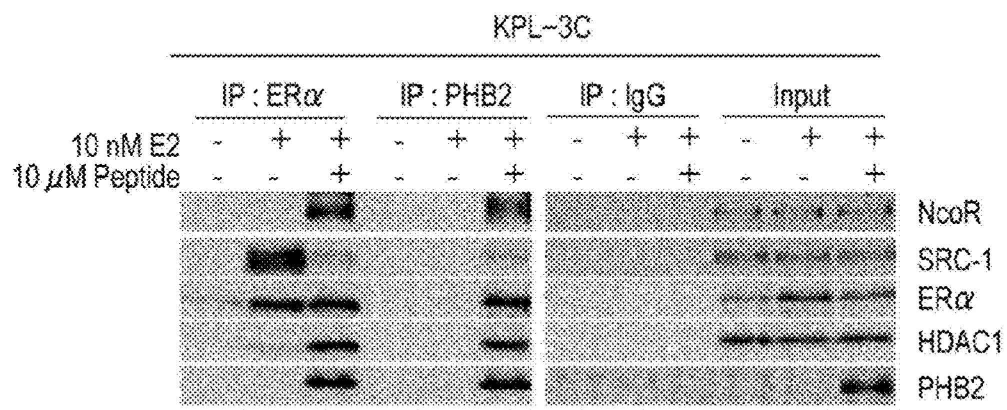
Figure 4:
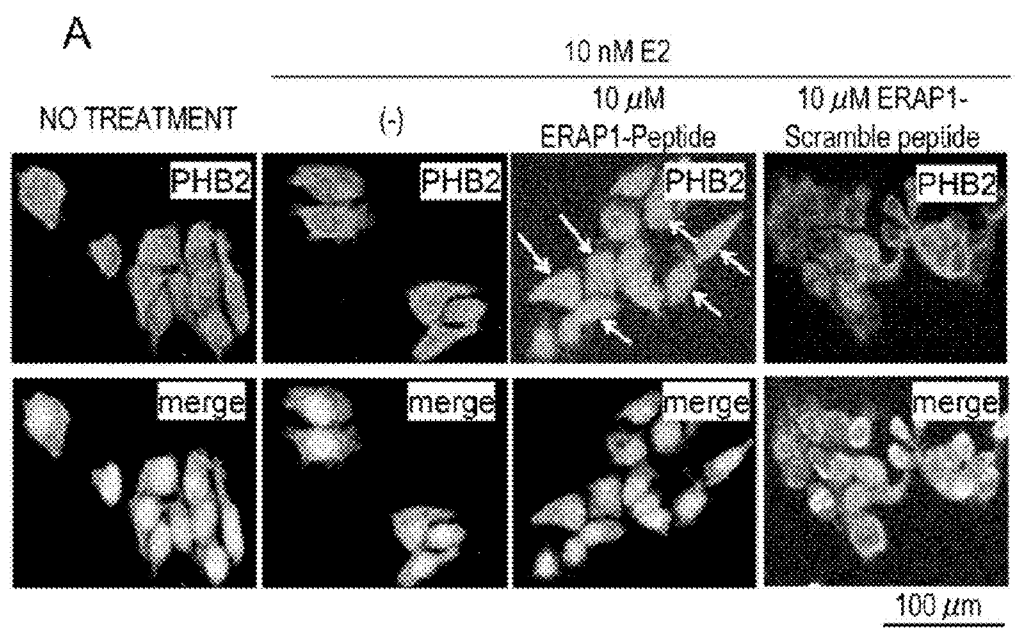
Figure 1:
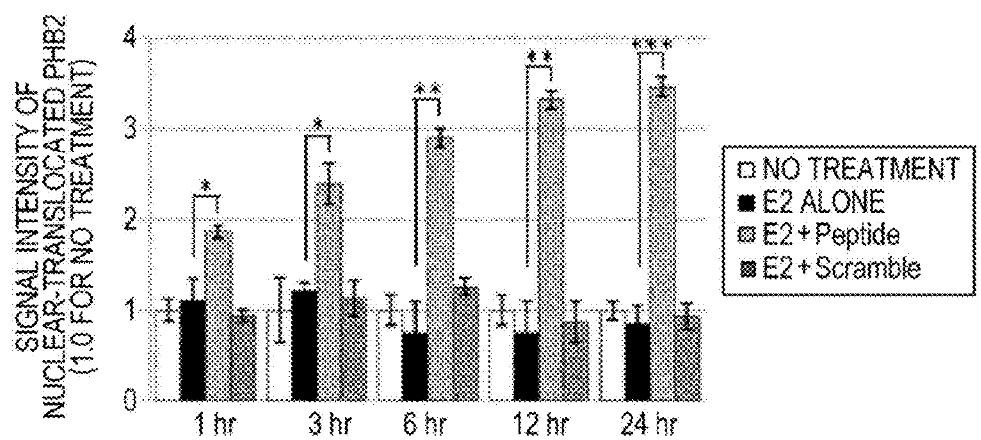
Figure 4:
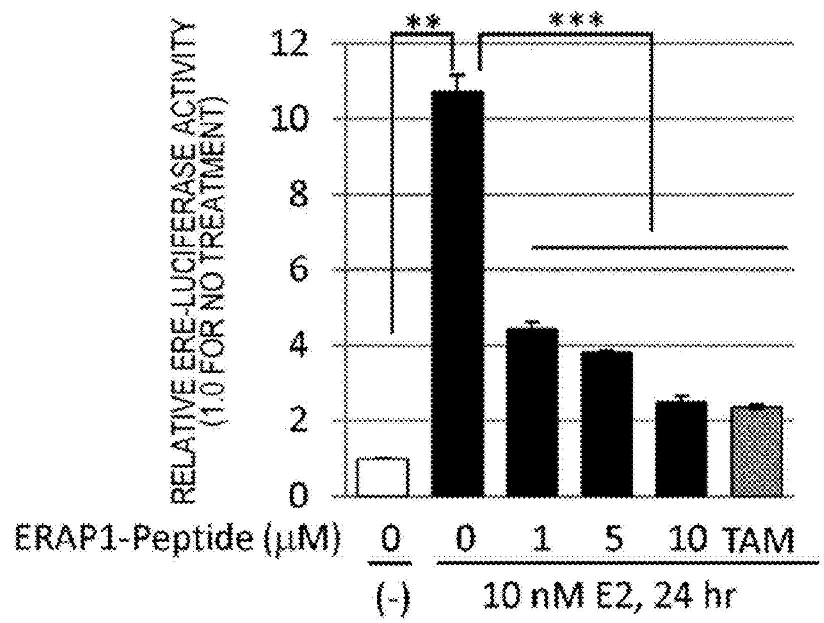
Figure 3:
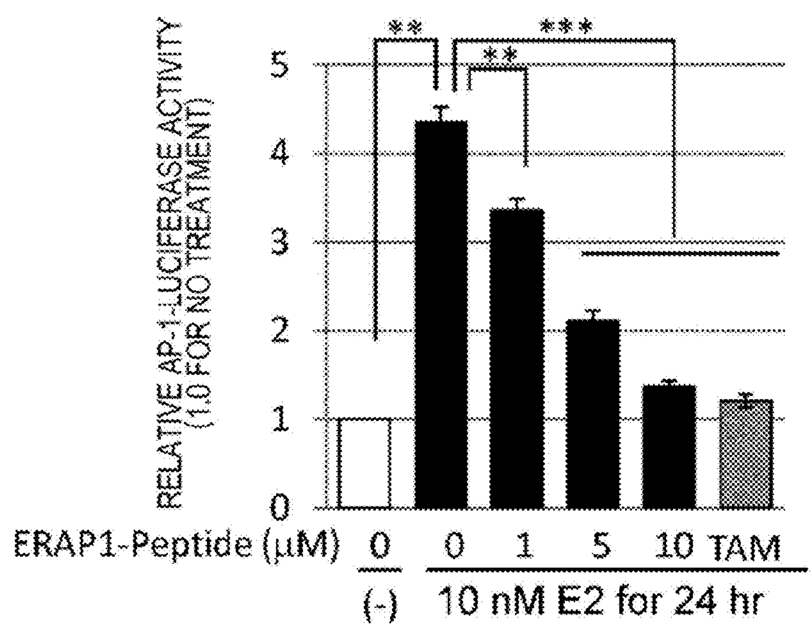
Figure 4:
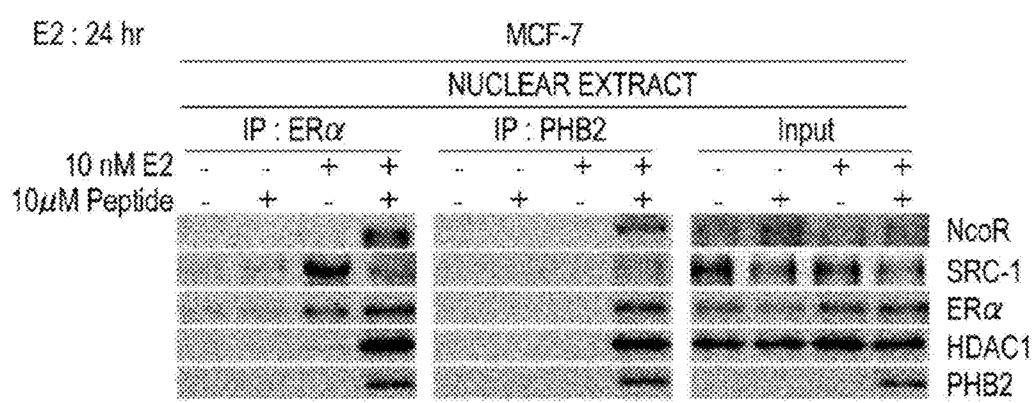
Figure 4:
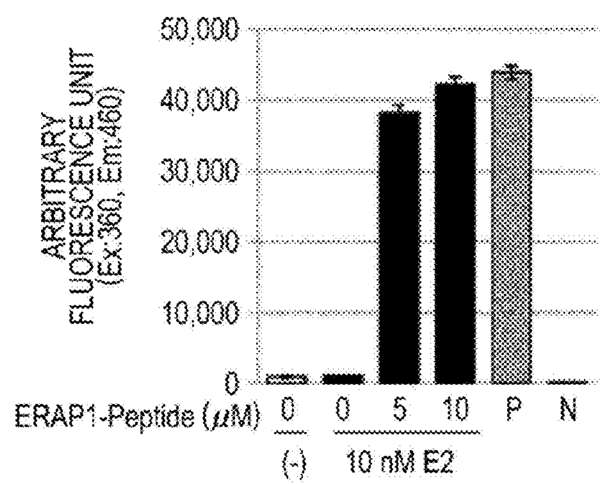
Figure 4:
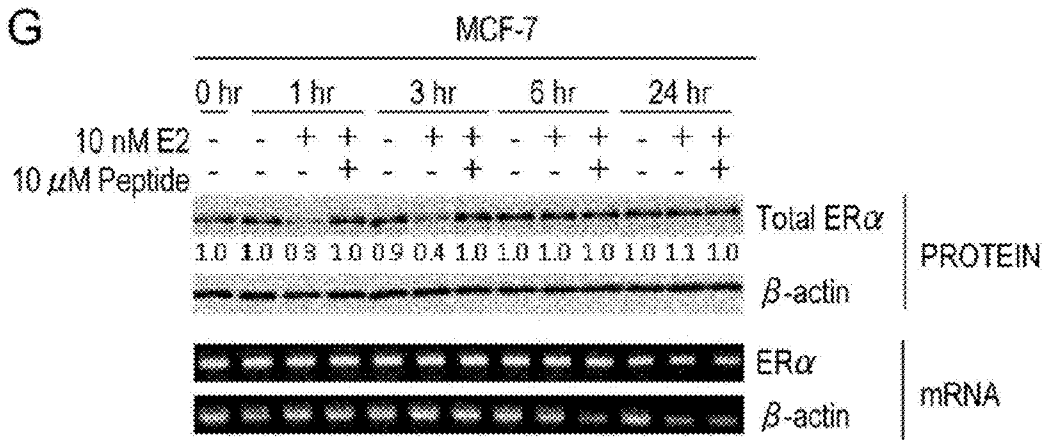

By having either one or both of the properties (i) and (ii) mentioned above, the peptide of the present invention suppresses activation of estrogen receptor in the ERAP1-expressed cell. As a result, the peptide of the present invention leads to suppression for cell proliferation of estrogen receptor-positive cells. The above-mentioned properties (i) and (ii) of the ERAP1 peptide can be evaluated in accordance with the methods described in Examples described later The PHB2 polypeptide is known to be a selective co-regulator for an estrogen receptor, and suppresses the transcriptional activation of the estrogen receptor by the interaction with the estrogen receptor (Kasashima K, J Biol Chem 2006; 281: 36401-10). On the other hand, the ERAP1 polypeptide disturbs nuclear translocation of the PHB2 polypeptide, and inhibits the interaction between the PHB2 polypeptide and the estrogen receptor in the nucleus by binding to the PHB2 polypeptide (FIGS. 3A, 3B, 4A and 4B). In addition, the ERAP1 polypeptide disturbs the binding of the estrogen receptor present on the cell membrane to the PHB2 polypeptide (FIGS. 3A, 3B and 4B). As results of these actions, in cells in which the ERAP1 polypeptide is excessively expressed, suppression for activation of estrogen receptor by the PHB2 polypeptide does not sufficiently work, and acceleration of the cell proliferation is induced.

The peptide of the present invention is characterized by a point that the peptide of the present invention competitively inhibits the binding of the ERAP1 polypeptide to the PHB2 polypeptide, and thus recovers the estrogen receptor activation-suppression function of the PHB2 polypeptide inhibited by the binding to the ERAP1 polypeptide. Thus, the peptide of the present invention desirably does not disturb nuclear translocation of the PHB2 polypeptide, and does not disturb the binding of the estrogen receptor to the PHB2 polypeptide. As described above, the fragment of the ERAP1 polypeptide comprising the binding site to the PHB2 polypeptide is suitable as the peptide of the present invention. However, a peptide close to the full-length of the ERAP1 polypeptide is likely to disturb nuclear translocation of the PHB2 polypeptide, or disturb the binding of the PHB2 polypeptide to the estrogen receptor although the degree is not as much as that of the ERAP1 polypeptide. Accordingly, the partial amino acid sequence of the ERAP1 polypeptide contained in the peptide of the present invention has preferably 100 residues or less, more preferably 80 residues or less, and further preferably 70 residues or less. In the more preferred embodiments, the partial amino acid sequence of the ERAP1 polypeptide contained in the peptide of the present invention has 50 residues or less, 40 residues or less, 30 residues or less, 25 residues or less, or 20 residues or less.

In addition, the peptide of the present invention may comprise other amino acid sequences than the amino acid sequence derived from the ERAP1 polypeptide as long as the activity of inhibiting the binding of the ERAP1 polypeptide to the PHB2 polypeptide is maintained. Also in this case, the peptide of the present invention desirably does not disturb nuclear translocation of the PHB2 polypeptide, and the binding of the PHB2 polypeptide to the estrogen receptor. Thus, the peptide of the present invention is preferably a peptide of 100 residues or less, 80 residues or less, or 70 residues or less. In the more preferred embodiments, the peptide of the present invention is a peptide of 50 residues or less, 40 residues or less, or 30 residues or less. Preferred examples of the amino acid sequence contained in the peptide of the present invention include amino acid sequences that constitute the transcellular peptide described later, and linker sequences for binding to other substances, but are not limited thereto.

In addition, the peptide of the present invention may be modified by other substances. Herein, the term "modified" used with respect to a peptide refers that other substance binds to the peptide directly or indirectly. Examples of the other substance modifying the peptide of the present invention include peptides, lipids, saccharides, and naturally occurring or synthetic polymers, but are not limited thereto. The peptide of the present invention may have any modification as long as the activity of inhibiting the binding of the ERAP1 polypeptide to the PHB2 polypeptide is maintained. In addition, the peptide of the present invention may be imparted additional function by the modification. Examples of the additional function include target-directing property, stability, and cell membrane permeability, but are not limited thereto.

Preferred examples of the modification in the present invention include introduction of a cell membrane permeable substance. The intracellular structure is commonly shielded from the external environment by a cell membrane. Thus, it is difficult to effectively introduce an extracellular substance into a cell. However, a certain substance has cell membrane permeability, and can be introduced into a cell without being blocked by a cell membrane. A substance not having cell membrane permeability can be imparted the cell membrane permeability by being modified with such a substance having cell membrane permeability (cell membrane permeable substance). Thus, the peptide of the present invention can be modified with a cell membrane permeable substance whereby to be effectively introduced into a cell. Furthermore, herein, "cell membrane permeability" refers to a property of permeating a cell membrane of a mammal to enter the cytoplasm. In addition, "cell membrane permeable substance" refers to a substance having the "cell membrane permeability".

Examples of the cell membrane permeable substance include membrane fusion liposomes, and cell membrane permeable peptides, but are not limited thereto. For example, the membrane fusion liposome is fused with a cell membrane, whereby to release the contents into the cell. The membrane fusion liposome can be prepared, for example, by modifying the liposome surface with a substance having membrane fusion property. Examples of the membrane fusion liposome include pH-sensitive liposome (Yuba E, et at, J. Control. Release, 149, 72-80 (2011)), Sendai virus membrane fusion liposome (WO97/016171), modified liposome with a cell membrane permeable peptide, and the like. The peptide of the present invention may be enclosed in the membrane fusion liposome for being effectively introduced into the cell. The enclosure of the peptide into the membrane fusion liposome is also encompassed in the "modification" of the peptide in the present invention.

With respect to the cell membrane permeable peptide, various naturally occurring or artificially synthesized peptides have been reported so far (Joliot A. & Prochian. A., Nat Cell Biol. 2004; 6: 189-96). Examples of the cell membrane permeable peptide include the peptides described below, but are not limited thereto.

Polyarginine (Matsushita et al., (2003) J. Neurosci.; 21, 6000-7.)

```
                                        (SEQ ID NO: 42)
Tat/RKKRRQRRR
(Frankel et al., (1988) Cel. 55, 1189-93.,
Green & Loewenstein (1988) Cell 55, 1179-88.);

                                        (SEQ ID NO: 57)
Penetratin/RQIKIWFQNRRMKWKK
(Derossi et al., (1994) J. Biol. Chem. 269,
10444-50.);

                                        (SEQ ID NO: 43)
Buforin II/TRSSRAGLQFPVCRVHRLLRK
(Park et al., (2000) Proc. Natl Acad. Sci. U.S.A.
97, 8245-50.);

                                        (SEQ ID NO: 44)
Transportan/GWTLNSAGYLLGKINLKALAALAKKIL
(Pooga et al., (1998) FASEB J. 12, 67-77.);

                                        (SEQ ID NO: 45)
MAP (Model Amphipathic Peptide)/KLALKLALKALKAALKLA
(Oehlke et al., (1998) Biochim. Biophys.
Acta. 1414, 127-39.);

                                        (SEQ ID NO: 46)
K-FGF/AAVALLPAVLLALLAP
(Lin et al., (1995) J. Biol. Chem. 270, 14255-8.);

                                        (SEQ ID NO: 47)
Ku70/VPMLK
(Sawada et al., (2003) Nature Cell Biol. 5,
352-7.);

                                        (SEQ ID NO: 48)
Ku70/PMLKE
(Sawada et al., (2003) Nature Cell Biol. 5,
352-7.);
```

-continued (SEQ ID NO: 49)
Prion/MANLGYWLLALFVTMWTDVGLCKKRPKP
(Lundberg et al., (2003) Biochem. Biophys. Res. Commun. 299, 85-90.);

(SEQ ID NO: 50)
pVEC/LLIILARRIRKQAHAHSK
(Elmquist et al., (2001) Exp. Cell Res. 269, 237-44):

(SEQ ID NO: 51)
Pep-1/KETWWETWWTEWSQPKKKRKV
(Morris et al., (2001) Nature Biotechnol. 19, 1173-6.);

(SEQ ID NO: 52)
SynB1/RGGRLSYSRRRFSTSTGR
(Rousselle et al., (2000) Mol. Pharmacol. 57, 679-86.);

(SEQ ID NO: 53)
Pep-7/SDLWEMMMVSLACQY
(Gao et al., (2002) Bioorg. Med. Chem. 10, 4057-65.);
and (SEQ ID NO: 54)
HN-1/TSPLNIHNGQKL;
(Hong & Clayman (2000) Cancer Res. 60, 6551-6).

The polyarginine mentioned above can be constituted from any number of arginine residues. For example, the polyarginine can be constituted from 5 to 20 arginine residues. The number of the arginine residues that constitute the polyarginine is not particularly limited as long as the activity of the present peptide of inhibiting the binding of the ERAP1 polypeptide to the PHB2 polypeptide is not disturbed, but, generally, a polyarginine consisting of 11 arginine residues (SEQ ID NO: 55) is often used.

The peptide of the present invention modified with the cell membrane permeable substance may be represented by the general formula described below:

[R]-[D]

In the formula, [R] represents a cell membrane permeable substance, and [D] represents "a peptide that inhibits the binding of the ERAP1 polypeptide to the PHB2 polypeptide, which comprises the binding site to the PHB2 polypeptide in the ERAP1 polypeptide". In the above-mentioned general formula, [R] and [D] may be directly linked, or indirectly linked through a linker and the like. When [R] and [D] are indirectly linked, a peptide, a compound having multiple functional groups, or the like may be used as a linker. For example, when [R] is a cell membrane permeable peptide, preferred examples of the linker include linkers consisting of glycine residues. The number of the glycine residues that constitute the linker is not particularly limited, but preferably 1 to 10 residues, more preferably 2 to 7 residues, and further preferably 3 to 5 residues. In addition, the cell membrane permeable substance may be indirectly linked to the "peptide that comprises the binding site to the PHB2 polypeptide in the ERAP1 polypeptide and inhibits the binding of the ERAP1 polypeptide to the PHB2 polypeptide" by being bonded to the surface of microparticles. [R] may be linked to any position of [D]. Examples of the position linked to [R] include the N-terminal or C terminal of [D] and side chains of amino acid residues that constitute [D]. Preferably, [R] is directly linked to the N-terminal or C terminal of [D], or indirectly linked through a linker. Furthermore, multiple [R] molecules may be linked to one [D] molecule. In this case, [R] molecule may be introduced into multiple different positions of [D] molecule. Alternatively, [D] may be modified with multiple [R] linked to each other.

In addition, it is known in the art that particularly useful various amino acid mimetics or non-naturally occurring amino acids are introduced in order to enhance in vivo stability of the peptide. Thus, such amino acid mimetics or non-naturally occurring amino acids may be introduced in order to enhance in vivo stability of the peptide of the present invention. The stability of the peptide may be confirmed using various biological culture mediums such as peptidase as well as human blood plasma and serum (e.g., see Coos Verhoef et al. (1986) Eur. J. Drug Metab Pharmacokin. 11: 291-302).

The peptide of the present invention is characterized by a point of having an activity of inhibiting the binding of the ERAP1 polypeptide to the PHB2 polypeptide. Whether the constructed peptide has an activity of inhibiting the binding of the ERAP1 polypeptide to the PHB2 polypeptide or not can be confirmed by comparing the binding levels of the ERAP1 polypeptide to the PHB2 polypeptide in the presence and in the absence of the peptide. Namely, when the binding level in the presence of the peptide is lower than the binding level in the absence of the peptide, the peptide can be determined to have "activity of inhibiting the binding of the ERAP1 polypeptide to the PHB2 polypeptide".

Measurement for the binding level of the ERAP1 polypeptide to the PHB2 polypeptide may be performed using various known methods. For example, the methods include immunoprecipitation using an anti-ERAP1 antibody or an anti-PHB2 antibody, affinity chromatography, and a biosensor using surface plasmon resonance phenomena.

As a specific method, for example, the ERAP1 polypeptide and the PHB2 polypeptide are incubated in the presence and in the absence of the test peptide. Then, the reaction solution is immunoprecipitated with anti-ERAP1 antibody or anti-PHB2 antibody. Furthermore, Western blotting analysis of the immunoprecipitate is performed. The binding level of the ERAP1 polypeptide to the PHB2 polypeptide can be confirmed by detecting at least one of the level of PHB2 polypeptide immunoprecipitated with anti-ERAP1 antibody or the level of ERAP1 polypeptide immunoprecipitated with anti-PHB2 antibody. The ERAP1 polypeptide and the PHB2 polypeptide used herein may be prepared by a known genetic engineering technique. In addition, the cell lysate of cells producing these polypeptides may be also used. As the cells producing these polypeptides, the cell lines as described in Examples of the specification may be used.

Alternatively, the methods as described in Examples of the specification may be used. Specifically, in the presence and in the absence of the test peptide, the estrogen receptor-positive cells are cultured. Then, the cells are lysed with an appropriate lysis buffer. Then, immunoprecipitation and Western blotting analysis may be performed using the cell lysate similarly as described above.

A peptide confirmed to have "activity of inhibiting the binding of the ERAP1 polypeptide to the PHB2 polypeptide" by any of the above-mentioned methods is determined as a peptide having "activity of inhibiting the binding of the ERAP1 polypeptide to the PHB2 polypeptide".

In addition, the peptide of the present invention may have either one or both of the properties (i) and (ii) described below as a desirable property:

(i) property of promoting nuclear translocation of the PHB2 polypeptide in the estrogen receptor-positive cells in which the ERAP1 polypeptide is expressed; and (ii) property of promoting the binding of the estrogen receptor present in the nucleus and/or on the cell membrane to the PHB2 polypeptide in the estrogen receptor-positive cells in which the ERAP1 polypeptide is expressed.

Whether or not the peptide of the present invention has the above-mentioned property can be confirmed by comparing (i) the level of nuclear translocation of the PHB2 polypeptide, and/or (ii) the level of the binding of the estrogen receptor to the PHB2 polypeptide in the presence and in the absence of the peptide of in the present invention. Namely, when the level in the presence of the peptide of the present invention is higher than the level in the absence of the peptide of the present invention, the peptide of the present invention can be determined to have the properties of the above-mentioned (i) and/or (ii).

As a specific method, for example, the method as described in Examples of the specification may be used. Specifically, when the property of the above-mentioned (i) is investigated, the estrogen receptor-positive cells are stimulated with estradiol for 24 hours with addition or without addition of the peptide of the present invention. Then, the cells are fractionated by specific gravity centrifugation. Then, the PHB2 polypeptide present in the nuclear fraction is detected by Western blotting analysis and the like. When the polypeptide level of the PHB2 polypeptide detected in the nuclear fraction increases in a case where the peptide of the present invention is added in comparison to a case where the peptide of the present invention is not added, it is determined that the peptide of the present invention has the property of the above-mentioned (i). In addition, the level of the PHB2 polypeptide present in the nucleus may be also detected by the immunochemical staining as described in Examples of the specification.

When the property of the above-mentioned (ii) is investigated, the estrogen receptor-positive cells are stimulated estradiol with for 24 hours, with addition or without addition of the peptide of the present invention. Then, the cells are fractionated by specific gravity centrifugation. Then, the cytoplasm and nuclear fractions are immunoprecipitated with anti-estrogen receptor antibody or anti-PHB2 antibody. Furthermore, Western blotting analysis of the immunoprecipitate is performed. As a result, when the binding level of the estrogen receptor to the PHB2 polypeptide increases in the cytoplasm fraction and/or the nuclear fraction in a case where the peptide of the present invention is added in comparison to a case where the peptide of the present invention is not added, it is determined that the peptide of the present invention has the properly of the above-mentioned (ii).

The peptide of the present invention can be manufactured using a method well known to one of ordinary skill in the art. For example, the peptide of the present invention can be obtained by chemical synthesis based on the amino acid sequence. The method for chemically synthesizing the peptide is known, and the peptide of the present invention can be chemically synthesized based on an amino acid sequence selected as the peptide of the present invention by one of ordinary skill in the art. The method for chemically synthesizing the peptide is described in, for example, the documents as described below;

(i) Peptide Synthesis, interscience, New York, 1966;

(ii) The Proteins, Vol. 2, Academic Press, New York, 1976;

(iii) Peptide synthesis, Maruzen Co., Ltd., 1975;

(iv) Fundamentals and Experiment of Peptide synthesis, Maruzen Co., Ltd., 1985;

(v) Development of Pharmaceuticals (second volume) (in Japanese), Vol. 14 (peptide synthesis), Hirokawa, 1991;

(vi) WO99/67288: and (vii) Barany G. & Merrifield R. B., Peptides Vol. 2, "Solid Phase Peptide Synthesis", Academic Press, New York, 1980, 100-118.

In addition, the peptide of the present invention may be obtained by genetic engineering technique (e.g., Morrison J, J Bacteriology 1977, 132: 349-51; Clark-Curtiss & Curtiss, Methods in Enzymology (eds. Wu et al.) 1983, 101: 347-62). For example, a polynucleotide encoding the peptide of the present invention is inserted into an appropriate expression vector, and the vector is introduced into an appropriate host cell to prepare a transformed cell. Then, the host cells are cultured to produce the peptide of the present invention, and the cell extract is prepared. In purification of the present peptide from the cell extract, a standard technique for purification of a protein may be used. For example, the present peptide may be purified by appropriately selecting and combining column chromatography, filter filtration, ultrafiltration, salting out, solvent precipitation, solvent extraction, distillation, immunoprecipitation, SDS-polyacrylic amide gel electrophoresis, isoelectric point electrophoresis, dialysis, and recrystallization. In addition, the peptide of the present invention may be also synthesized by an in vitro translation system in which elements necessary for protein synthesis are reconstituted in vitro.

When a genetic engineering technique is used, the peptide of the present invention may be also expressed as a fusion protein with other peptide. A polynucleotide encoding the peptide of the present invention and a polynucleotide encoding the other peptide are linked to become an inframe, and inserted into an appropriate expression vector, and the vector is introduced into an appropriate host cell, and the transformed cells are prepared. Then, the host cells are cultured to produce a fusion protein of the peptide of the present invention with the other peptide, and the cell extract is prepared. Purification of the fusion protein from the cell extract may be performed, for example, by capturing the fusion protein with an affinity chromatography using a column to which a substance having affinity to the fusion protein is bound. In addition, if the peptide of the present invention and the other peptide are bound in advance through a linker sequence that can be cut by an enzyme such as peptidase, protease and proteasome, the fusion protein captured on the column can be treated with these enzymes to separate the peptide of the present invention from the column. Examples of the other peptide that can be used in formation of the fusion protein include peptides as described below, but are not limited thereto:

FLAG (Hopp et al, (1988) BioTechnology 6, 1204-10);

6×His or 10×His consisting of histidine (His) residues:

Influenza hemagglutinin (HA);

Human c-myc fragment, VSV-GP fragment; p18 HIV fragment;

T7 tag; HSV tag;

E tag: SV40 T antigen fragment:

Ick tag;

α-tubulin fragment;

B tag;

Protein C fragment;

GST (glutathione-S-transferase);

HA (influenza hemagglutinin)

immunoglobulin constant region;

β-galactosidase; and;

MBP (maltose-binding protein).

2. Polynucleotide Encoding the Peptide of the Present Invention, Vector, and Host Cell The present invention also provides a polynucleotide encoding the peptide of the present invention. In addition, the present invention also provides a vector comprising the polynucleotide, and a host cell comprising the vector. The polynucleotide, the vector, and the host cell may be used for manufacturing the peptide of the present invention.

The polynucleotide of the present invention may be manufactured by a method known to one of ordinary skill in the art. For example, the polynucleotide of the present invention can be synthesized using solid phase techniques such as those described in Beaucage S L & Iyer R P, Tetrahedron 1992, 48: 2223-311; and Matthes et al., EMBO J 1984, 3: 801-5. In addition, the polynucleotide of the present invention may be also prepared using a genetic engineering technique. For example, a primer is constructed based on a partial base sequence of the ERAP1 gene encoding the amino acid sequence selected as the peptide of the present invention (SEQ ID NO: 34), and reverse transcription PCR is performed using mRNA extracted from cells expressing the ERAP1 polypeptide as a template. This enables amplification of the polynucleotide of the present invention.

The polynucleotide of the present invention is inserted into an appropriate expression vector, and the vector may be introduced into an appropriate host cell, to produce the peptide of the present invention in the host cell.

For example, when *Escherichia coli* is selected as a host cell, and a vector is amplified in a large quantity in the *Escherichia coli* (e.g., JMI09, DH5α, HB101, or XL1Blue), the vector needs to have "ori" for amplification in *Escherichia coli*, and a marker gene for selection of the transformed *Escherichia coli* (e.g., drug-resistant gene selected by a drug such as ampicillin, tetracycline, kanamycin and chloramphenicol). For example, a vector of M13 series, a vector of pUC series, pBR322, pBluescript, or pCR-Script may be used. When a vector is used for production of the peptide of the present invention, an expression vector is particularly useful. For example, an expression vector for expression in *Escherichia coli* needs to have the above-mentioned characteristics for amplification in *Escherichia coli*. When an *Escherichia coli* such as JM109, DH5α, HB101, or XL1Blue is used as a host cell, the vector needs to have a promoter that can effectively express a desired gene in *Escherichia coli*, for example, lacZ promoter (Ward, et al., Nature 341: 544-6 (1989); FASEB J 6: 2422-7 (1992)), araB promoter (Better, et al., Science 240: 1041-3 (1988)), or T7 promoter. Furthermore, the vector can also comprise a signal sequence for secretion of the polypeptide. One example of the signal sequence commanding secretion of the polypeptide to the periplasm of *Escherichia coli* is pelB signal sequence (Lei, et al., J Bacteriol 169: 4379-83 (1987)). Examples of means for introducing the vector into a target host cell include a calcium chloride method and an electroporation method.

Besides *Escherichia coli*, for example, useful vectors include mammal cell-derived expression vectors (e.g., pcDNA3 (Invitrogen) and pEGF-BOS (Mizushima S., Nucleic Acids Res 18(17): 5322 (1990)), pEF, pCDM8), insect cell-derived expression vectors (e.g., "Bac-to-BAC vaculovirus expression system" (GIBCO BRL), pBacPAK8), plant-derived expression vectors (e.g., pMH1, pMH2), animal virus-derived expression vectors (e.g., pHSV, pMV, pAdexLcw), retrovirus-derived expression vectors (e.g., pZIpneo), yeast-derived expression vectors (e.g., "*Pichia* expression kit" (Invitrogen), pNVII, SP-Q01), and *Bacillus subtilis*-derived expression vectors (e.g., pPL608, pKTH50).

In order to express a vector in animal cells such as CHO cells, COS cells or NIH3T3 cells, the vector needs to have a promoter necessary for expression in this kind of cells, for example, SV40 promoter (Mulligan, et al., Nature 277: 108-14 (1979)), MMLV-LTR promoter, EF1α promoter (Mizushima, et al., Nucleic Acids Res 18: 5322 (1990)) or CMV promoter. In addition, the vector preferably has a marker gene for selecting a transformant (e.g. a drug-resistant gene selected by a drug (e.g., neomycin, G418)). Examples of known vectors having these characteristics include pMAM, pDR2, pBK-RSV, pBK-CMV, pOPRSV, and pOP13.

In addition, the polynucleotide of the present invention may be inserted into an appropriate vector, and introduced into a target cell for production of the peptide of the present invention in a target cell. The peptide of the present invention produced in the target cell inhibits the binding of the ERAP1 polypeptide to the PHB2 polypeptide, and induces suppression for the cell proliferation of the target cell. In this case, a vector into which the polynucleotide the polynucleotide of the present invention is inserted, may be a vector for stably inserting the polynucleotide of the present invention into the genome of the target cell (e.g., see Thomas K R & Capecchi M R, Cell 1987, 51: 503-12 with respect to description of a homologous recombinant cassette vector). For example, see Wolff et al., Science 1990, 247: 1465-8; U.S. Pat. No. 5,580,895; U.S. Pat. No. 5,589,466: U.S. Pat. No. 5,804,566; U.S. Pat. No. 5,739,118; U.S. Pat. No. 5,736,524; U.S. Pat. No. 5,679,647; and WO98/04720, In addition, the polynucleotide of the present invention may be also inserted into an expression vector such as a viral vector or a bacterial vector. Examples of the expression vector include attenuated virus hosts such as cowpox or avianpox (e.g., see U.S. Pat. No. 4,722,858). Other examples of the vector that may be used, include Bacille Calmette Guerin (BCG) (Stover et al., Nature 1991, 351: 456-60). Other examples include adenovirus vectors and adeno-associated virus vectors, retrovirus vectors, *Salmonella typhi* vectors, detoxicated anthrax toxin vectors, etc. (Shata et al., Mol Med Today 2000, 6: 66-71: Shedlock et al. J Lekoc Biol 2000, 68: 793-806; and Hipp et al., In Vivo 2000, 14: 571-85).

3. Pharmaceutical Composition Comprising the Peptide or Polynucleotide of the Present Invention and Use Thereof The present invention also provides a pharmaceutical composition comprising the peptide of the present invention or a polynucleotide encoding the peptide of the present invention.

The peptide of the present invention inhibits the binding of ERAP1 polypeptide to PHB2 polypeptide, and thus induces suppression for activation of estrogen receptor by the PHB2 polypeptide. As a result, the peptide of the present invention leads to suppression for cell proliferation in estrogen receptor-positive cells. Thus, the pharmaceutical composition of the present invention is useful for treating and/or preventing cell proliferative diseases due to activation of estrogen receptor. Examples of such cell proliferative disease include cancers.

It is known that particularly breast cancer among cancers is deeply related to activation of estrogen receptor. An ERAP1 polypeptide is a novel regulation factor for estrogen receptor activation, and expressed in high frequency in many breast cancer samples and breast cancer cells. On the other hand, it is confirmed that nearly no expression is recognized in normal tissues (Kim J W, Akiyama M, Park J H, et al Cancer Sci. 2009; 100: 1468-78.). Thus, it is considered that suppression function of the PHB2 polypeptide on activation of estrogen receptor is inhibited by expression of the ERAP1 polypeptide in breast cancer, and as a result, proliferation of breast cancer cells is promoted. Accordingly, the pharmaceutical composition of the present invention is particularly suitable for treating and/or preventing breast cancer. In addition, the pharmaceutical composition of the present invention is particularly useful for a breast cancer which is estrogen receptor-positive, and in which the ERAP1 polypeptide is expressed among breast cancers. However, the pharmaceutical composition of the present invention is not limited to breast cancer, but the pharmaceutical composition of the present invention may be used for cancer which is estrogen receptor-positive, and in which the ERAP1 polypeptide is expressed. Examples of the estrogen receptor-positive cancer besides breast cancer include uterine cancer, ovarian cancer, prostate cancer (Nelles J L, et al., Expert Rev Endocrinol Metab. 2011 May; 6(3): 437-451.), lung cancer (particularly non-small cell lung cancer) (Stabile L P, et al., Cancer Res. 2005 Feb. 15; 65(4): 1459-70.; Marquez-Garban D C, et al., Steroids. 2007 February; 72 (2): 135-43.), etc., but are not limited thereto.

In addition, the peptide of the present invention has suppression effect not only on estrogen-dependent cell proliferation in estrogen receptor-positive cells, but also on estrogen-independent cell proliferation (Example 3). Among the estrogen receptor-positive breast cancers, 60 to 70% is estrogen-dependent breast cancer, and the rest is estrogen-independent breast cancer. The estrogen-independent breast cancer is refractory or resistant with respect to conventional hormone therapy agents such as tamoxifen and aromatase inhibitors, and cannot be treated with the conventional hormone therapy agent. It is considered, that in such estrogen-independent breast cancer, the estrogen receptor is activated by other factors than estrogen (e.g., growth factor (EGF, IFGF, etc.), mutation of the estrogen receptor, phosphorylation of the estrogen receptor, etc.), and cell proliferation is promoted. The peptide of the present invention also has suppression effect on estrogen-independent cell proliferation of the estrogen receptor-positive breast cancer, and thus the pharmaceutical composition of the present invention can be also applied to treating and/or preventing estrogen-independent estrogen receptor-positive breast cancer.

Figure 40:
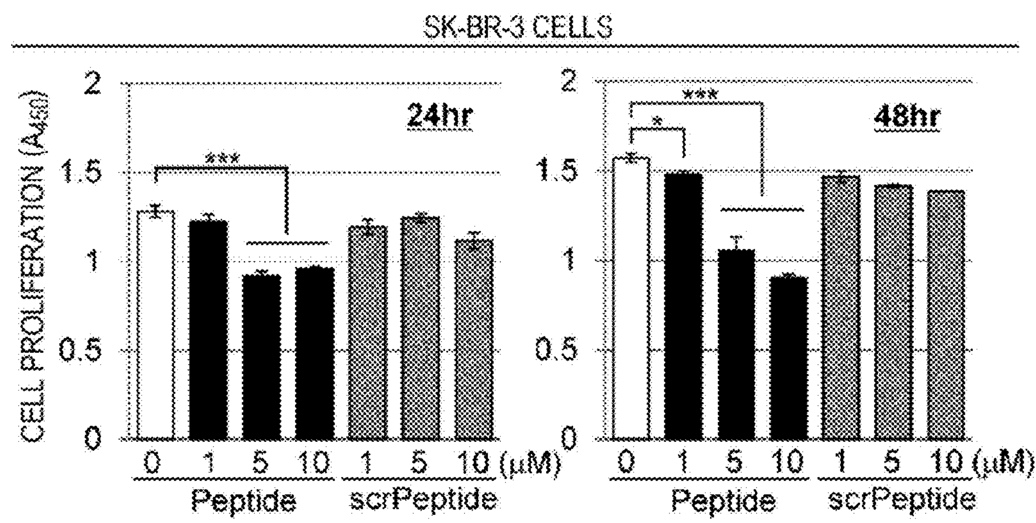
FIG. 40 is a diagram illustrating the results of MTT assay by which proliferation suppression effect of the ERAP1-peptide in ERα negative breast cancer cell lines, SK-BR-3 cells was evaluated. SK-BR-3 cells were treated with the ERAP1-peptide (Peptide) or the ERAP1-scramble peptide (scrPeptide) for 24 hours or for 48 hours. The data show the mean±SE of three independent experiments. *P<0.05, ***P<0.001.

Furthermore, it is confirmed that the peptide of the present invention has cell proliferation suppression effect also with respect to estrogen receptor-negative breast cancer cells (FIG. 40). Thus, the pharmaceutical composition of the present invention can be also applied to treating and/or preventing estrogen receptor-negative breast cancer.

In addition, the peptide of the present invention effectively suppresses the cell proliferation of tamoxifen-resistant breast cancer cells (Example 2 and Example 8). Tamoxifen is ant antiestrogen, and considered to suppress estrogen-dependent cell proliferation by binding to the estrogen receptor in competition with estrogen. Tamoxifen is widely used in postoperative adjuvant therapy or standard treatment of advanced/relapsed breast cancer, but about 30% of the estrogen receptor-positive breast cancer is tamoxifen-refractory. In addition, by long term use, breast cancer may become resistant to tamoxifen. The peptide of the present invention has a suppression effect on the cell proliferation of tamoxifen-resistant breast cancer cells, and thus the pharmaceutical composition of the present invention can be suitably applied to such tamoxifen-resistant breast cancer.

In addition, when the peptide of the present invention was used in combination with tamoxifen, the cell proliferation suppression effect in the estrogen receptor-positive cell, and the antitumor effect in vivo were remarkably promoted (Example 4). As described above, tamoxifen is an antiestrogen, and has a different mechanism for exerting cell proliferation suppression effect compared to the peptide of the present invention. Thus, it is considered that by concomitant use of tamoxifen with the peptide of the present invention, the peptide of the present invention potentiates the therapeutic effects of tamoxifen on cancer. Thus, the pharmaceutical composition of the present invention is suitably used in treating and/or preventing cancer as concomitant use with tamoxifen for the purpose of potentiating the therapeutic effects of tamoxifen on cancer. In addition, the pharmaceutical composition of the present invention may be also used concomitantly with other hormone therapy agents than tamoxifen. Herein, the term "hormone therapy agent" refers to a medicine that suppresses estrogen-dependent cell proliferation by suppressing actions of estrogen or production of estrogen in vivo. Examples of the hormone therapy agent include an aromatase inhibitor, an LH-RH agonist preparation, and a progesterone preparation, but are not limited thereto. These conventional hormone therapy agents have different mechanisms for inducing cancer treatment compared to the peptide of the present invention, and thus concomitant use with the pharmaceutical composition of the present invention can be expected to potentiate the therapeutic effects thereof on cancer.

Hence, the present invention provides, for example, the pharmaceutical compositions described in (1) to (7) below:

(1) A pharmaceutical composition comprising at least one ingredient selected from a group consisting of a peptide of the present invention, a polynucleotide encoding the peptide, and a pharmaceutically acceptable salt of the peptide;

(2) The pharmaceutical composition described in (1) for treating and/or preventing cancer;

(3) The pharmaceutical composition described in (2), wherein the cancer is breast cancer;

(4) The pharmaceutical composition described in (1) or (2), wherein the cancer is estrogen receptor-positive;

(5) The pharmaceutical composition described in (4), wherein the cancer is tamoxifen-resistant;

(6) A pharmaceutical composition comprising a peptide of the present invention or a polynucleotide encoding the peptide for potentiating the therapeutic effects of a hormone therapy agent on cancer; and (7) A pharmaceutical composition comprising the peptide of the present invention or a polynucleotide encoding the peptide for suppressing activation of estrogen receptor in estrogen receptor-positive cells.

Examples of the pharmaceutically acceptable salt of the peptide of the present invention, which can be used in the present invention, include salts with a pharmaceutically acceptable acid (e.g., inorganic acid or organic acid) or base (e.g., alkali metal, alkali earth metal, or amine). Examples of the preferred embodiments include pharmaceutically acceptable acid addition salts. Examples of such salts include salts with an inorganic acid (e.g., hydrochloric acid, phosphoric acid, hydrobromic acid, sulfuric acid, or acetic acid), or salts with an organic acid (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid, or meglumine acid). Preferred examples of the pharmaceutically acceptable salt of the peptide of the present invention include acetic acid salt, hydrochloric acid salt, meglumine acid salt, and ammonium salt.

In addition, the present invention provides use of the peptide of the present invention or a polynucleotide encoding the peptide in manufacture of the pharmaceutical composition described in any one of the above-mentioned (1) to (7). In addition, the present invention further provides a method or process for manufacturing the pharmaceutical composition described in any one of the above-mentioned (1) to (7). The method or process includes a step of prescribing a pharmaceutically acceptable carrier and the peptide of the present invention or a polynucleotide encoding the peptide as an active ingredient. In addition, the present invention provides a method or process for manufacturing the pharmaceutical composition described in any one of the above-mentioned (1) to (7). The method or process comprises a step of mixing an active ingredient with a pharmaceutically acceptable carrier, where this active ingredient is the peptide of the present invention or a polynucleotide encoding the peptide. In addition, the present invention provides the peptide of the present invention or a polynucleotide encoding the peptide for use in treatment of cancer, potentiation of the therapeutic effects of a hormone therapy agent on cancer, or suppression for activation of estrogen receptor in estrogen receptor-positive cells.

In addition, the present invention provides a method for treating and/or preventing a cell proliferative disease due to activation of estrogen receptor, which comprises a step of administering the peptide of the present invention or a polynucleotide encoding the peptide to a subject. Examples of the cell proliferative disease treated and/or prevented by the method of the present invention include cancer. The cancer suitable for application of the method of the present invention is similar to those described above for the pharmaceutical composition of the present invention. Namely, the method of the present invention is preferably applied to cancer which is estrogen receptor-positive, and in which the ERAP1 polypeptide is expressed. In addition, the present invention provides a method for suppressing activation of estrogen receptor, which comprises a step of bringing the peptide of the present invention or a polynucleotide encoding the peptide into contact with estrogen receptor-positive cells.

The pharmaceutical composition of the present invention is preferably administered to human, but may be administered to other mammals, e.g., a mouse, a rat, a guinea pig, a rabbit, a cat, a dog, a sheep, a pig, a cow, a monkey, a baboon, and a chimpanzee.

The pharmaceutical composition of the present invention contains a pharmaceutically effective amount of the peptide of the present invention or a polynucleotide encoding the peptide as an active ingredient. The "pharmaceutically effective amount" is a sufficient amount for achieving the purpose of the pharmaceutical composition of the present invention. For example, when the pharmaceutical composition of the present invention is a pharmaceutical composition for treating and/or preventing cancer, one example of the pharmaceutically effective amount may be an amount of inducing suppression for cancer proliferation speed, suppression for metastatic ability, extension of life time, suppression or delay of cancer generation, or alleviation of various clinical symptoms involved in cancer when administered to a patient. The suppression for cancer proliferation speed may be suppression by, e.g., about 5% or more in comparison to the case where the pharmaceutical composition of the present invention is not administered. The suppression for cancer proliferation speed may be preferably about 10% or more, 20% or more, 30% or more, 40% or more, 50% or more, 75% or more, 80% or more, 90% or more, or 100% or more.

In addition, when the pharmaceutical composition of the present invention is a pharmaceutical composition for potentiating the therapeutic effects of a hormone therapy agent on cancer, one example of the pharmaceutically effective amount may be an amount of inducing potentiation of the therapeutic effects of a hormone therapy agent on cancer when administered to a patient in comparison to the case where the pharmaceutical composition of the present invention is not administered. The therapeutic effects of a hormone therapy agent on cancer to be compared may be, e.g., suppression for cancer proliferation speed, suppression for metastatic ability, extension of life time, suppression or delay of cancer generation, or alleviation of various clinical symptoms involved in cancer. For example, the pharmaceutically effective amount may be an amount for potentiating suppression effect of cancer proliferation speed by a hormone therapy agent by about 5% or more in comparison to the case where the pharmaceutical composition of the present invention is not administered. The potentiation of suppression effect of cancer proliferation speed by a hormone therapy agent may be preferably about 10% or more, 20% or more, 30% or more, 40% or more, 50% or more, 75% or more, 80% or more, 90% or more, or 100% or more.

In addition, when the pharmaceutical composition of the present invention is a pharmaceutical composition for suppressing activation of estrogen receptor in estrogen receptor-positive cells, one example of the pharmaceutically effective amount may be an amount to induce suppression for activation of estrogen receptor in estrogen receptor-positive cells when administered to a patient, in comparison to the case where the pharmaceutical composition of the present invention is not administered. The suppression for activation of estrogen receptor can be confirmed by, e.g., detecting suppression for the expression level of a target gene for transcriptional activation by estrogen receptors (gene having estrogen responsible element (ERE)), suppression for the phosphorylation level of the estrogen receptor, suppression for the phosphorylation level of a signal molecule such as IGF-1Rβ, Shc, Akt, PI3K and MAK, and the like. For example, the pharmaceutically effective amount may be an amount to suppress any of the levels exemplified above by about 5% or more, in comparison to the case where the pharmaceutical composition of the present invention is not administered. The suppression for any of the levels exemplified above may be preferably by about 10% or more, 20% or more, 30% or more, 40% or more, 50% or more, 75% or more, 80% or more, 90% or more, or 100% or more.

The pharmaceutically effective amount may depend on many factors including the age and the sex of a subject, the purpose of administration, the severity of disease and administration route. However, determination of the pharmaceutically effective amount in the pharmaceutical composition of the present invention may be performed sufficiently by one of ordinary skill in the art. For example, the pharmaceutically effective amount in the pharmaceutical composition of the present invention may be first roughly estimated from a cell culture assay and/or animal model. For example, the pharmaceutically effective amount can be prescribed in an animal model so as to reach the circulation concentration covering IC50 (dose by which 50% of the cells show desired effects) determined in the cell culture. The pharmaceutically effective amount can be also determined by, e.g., standard pharmaceutical procedures for determining LD50 (dose by which 50% of a population is led to death) and ED50 (dose by which 50% of a population is effectively treated) in a cell culture or experiment animal. The ratio of the dose for toxic actions to the dose for the therapeutic effects is the therapeutic index (namely, the ratio of LD50 and ED50). In prescription of a dose range for use in human, the data obtained from such cell culture assay and animal test can be used. The dose of such polypeptide and polynucleotide may be within a range of the circulation concentration which has nearly no or absolutely no toxicity, and covers ED50. The dose in this range may be changed depending on a unit dosage form to be used and administration route to be used. Exact prescription, administration route, and dose may be selected by an individual physician in consideration of the state of a patient (e.g., see Fingl et al. (1975) in "The Pharmacological Basis of Therapeutics", Ch. 1 p1), The dose and the administration interval may be regulated individually so as to obtain sufficient plasma concentration of the active ingredient for maintaining desirable effects.

As for the exemplary dose, e.g., the peptide of the present invention or a polynucleotide encoding the peptide may be administered in a dose of about 0.1 to about 250 mg/kg/day. The dose is preferably about 0.5 to about 200 mg/kg/day, more preferably about 1.0 to about 150 mg/kg/day, and further preferably about 3.0 to about 100 mg/kg/day. The dose range for an adult (60 kg body weight) is commonly about 5 rug to about 17.5 g/day preferably about 5 mg to about 10 g/day, and more preferably about 100 mg to about 3 g/day. The pharmaceutical composition of the present invention may contain the peptide of the present invention or a polynucleotide encoding the peptide in the amount described above in a tablet or other unit dosage form provided as an individual unit. Alternatively, the pharmaceutical composition of the present invention may contain the dose described above, for example, in a unit containing about 5 mg to about 500 mg, preferably about 50 mg to about 500 mg as multiple preparations.

The pharmaceutical composition of the present invention may optionally contain other therapeutic substances as an active ingredient. For example, the pharmaceutical composition of the present invention may contain other hormone therapy agents (tamoxifen, an aromatase inhibitor, an LH-RH agonist preparation, a progesterone preparation, etc.). As shown in Examples, it is confirmed that when the peptide of the present invention is administered together with tamoxifen, antitumor effect increases in comparison to the case where they are administered individually (Example 4). Thus, a pharmaceutical composition comprising the peptide of the present invention and other hormone therapy agent is exemplified as the preferred embodiment of the pharmaceutical composition of the present invention. In addition, the pharmaceutical composition of the present invention may contain, e.g., an anti-inflammatory agent, an analgesic, a chemical therapy agent, and the like. These various preparations to be blended with the ERAP1 peptide may be blended in a form of a prodrug or a pharmaceutically acceptable salt.

In addition to the fact that the pharmaceutical composition of the present invention contains other therapeutic substance as it is, the pharmaceutical composition of the present invention may be administered with one or more kinds of other pharmaceutical compositions at the same time or successively. As described above, when the peptide of the present invention is used in combination with other hormone therapy agent, increase of the antitumor effect is expected in comparison to the case where they are administered individually. Thus, the present invention includes the methods described below as the preferred embodiments:

a method for treating and/or preventing cancer, which comprises a step of administering the peptide of the present invention or a polynucleotide encoding the peptide to a subject, and a step of administering a hormone therapy agent to a subject; and a method for potentiating the therapeutic effects of a hormone therapy agent on breast cancer in a subject, which comprises (a) and (b) steps described below:

(a) a step of administering a hormone therapy agent to a subject; and (b) a step of administering the peptide of the present invention or a polynucleotide encoding the peptide to a subject.

Namely, the present invention provides a method for potentiating therapeutic effects of either one or both of a hormone therapy agent and a chemical therapy agent, which comprises a step of administering the ERAP1 peptide to a subject to which either one or both of a hormone therapy agent and a chemical therapy agent has been administered. Alternatively, the present invention relates to use of any ingredient selected from a group consisting of (a) to (c) described below in manufacture of a pharmaceutical composition for potentiating therapeutic effects of either one or both of a hormone therapy agent and a chemical therapy agent:

(a) the ERAP1 peptide of the present invention;
(b) a polynucleotide encoding the peptide; and
(c) a pharmaceutically acceptable salt of the peptide.

Further, the present invention provides a pharmaceutical composition for potentiating therapeutic effects of either one or both of a hormone therapy agent and a chemical therapy agent, which comprises any ingredient selected from a group consisting of the above-mentioned (a) to (c) and a pharmaceutically acceptable carrier In addition, the present invention provides a method for manufacturing a pharmaceutical composition for potentiating therapeutic effects of either one or both of a hormone therapy agent and a chemical therapy agent, which comprises a step of blending any ingredient selected from a group consisting of the above-mentioned (a) to (c) and a pharmaceutically acceptable carrier. A disease for which potentiation of the therapeutic effects by the present invention is expected, is cancer which is estrogen receptor-positive, and in which the ERAP1 polypeptide is expressed. Examples of such cancer include human breast cancer.

In one embodiment of the present invention, the pharmaceutical composition of the present invention may be contained in a manufactured article and/or kit comprising a material useful for treating and/or preventing cancer. More specifically, encompassed in the kit of the present invention is a kit for treating cancer which is estrogen receptor-positive, and in which the ERAP1 polypeptide is expressed, which comprises (i) either one or both of a hormone therapy agent and a chemical therapy agent, and (ii) any ingredient selected from a group consisting of the following (a)-(c):

(a) the ERAP1 peptide of the present invention;
(b) a polynucleotide encoding the peptide; and
(c) a pharmaceutically acceptable salt of the peptide.

A manufactured article may comprise a container for any pharmaceutical composition of the present invention together with a label. Examples of an appropriate container include a bottle, a vial, and a test tube. The container may be formed from various materials such as glass or plastic. The label of the container must indicate that the pharmaceutical composition is used for treating and/or preventing one or more conditions of a disease. The label may also indicate indications of administration, etc.

The kit comprising the pharmaceutical composition of the present invention may further optionally comprise a second container accommodating a pharmaceutically acceptable diluent in addition to the above-mentioned container. The kit may further contain other materials desired from the commercial viewpoint and the user viewpoint, which include another buffer, a diluent, a filter, a needle, a syringe, and an attached document having instruction.

The pharmaceutical composition of the present invention may be put into a package or dispenser device as necessary which may comprise one or more unit dosage forms comprising an active ingredient. The package may contain a metal foil or a plastic foil such as a blister package. The package or dispenser device may be attached with administration instruction.

The pharmaceutical composition of the present invention may be also provided as a kit with other pharmaceutical composition useful for treating and/or preventing cancer. The pharmaceutical composition that may be combined with the pharmaceutical composition of the present invention in the kit includes, e.g., hormone therapy agents and chemical therapy agents, but is not limited thereto. In the preferred embodiments, the pharmaceutical composition of the present invention may be provided as a kit with other hormone therapy agent. Thus, a kit comprising the pharmaceutical composition of the present invention and other hormone therapy agent is also encompassed by the present invention. Alternatively, the present invention relates to use of a combination of (i) and (ii) described below in treatment of cancer which is estrogen receptor-positive, and in which the ERAP1 polypeptide is expressed in a subject:

(i) either one or both of a hormone therapy agent and a chemical therapy agent, and (ii) any ingredient selected from a group consisting of the following (a)-(c)

(a) the ERAP1 peptide of the present invention;

(b) a polynucleotide encoding the peptide; and (c) a pharmaceutically acceptable salt of the peptide.

In the preferred embodiments of the present invention, examples of the cancer that can be a subject for the treatment include human breast cancer.

The peptide of the present invention or a polynucleotide encoding the peptide may be administered directly together with an appropriate carrier to a subject, or formulated into an appropriate dosage form using a known method for preparing a medicine. Alternatively, a pharmaceutically acceptable salt of the peptide of the present invention may be also administered together with an appropriate carrier to a subject, or may be formulated for administration like the peptide. For example, the pharmaceutical composition of the present invention can be formulated into a form suitable for oral, rectal, intranasal, local (including buccal and sublingual), vaginal, or parenteral (including intramuscular, subcutaneously, and intravenous) administration, or administration by inhalation or blowing. For example, as necessary, the pharmaceutical composition of the present invention may be administered orally as a sugar-coated tablet, a capsule, an elixir, and a microcapsule, or may be administered parenterally in a form of an injection that is a sterilized solution or suspension with water or any other pharmaceutically acceptable carrier. For example, the pharmaceutical composition of the present invention may be mixed together with a pharmaceutically acceptable carrier or medium, specifically sterilized water, physiological saline, vegetable oil, an emulsifying agent, a suspending agent, a surfactant, a stabilizing agent, a flavoring agent, an excipient, a solvent agent, a preservative, a binding agent, etc, in a unit dosage form that is required for use in a conventionally accepted drug. The phrase "pharmaceutically acceptable carrier" refers to an inert substance that is used as a diluent or solvent agent for a drug. Thus, the pharmaceutical composition of the present invention may comprise any pharmaceutically acceptable carrier in addition to the peptide of the present invention or a polynucleotide encoding the peptide.

Examples of additives that may be mixed with a tablet and a capsule include binding agents (gelatin, cornstarch, tragacanth gum, and gum Arabic, etc.); excipients (crystalline cellulose, etc.); expanding agents (cornstarch, gelatin, and alginic acid, etc.); lubricants (magnesium stearate, etc.); sweeteners (sucrose, lactose, or saccharin); and flavoring agents (peppermint, Akamono oil, and cherry, etc.). When the unit dosage form is a capsule, a liquid carrier (oil, etc.) may be also further encompassed in the above-mentioned ingredients. Sterilized ingredients for injection may be formulated using a solvent agent such as distilled water for injection according to conventional medicine use.

Other isotonic solutions including physiological saline, as well as adjuvants such as glucose, D-sorbitol, D-mannose, D-mannitol and sodium chloride may be used as an aqueous solution for injection. These may be used along with appropriate solubilizing agents such as an alcohol, specifically ethanol, a polyalcohol (e.g., propylene glycol and polyethylene glycol) and a non-ionic surfactant (e.g., polysorbate 80 (trademark) and HCO-50)).

Sesame oil or soybean oil may be used as an oily solution, and may be used along with benzyl benzoate or benzyl alcohol as a solubilizing agent, and may be formulated using a buffer (phosphate buffer and sodium acetate buffer, etc.); analgesics (procaine hydrochloride, etc.); a stabilizing agent (benzyl alcohol, phenol, etc.); and an antioxidant. Prepared injection solution may be filled into an appropriate ampule.

A pharmaceutical preparation suitable for oral administration includes, but not limited to, a capsule, a cachet, and a tablet, which contain a prescribed amount of an active ingredient, respectively. The preparation also includes a drug, a liquid, a gel, a syrup, a slurry, a pill, powders, granules, a solution, a suspension, an emulsion, etc. The active ingredient is optionally administered as bolus, a lozenge, or a paste. The tablet and the capsule for oral administration may contain conventional excipients such as a binding agent, an extender, a lubricant, a disintegrator, and a wetting agent. Appropriate excipient includes, particularly, extenders, for example, sugars including lactose, sucrose, mannitol, and sorbitol; cellulose preparations, e.g., cornstarch, wheat starch, rice starch, potato starch, gelatin, tragacanth gum, methyl cellulose, hydroxypropylmethylcellulose and sodium carboxymethyl cellulose, and polyvinyl pyrrolidone (PVP). A disintegrator such as cross-linking polyvinyl pyrrolidone, agar, and alginic acid or a salt thereof e.g., sodium alginate may be added as necessary.

A tablet may be manufactured by compressing or molding optionally together with one or more kinds of preparation ingredients. A compressed tablet may be prepared by mixing an active ingredient in a freely flowable form such as powders or granules optionally with a binding agent, a lubricant, an inert diluent, a lubricant, a surfactant or a dispersant, and compressing the mixture in an appropriate machine. A tablet triturate may be manufactured by molding a mixture of powder compounds moistened with an inert liquid diluent in an appropriate machine. A tablet may be coated in accordance with a method well known in the art. Oral liquid preparations may be in a form, e.g., an aqueous or oily suspension, a solution, an emulsion, a syrup, or an elixir agent, or may be provided as a dry product for reconstitution with water or other appropriate vehicle before use. Such liquid preparations may contain conventional additives such as a suspending agent, an emulsifying agent, a non-aqueous vehicle (edible oil may be encompassed), and a preservative.

Preparations for parenteral administration include aqueous and non-aqueous, sterilized injections that may contain an antioxidant, a buffer agent, a bacteriostatic and a solute that renders the blood of a subject recipient isotonic to the preparation, and aqueous and non-aqueous sterilized suspensions that may contain a suspending agent and a thickener. The preparation may be provided as filled in a container, e.g. sealed ampule or vial in a unit dosage or plural dosage, and may be conserved in the freeze-dried state that may be simply added with a sterilized liquid carrier, e.g., physiological solution and water for injection just before use. Alternatively, the preparation may be provided as a continuous infusion. A solubilizing solution and suspension for instant injection may be prepared from sterilized powders, granules, and a tablet as described above.

Preparations for rectal administration include suppositories using standard carriers such as cocoa butter or polyethylene glycol. Preparations for intraorally administering, e.g., locally administering buccally or sublingually include a lozenge comprising an active ingredient in a flavoring base such as sucrose, and gum Arabic or tragacanth gum, and a troche comprising an active ingredient in a base such as gelatin, glycerin, sucrose, or gum Arabic. A liquid spray or dispersible powder or drop form may be used in order to intranasally administer the active ingredient. The drops may be prescribed using an aqueous or non-aqueous base also containing one or more kinds of a dispersant, a solubilizing agent, or a suspending agent.

For administration by inhalation, the pharmaceutical composition of the present invention may be delivered by an inhalator, a nebulizer, a pressure pack, or other appropriate means for delivering aerosol spray. The pressure pack may comprise appropriate spray agents (dichlorodifluoromethane, trichlorofluoromethane, dichlorotetrafluoroelthane, carbon dioxide, or other appropriate gas). A dosage unit in the pressure aerosol may be determined by providing a valve for delivering a fixed amount. Alternatively, in administration by inhalation or blowing, the pharmaceutical composition of the present invention may be a form of a dry powder composition, e.g. a powder mixture of the peptide of the present invention, and a suitable powder base such as lactose or starch. The powder composition may be provided in a unit dosage form in, e.g., a capsule, a cartridge, gelatin, or a blister pack, and the powders may be administered using an inhalator or blower therefrom.

The preparations described above adapted so as to sustainably release the peptide of the present invention as necessary may be used. The pharmaceutical composition of the present invention may also contain other active ingredients such as an antibacterial agent, an immune-suppressing agent, or a preservative.

It is to be understood that the preparation of the present invention may comprise conventional other substances in the art in consideration of the kind of the preparation in addition to the ingredients described above. For example, a preparation suitable for oral administration may comprise a flavoring agent.

The pharmaceutical composition of the present invention is preferably administered parenterally as an injection so as to avoid the active ingredient, i.e., the peptide or the polynucleotide from being digested by gastric acid or an intestinal enzyme. For example, the pharmaceutical composition of the present invention may be administered by intraarterial injection, intravenous injection, intradermal injection, subcutaneous injection or intra-tumor injection using a method well known to one of ordinary skill in the art. In the preferred embodiments, the pharmaceutical composition of the present invention is administered by intravenous injection in a form in which the active ingredient is enclosed in an appropriate delivery reagent such as a liposome. The enclosure of the active ingredient into a delivery reagent such as a liposome may be performed by a method known to one of ordinary skill in the art.

When the active ingredient is a polynucleotide encoding the peptide of the present invention, the pharmaceutical composition of the present invention may contain a vector for gene therapy into which the polynucleotide is inserted as an active ingredient. In this case, the pharmaceutical, composition of the present invention may comprise an appropriate transfection-potentiating agent in order to introduce the vector into the cell.

4. Method for Determining Prognosis of Cancer

As shown in Examples of the specification, the expression of the ERAP1 polypeptide significantly correlates with the relapse-free survival period of breast cancer (Example 7). Thus, the present invention also provides a method for determining the prognosis of a patient having cancer using the expression of the ERAP1 polypeptide as an index.

Specifically, the present invention provides the methods of [1] to [8] described below:

[1] a method for determining the prognosis of a patient having cancer, which comprises the steps (a) to (c) described in (A) or (B) described below:

(A)

(a) a step of detecting the expression level of the ERAP1 gene in a biological sample collected from the subject;

(b) a step of comparing the expression level detected in the step (a) with a control level;

(c) a step of determining the prognosis of the subject on the basis of the comparison of the step (b);

(B)

(a) a step of isolating or collecting a subject-derived biological sample;

(b) a step of bringing the subject-derived biological sample into contact with an oligonucleotide that is hybridized with the ERAP1 polynucleotide, or an antibody that binds to the ERAP1 polypeptide for detecting, measuring, or determining the expression level of the ERAP1 gene;

(c) a step of detecting, measuring, or determining the expression level of the ERAP1 gene on the basis of the contact;

(d) a step of comparing the expression level detected in the step (c) with a control level; and (e) a step of determining the prognosis of the subject on the basis of the comparison of the step (d);

[2] the method described in [1], wherein the above-mentioned control level is a good prognosis control level, and increase of the above-mentioned expression level in comparison to the control level is determined as poor prognosis;

[3] the method described in [1] or [2], wherein the above-mentioned expression level is obtained by either one of the method (a) or (b) described below:

(a) detecting mRNA encoding the ERAP1 polypeptide; and (b) detecting the ERAP1 polypeptide;

[4] the method described in [3], wherein the above-mentioned expression level is obtained by immunohistochemical staining;

[5] the method described in any one of [1] to [4], wherein the above-mentioned biological sample is a resected specimen of cancer;

[6] the method described in any one of [1] to [5], wherein the cancer is estrogen receptor-positive;

[7] the method described in [6], wherein the cancer is breast cancer, and

[8] the method described in any one of [1] to [7], wherein the prognosis to be determined is relapsing after surgery.

Hereinafter, the method of the present invention will be described in detail.

Herein, the term "prognosis" represents an estimate regarding expected outcome of disease, possibility of recovery from disease, and possibility of relapsing of disease. Thus, no good, or poor prognosis is prescribed by decrease of the lifetime or survival rate after the treatment or increase of the relapsing rate after the treatment or shortening of the time period to the relapsing. To the contrary, good prognosis is prescribed by increase of the lifetime or survival rate after the treatment, or decrease of the relapsing rate after the treatment or extension of the time period to the relapsing.

Herein, the phrase "determining the prognosis" includes analysis for estimation and expectation of the progress of cancer, particularly relapsing of cancer, spread of metastasis and relapsing of disease. The method for determining the prognosis of the present invention is intended to be clinically used in making conclusion, for treatment method, including therapeutic intervention, diagnostic criteria, e.g. classification of the disease stage, and disease monitoring and supervision for metastasis or relapsing of neoplastic disease. In the preferred embodiments, the prognosis estimated by the method of the present invention may be relapsing after surgery. Thus, by the method of the present invention, it becomes possible to estimate possibility of cancer relapsing in a patient who has received cancer-resection surgery.

The cancer that is determined for the prognosis by the method of the present invention is preferably estrogen receptor-positive cancer. Examples of the estrogen receptor-positive cancer include breast cancer, uterine cancer, ovarian cancer, prostate cancer, and lung cancer (particularly non-small cell lung cancer), but are not limited thereto. In the preferred embodiments, the cancer determined for the prognosis by the method of the present invention is breast cancer.

The biological sample collected from a patient, which is used in the method of the present invention, is not particularly limited, but preferably includes patient-derived cancer cells. Preferred examples of the biological sample include cancer-resected specimens resected by surgical procedure or the like. For example, when the cancer determined for the prognosis is breast cancer, preferred examples of the biological sample include breast cancer-resected specimens. The biological sample may be collected from a patient at various time points including the times before, during and after the treatment. For example, breast cancer cells derived from a patient to be determined for the prognosis is particularly preferred as the biological sample of the present invention.

The "control level" used for comparison in the method of the present invention may be the expression level of the ERAP1 gene detected before any kind of treatment, e.g., in individuals or population of individuals that have showed good prognosis of cancer after the treatment. The control level in this case is referred herein to as the "good prognosis control level". In addition, the "control level" may be the expression level of the ERAP1 gene detected before any kind of the treatments in individuals or population of individuals that have showed poor prognosis of cancer after the treatment. In this case, the control level is referred herein to as the "poor prognosis control level". The "control level" may be single expression pattern or plural expression patterns derived from single reference population. Thus, the control level can be obtained based on the expression level of the ERAP1 gene detected before any kind of the treatments in a patient, or a patient population whose prognosis of cancer has been known. Alternatively, a standard value of the expression level of the ERAP1 gene in a patient group whose prognosis has been known, is used. The standard value may be obtained by any method known in the technical field. For example, a range of the mean±2S.D. or the mean±3S.D. may be used as the standard value.

The control level may be obtained at the same time as a test biological sample by using samples collected and conserved so far from a patient or a patient group whose prognosis of cancer has been known before any kind of the treatment.

Alternatively, the control level may be obtained by a statistical method on the basis of results obtained by analysis of the expression level of the ERAP1 gene in samples collected and conserved so far from the control group. Furthermore, the control level may be a database of the expression pattern of a patient group collected so far whose prognosis has been known. In addition, according to one embodiment of the present invention, the expression level of the ERAP1 gene in a patient-derived biological sample may be compared with multiple control levels obtained from multiple reference samples. In the preferred embodiments, a control level obtained from a reference sample that is derived from the same tissue type as the biological sample collected from a patient, is used.

In the method of the present invention, when the expression level of the ERAP1 gene in the patient-derived biological sample is similar to the good prognosis control level, the prognosis of the patient is determined as good. On the other hand, when the expression level of the ERAP1 gene in the patient-derived biological sample increases in comparison to the good prognosis control level, the prognosis of the patient is determined as no good or poor. In addition, when the expression level of the ERAP1 gene in the patient-derived biological sample decreases in comparison to the poor prognosis control level, the prognosis of the patient is determined as good. On the other hand, when the expression level of the ERAP1 gene in the patient-derived biological sample is similar to the poor prognosis control level, the prognosis of the patient is determined as no good or poor. Preferred examples of the good prognosis control sample include, e.g., breast cancer cells that are derived from a patient who has shown good prognosis after the treatment. Alternatively, preferred examples of the poor prognosis control sample include breast cancer cells that are derived from a patient who has shown poor prognosis.

The expression level of the ERAP1 gene in a biological sample can be considered to have changed (i.e., increased or decreased) when the expression level of the ERAP1 gene is different from the control level by 1.0 time or more, 1.5 times or more, 2.0 times or more, 5.0 times or more, 10.0 times or more, or higher.

The difference of the expression level between the level of a test biological sample and the control level may be normalized by control, e.g. housekeeping gene. For example, a polynucleotide the expression level of which is known not to be different between cancer cells and non-cancer cells (e.g., β actin glyceraldehyde 3 phosphoric acid dehydrogenase, ribosome protein P1 encoding gene) may be used for normalizing the expression level of the ERAP1 gene.

The expression level can be obtained by detecting a transcription product (mRNA) or translation product (protein) of the ERAP1 gene in a biological sample collected from a patient using a method known in the technical field.

For example, mRNA of the ERAP1 gene can be detected by hybridization, e.g., northern blotting hybridization analysis with a probe having a complementary sequence to the mRNA. The detection may be performed on a chip or array. Alternatively, a detection method based on amplification using a primer specific for mRNA of the ERAP1 gene, e.g., reverse transcription polymerase chain reaction (RT-PCR) may be used in the detection. The probe or primer specific for the ERAP1 gene can be designed and prepared using a conventional technique by making reference to the whole sequence of the base sequence of the ERAP1 gene (SEQ ID NO: 34). For example, the primers used in Examples (SEQ ID NO: 17 and SEQ ID NO: 18) can be used in detection by RT-PCR, but the primer is not limited thereto.

The probe or primer used in the method of the present invention is hybridized with mRNA of the ERAP1 gene under stringent, moderate stringent, or low stringent condition. Herein, the phrase "stringent (hybridization condition)" represents a condition where the probe or primer is hybridized with a target sequence, but not hybridized with other sequences. The stringent condition is dependent on the sequence, and varies under various circumstances. Specific hybridization of a long sequence is observed at higher temperature than specific hybridization of a short sequence. Generally, the temperature of the stringent condition is selected to be lower by about 5° C. than the thermal melting point (Tm) of a particular sequence at prescribed ionic strength and pH. Tm is a temperature at which 50% of a probe complementary to a target sequence is hybridized with the target sequence in the equilibrium state (in prescribed ionic strength, pH and nucleic acid concentration). Generally at Tm, the target sequence is excessively present, and 50% of the probe is occupied in the equilibrium state. Typically, for the stringent condition, the concentration of the salts is less than about 1.0 M of sodium ion, typically about 0.01 M to 1.0 M of sodium ion (or the salt) at pH 7.0 to 8.3, and the temperature is at least about 30° C. for a short probe or primer (e.g., 10 to 50 nucleotides), and at least about 60° C. for a long probe or primer. The stringent condition may be achieved by addition of a destabilization agent, e.g., formamide.

In the method of the present invention, a translation product of the ERAP1 gene may be also detected for obtaining the expression level of the ERAP1 gene. For example, the amount of the ERAP1 polypeptide may be obtained. Examples of the method for obtaining the amount of the ERAP1 polypeptide as a translation product include an immunoassay method using an antibody that specifically recognizes the ERAP1 polypeptide. The antibody may be monoclonal or polyclonal. Furthermore, any fragment or modified fragment (e.g., chimera antibody, scFv, Fab, F(ab')2, Fv and the like) of the antibody may be used in the detection if the fragment keeps the binding ability to the ERAP1 polypeptide. A method for preparing these kinds of the antibody is known in the technical field, and any method may be used for preparing such antibody and an equivalent thereof.

In the preferred embodiments, the expression level of the ERAP1 gene may be obtained by immunohistochemical staining using an antibody for the ERAP1 polypeptide. A cancer-resected specimen is preferably used as a sample for the immunohistochemical staining. The abundance of the ERAP1 polypeptide that correlates with the expression level of the ERAP1 gene may be evaluated by observing the intensity of the immunohistochemical staining. Namely, when the cancer tissue is almost uniformly and strongly stained, it indicates that the abundance of the ERAP1 polypeptide is high, and the expression level of the ERAP1 gene is high. For example, when the cancer tissue is almost uniformly and strongly stained, it is determined as strong positive, and the prognosis of the patient from which the tissue is collected may be determined as no good.

In addition, the method of the present invention may also give intermediate results in addition to other test results for determining the prognosis of a patient. Such intermediate results may help determination, decision or prediction of the prognosis of the patient by a doctor, a nurse or another therapist. Examples of additional information that can be considered in combination with the intermediate results obtained by the present invention for determining the prognosis include the clinical symptoms and the body state of a patient.

In other words, the expression level of the ERAP1 gene is a prognosis marker useful for evaluating, estimating, or determining the prognosis of a subject affected with estrogen receptor-positive cancer (e.g., breast cancer, uterine cancer, ovarian cancer, prostate cancer, lung cancer (particularly non-small cell lung cancer)). Thus, the present invention also provides a method for detecting a prognosis marker for evaluating, estimating, or determining the prognosis of a subject affected with estrogen receptor-positive cancer, wherein the method comprises a) a step of detecting or measuring the expression level of the ERAP1 gene in a subject-derived biological sample, and b) a step of correlating the expression level detected or measured in the step a) with the prognosis of the subject.

Specifically, according to the present invention, increase of the expression level in comparison to the control level indicates possibility or suspicion of the poor prognosis (low survival rate).

In another embodiment of the method of the present invention, the present invention further provides a method of detecting the expression level of the ERAP1 gene in a biological sample collected from a patient having cancer, as a marker for determining the prognosis of a patient having cancer. When the detected expression level of the ERAP1 gene increases in comparison to the good prognosis control level, it indicates no good, or poor prognosis of the patient.

In addition, in another embodiment of the method of the present invention, the present invention further provides use of an antibody that specifically binds to a nucleic acid complementary to mRNA of the ERAP1 gene or the ERAP1 polypeptide in manufacture of a reagent for determining the prognosis of a patient having cancer.

In addition, in another embodiment of the method of the present invention, the present invention further provides an antibody that specifically binds to a nucleic acid complementary to mRNA of the ERAP1 gene or the ERAP1 polypeptide for determining the prognosis of a patient having cancer 5. Kit for Evaluating the Prognosis of Cancer The present invention provides a kit for evaluating or determining the prognosis of cancer. Specifically, the present kit comprises at least one reagent for detecting the expression of the ERAP1 gene in a patient-derived biological sample, which is selected from the group described below.

The cancer in the present invention is preferably estrogen receptor-positive cancer, more preferably breast cancer.

(a) a reagent for detecting mRNA of the ERAP1 gene (b) a reagent for detecting ERAP1 protein Examples of a reagent suitable for detecting mRNA of the ERAP1 gene include nucleic acids that specifically bind to ERAP1 mRNA or identify ERAP1 mRNA, such as oligonucleotides having a sequence complementary to a portion of the ERAP1 mRNA. Such kind of the oligonucleotides is illustrated by primers and probes specific for ERAP1 mRNA. Such kind of the oligonucleotides may be prepared on the basis of a method well known in the art. The reagent for detecting ERAP1 mRNA may be immobilized on a solid substrate as necessary. Furthermore, two or more reagents for detecting ERAP1 mRNA may be contained in a kit.

The probe or primer of the present invention typically comprises substantially purified oligonucleotides. The oligonucleotide typically comprises a consecutive sense chain nucleotide sequence of at least about 2000, 1000, 500, 400, 350, 300, 250, 200, 150, 100, 50, or 25 of nucleic acids comprising the ERAP1 sequence, or an antisense chain nucleotide sequence of nucleic acids comprising the ERAP1 sequence, or a region of a nucleotide sequence that is hybridized with a naturally occurring mutant of these sequences under the stringent condition. Specifically, in the preferred embodiments, e.g., an oligonucleotide having a length of 5 to 50 may be used as a primer for amplifying the gene to be detected. Alternatively, in a detection method based on the hybridization, a polynucleotide having a base length of hundreds (e.g., about 100 to 200) to a base length of thousands (e.g., about 1000 to 2000) may be used as a probe (e.g., northern blotting assay or DNA microarray analysis).

On the other hand, examples of the reagent suitable for detecting the ERAP1 protein include antibodies for ERAP1 protein. The antibody may be monoclonal or polyconal. Furthermore, any fragment or modified form (e.g. chimera antibody, scFv, Fab, F(ab')2, Fv and the like) of the antibody may be used as long as the fragment keeps the binding ability to the ERAP1 polypeptide. A method for preparing such kind of the antibody for detecting a protein is well known in the art, and such antibody and the equivalent thereof may be prepared using any method in the present invention. Furthermore, the antibody may be labeled with signal generation molecules by direct linkage or indirect labeling technique. The label, a method for labeling an antibody, and a method for detecting binding of the target to an antibody are well known in the art, and any label and any method may be used for the present invention. Furthermore, two or more reagents for detecting ERAP1 protein may be contained in a kit.

The kit may comprise one or more of the above-mentioned reagents. Furthermore, the kit may comprise a solid substrate and reagent for binding a probe for the ERAP1 gene or an antibody for ERAP1 protein, a culture medium and a container for culturing cells, positive and negative control reagents, and a secondary antibody for detecting antibody for ERAP1 protein. For example, a tissue sample obtained from a patient having good prognosis or poor prognosis may serve as a useful control reagent. The kit of the present invention comprises a buffer agent, a diluent, a filter, a needle, a syringe, and a package enclosure having instruction (e.g., document, tape, CD-ROM, etc.), and may further comprise other desirable materials from commercial viewpoint and user's viewpoint. These reagents, etc. may be contained in a container attached with a label. Examples of an appropriate container include a bottle, a vial, and a test tube. The container may be formed from various materials such as glass or plastic.

In one embodiment of the present invention, when the reagent is a probe for ERAP1 mRNA, the reagent may be immobilized on a solid substrate such as a porous strip and at least one detection site may be formed. The measurement or detection region of the porous strip may comprise multiple sites comprising nucleic acids (probe), respectively. The test strip may also comprise sites for negative and/or positive control. Alternatively, the control site may be positioned on other strip than the test strip. Optionally, different detection sites may contain different amounts of immobilized nucleic acid. Namely, a first detection site may contain larger amount of immobilized nucleic acid, and the following sites may contain smaller amount of immobilized nucleic acid. When a test sample is added, a quantitative index for the amount of ERAP1 mRNA present in the sample is provided by the number of the sites presenting detectable signal. The detection site can be constituted in any appropriately detectable shape, and typically, is a stripe or dot shape over the full width of the test strip.

The kit of the present Invention may further comprise a control sample showing good prognosis, a control sample showing poor prognosis, or both of them. The control sample showing good prognosis may be, e.g., a sample derived from an individual or a population having good progress after cancer treatment. On the other hand, the control sample showing poor prognosis may be a sample derived from an individual or a population having no good progress after cancer treatment.

In the preferred embodiments, the control sample showing good prognosis may be a clinical cancer tissue derived from a cancer patient having good progress after cancer treatment. The cancer is preferably estrogen receptor-positive cancer. Examples of the estrogen receptor-positive cancer include breast cancer, uterine cancer, ovarian cancer, prostate cancer and lung cancer (particularly non-small cell lung cancer), but are not limited thereto. Alternatively, the control sample showing good prognosis of the present invention is preferably a sample containing a lower amount of ERAP1 mRNA or protein than the cutoff value. The cutoff value in the present invention refers to a value distinguishing a range of good prognosis from a range of poor prognosis. The cutoff value may be determined using, e.g., Receiver Operating Characteristic (ROC) curve. An ERAP1 standard sample of the present invention may comprise an amount of ERAP1 mRNA or polypeptide corresponding to the cutoff value.

On the other hand, the control sample showing poor prognosis may be a clinical cancer tissue derived from a cancer patient having no good progress after cancer treatment. The control sample showing poor prognosis in the present invention is preferably a sample comprising a greater amount of ERAP1 mRNA or protein than the cutoff value.

6. Method for Screening Candidate Material for Treating and/or Preventing Cancer The present invention also provides a method for screening a candidate material for treating and/or preventing cancer.

As shown in Examples of the specification, phosphorylation of Ser39 of PHB plays an important role in the function of suppressing the estrogen receptor activation of PHB. However, phosphorylated Ser39 of PHB is dephosphorized by PP1α through the binding to PP1α via ERAP1 (Example 8). As a result, the function of suppressing the estrogen receptor activation of PHB is decreased, and proliferation of cancer cells is promoted. Thus, by inhibition of the binding of ERAP1 to PP1α, the interaction between PP1α and PHB is inhibited. As a result, dephosphorylation of PHB2 can be suppressed, and PBH2 can therefore maintain its function of suppressing the activation of estrogen receptor. Thus, a substance inhibiting the binding of ERAP1 to PP1α can be a candidate material for treating and/or preventing cancer.

In addition, as shown in Examples of the specification, it was confirmed that ERAP1 is phosphorylated by PKA and PKB, to accentuate the phosphatase activity of PP1α that is bound to ERAP1 (Example 8). Thus, inhibition of the binding of PKA and PKB to ERAP1 inhibits phosphorylation of ERAP1, and suppresses acceleration of the phosphatase activity of PP1α. As a result, dephosphorylating of PHB2 can be suppressed, and PHB2 can therefore maintain its function of suppressing the activation of estrogen receptor.

Accordingly, the present invention provides a method for screening a candidate material for treating and/or preventing cancer using inhibition of the binding of the ERAP1 polypeptide, and the PP1α polypeptide, the PKA polypeptide, or the PKB polypeptide as an index.

Examples of the test substance screened by the screening method of the present invention include any compounds, or compositions comprising several compounds. Furthermore, the test substance exposed to a cell or protein by the screening method of the present invention may be a single compound or a combination of compounds. When a combination of compounds is used in the screening method of the present invention, the compounds may be brought into contact sequentially, or may be brought into contact at the same time.

For example, any test substance such as a cell extract, a cell culture supernatant, a fermented microbiological product, a marine organism extract, a plant extract, a purified protein or rude protein, a peptide, a non-peptide compound, a synthetic micromolecule compound (including nucleic acid constructs such as antisense RNA, siRNA, ribozyme, and aptamer and the like), and a naturally occurring compound may be used in the screening method of the present invention. The test substance of the present invention is available using any of many approaches of combinatorial library methods known in the art. Examples of such approach include (1) biological library, (2) spatially addressable parallel solid phase or liquid phase library, (3) synthetic library method demanding deconvolution, (4) "one-bead one-compound" library method, and (5) synthetic library method using affinity chromatography selection. The biological library method using the affinity chromatography selection is limited to a peptide library. The other four approaches can be applied to the peptide library, the non-peptide oligomer library, or the low molecular library of compounds (Lam, Anticancer Drug Des 1997, 12: 145-67). Examples of a method for synthesizing the molecular library can be found in the art (DeWitt et al, Proc Natl Acad Sci USA 1993, 90: 6909-13; Erb et al., Proc Natl Acad Sci USA 1994, 91: 11422-6: Zuckernman et al., J Med Chem 37: 2678-85, 1994; Cho et al., Science 1993, 261: 1303-5; Carell et al., Angew Chem Int Ed Engl 1994, 33: 2059; Carell et al., Angew Chem Int Ed Engl 1994, 33: 2061: Gallop et al., J Med Chem 1994, 37: 1233-51). The library of compounds can be presented in a solution (see, Houghten, Bio/Techniques 1992, 13: 412-21), or on beads (Lamn, Nature 1991, 354: 82-4), on a chip (Fodor, Nature 1993, 364: 555-6), on bacteria (U.S. Pat. No. 5,223,409), on spores (U.S. Pat. No. 5,571,698; U.S. Pat. No. 5,403,484, and U.S. Pat. No. 5,223,409), on a plasmid (Cull et al., Proc Natl Acad Sci USA 1992, 89: 1865-9), or on a phage (Scott and Smith, Science 1990, 249: 386-90; Devlin, Science 1990, 249: 404-6; Cwirla et al., Proc Natl Acad Sci USA 1990, 87: 6378-82; Felici, J Mol Biol 1991, 222: 301-10. US patent application No. 2002103360).

Compounds converted by adding, deleting and/or substituting a portion of the structure of compounds screened by the screening method of the present invention are encompassed in the test substance identified by the screening method of the present invention.

Furthermore, when the screened test substance is a protein, in order to obtain DNA encoding the protein, a complete amino acid sequence of the protein can be determined to deduce a nucleic acid sequence encoding the protein. Alternatively, DNA encoding the protein can be isolated by analyzing a partial amino acid sequence of the identified protein, and preparing as a probe oligoDNA based on the sequence, and screening the cDNA library using the probe. The isolated DNA may be used in preparation of a test substance that is a candidate material for treating or preventing cancer.

The test substance that is screened in the screening method of the present invention may be an antibody that specifically binds to the ERAP1 polypeptide, the PP1 polypeptide, the PKA polypeptide or the PKB polypeptide, or may be an antibody that specifically binds to a partial peptide that is lack of the biological activity of the original protein in vivo. Alternatively, the test substance may be dominant negative peptides of the PP1α polypeptide, the PKA polypeptide or the PKB polypeptide that specifically binds to the binding site of the ERAP1 polypeptide to the PP1α polypeptide, the PKA polypeptide or the PKB polypeptide. Alternatively, the test substance may be dominant negative peptides of the ERAP1 polypeptide that specifically binds to the binding site of the PP1α polypeptide, the PKA polypeptide or PKB polypeptide to the ERAP1 polypeptide.

Construction of the test substance library is well known in the art, and further guidelines for a method for identifying a test substance for the screening method of the present invention, and construction of the test substance library are shown below.

(i) Molecular Modeling

Construction of the test substance library is easy from knowledge of molecular structures of compounds that are known to have properties to be obtained, and/or molecular structures of the ERAP1 polypeptide, and the PP1α polypeptide, the PKA polypeptide or the PKB polypeptide. As one approach for preliminarily screening a suitable test substance, computer modeling for the interaction between the test substance and the target may be used.

A computer modeling technology enables visualization of the three-dimensional atom structure of a selected molecule, and reasonable design of a new compound that interacts with the molecule. A three-dimensional construct typically depends on X ray crystallographic analysis of the selected molecule or data from NMR imaging. Molecular dynamics demands force field data. The computer graphic system enables estimation how a new compound binds to a target molecule, and experimental operation of the structures of the compound and the target molecule for perfecting the binding specificity. In order to estimate how the molecule-compound interaction changes when a minor change is added to one or both of them, a molecular dynamics software and calculation collection type computer are necessary. They are commonly linked to an interface of user-friendly menu mode between a molecular design program and a user.

Examples of the molecular modeling system outlined above include CHARMM program and QUANTA program, Polygen Corporation, Waltham and Mass. CHARMM carries out energy minimization and functions of molecular dynamics. QUANTA carries out construction of molecular structure, graphic modeling, and analysis. QUANTA enables interactive construction, alteration, visualization, and analysis of intermolecular behavior.

For a subject of computer modeling of a drug interacting with a particular protein, many articles are published. Examples thereof include Rotivinen et al. Acta Pharmaceutica Fennica 1988, 97: 159-66; Ripka, New Scientist 1988, 54-8; McKinlay & Rossmnanna, Annu Rev Pharmacol Toxiciol 1989, 29: 111-22; Perry & Davies, Prog Clin Biol Res 1989, 291: 189-93; Lewis & Dean, Proc R Soc Lond 1989, 236: 125-40, 141-62; and Askew et al., J Am Chem Soc 1989, 111: 1082-90, which is related to model receptor of nucleic acid ingredients.

Other computer programs for screening and illustrating a chemical substance are available from companies such as BioDesign, Inc. (Pasadena, Calif.), Allelix, Inc. (Mississauga, Ontario, Canada), and Hypercube, Inc. (Cambridge, Ontario). For example, see DesJarlais et al., J Med Chem 1988, 31: 722-9; Meng et al., J Computer Chem 1992, 13: 505-24; Meng et al., Proteins 1993, 17: 266-78; Shoichet et al., Science 1993, 259: 1445-50.

If a deduced inhibitor is identified, combinatorial chemistry technology may be used for constructing many variants based on the chemical structure of the identified, deduced inhibitor as elaborated below. The library of the deduced inhibitors or "test substances" obtained as a result can be screened using the method of the present invention for identifying a candidate material for treating and/or preventing cancer.

(ii) Combinatorial Chemical Synthesis

A combinatorial library of test substances can be manufactured as a portion of a reasonable drug design program, which comprises knowledge of the core structure present in a known inhibitor. This approach enables a moderate size of the library to be maintained to facilitate high-throughput screening. Alternatively, by simply synthesizing complete permutation of a molecular family that constitutes the library, it is possible to construct a simple, particularly short, polymer molecule library. One example of the latter approach is a library of a complete peptide having 6 amino acid length. Such peptide library may comprise every permutation of the 6 amino acid sequence. This kind of the library is referred to as the linear combinatorial chemical library.

Manufacture of the combinatorial chemical library is well known to one of ordinary skill in the art, and can be performed by either one of chemical synthesis or biological synthesis. Examples of the combinatorial chemical library include a peptide library (e.g., see U.S. Pat. No. 5,010,175: Furka, Int J Pept Prot Res 1991, 37: 487-93; Houghten et al., Nature 1991, 354: 84-6), but are not limited thereto. The other chemical techniques for manufacturing a chemical diversity library may be used. Examples of such chemical techniques include peptides (e.g., WO91/19735), encoded peptides (e.g., WO93/20242), random biooligomers (e.g., WO92/00091), benzodiazepine (e.g., U.S. Pat. No. 5,288,514), diversomers such as hydantoin, benzodiazepine and dipeptide (DeWitt et al., Proc Nat Acad Sci USA 1993, 90: 6909-13), vinylogous polypeptide (Hagihara et al., J Amer Chem Soc 1992, 114: 6568), nonpeptidic peptide mimetics having a glucose scaffold. (Hirschmann et al., J Amer Chem Soc 1992, 114: 9217-8), analogous organic compounds of a low molecular compounds library (Chen et al., J. Amer Chem Soc 1994, 116: 2661), oligocarbamate (Cho et al., Science 1993, 261: 1303), and/or peptidyl phosphonate (Campbell et al., J Org Chem 1994, 59: 658), a nucleic acid library (see Ausubel, Current Protocols in Molecular Biology 1995 supplement; Sambrook et al., Molecular Cloning: A Laboratory Manual, 1989, Cold Spring Harbor Laboratory, New York, USA), a peptide nucleic acid library (e.g., see U.S. Pat. No. 5,539,083), an antibody library (e.g., see Vaughan et al., Nature Biotechnology 1996, 14(3): 309-14 and WO97/271), a carbohydrate library (e.g., see Liang et al, Science 1996, 274: 1520-22; U.S. Pat. No. 5,593,853), and an organic low molecular library (e.g., see benzodiazepine, Gordon E M. Curr Opin Biotechnol. 1995 Dec. 1; 6(6): 624-31.; isoprenoid, U.S. Pat. No. 5,569,588; thiazolidinone and metathiazanone. U.S. Pat. No. 5,549,974; pyrrolidine, U.S. Pat. No. 5,525,735 and U.S. Pat. No. 5,519,134; morpholino compounds, U.S. Pat. No. 5,506,337; benzodiazepine, U.S. Pat. No. 5,288,514 and the like), but are not limited thereto.

A device for preparing the combinatorial library is commercialized (e.g., see 357 MPS, 390 MPS (Advanced Chem. Tech, Louisville Ky.), Symphony (Rainin, Woburn, Mass.), 433A (Applied Biosystems, Foster City, Calif.), 9050 Plus (Millipore, Bedford, Mass.)). Furthermore, the combinatorial library itself is also commercialized in great numbers (e.g., see ComGenex, Princeton, N.J. Tripos, Inc., St. Louis, Mo., 3D Pharmaceuticals, Exton, Pa., Martek Biosciences, Columbia, Md. and the like).

(iii) Other Candidates

Another approach uses a recombinant bacteriophage for manufacturing the library. By using "phage method" (Scott & Smith, Science 1990, 249: 386-90; Cwirla et al., Proc Natl Acad Sci USA 1990, 87: 6378-82; Devlin et al. Science 1990, 249: 404-6), it is possible to construct a very great library (e.g., 106 to 108 chemical substances). A second approach mainly uses chemical method, for example, the method of Geysen (Geysen et al., Molecular Immunology 1986, 23: 709-15; Geysen et al., J Immunologic Method 1987, 102: 259-74); and the method of Fodor et, al. (Science 1991, 251: 767-73). Furka et, al. (14th International Congress of Biochemistry 1988, Volume #5, Abstract FR: 013; Furka, Int J Peptide Protein Res 1.991, 37: 487-93), Houghten (U.S. Pat. No. 4,631,211), and Rutter et, al. (U.S. Pat. No. 5,010,175) describe methods for manufacturing a peptide mixture that can be tested as an agonist or an antagonist, An aptamer is a macromolecule consisting of nucleic acids, which strongly binds to a particular molecular target. Tuerk and Gold (Science. 249: 505-510 (1990)) discloses SELEX (Systematic Evolution of Ligands by Exponential Enrichment method for selecting an aptamer. In SELEX method, a great library of nucleic acid molecules (e.g., 1015 different molecules) can be used in the screening.

(vi) Method for screening substance decreasing binding level between ERAP1 polypeptide and PP1α polypeptide, PKA polypeptide or PKB polypeptide As described above, the present invention provides a candidate material for suppressing proliferation of cancer cells, or a method for screening a candidate material for treating and/or preventing cancer using inhibition of binding between the ERAP1 polypeptide and the PP1α polypeptide, the PKA polypeptide or the PKB polypeptide as an index. A cancer to which a candidate materials identified by the screen inn method of the present invention can be applied is cancer in which the ERAP1 polypeptide is expressed, more preferably estrogen receptor-positive cancer. Examples of such cancer include, e.g., breast cancer in addition, by the candidate material identified by the screening method of the present invention, it is possible to effectively suppress proliferation of particularly estrogen-dependent cancer cells.

More specifically, the method of the present invention comprises the steps described below:

(a) a step of bringing the ERAP1 polypeptide or a functional equivalent thereof into contact with PP1α polypeptide, PKA polypeptide or PKB polypeptide, or a functional equivalent thereof in the presence of a test substance:

(b) a step of detecting the binding level between the above-mentioned polypeptides in (a); and (c) a step of selecting a test substance that decreases the binding level between the above-mentioned polypeptides in comparison to the binding level detected in the absence of the test substance.

By the method of the present invention, it is possible to evaluate the suppression effect on the cancer cell proliferation or therapeutic effects on cancer of a test substance subjected to the screening. Thus, the present invention also provides a method for evaluating suppression effect for the cancer cell proliferation or treatment or prevention effect for cancer of a test substance.

More specifically, the above-mentioned method comprises the steps described below:

(a) a step of bringing the ERAP1 polypeptide or a functional equivalent thereof into contact with the PP1α polypeptide, the PKA polypeptide or the PKB polypeptide, or a functional equivalent thereof in the presence of a test substance;

(b) a step of detecting the binding level between the above-mentioned polypeptides in (a);

(c) a step of comparing the binding level between the above-mentioned polypeptides detected in (b) with the binding level detected in the absence of the test substance; and (d) a step of correlating the decrease rate of the binding level between the above-mentioned polypeptides by the test substance obtained by the comparison in (c), with suppression effect on the cancer cell proliferation or treatment or prevention effect on cancer of the test substance.

For example, when a test substance decreases the binding level of the ERAP1 polypeptide or a functional equivalent thereof and the PP1α polypeptide, the PKA polypeptide or the PKB polypeptide, or a functional equivalent thereof in comparison to the binding level detected in the absence of the test substance, the test substance can be identified or selected as a candidate material having suppression effect on the cancer cell proliferation or treatment or prevention effect on cancer. Alternatively, when a test substance does not decrease the binding level of the ERAP1 polypeptide or a functional equivalent thereof and the PP1α polypeptide, the PKA polypeptide or the PKB polypeptide, or a functional equivalent thereof in comparison to the binding level detected in the absence of the test substance, the test substance can be identified as a substance not having significant suppression effect on the cancer cell proliferation, or a substance not having significant treatment or prevention effect on cancer.

The term "functional equivalent of the ERAP1 polypeptide" used for the screening method of the present invention refers to a mutant of the ERAP1 polypeptide, a fragment polypeptide, a mutant of a fragment polypeptide, and a tagged polypeptide thereof and the like that keep the binding ability to the PP1α polypeptide, the PKA polypeptide, or the PKB polypeptide. Thus, when inhibition of the binding with the PP1α polypeptide is used as an index, the functional equivalent of the ERAP1 polypeptide is a mutant of the ERAP1 polypeptide, a fragment polypeptide, a mutant of a fragment polypeptide, and a tagged polypeptide thereof and the like that keep the binding ability to the PP1α polypeptide. Examples of such functional equivalent of ERAP1 include polypeptides comprising a binding domain of the ERAP1 polypeptide to the PP1α polypeptide. Specifically, examples of such functional equivalent include polypeptides comprising the amino acid sequence described in SEQ ID NO: 66, or polypeptide comprising the amino acid sequence described in SEQ ID NO: 67.

In addition, when inhibition of the binding of the ERAP1 polypeptide and the PKA polypeptide is used as an index, the functional equivalent of the ERAP1 polypeptide is a mutant of the ERAP1 polypeptide, a fragment polypeptide, a mutant of a fragment polypeptide, and a tagged polypeptide thereof and the like that keep the binding ability to the PKA polypeptide. Examples of such functional equivalent of the ERAP1 polypeptide include polypeptides comprising a binding domain of the ERAP1 polypeptide to the PKA polypeptide. In addition, when inhibition of the binding of the ERAP1 polypeptide and the PKB polypeptide is used as an index, the functional equivalent of the ERAP1 polypeptide is a mutant of the ERAP1 polypeptide, a fragment polypeptide, a mutant of a fragment polypeptide, and a tagged polypeptide thereof and the like that keep the binding ability to the PKB polypeptide. Examples of such ERAP1 functional equivalent include polypeptides comprising a binding domain of the ERAP1 polypeptide to the PKB polypeptide.

In addition, the term "functional equivalent of the PP1α polypeptide" used for the screening method of the present invention refers to a mutant of the PP1α polypeptide, a fragment polypeptide, a mutant of a fragment polypeptide, and a tagged polypeptide thereof and the like that keep the binding ability to the ERAP1 polypeptide. Examples of such functional equivalent of the PP1α polypeptide include polypeptides comprising a binding domain of the PP1α polypeptide to the ERAP1 polypeptide.

In addition, the term "functional equivalent of the PKA polypeptide" used for the screening method of the present invention refers to a mutant of the PKA polypeptide, a fragment polypeptide, a mutant of a fragment polypeptide, and a tagged polypeptide thereof and the like that keep the binding ability to the ERAP1 polypeptide. Examples of such functional equivalent of the PKA polypeptide include polypeptides comprising a binding domain of the PKA polypeptide to the ERAP1 polypeptide.

In addition, the term "functional equivalent of the PKB polypeptide" used for the screening method of the present invention refers to a mutant of the PKB polypeptide, a fragment polypeptide, a mutant of a fragment polypeptide, and a tagged polypeptide thereof and the like that keep the binding ability to the ERAP1 polypeptide. Examples of such functional equivalent of the PKB polypeptide include polypeptides comprising a binding domain of the PKB polypeptide to the ERAP1 polypeptide.

As described in the item of "1. ERAP1 peptide", alteration of one, two, or several amino acids in a protein does not generally have influence on the functions of the protein. Thus, the functional equivalents of the ERAP1 polypeptide, the PP1α polypeptide, the PKA polypeptide and the PKB polypeptide may be polypeptides comprising amino acid sequences in which one, two, or several amino acid residues are substituted, deleted, inserted, and/or added in the amino acid sequences of the ERAP1 polypeptide, the PP1α polypeptide, the PKA polypeptide, and the PKB polypeptide, respectively. These functional equivalents may be those comprising the amino acid sequence having a homology (also called "a sequence identity") of at least about 80%, more preferably at least about 90% to 95%, further more preferably at least about 96%, 97%, 98% or 99% with respect to the ERAP1 polypeptide, the PP1α polypeptide, the PKA polypeptide, and the PKB polypeptide, respectively. The "% homology" (also called "% identity") can be typically calculated based on the comparison between optimally aligned two sequences. A method for aligning the sequence for the comparison is well known in the art. Optimal alignment of the sequence and the comparison can be implemented using the algorithm in, e.g., "Wilbur and Lipman, Proc Natl Acad Sci USA 80: 726-30 (1983)".

The number of the amino acid mutation is not particularly limited as long as the binding ability of the ERAP1 polypeptide to the PP1α polypeptide, the PKA polypeptide, or the PKB polypeptide is maintained, or as long as the binding ability of the PP1α polypeptide, the PKA polypeptide, or the PKB polypeptide to the ERAP1 polypeptide is maintained. However, the number of the amino acid mutation is generally preferably 5% or less of the amino acid sequence. Thus, in the preferred embodiments, the number of amino acid residues mutated in the functional equivalents of the above-mentioned polypeptides may be 30 amino acids or less, 20 amino acids or less, 10 amino acids or less, 5 or 6 amino acids or less, or 3 or 4 amino acids or less.

In addition, when the kind of the amino acid mutation is "substitution", the substitution is preferably conservative amino acid substitution. However, the substitution may be non-conservative amino acid substitution as long as the binding ability of the ERAP1 polypeptide to the PP1α polypeptide, the PKA polypeptide or the PKB polypeptide is maintained, or as long as the binding ability of the PP1α polypeptide, the PKA polypeptide, or the PKB polypeptide to the ERAP1 polypeptide is maintained.

Alternatively, the functional equivalents of the ERAP1 polypeptide, the PP1α polypeptide, the PKA polypeptide, and the PKB polypeptide may be encoded by polynucleotides that are hybridized, respectively to naturally occurring polynucleotides of each of the ERAP1 gene, the PP1α gene, the PKA gene, and the PKB gene under the stringent condition.

The term "stringent (hybridization) condition" means a condition where a nucleic acid molecule is typically hybridized with a target sequence in a complex mixture of nucleic acids, but is not hybridized with other sequences in a detectable degree. The stringent condition is dependent on the sequence, and varies depending on conditions such as ionic strength, pH and the concentration of nucleic acids. As the sequence is longer, the temperature for specific hybridization is higher. A broad guideline for the hybridization of nucleic acids is found in Tijssen, Techniques in Biochemistry and Molecular Biology-Hybridization with Nucleic Probes, "Overview of principles of hybridization and the strategy of nucleic acid assays" (1993). The stringent condition is commonly selected so as to be about 5 to 10° C. lower than the thermal melting point (Tm) of a particular sequence in prescribed ionic strength and pH. Tm is a temperature where 50% of a probe complementary to a target is hybridized with a target sequence in the equilibrium state (under prescribed ionic strength, pH, and nucleic acid concentration) (since the target sequence is excessively present, 50% probe is occupied in the equilibrium state at Tm). The stringent condition may be realized by adding a destabilization agent such as formamide. In selective hybridization or specific hybridization, the positive signal is at least 2 times of the background hybridization signal, and preferably 10 times of the background hybridization signal. Exemplary stringent hybridization condition as described below is possible: 50% formamide, 5×SSC, and 1% SDS, incubation at 42° C., or 5×SSC, 1% SDS, incubation at 65° C., 0.2×SSC and 0.1% SDS, and washing at 50° C.

Hybridization conditions for isolating DNA encoding a functionally equivalent polypeptide with respect to the ERAP1 polypeptide, the PP1α polypeptide, the PKA polypeptide, and the PKB polypeptide can be selected according to an ordinary method by one of ordinary skill in the art. For example, the hybridization can be implemented by performing prehybridization for 30 minutes or more at 68° C. using "Rapid-hyb buffer" (Amersham LIFE SCIENCE), adding a labeling probe, and heating for 1 hour or more at 68° C. The following washing step can be performed, e.g. under a low stringent condition. Examples of the low stringent, condition include 42° C., 2×SSC and 0.1% SDS, and 50° C., 2×SSC and 0.1% SDS. Alternatively, the following washing step can be more suitably performed under high stringent condition. Examples of the high stringent condition include, e.g., three washings in 0.01% SDS for 20 minutes at room temperature and 2×SSC, and then three washing in 0.1% SDS at 37° C. for 20 minutes and 1×SSC, and two washings in 0.1% DSD at 50° C. for 20 minutes and 1×SSC. However, several factors such as the temperature and the salt concentration may have influence on the stringency of the hybridization. These factors may be appropriately selected to achieve necessary stringent condition by one of ordinary skill in the art.

The term "tagged polypeptide" used for the screening method of the present invention refers to a polypeptide in which any epitope of a monoclonal antibody having clear specificity is added to the N-terminal or C terminal of the polypeptide. As such epitope, a commercially available epitope-antibody system may be used (Experimental Medicine 1995, 13: 85-90). For example, β-galactosidase, maltose-bound protein, glutathione S-transferase (GST), green fluorescence protein (GFP), polyhistidine (His-tag), influenza aggregate HA, human c-myc, FLAG, vesicular stomatitis virusglycoprotein (VSV-GP), T7 gene 10 protein (T7-tag), human simple herpes virus glycoprotein (HSV-tag), E-tag (epitope on a monoclonal phage) and the like may be suitably used as a tag (Experimental Medicine 13: 85-90 (1995)).

The ERAP1 polypeptide, the PP1α polypeptide, the PKA polypeptide and the PKB polypeptide, and functional equivalents thereof can be manufactured using a method well known to one of ordinary skill in the art such as those described in "1. ERAP1 peptide". In the preferred embodiments, the above-mentioned polypeptide used in the screening method of the present invention is isolated, and purified.

In addition, the ERAP1 polypeptide, the PP1α polypeptide, the PKA polypeptide and the PKB polypeptide, and functional equivalents thereof used in the screening method of the present invention may be linked to other substance as long as they keep the binding ability. Examples of the substance that can be linked include a peptide, a lipid, a sugar and a sugar chain, an acetyl group, and naturally occurring and synthetic polymers. The linkage of these substances may be implemented for imparting additional function to the polypeptide, or for stabilizing the polypeptide.

As the method for screening a substance that inhibits the binding between the ERAP1 polypeptide or a functional equivalent thereof and the PP1α polypeptide, the PKA polypeptide or the PKB polypeptide, or functional equivalents thereof, a method well known to one of ordinary skill in the art may be used. For example, such screening can be implemented by in vitro assay system. More specifically, first, the ERAP1 polypeptide or a functional equivalent thereof is bound to a support, and the PP1α polypeptide, the PKA polypeptide or the PKB polypeptide, or a functional equivalent thereof is added together with a test substance. Then, the mixture is incubated, and then washed, and the PP1α polypeptide, the PKA polypeptide or the PKB polypeptide, or a functional equivalent thereof that is bound to the support is detected or measured. A test substance that decreases the detected amount of the PP1α polypeptide, the PKA polypeptide or the PKB polypeptide, or a functional equivalent thereof may be selected as a candidate material for suppressing proliferation of cancer cells, and/or a candidate material for treating and/or preventing cancer, Alternatively, the PP1α polypeptide, the PKA polypeptide or the PKB polypeptide, or a functional equivalent thereof may be bound to a support, and the ERAP1 polypeptide or a functional equivalent thereof may be added thereto together with a test substance. In this case, a test substance that decreases the detected amount of the ERAP1 polypeptide or a functional equivalent thereof may be selected as a candidate material for suppressing proliferation of cancer cells, and/or a candidate material for treating and/or preventing cancer.

Examples of the support that can be used for binding the above-mentioned polypeptide include insoluble polysaccharides such as agarose, cellulose and dextran; and synthesis resins such as polyacrylic amide, polystyrene and silicone, Commercially available beads and plates prepared from the above-mentioned materials (e.g., multi-well plates, biosensor chips and the like) can be suitably used. When the bead is used, the bead may be filled into a column. Alternatively, if magnetic beads known in the art are used similarly, polypeptides that are bonded on the beads can be easily isolated by the magnetic.

The binding of the polypeptide to the support can be implemented by a method known in the art such as chemical binding and physical adsorption. Alternatively, the polypeptide may be bound to the support through an antibody specifically recognizing the polypeptide. In addition, when the polypeptide is a tagged polypeptide, the tagged polypeptide may be bound to the support through an antibody specifically recognizing the tag. Furthermore, the binding of the polypeptide to the support can be also implemented by avidin and biotin. The binding between the polypeptides can be implemented in a buffer such as a phosphate buffer or tris buffer as long as the buffer does not inhibit the binding between the polypeptides.

As a means for detecting or quantifying the binding between the polypeptides, a biosensor using surface plasmon resonance phenomena can be used. When such biosensor is used, the binding between the polypeptides can be observed in real time as the surface plasmon resonance signal using a trace amount of the polypeptides without labeling (e.g., BIAcore, Pharmacia). Then, using a biosensor such as BIAcore, the binding between the polypeptides can be evaluated.

Alternatively, the ERAP1 polypeptide or a functional equivalent thereof may be labeled, and the label can be used for detecting or measuring the binding between the polypeptides. Alternatively, the PP1α polypeptide, the PKA polypeptide or the PKB polypeptide, or a functional equivalent thereof may be labeled, and the label can be used for detecting or measuring the binding between the polypeptides. Specifically, one of the polypeptides to be detected for the binding is labeled, and then, the labeled polypeptide is brought into contact with the other polypeptide in the presence of a test substance. Then, after washing, the bound polypeptide is detected or measured by the label. A labeling substance such as a radioisotope (e.g., 3H, 14C, 32P, 33P, 35S, 125I, 131I), an enzyme (e.g. alkaline phosphatase, horseradish peroxidase, β-galactosidase, β-glucosidase), a fluorescence substance (e.g., fluorescein isothiocyanate (FLTC), rhodamine) and biotin/avidin may be used for the labeling of the polypeptide in the present method. When the polypeptide is labeled by a radioisotope, detection or measurement of the labeled polypeptide bound can be implemented by liquid scintillation. When the polypeptide is labeled by an enzyme, a substrate for the enzyme is added. Subsequently, the change of the substrate by an enzyme such as the color development can be detected by an absorptiometer and the like, whereby to detect or measure the labeled polypeptide that is bound. Furthermore, when a fluorescence substance is used as a label, bound labeled polypeptide can be detected or measured using a fluorescence photometer.

Furthermore, the binding between the ERAP1 polypeptide or a functional equivalent thereof and the PP1α polypeptide, the PKA polypeptide or the PKB polypeptide, or a functional equivalent thereof can be detected or measured using an antibody for the ERAP1 polypeptide, the PP1α polypeptide, the PKA polypeptide, the PKB polypeptide, or a functional equivalent thereof. For example, the ERAP1 polypeptide or a functional equivalent thereof immobilized on a support is brought into contact with the PP1α polypeptide, the PKA polypeptide, or the PKB polypeptide, or a functional equivalent thereof together with a test substance. Then, the mixture is incubated. Then, the mixture is washed, and the PP1α polypeptide, the PKA polypeptide, or the PKB polypeptide, or a functional equivalent thereof that is bound to the ERAP1 polypeptide or a functional equivalent thereof can be detected or measured using an antibody for the PP1α polypeptide, the PKA polypeptide, or the PKB polypeptide, or a functional equivalent thereof.

Alternatively, the PP1α polypeptide, the PKA polypeptide or the PKB polypeptide, or a functional equivalent thereof is immobilized on a support, and brought into contact with the ERAP1 polypeptide or a functional equivalent thereof together with a test substance. Then, the ERAP1 polypeptide or a functional equivalent thereof that is bound to the PP1α polypeptide, the PKA polypeptide or the PKB polypeptide, or a functional equivalent thereof may be detected or measured using an antibody for the ERAP1 polypeptide or a functional equivalent thereof. When an antibody is used in the screening method of the present invention, preferably, the antibody is labeled by one of the above-mentioned labeling substances, and can be detected or measured based on the labeling substance. Alternatively, an antibody for the above-mentioned polypeptide may be used as a primary antibody that is detected by a secondary antibody labeled with a labeling substance. Furthermore, when the antibody is used, the antibody that is bound to the polypeptide can be detected or measured using protein G column or protein A column.

Alternatively, in other embodiments, the two-hybrid system using cells may be used ("MATCHMAKER Two-Hybrid system", "Mammalian MATCHMAKER Two-Hybrid Assay Kit" "MATCHMAKER one-Hybrid system" (Clontech); "HybriZAP Two-Hybrid Vector System" (Stratagene); reference document "Dalton and Treisman, Cell 68: 597-612 (1992)", "Fields and Sternglanz, Trends Genet. 10: 286-92 (1994)").

In the two-hybrid system, e.g., the ERAP1 polypeptide or a functional equivalent thereof is fused with an SRF-binding region or GAL4-binding region. Then, the resultant is expressed in yeast cells. The PP1α polypeptide, the PKA polypeptide or the PKB polypeptide or a functional equivalent thereof is fused with VP16- or GAL4-transcriptional activation region. Then, the resultant is expressed similarly in yeast cells in the presence of a test substance. Alternatively, the PP1α polypeptide, the PKA polypeptide or the PKB polypeptide, or a functional equivalent thereof is fused with SRF-binding region or GAL4-binding region. In addition, the ERAP1 polypeptide or a functional equivalent thereof may be fused with VP16- or GAL4-transcriptional activation region. The binding of the ERAP1 polypeptide or a functional equivalent thereof to the PP1α polypeptide, the PKA polypeptide or the PKB polypeptide, or a functional equivalent thereof enables activation of a reporter gene and detection of a positive clone. As the reporter gene, e.g., Ade2 gene, lacZ gene, CAT gene, luciferase gene and the like may be used in addition to HIS3 gene.

The term "decreasing the binding level" used for the screening method of the present invention refers to decreasing the binding level between the polypeptides by at least 10% or more, preferably 25% or more, more preferably 50% or more, further preferably 75%, 80%, 85%, 90% or 95% or more in comparison to the binding level detected in the absence of a test substance. Thus, when the test substance decreases the binding level between the polypeptides by at least 10% or more, the test substance is characterized as a substance "decreasing the binding level".

The candidate material identified or selected by the screening method of the present invention can be further evaluated by tests for the suppression effect on the cancer cell proliferation or treatment or prevention effect on cancer. Thus, the screening method of the present invention may comprise the steps described below:

(a) a step of bringing the ERAP1 polypeptide or a functional equivalent thereof into contact with the PP1α polypeptide, the PKA polypeptide or the PKB polypeptide, or a functional equivalent thereof in the presence of a test substance;

(b) a step of detecting the binding level between the above-mentioned polypeptides in (a); and (c) a step of selecting a test substance that decreases the binding level between the above-mentioned polypeptides in comparison to the binding level detected in the absence of the test substance;

(d) a step of confirming the suppression effect on the cancer cell proliferation with respect to the test substance selected in (c); and (e) a step of selecting the test substance confirmed for the suppression effect on the cancer cell proliferation in (d) as a substance for suppressing proliferation of cancer cells, or a candidate material for treating and/or preventing cancer.

Confirmation for the suppression effect on the cancer cell proliferation can be performed by in vitro test or in vivo test. In the preferred embodiments, cancer cells that can be used in such in vitro test and in vivo test are estrogen receptor-positive cancer cells in which the ERAP1 polypeptide is expressed. Examples of such cancer cells include estrogen receptor-positive breast cancer cells. In addition, the suppression effect on the cancer cell proliferation evaluated in the in vitro test or in vivo test is preferably the suppression effect on estrogen-dependent cell proliferation.

With respect to the identified or selected candidate material, in vitro test can be implemented to confirm the suppression effect on the cancer cell proliferation. In this in vitro test, e.g., cancer cells or normal cells are cultured in the presence of the candidate material, and the proliferation speed is measured. Similarly, the in vitro test can be implemented to evaluate the suppression effect on estrogen-dependent cell proliferation. In this case, cancer cells are treated with estrogen, and then cultured in the presence of the candidate material. Alternatively, cancer cells are cultured in the presence of estrogen and the candidate material. Then, the proliferation speed of cancer cells is measured. The in vivo test can be implemented with respect to the identified or selected candidate material to confirm the suppression effect on the cancer cell proliferation. In this in vivo test, e.g., a mouse is transplanted with cancer cells, and administered with the candidate material, and confirmed for proliferation of the transplanted cancer cells. Similarly, the in vivo test can be implemented to evaluate the suppression effect on estrogen-dependent cell proliferation. In this case, the mouse transplanted with the cancer cells is administered with estrogen and the candidate material at the same time or sequentially, and confirmed for proliferation of the transplanted cancer cells. Methods for such in vitro test and in vivo test are exemplified in EXAMPLES in the specification.

The term "confined for the suppression effect on the cancer cell proliferation" in the above-mentioned screening method means that the proliferation speed of cancer cells is suppressed in the presence of a test substance by at least 10% or more, preferably 25% or more, more preferably 50% or more, further preferably 75%, 80%, 859%, 90% or 95% or more, in comparison to the proliferation speed detected in the absence of the test substance. Thus, when the test substance suppresses the proliferation speed of cancer cells by at least 10% or more, the test substance is characterized as a substance "confirmed for the suppression effect on the cancer cell proliferation".

Hereinafter, the present invention will be further described in detail in reference to Examples. However, the materials, the methods, and the examples described below are only examples in various aspects of the present invention, and the scope of the present invention is not limited thereto at all. Therefore, similar or equivalent methods and materials to those described in the specification may be used for implementing or investigating the present invention.

EXAMPLES

Hereinafter, the present invention will be further specifically described using Examples. However, the technical scope of the present invention is not limited to these Examples.

[Example 1] Effect on Estrogen-Dependent Breast Cancer

1. Materials and Methods

Cell Line and Clinical Sample

Human breast cancer cell lines (MCF-7, ZR-75-1, HCC1500, BT-474, YMB-1 and T47D) and COS-7 were purchased from Americain Type Culture Collection (ATCC, Rockville, Md., USA), KPL-1 and KPL-3C were provided from Dr. Junichi Kurebayashi (Kawasaki Medical School, Okayama, Japan) under Material transfer agreement. HBC4 and HBC5 were provided from Dr. Takao Yamori (Japanese Foundation For Cancer Research, Cancer Chemotherapy Center, Department of Molecular Pharmacology) under Material transfer agreement. All of the cell lines were cultured under the conditions recommended by each depositor.

Treatment of Cell

MCF-7 cells were suspended in MEM (Invitrogen, Carlsbad, Calif., USA) reinforced with 10% FBS (Nichirei Biosciences, Tokyo, Japan), 1% antibiotic/antimycotic solution (Invitrogen), 0.1 mM NEAA (Tnvitrogen), 1 mM sodium pyruvate and 10 μg/ml insulin (Sigma, St. Louis, Mo., USA). Then, the cell suspension was seeded in a 48-well plate ($2\times10^4$ cells/200 μl), a 24-well plate ($1\times10^5$ cells/1 ml), a 6-well plate ($5\times10^5$ cells/2 ml) or 10 cm dish ($2\times10^6$ cells/10 ml). The cells were maintained at 37° C. in humidified atmosphere containing 5% carbon dioxide. On the next day of the seeding, the culture medium was exchanged with phenol red-free DMEM/F12 (Invitrogen) reinforced with FBS, an antibiotic/antimycotic solution, NEAA, sodium pyruvate and insulin. After 24 hours, the cells were treated with 10 nM 17β estradiol (E2, Sigma). The ERAP-1 peptide was added just before the E2 stimulation in the inhibition test.

Western Blotting Analysis

The cells were lysed with a lysis buffer (50 mM Tris-HCl: pH 8.0, 150 mM NaCl, 0.1% NP-40, and 0.5% CHAPS) containing 0.1% protease inhibitor cocktail III (Calbiochem, San Diego, Calif., USA). The cell lysate was subjected to electrophoresis, blotted on a nitrocellulose membrane, and blocked with a 4% BlockAce solution (Dainippon Pharmaceutical, Osaka, Japan) for 1 hour. The membrane was incubated in the presence of the antibodies described below for 1 hour:

Anti-ERAP1 antibody (Kim J W, et al. Cancer Sci. 2009; 100; 1468-78);

Anti-PHB2 antibody (Abcam, Cambridge, UK);

Anti-NcoR antibody (Abcam, Cambridge, UK);

Anti-phosphorylation ERα antibody (Tyr537) (Abcam, Cambridge, UK);

Anti-ERα (AER314) antibody (Thermo Fisher Scientific, Fremont, Calif., U.S.A);

Anti-SRC-1 (128E7) antibody (Cell Signaling Technology, Danvers, Mass., USA);

Anti-Shc antibody (Cell Signaling Technology, Danvers, Mass., USA);

Anti-α/β-tubulin antibody (Cell Signaling Technology, Danvers, Mass., MA, USA);

Anti-Akt antibody (Cell Signaling Technology, Danvers, Mass., USA);

Anti-phosphorylation Aki antibody (Ser473) (587F11) (Cell Signaling Technology, Danvers, Mass., USA);

Anti-p44/42 Map Kinase antibody (Cell Signaling Technology, Danvers, Mass., USA);

Anti-phosphorylation p44/42 Map Kinase antibody (Thr202/Tyr204) (Cell Signaling Technology, Danvers, Mass., USA);

Anti-phosphorylation ERα antibody (Ser104/106) (Cell Signaling Technology, Danvers, Mass., USA);

Anti-HDAC1 (H-11) antibody (Santa Cruz Biotechnology, Santa Cruz, Calif., USA);

Anti-IGF-1Rβ antibody (Santa Cruz Biotechnology, Santa Cruz, Calif., USA);

Anti-P13-kinase p85α (U13) antibody (Santa Cruz Biotechnology, Santa Cruz, Calif., USA);

Anti-Ub (P4D1) antibody (Santa Cruz Biotechnology, Santa Cruz, Calif., USA);

Anti-lamin B1 antibody (Santa Cruz Biotechnology, Santa Cruz, Calif., USA);

Anti-phosphorylation ERα antibody (Ser118) (Santa Cruz Biotechnology, Santa Cruz Calif., USA);

Anti-phosphorylation ERα antibody (Ser167) (Santa Cruz Biotechnology, Santa Cruz. Calif., USA);

Anti-phosphorylation ERα antibody (Ser305) antibody (Millipore, Billerica, Mass. USA);

Anti-β-actin (AC-15) antibody (Sigma);

Anti-FLAG-tag M2 antibody (Sigma);

Anti-HA-tag antibody (Roche, Mannheim, Germany); or

Anti-phosphorylation tyrosine antibody (Zymed, San Francisco, Calif., USA).

Next, the membrane was incubated in the presence of HRP-binding secondary antibody (Santa Cruz Biotechnology) for 1 hour. Then, the membrane was developed with enhanced chemiluminescence system (GE Healthcare, Buckinghamshire, UK). The blotting was scanned using an Image Reader LAS-3000 mini (Fujifim, Tokyo, Japan).

Immunoprecipitation

As described in the item of "Western blotting analysis", the cells were lysed with a 0.1% NP-40 lysis buffer. The cell lysate was precleaned using normal IgG and rec-Protein G Sepharose 4B (Zymed, San Francisco, Calif., USA) at 4° C. for 3 hours. After centrifuge separation, the supernatant was incubated in the presence of an anti-ERAP1 antibody, an anti-PHB2 antibody and an anti-ERα antibody at 4° C. for 6 hours. Then, the supernatant was incubated in the presence of rec-Protein G Sepharose 4B at 4° C. for 1 hour, to precipitate an antigen-antibody complex. The immunoprecipitated protein complex was washed with a lysis buffer three times, and separated by SDS-PAGE. Then, Western blotting analysis was performed by the method described previously (Kim J W, et al. Cancer Sci. 2009; 100: 1468-78.).

Identification of PHB-2 Binding Region in ERAP1 Protein

In order to determine the PHB2-binding region in ERAP1, five different constructs corresponding to partial peptides ($ERAP1_{1-434}$, $ERAP1_{435-2177}$, $ERAP1_{1468-2177}$, $ERAP1_{1-250}$, $ERAP1_{1-100}$) of the ERAP1 protein were cloned into appropriate sites of an N-terminal Flag-tagged pCAGGS vector. COS-7 cells were transfected with each plasmid of FLAG-ERAP1 and HA-PHB2 using FuGENE6 transfection reagent (Roche). After 48 hours from the transfection, the cells were lysed with a 0.1% NP-40 lysis buffer as described above. The cell lysate was precleaned at 4° C. for 3 hours, and then the cell lysate was incubated at 4° C. for 6 hours in the presence of anti-Flag M2 agarose (Sigma). Then, the immunoprecipitated protein or the cell lysate was subjected to electrophoresis, and blotted on a nitrocellulose membrane. The membrane was incubated in the presence of the anti-FLAG-tag M2 antibody or the anti-HA-tag antibody.

Dominant Negative Effect of ERAP1-Deleted Variant (1-434) on Binding of ERAP1 and REA The influence of ERAP1-deleted variant (1-434) on the interaction between ERAP1 and PHB2, and the influence of E2 stimulation on ERE activity were investigated using an expression vector construct ($ERAP_{1-434}$) consisting of 1-434 amino acid residues of ERAP1 (SEQ ID NO: 33), which were estimated to be important for the interaction between ERAP1 and PHB2. In the binding-inhibition test, COS-7 cells were transfected with Flag-ERAP1 together with HA-PHB2 by FuGENE6 transfection reagent (Roche). After 48 hours, the cells were lysed with a 0.1% NP-40 lysis buffer. The cell lysate was precleaned at 4° C. for 3 hours, and then, the cell lysate was incubated at 4° C. for 6 hours in the presence of an anti-HA antibody. Then, the immunoprecipitated protein or the cell lysate was subjected to electrophoresis, and blotted on a nitrocellulose membrane. The membrane was incubated in the presence of the anti-FLAG-tag M2 antibody or the anti-HA-tag antibody. In addition, in ERE activity inhibition test. COS-7 cells were transfected with $ERAP1_{1-434}$, ERAP1, PHB2, ERα, and each plasmid of the ERE-luciferase vectors by FuGENE6 transfection reagent. At the same time, the cells were stimulated with E2 for 48 hours. The cells were harvested, and activities of luciferase and *Renilla*-luciferase were evaluated using Promega dual luciferase reporter assay (Tokyo, Japan). All of the data were standardized by the activity of *Renilla*-luciferase in consideration of the transfection efficiency.

Dominant Negative Peptide

To the amino terminal of the peptide consisting of 13 amino acids derived from PHB2-binding domain of ERAP1 (codon 165-177: QMLSDLTLQLRQR (SEQ ID NO: 27)), a polyarginine sequence (11R) consisting of 11 cell membrane-permeable arginines were covalently bonded. The ERAP1-scramble peptide (DRQLQLSTLQRML (SEQ ID NO: 28)) and the ERAP1-mutant peptide (AMLSALTLALRQR (SEQ ID NO: 29)) were synthesized as a control. In order to test the influence of the 11R-bound ERAP1-peptide on inhibition of formation of ERAP1-PHB2 complex, MCF-7 cells were treated with 10 μM ERAP1 peptide in the presence of 10 μM E2. After 24 hours, the cells were lysed with a 0.1% NP-40 lysis buffer. Then, as described in the item of "Immunoprecipitation", the cell lysate was incubated in the presence of an anti-ERAP1 antibody and an anti-PHB2 antibody. Then, the immunoprecipitated protein or the cell lysate was subjected to electrophoresis, and blotted on a nitrocellulose membrane. Finally, Western blotting analysis was performed using an anti-ERAP1 antibody or an anti-PHB2 antibody, and inherent ERAP1 or PHB2 protein was detected, respectively.

Chemical Staining of Immune Cell

MCF-7 cells were seeded in an 8-well chamber (Laboratory-Tek II Chamber Slide System, Nalgen Nunc International, Naperville, Ill., USA) in $5\times10^4$ cells/well, and cultured under estrogen-free condition for 24 hours. After 24 hours from exposure to E2 and/or the ERAP1-peptide, the cells were treated with 4% paraformaldehyde at 40° C. for 30 minutes to fix the cells, and treated with 0.1% Triton X-100 for 2 minutes whereby to make the cells permeable. Then, the cells were coated with 3% BSA to block non-specific hybridization. Then, the cells were incubated further for 1 hour in the presence of an anti-PHB2 antibody. The cells were washed with PBS; and then incubated in the presence of Alexa 594-binding anti-rabbit antibody (Molecular Probe, Eugene, Oreg., USA) for 1 hour whereby to stain the cells. The nucleus was counterstained with 4,6-diamidine-2'-phenylindole dihydrochloride (DAPI, Vectashield, Vector Laboratories, Burlingame, Calif. USA). The fluorescence image was obtained under Olympus IX71 microscope (Tokyo, Japan).

Fractionation of Nucleus/Cytoplasm

In order to evaluate the locality of PHB2, MCF-7 cells were treated as described above. Then, immunoprecipitation was performed using an anti-ERAP1 antibody, an anti-PHB antibody and an anti-ERα antibody in the presence of rec-protein G sepharose using the extracts of the nucleus and the cytoplasm of MCF7 cells. The extracts of the nucleus and the cytoplasm were prepared in accordance with the instruction of the manufacturer using NE-PER nuclear and cytoplasmic extraction reagent (Thermo Fisher Scientific). The protein contents of the cytoplasm and nuclear fractions were evaluated with Comassie brilliant blue staining.

Luciferase Reporter Assay

For ERE reporter assay, MCF-7 cells were transfected with ERE reporter (SABiosciences, Frederick, Md., USA) in accordance with the instruction of the manufacturer. For AP-1 reporter assay, MCF-7 cells were transfected with AP-1 reporter (mouse IL-11 promoter comprising two tandem AP-1 sites subcloned into PGL2-basic vector), c-fos, c-Jun and pRL-TK as an internal standard. After 16 hours from the transfection, the culture medium was exchanged with an assay culture medium (Opti-MEM, 10% FBS, 0.1 mM NEAA, 0.1 mM Sodium pyruvate and 10 μg/ml insulin) After 24 hours from the transfection, the cells were treated with E2 and/or the ERAP1-peptide or 24 hours. The cells were harvested, and the activities of luciferase and *Renilla*-luciferase were evaluated using Promega dual luciferase reporter assay (Tokyo, Japan). In consideration of the transfection efficiency, all of the data were standardized by the activity of *Renilla*-luciferase.

Deacetylation Assay

HDAC assay was performed using HDAC Fluorescent Activity Assay/Drug Discovery Kit (Enzo Life Sciences, Plymouth Meeting, Pa., USA) in accordance with the instruction of the manufacturer. MCF-7 cells were treated with E2 and/or the ERAP1 peptide(s) for 24 hours in a 6-well plate. Then, the cell extract was immunoprecipitated with anti-PHB2 antibody. Furthermore, the immunoprecipitated cell extract was incubated for 30 minutes in the presence of a substrate at 30° C. After the incubation, the reaction was stopped, and the fluorescence was analyzed with a microplate fluorometer (Infinite M200, Tecan, Mannedorf, Switzerland).

Semi-Quantitative Reverse Transcriotion PCR

Down-regulation of ERα was evaluated by semi-quantitative reverse transcription PCR. Complete RNA was extracted using RNeasy Mini purification kit (Qiagen) from E2-treated cells in the presence or in the absence of the ERAP1 peptide, and reverse-transcribed into cDNA using Superscript II reverse transcriptase (Invitrogen), oligo dT primer (nvitrogen) and 25 mM dNTP Mixture (Invitrogen). mRNAs of ERα and β-actin were measured with GeneAmp PCR system (Applied Biosystems, Foster, Calif., USA). The primers are as described below:

```
                                    (SEQ ID NO: 1)
ERα: 5'-GCAGGGAGAGGAGTTTGTGTG-3'
and
                                    (SEQ ID NO: 2)
5'-TGGGAGAGGATGAGGAGGAG-3'
                                    (SEQ ID NO: 3)
β-actin: 5'-GAGGTGATAGCATTGCTTTCG-3'
and
                                    (SEQ ID NO: 4)
5'-CAAGTCAGTGTACAGGTAAGC-3'.
```

Real Time PCR

Expressions of target genes of ERα (pS2, cyclin D1, c-myc, SP-1, E2F1 and PgR). ERAP1 and PHB2 were evaluated with real time PCR. In addition, the expression amount of PHB32 not reported as a target of ERα was also measured as a negative control. β2-MG was used as an internal standard control. Extraction of complete RNA and the following cDNA synthesis were performed as described above. cDNA was analyzed with real time PCR in 500 Real Time PCR. System (Applied Biosystems) using SYBR® Premix Ex Taq (Takara Bio, Shiga, Japan) in accordance with the instructions of the manufacturer. Each sample was standardized with the mRNA content of β2-MG. The primers used for the amplification are as described below:

```
                                     (SEQ ID NO: 5)
pS2: 5'-GGCCTCCTTAGGCAAATGTT-3'
and

                                     (SEQ ID NO: 6)
5'-CCTCCTCTCTGCTCCAAAGG-3';

                                     (SEQ ID NO: 7)
cyclin D1: 5'-CAGAAGTGCGAGGAGGAGGT-3'
and

                                     (SEQ ID NO: 8)
5'-CGGATGGAGTTGTCGGTGT-3';

                                     (SEQ ID NO: 9)
c-myc: 5'-CGTCTCCACACATCAGCACA-3'
and

                                    (SEQ ID NO: 10)
5'-GCTCCGTTTTAGCTCGTTCC-3';

                                    (SEQ ID NO: 11)
SP-1: 5'-TGCTGCTCAACTCTCCTCCA-3'
and

                                    (SEQ ID NO: 12)
5'-GCATCTGGGCTGTTTTCTCC-3';

                                    (SEQ ID NO: 13)
E2F1: 5'-TACCCCAACTCCCTCTACCC-3'
and

                                    (SEQ ID NO: 14)
5'-CCCACTCACCTCTCCCATCT-3';

                                    (SEQ ID NO: 15)
PgR: 5'-CCCCGAGTTAGGAGACGAGA-3'
and

                                    (SEQ ID NO: 16)
5'-GCAGAGGGAGGAGAAAGTGG-3';

                                    (SEQ ID NO: 17)
ERAP1: 5'-CTTGACAAGGCCTTTGGAGT-3'
and

                                    (SEQ ID NO: 18)
5'-CAATATGCTTTTCCCGCTTT-3';

                                    (SEQ ID NO: 19)
PHB2: 5'-GGATCTGCTTCTCCAGTTTT-3'
and

                                    (SEQ ID NO: 20)
5'-ACTGAGAAATCACGCACTGT-3';

                                    (SEQ ID NO: 21)
β2-MG: 5'-AACTTAGAGGTGGGGAGCAG-3'
and

                                    (SEQ ID NO: 22)
5'-CACAACCATGCCTTACTTTATC-3'.
```

Cell Proliferation Assay

Using Cell-Counting Kit-8 (CCK-8, Dojindo, Kumamoto, Japan), the cell proliferation assay was performed. The cells were harvested, and plated in $2\times10^4$ cells/well on a 48-well plate, and maintained at 37° C. in a humidified incubator. At the indicated time points, the cells were added with a CCK-8 solution diluted to 1:10, and incubated for 1 hour. Then, the absorbance at 450 nm was measured and the number of living cells in each well was calculated.

Cell Cycle

The cells were fixed with cold 70% ethanol, and stained with 20 μg/ml propidium iodide (Sigma) and 1 mg/ml ribonuclease A (Sigma), and analyzed with FACSCalibur (BD, Franklin Lakes, N.J., USA). The cell cycle was evaluated using CellQuest software (BD).

Inhibition of Tumor Proliferation In Vivo

KPL-3C cell suspension ($1\times10^7$ cells/mouse) was mixed with the same amount of Matrigel (BD). This mixture was injected into the breast fat body of 6 weeks old female BALB/c nude mouse (CLEA Japan, Tokyo, Japan). The mouse was kept in a sterile isolated facility with a cycle of 12 hour light period/12 hour dark period, and freely fed with rodent food and water. The tumor was grown over 1 week until the size thereof reached 50 to 80 mm$^3$ (calculated as $\frac{1}{2}\times$(width$\times$length$^2$)). Then, the mice were randomly divided into nine treatment groups (5 individuals/group): no treatment group, 6 μg/day E2 treatment group, E2+0.28 mg/day ERAP1-peptide treatment group, E2+0.7 mg/day ERAP1-peptide treatment group, E2+1.4 mg/day ERAP1-peptide treatment group, E2+0.28 mg/day of the scramble peptide treatment group, E2+0.7 mg/day of the scramble peptide treatment group, E2+1.4 mg/day of the scramble peptide treatment group, and E2+83 μg/day tamoxifen treatment group. The mouse was treated every day with 6 μg/day E2 solution (100 μl $2.2\times10^{-4}$ M) on the neck skin. The ERAP1-peptide or the scramble peptide was administered to the mouse in 0.28, 0.7, or 1.4 mg/day (14, 35, 70 mg/kg) by intraperitoneal injection every day. Tamoxifen was also administered intraperitoneally to the mouse in a dose of 4 mg/kg, every day. The tumor volume was measured over 2 weeks using calipers. When the test was completed, the animal was killed, and further the tumor was removed for performing analysis of ERα target gene expression, and freezed with liquid nitrogen. In vivo data were indicated as the average value of the tumor volume±the standard error of average value. The P value when the test was completed, was calculated using Students t-test. All of the tests were performed in accordance with the guideline of the animal facility of The University of Tokushima.

ChIP Assay

ChIP analysis was performed according to the instructions of the manufacturer using EZ-ChIP (Millipore, Billerica, Mass., USA). MCF-7 cells were treated with E2 and/or the ERAP1-peptide for 24 hours. Then, the cells were fixed with 37% formaldehyde, and resuspended in a lysis buffer, and crushed with ultrasonic waves in 10 seconds×10 with Microson XL-2000 (Misonix Farmingdale, N.Y., USA). The supernatant was precleared with protein G agarose beads, and 1% input was collected. Immunoprecipitation (for each $1\times10^6$ cells) was performed (overnight, 4° C.) using an anti-ERα antibody, an anti-PHB2 antibody, an anti-HDAC1 antibody and an anti-NCoR antibody, and an anti-SRC-1 antibody, and normal mouse IgG as a control. The DNA-protein complex was pulled-down with protein G agarose beads (1 hour, 4° C.) and washed. The immunoprecipitate was resuspended in Elution buffer. Then, the obtained suspension was incubated at 65° C. for 5 hours in order to release the cross-linking. Then, the imnunoprecipitate was purified using the accessory purification column. The DNA fragment was detected with 25 to 28 cycles of PCR. As the primers for ERE region of ERAP1 genome,

```
                                    (SEQ ID NO: 23)
5'-GGGGTACCTTATATCACTAGTCGACA-3'
and

                                    (SEQ ID NO: 24)
5'-CCGCTCGAGAGAACTAGAGCAGACAA-3'
```

were used.

Statistical Analysis

For determining the statistical significance of the difference between the test groups, Student's t-test was used. P value<0.05 was regarded as significant.

Estimation of Interaction Site

The interaction site of ERAP1 and PHB2 was estimated using PSIVER. PSIVER (Protein-protein interaction SItes prediction serVER) is a calculation method for estimating residues binding to other proteins using only characteristics of the sequence (site-specific score matrix and estimated solvent-contact surface area). For the calculation method, Naive Bayes classifier provided with the deduced kernel density is used, and the estimation server is opened on the internet. 0.390, which was the threshold of the default, was used in the present invention.

Recombinant PHB2 Protein

The partial sequence of human PHB2 (residues 77-244) was cloned into NcoI and XhoI sites of pTAT6 expression vector (see gift by Dr. Marko Hyvonen, University of Cambridge.: Peranen J, et al., (1996). Anal Biochem. 236, 371-373.) so as to become inframe with the hexahistidine tag, thioredoxin (TrxA) and TEV protease cut site (TEV site) at the amino terminal. The recombinant protein was expressed in *Escherichia coli* BL21 star (DE3) cell line (Invitrogen, Carlsbad, Calif.), and purified using Hi-Trap Kit (GE Healthcare). Finally, the recombinant protein was purified according to the protocol of the supplier using superdex 200 gel filtration column (GE Healthcare) with high performance liquid chromatography (HPLC).

2. Result

Identification of Peptide Inhibiting ERAP1-PHB2/REA Binding

The present inventors performed the experiments described below for the purpose of aiming to develop an inhibitor targeting the interaction of ERAP1 and PHB2/REA. First, determination of the binding region in ERAP1 to PHB2/REA was tried. Three expression vector constructs ($ERAP1_{1468-2177}$: 1-434 amino acids, $ERAP1_{435-2177}$: 435-2177 amino acids, and $ERAP1_{1468-2177}$: 1468-2177 amino acids) were manufactured (FIG. 1A) so as to cover the full-length of the ERAP1 protein, and the binding region was examined with the immunoprecipitation-Western blotting method using these. As a result, specific binding with PHB2/REA through the region of 1-434 amino acid residues of ERAP1 was confirmed (FIG. 1B). Further refining of the binding region was performed in $ERAP1_{1-434}$ confirmed for this binding with PHB2/REA. Expression vector constructs ($ERAP1_{1-250}$: 1-250 amino acids, and $ERAP1_{1-100}$: 1-100 amino acids) were further manufactured (FIG. 1C), and using these, the binding region was examined similarly with the immunoprecipitation-Western blotting method. As a result, specific binding with PHB2/REA was confirmed through the region of the amino acid residues 101-250 of ERAP1 (FIG. 1D).

Next, in order to verify these results, the influences of the expression vector construct $ERAP1_{1-434}$ (1-434 amino acids) on the binding of ERAP1-PHB2 and ERE transcriptional activity of ERα were examined. COS-7 cells were transfected with an ERAP1-deleted variant construct (ΔERAP1:$ERAP1_{1-434}$) in the concentrations shown in FIG. 1E together with Flag-full-length ERAP1 and an A-PHB2 construct. The cells were lysed after 48 hours from the transfection. Then, HA-tagged PHB2 was immunoprecipitated from the cell lysate with anti-HA antibody. As a result, the binding to ERAP1 and PHB2/REA was inhibited depending on the dose of the introduced ERAP1-deleted variant construct (ΔERAP1: $ERAP1_{1-434}$) (FIG. 1E). In addition, it was also recognized that ERE transcriptional activity of ERα was suppressed by introduction of the ERAP1-deleted variant construct (ΔERAP1: $ERAP1_{1-434}$) (FIG. 1F).

In order to determine further detailed binding amino acid sequence, the estimated site for the interaction of ERAP1 was examined using protein-protein interaction estimation system PSIVER (5), which was developed by Mizuguchi et at, of National Institute of Biomedical Innovation. As a result, 157-173 amino acids were estimated as the most promising region. Furthermore, among them, the glutamine at position 165 (Q), the aspartic acid at position 169 (D) and the glutamine at position 173 showed the highest score as the estimated amino acid residues for the interaction (FIG. 1G). In addition, from the estimated steric structure of the region, it was found that these 3 amino acid residues were present on the α helix structure, and the side chain thereof was exposed to the protein surface in the same direction (FIG. 1H). On the basis of this estimation, an expression vector construct (ERAP1 mutant) in which these 3 amino acid residues were substituted with alamine (A), was manufactured, and the binding to PHB2/REA was examined with the immunoprecipitation-Western blotting method. As a result, it was shown that the binding to PHB2/REA was dramatically inhibited by substitution of these 3 amino acid residues (FIG. 1I).

The present inventors considered that the region in the vicinity of these 3 amino acid residues of ERAP1 is important for the interaction between PHB2/REA, and focused on 13 amino acid residues (165-177 amino acid residues: QMLSDLTLQLRQR (SEQ ID NO: 27)) on the a helix structure comprising these 3 amino acid residues. Then, the present inventors synthesized the dominant negative peptide (the ERAP1-peptide) in which 11 arginine residues having the transcellular function were added to the N-terminal of the 13 amino acid residues. In addition, the present inventors also synthesized a peptide in which 13 amino acid residue sequences were randomly sorted (the ERAP1-scramble peptide: DRQLQLSTLQRML (SEQ ID NO: 28)) as a control, and a peptide in which the 3 amino acid residues important for the binding were all substituted with alanine (the ERAP1-mutant peptide: AMLSALTLALRQR (SEQ ID NO: 29)), respectively (FIG. 1J). Using these peptides, inhibition of the binding of ERAP1 and PHB2/REA was investigated with the immunoprecipitation-Western blotting method using an anti-ERAP1 antibody and an anti-PHB2/REA antibody. It was found that when the ERAP1-peptide was added to MCF-7 (FIG. 1K, the upper panel) and KPL-3C (FIG. 1K, the lower panel), which are ERα-positive breast cancer cells, the binding of inherent ERAP1 and inherent PHB2/REA was remarkably inhibited. On the other hand, when the ERAP1-scramble peptide or the ERAP1-mutant peptide was added, inhibition of the binding of inherent ERAP1 and inherent PHB2/REA was not recognized in any of the cells (FIG. 1K).

Figures 1, 2:
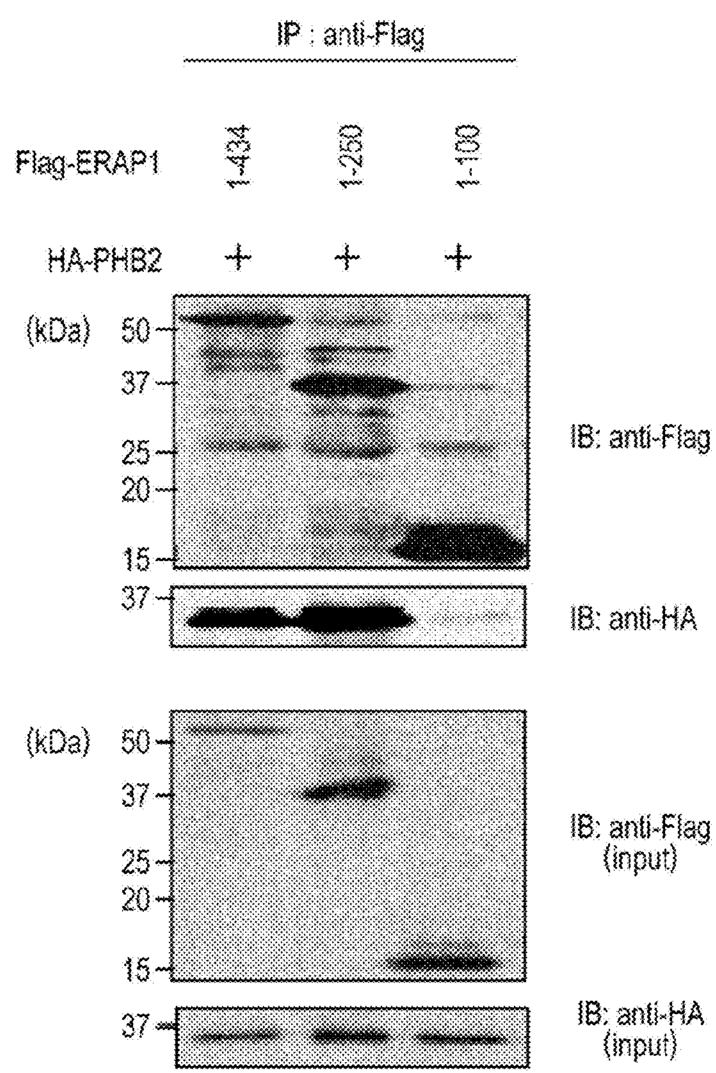
Figure 2:
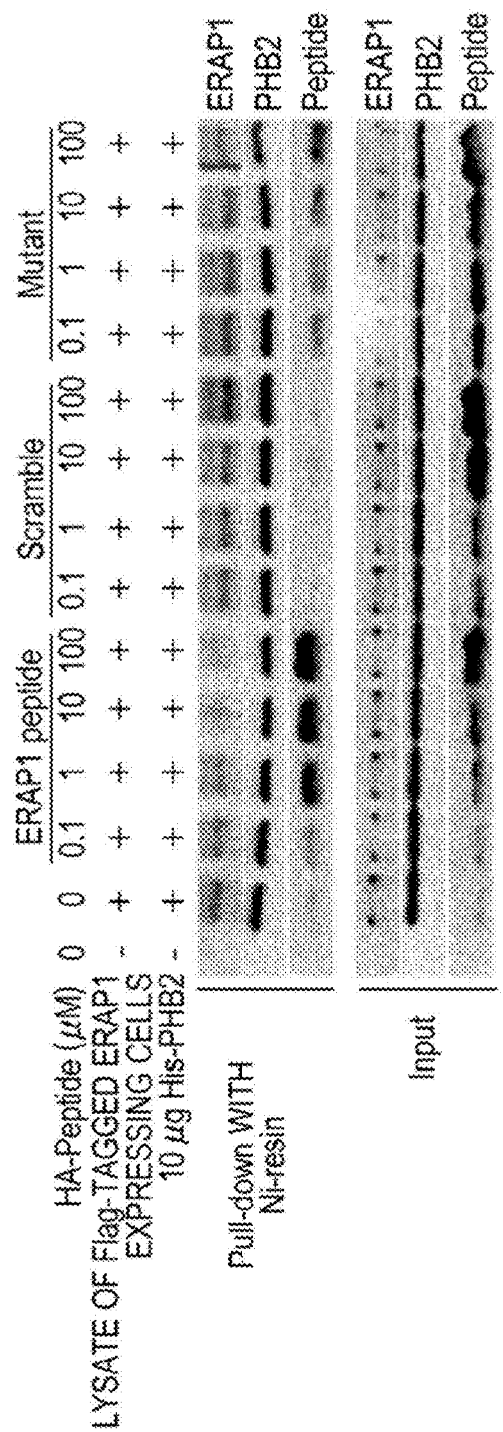

Next, it was examined whether the ERAP1-peptide directly inhibited the binding of ERAP1-PHB2/REA protein. PHB2/REA recombinant protein (6×His-PHB2/REA) to which histidine tag (His) prepared in an expression system for *Escherichia coli* was added, was mixed with the cell lysate of COS7 cells after forced expression of ERAP1 (Flag-ERAP1). To this mixture, HA tag-added peptide (ERAP1-HA-peptide) was added in each concentration. Then, inhibition of the binding was examined with Ni-resin pull-down and Western method. As a result, ERAP1-HA-peptide directly bound to His-PHB2/REA, depending on the concentration. As a result, it was found that the binding of Flag-ERAP1 and His-PHB2/REA was competitively inhibited (FIG. 2). As described above, it was found that ERAP-peptide directly inhibited the binding of ERAP1 and PHB2/REA, specifically to the sequence.

Influence of ERAP1-Peptide on Transcriptional Activation of ERα

PHB2/REA has been reported so far to have a function of suppressing the transcriptional activity of ER with nuclear translocation from the cytoplasm (Montano M M, et al., Proc Natl Acad Sci USA, 1999; 96: 6947-52); to be localized in the mitochondria membrane and have a function of maintaining the form of the mitochondria and bio-synthesizing the mitochondria and regulating the apoptosis (Kasashima K, et al., J Biol. Chem. 2006; 281: 36401-10; Artal-Sanz M and Tavernarakis N. Trends Endocrinol Metab. 2009; 21: 394-401); and to be related to regulation of the sister-chromatid cohesin (Artal-Sanz M and Tavernarakis N. Trends Endocrinol Metab. 2009; 20: 394-401; Tanaka H, et al., Current Biology. 2007; 17: 1356-61), and is considered as a multifunctional protein. Thus, the intracellular localization thereof is still under discussion. As described above, the locality of inherent PHB2/REA in breast cancer cells, and the change of the locality of PHB2/REA by E2 stimulation or the ERAP1-peptide administration were investigated. The fractions of the mitochondria, the cytoplasm and the nucleus of breast cancer cells MCF-7 in each condition of E2 treatment, no treatment or ERAP1-peptide treatment were collected, respectively, and the locality of inherent PHB2/REA was examined with Western method. As a result, the locality of inherent PHB2/REA was recognized in both of the cytoplasm and mitochondria, and the change of the locality was not recognized even after E2 treatment. On the other hand, when E2 and the ERAP1-peptide were administered at the same time, remarkable translocation of PHB2/REA from the cytoplasm into the nucleus was recognized. In addition, some decrease of the protein amount of PHB2/REA in the mitochondria was recognized with addition of the ERAP1-peptide in E2-dependent manner, and the translocation of PHB2/REA from the mitochondria into the cytoplasm or the nucleus was suggested (FIG. 3A).

Next, translocation of PHB2/REA from the cytoplasm into the nucleus by the ERAP1-peptide was temporally investigated. Prompt nuclear translocation of inherent PHB2/REA at 1 hour after the ERAP1-peptide administration to the MCF-7 cells was recognized, and the translocation temporally increased up to 24 hours (FIGS. 4A and 4B). On the other hand, nuclear translocation of PHB2/REA was not recognized with the ERAP1-scramble peptide (FIGS. 4A and 4B). In addition, ERAP1-peptide to which HA tag was added (ERAP1-HA-peptide) was synthesized in order to investigate the behavior of the ERAP1-peptide, and the behavior was examined using the peptide. Thus, it was recognized that ERAP1-HA-peptide directly bound to PHB2/REA and was nuclear-translocated at the same time (FIGS. 3B and 3C).

Figure 30:
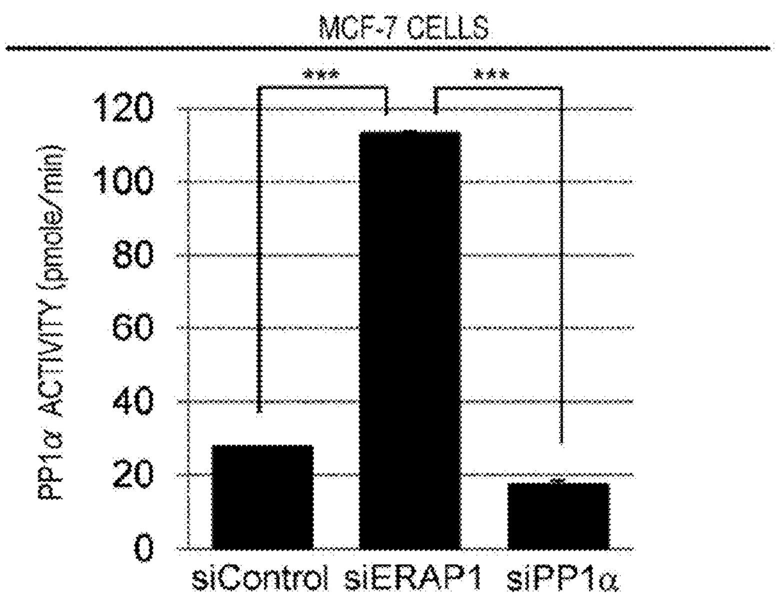
Figure 1:
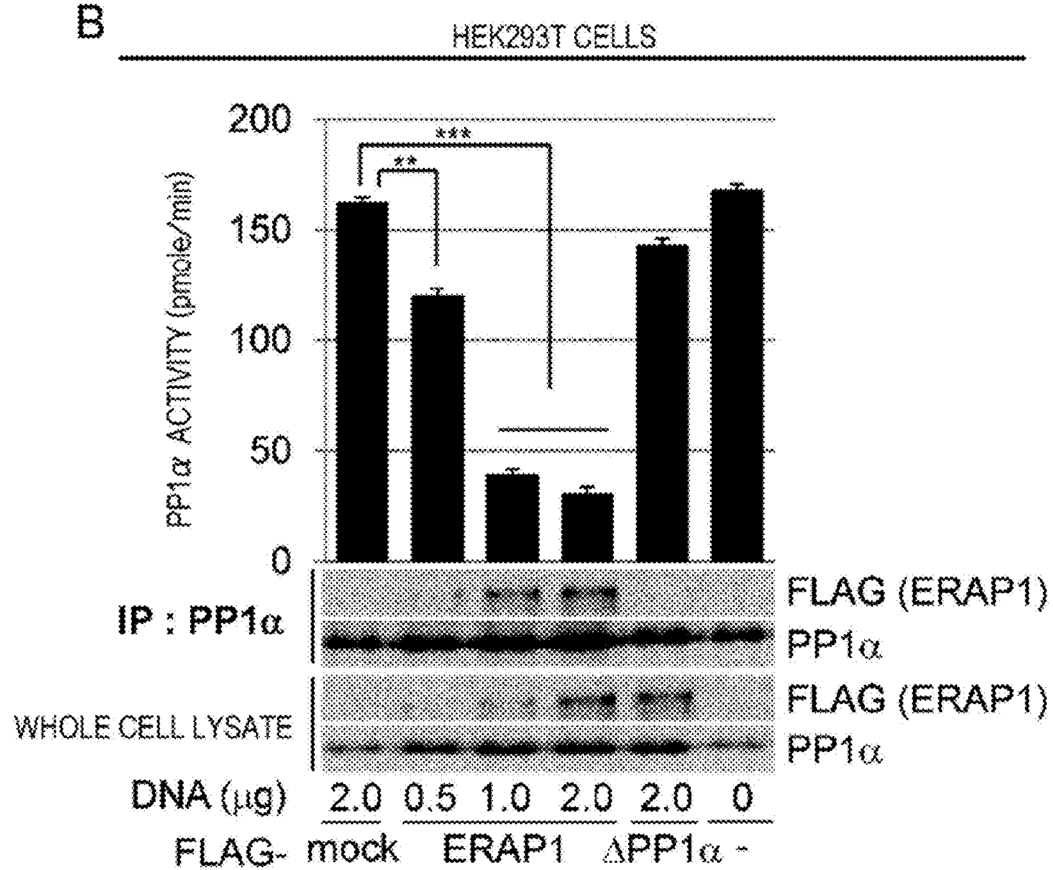

Subsequently, the influence of the ERAP1-peptide administration on the transcriptional activity of ERα was investigated with reporter assay of ERE (Estrogen-responsible element) and AP-1 binding sequence using MCF-7 cells. As a result, it was confirmed that the ERAP1-peptide (or ERAP1-HA-peptide) suppressed the transcriptional activity of ERα in ERE (FIG. 4C, and FIGS. 3D and 3E) and AP-1 (FIG. 4D and FIG. 3F), respectively depending on the concentration. However, no change was recognized in the cells added with ERAP-scramble peptide or ERAP-mutant peptide (FIGS. 3E and 3F). Furthermore, suppression for the transcriptional activity of ERE-ERα was recognized similarly by administration of the ERAP1-peptide also in KPL-3C, which is another ERα-positive cell line (FIG. 30). From these, it was found that the ERAP1-peptide led to E2-dependent nuclear translocation of PHB2/REA, and as a result, suppressed both of classical (ERE) and non-classical (AP-1) transcriptional activations of ERα.

It has been reported so far that PHB2/REA suppresses the transcription of ERα by being translocated into the nucleus and binding to ERα, and forming a complex with a transcription coupling suppression factor NcoR; and interacting with a histone deacetylation enzyme HDAC1 (Hurtev V, et. al., J Biol Chem. 2004; 279: 24834-43). From those described above, the influence of administration of the ERAP1-peptide on the interaction between ERα and these transcription suppression factors was investigated using MCF-7 cells, which are ERα-positive cells. It was recognized that when E2 was administered, ERα bound to a transcriptional activator SRC-1 as reported so far (Tai H, et al., Biochern Biophys Res Commun. 2000; 267: 311-6). On the other hand, it was found that when the ERAP1-peptide was administered, the binding of ERα and SRC-1 decreased, whereas ERα interacted with PHB2/REA, and further recruited NcoR and HDAC1 to form a complex (FIG. 4E). Similarly, it was found also in KPL-3C cells that when the ERAP1-peptide was administered, ERα recruited NcoR and HDAC1 to form a complex (FIG. 3H). In addition, it was recognized that when the ERAP1-peptide was administered, the activity of HDAC1 was accelerated dose-dependently (FIG. 4F), suggesting that ERα recruited these factors to form a complex, whereby to cause deacetylation of histone and as a result, agglutinate the chromatin and suppress the transcriptional activity of ERα.

Influence of ERAP1-Peptide on ERα Decomposition Mechanism

It has been reported in recent years that estrogen-dependent ERα down-regulation is essential for the transcriptional activation of ERα (Nawaz Z, et al., Proc Natl Acad Sci USA, 1999; 96: 1858-62; Lonard D M, et al, Mol. Cell. 2000; 5: 939-48; Reid G, et al., Mol Cell, 2003; 11: 695-707. Tateishi Y. et al., EMBO J. 2004; 23: 4813-23). It is known that this is due to decomposition of ERα by the ubiquitin-proteasome system, and thus is an important regulation mechanism in the cycle of binding and dissociation on the estrogen responsible element (ERE) of ERα after the transcriptional activation (Tai H, et al., Biochem Biophys Res Commun. 2000; 267: 311-6; Nawaz Z, et al., Proc Natl Acad Sci USA. 1999; 96: 1858-62; Lonard D M, et al., Mol. Cell. 2000; 5: 939-48; Reid G. et al., Mol. Cell. 2003; 11: 695-707). Accordingly, the influence of the ubiquitin-proteasome system of the ERAP1-peptide on ERα decomposition mechanism was examined. As reported already, when estrogen was administered to MCF-7 cells, decrease in the protein level of ERα was recognized after 1 to 3 hours.

Figure 5:
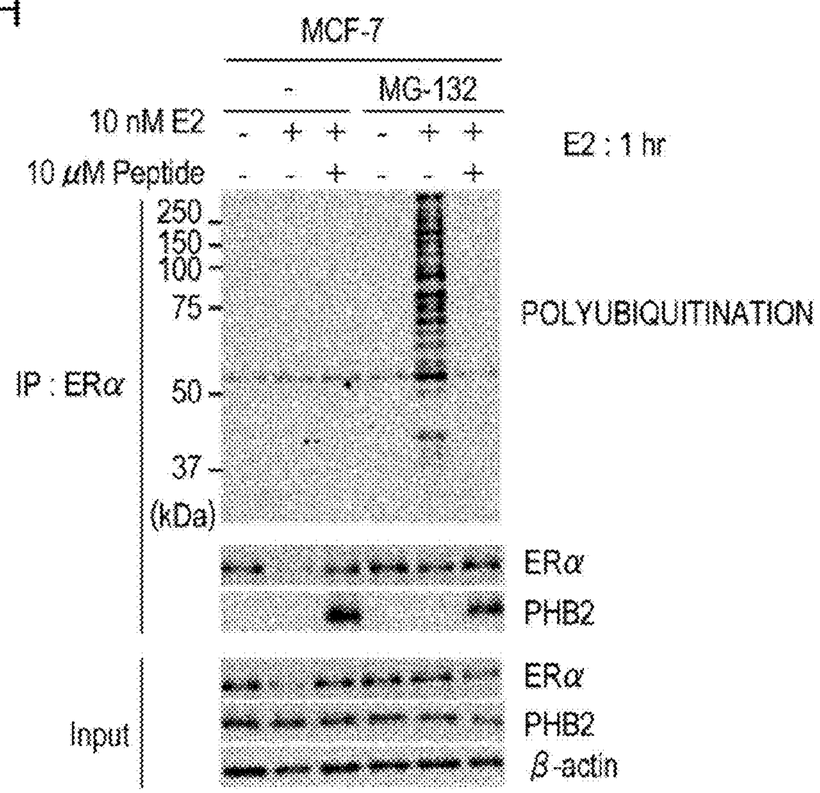
Figure 5:
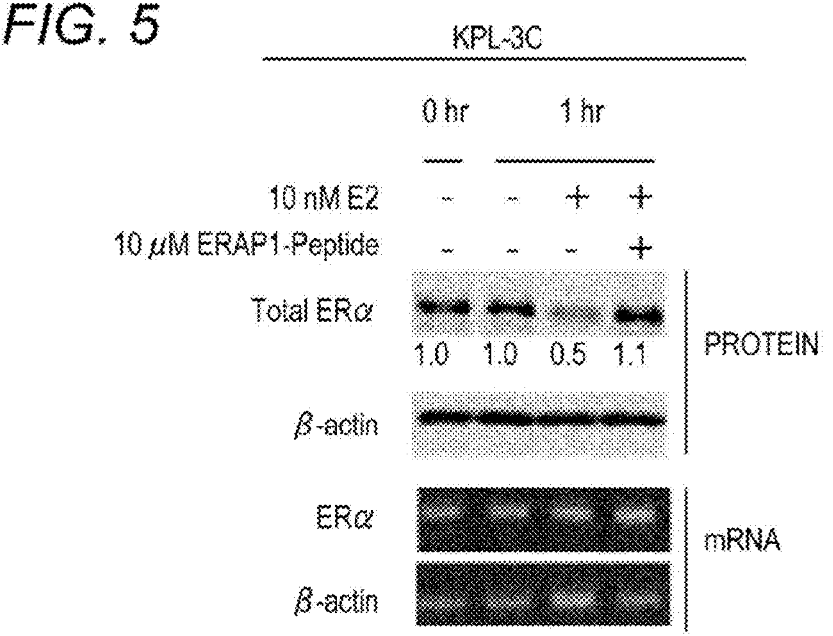
Figure 5:
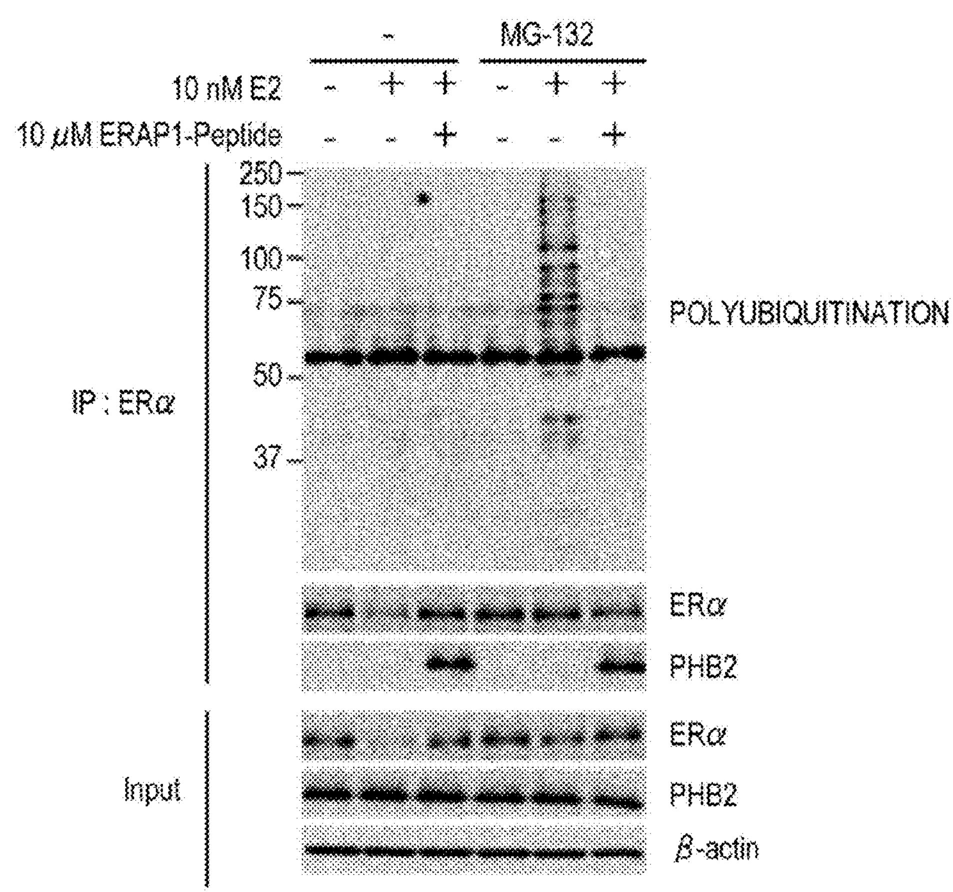

On the other hand, it was found that when the ERAP1-peptide was administered, the decrease thereof was suppressed (FIG. 40). Then, polyubiquitination of ERα was investigated. MCF-7 cells were treated with E2 in the presence of 26S proteasome inhibitor MG132. As a result, the protein decrease of ERα was suppressed and polyubiquitination of ERα was recognized. However, when the ERAP1-peptide was administered, polyubiquitination of ERα was inhibited in spite of the presence of MG132, and decrease of ERα was also inhibited (FIG. 4H). Also in the KPL-3C cells (ERα-positive), suppression for protein decrease of ERα was similarly recognized with inhibition of polyubiquitination by administration of the ERAP1-peptide in the presence of MG132 (FIG. 5). As described above, it was suggested that PHB2/REA was dissociated from ERAP1 by administration of the ERAP1-peptide and promptly nuclear-translocated, and directly bound to ERα, whereby to inhibit polyubiquitination of ERα and suppress the cycle of the binding and the dissociation of ERα on the estrogen responsible element (ERE), and finally lead to suppression for the transcriptional activation. This might be due to the fact that PHB2/REA binds to the lysine residues at positions 302 and 304, which were reported as the ubiquitination site of ERα (Berry N B, et al., Mol Endocrinology. 2008; 22: 1535-51), whereby to cause suppression for polyubiquitination onto these lysine residues.

Influence of ERAP1-Peptide on Cell Proliferation

Figures 2, 6:
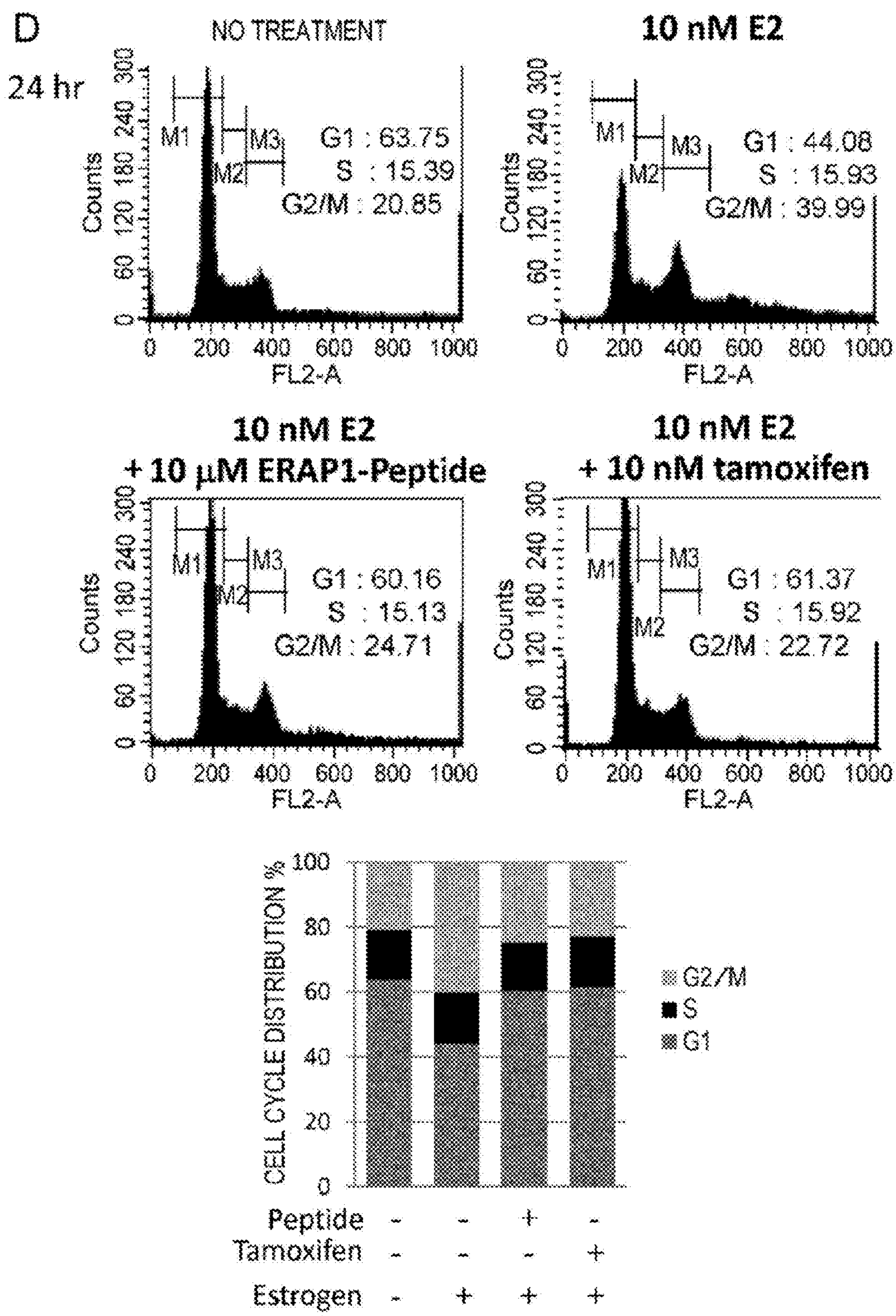
Figures 3, 6:
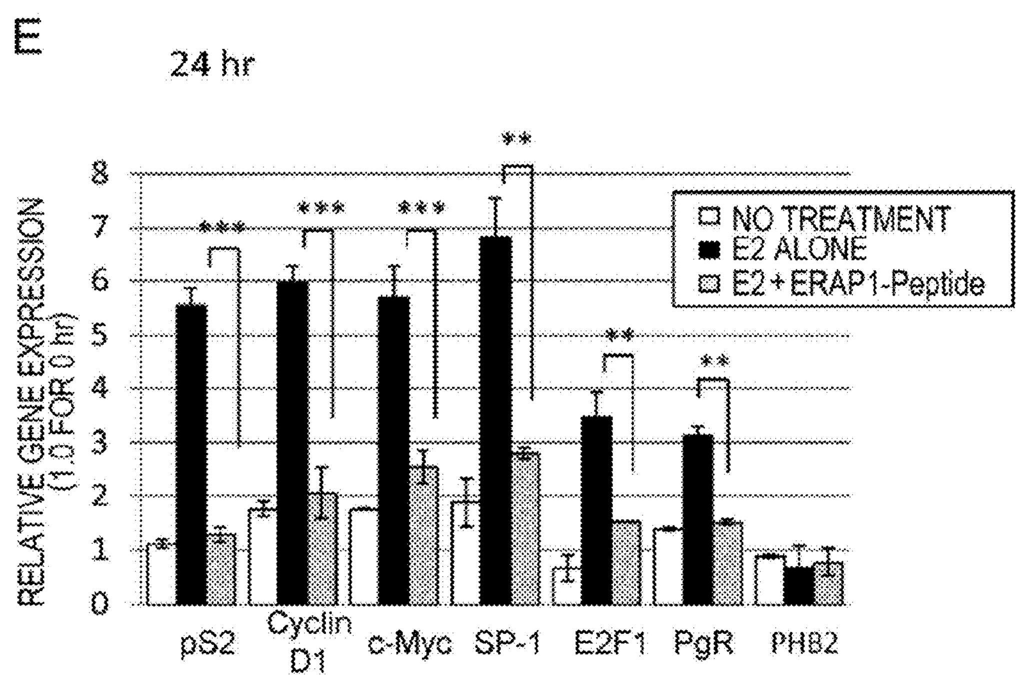
Figure 7:
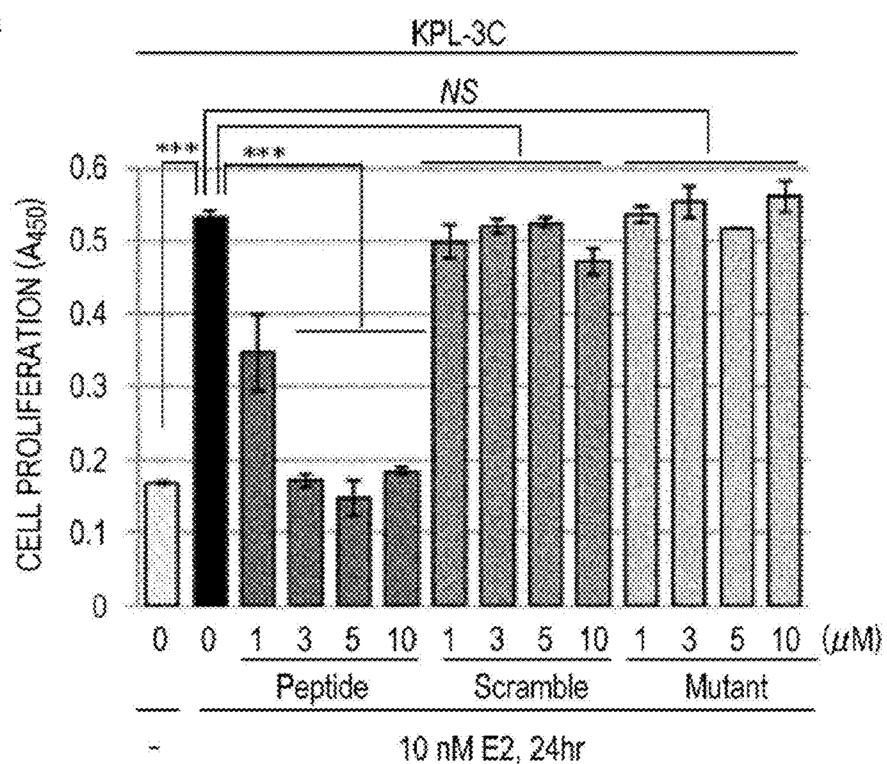
Figure 1:
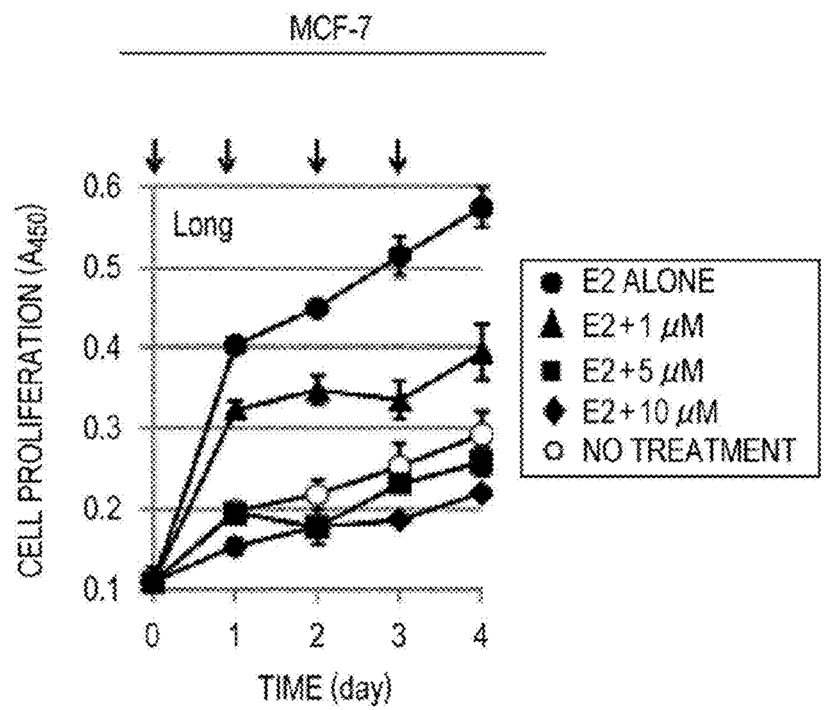
Figures 2, 7:
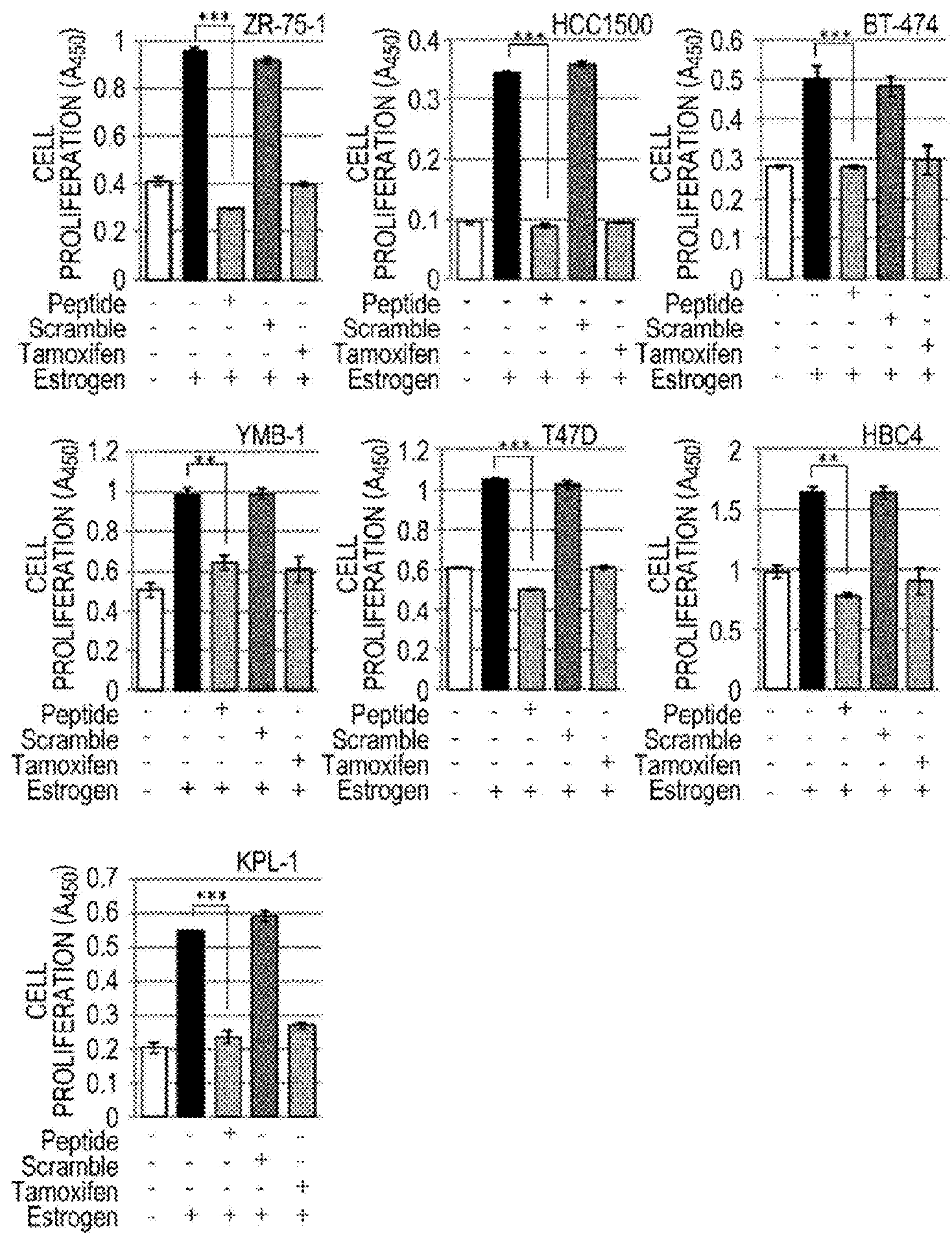
Figures 3, 7:
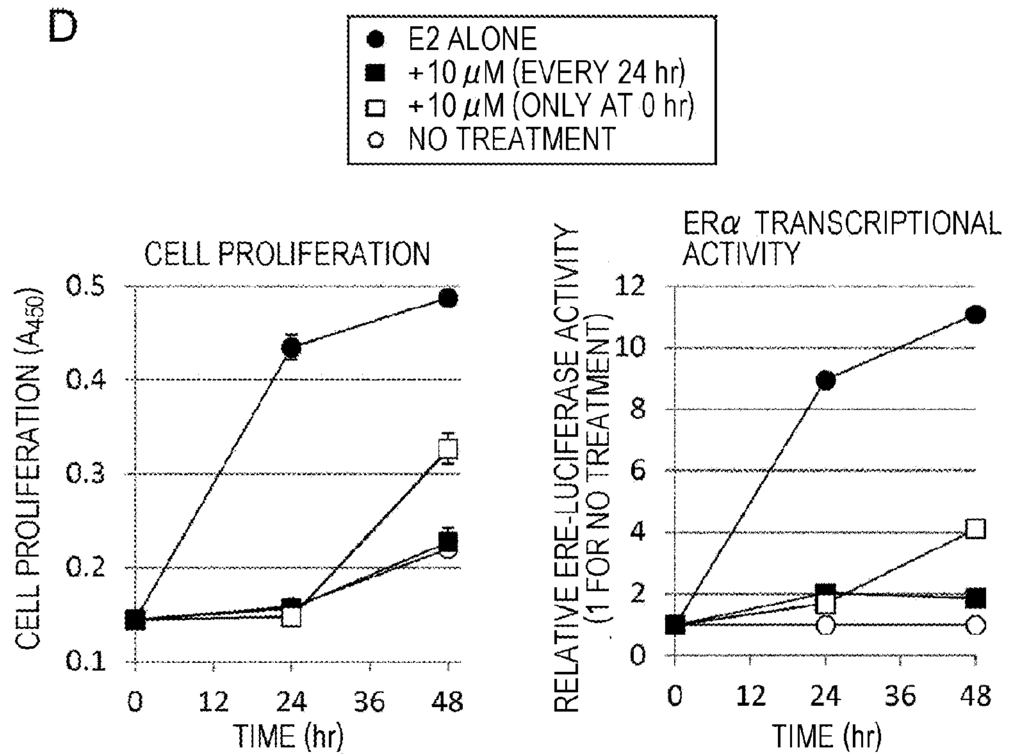
Figures 4, 7:
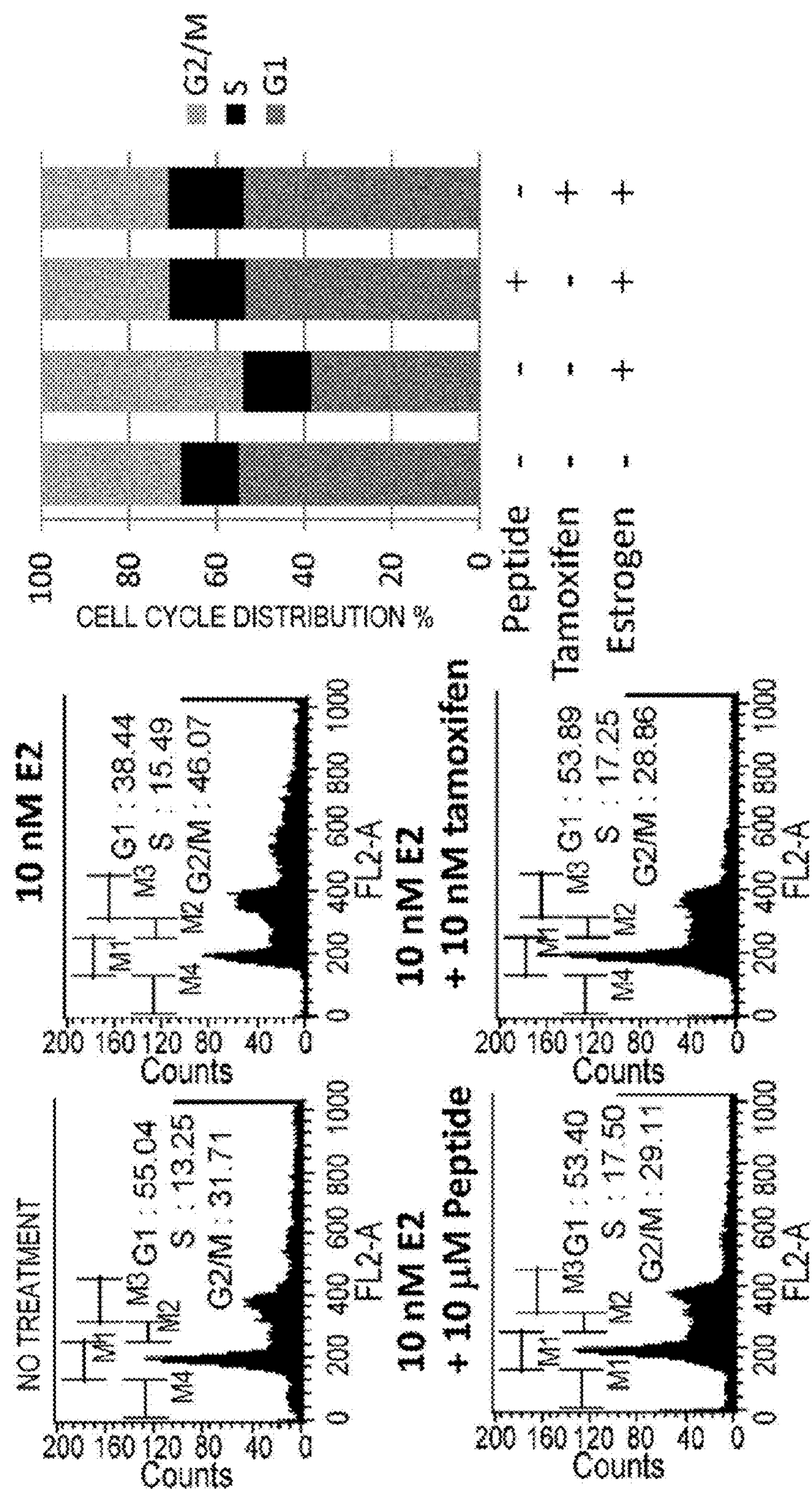

The influence of the ERAP1-peptide on cell proliferation was investigated using MCF7 cells positive for both of ERα and ERAP1. It was recognized that administration of the ERAP1-peptide dose-dependently suppressed the E2-dependent cell proliferation tip to 24 hours (FIG. 6A). On the other hand, administration of the ERAP1-scramble peptide or the ERAP1-mutant peptide was not recognized to provide the cell proliferation suppression effect (FIG. 6B). Furthermore, IC50 of suppression effect for the cell proliferation in MCF-7 cells for 24 hours was 2.18 μM. Similar results were obtained also in the KPL-3C cells (FIG. 7A). In addition, from tests in which the ERAP1-peptide was administered for four days successively every 24 hours, it was found that proliferation of the E2-dependent breast cancer cells was completely suppressed with the ERAP1-peptide in concentrations of 5 μM and 10 μM (FIG. 7B). However, the ERAP1-peptide had no influence on the cell proliferation at all in MCF-10A cells, which were normal epithelial cell lines negative for both of ERα and ERAP1 (FIG. 6C). Subsequently, with respect to 7 kinds of other breast cancer cell lines positive for both of ERα and ERAP1 (ZR-75-1, HCC1500, BT474, YMB-1, Y47D, KPL-1, HBC4), the influence of 10 μM ERAP1-peptide on the cell proliferation was examined similarly. Thus, the ERAP1-peptide showed remarkable E2-dependent proliferation suppression effect in all of the cells (FIG. 7C).

Next, the stability of the ERAP1-peptide was investigated. The cell proliferation suppression effect of the ERAP1-peptide in MCF-7 cells was temporally measured. As a result, complete E2-dependent proliferation suppression effect was recognized up to 24 hours (FIG. 7D, left panel). However, it was found that the cell proliferation was recovered by about 1.5 times in 48 hours, and ERE-ERα reporter activity was also recovered (FIG. 7D, right panel). From those described above, it was found that the ERAP1-peptide continuously suppressed proliferation of the E2-dependent breast cancer cells up to 24 hours.

Subsequently, the influence of the ERAP1-peptide administration on the cell cycle was examined. E2 and 10 μM of the ERA 1-peptide or anti-E2 inhibitor tamoxifen (TAM) were administered to MCF-7 cells at the same time, and FACS analysis was performed after 24 hours. As a result, stop of the cell cycle in the G1 phase was observed in the same way as administration of 10 nM TAM (FIG. 6D). When KPL-3C was used, similar results were recognized (FIG. 7E). From those described above, it was found that the ERAP1-peptide induced stop of the G1 phase whereby to cause the cell proliferation suppression effect.

Figures 1, 8:
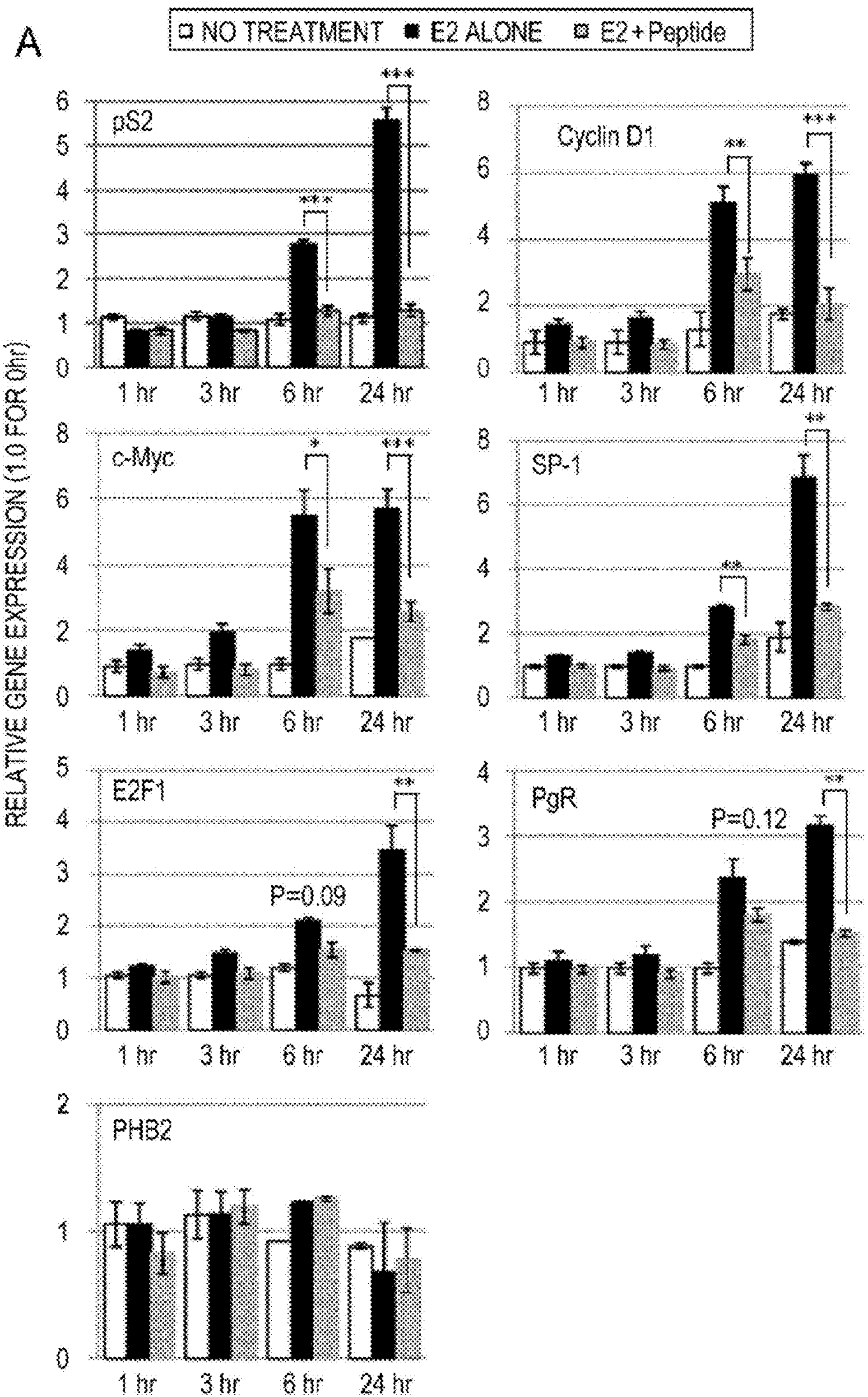
Figures 2, 8:
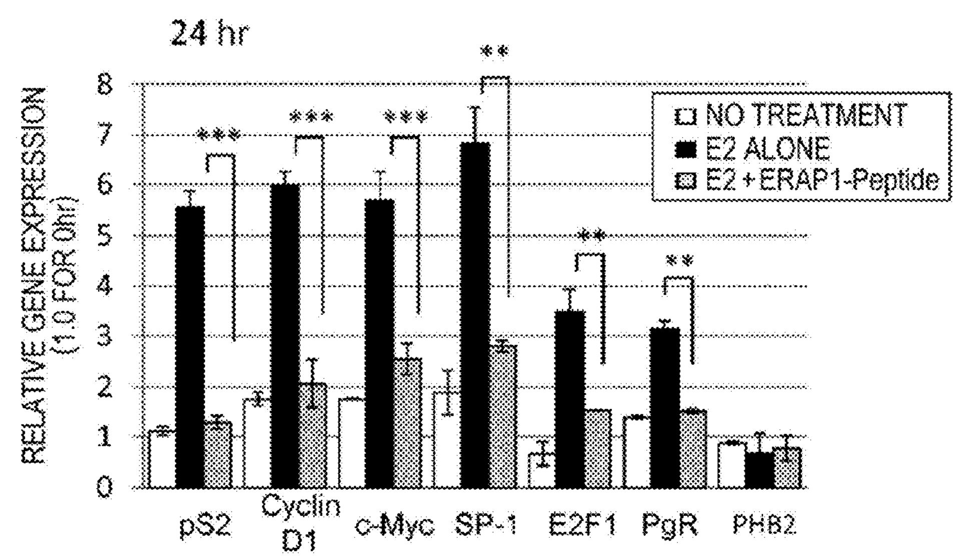

Next, the influence of the ERAP1-peptide on the expression of each gene of pS2, cyclin D1, c-Myc, SP-1, E2F1, and PgR, which were reported to be related to the proliferation as a target gene of ERα, were investigated. The ERAP1-peptide was added to MCF-7 cells, and the expression of each gene was examined after 24 hours with quantitative RT-PCR method. As a result, it was recognized that expression of any of the genes was remarkably suppressed with addition of the ERAP1-peptide (FIG. 6E). Furthermore, temporal suppression effect for expression of these target genes was examined. As a result, significant expression suppression effect was first recognized for any of the genes 6 hours after addition of the peptide (FIG. 8A). In addition, remarkable suppression for expression of all of these genes was recognized similarly also in ERα-positive breast cancer cell line KPC-3C, with addition of the ERAP1-peptide (FIG. 8B). As described above, it was suggested that the ERAP1-peptide suppressed the transcriptional activity of ERα, and as a result, suppressed the expression of the target gene whereby to induce suppression for the cell proliferation.

Influence of ERAP1-Peptide on Non-Genomic Activation Route

ERα is known to be localized on the cell membrane (or directly under cell membrane), and so called "xon-genomic ER activation route" is reported in which ERα interacts with membrane type growth factor receptors IGF-1Rβ (Insulin-like growth factor-1 receptor β). HER2 and EGFR by E2 stimulation, to rapidly activate cellular signal cascade and promote cell proliferation (Osborne C K, Schiff R. J Clin Oncol. 2005; 23: 1616-22; Yager J D, Davidson N E, N Engl J. Med. 2006; 354: 270-82: Johnston S R. Clin Cancer Res. 2010; 16: 1979-87). Past results show that administration of the ERAP1-peptide induces remarkable nuclear translocation of PHB2/REA, and as a result, suppresses "genomic activation route". However, it was thought that the majority of PHB2/REA was dissociated from ERAP1 and nuclear-translocated after addition of the ERAP1-peptide, but a portion thereof bound to cell membrane ER activated by estrogen whereby to remain in the cytoplasm as it was (FIGS. 3A and 3B, and FIG. 4B). From those described above, the influence of the ERAP1-peptide on the non-genomic activation route (MAPK or AKT route) was examined.

Figure 9:
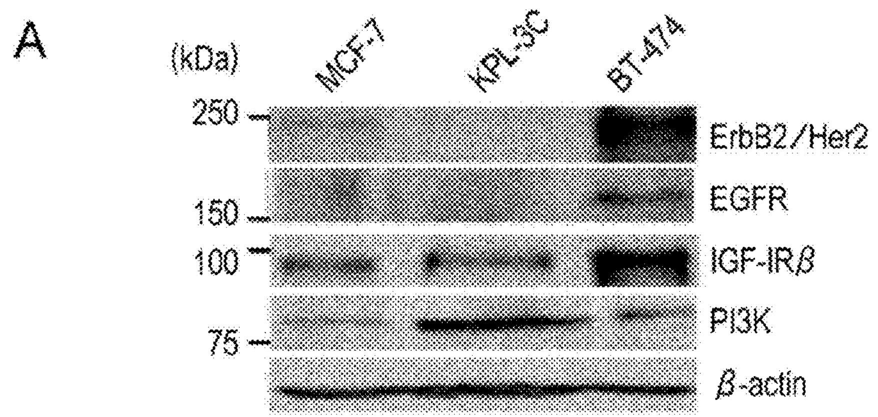
Figure 1:
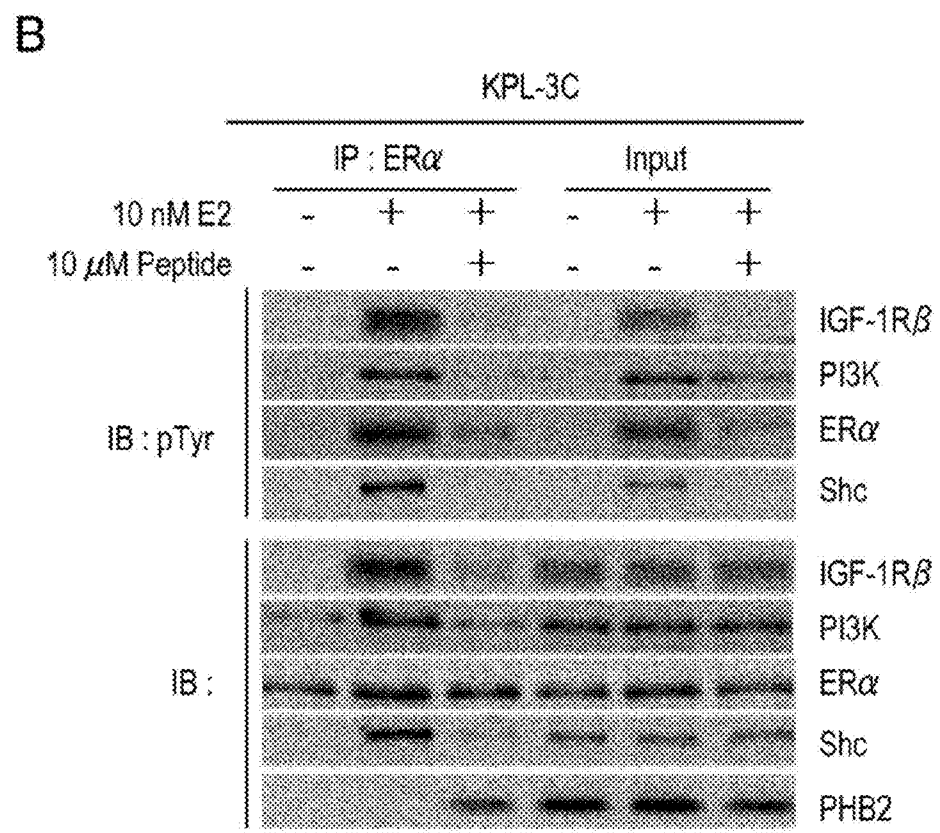
Figure 10:
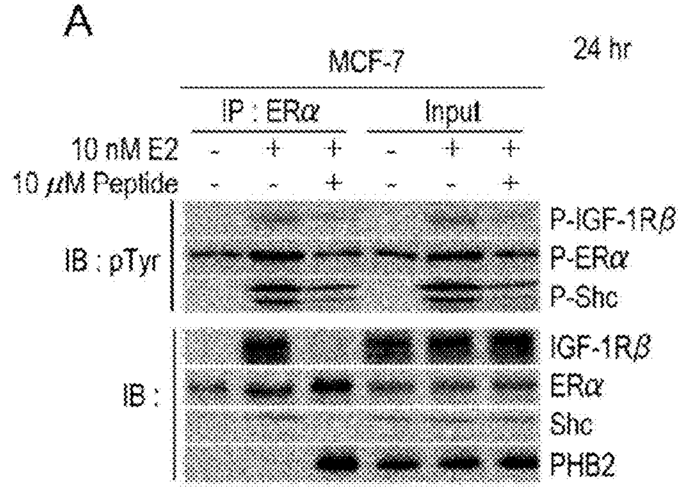
Figure 1:
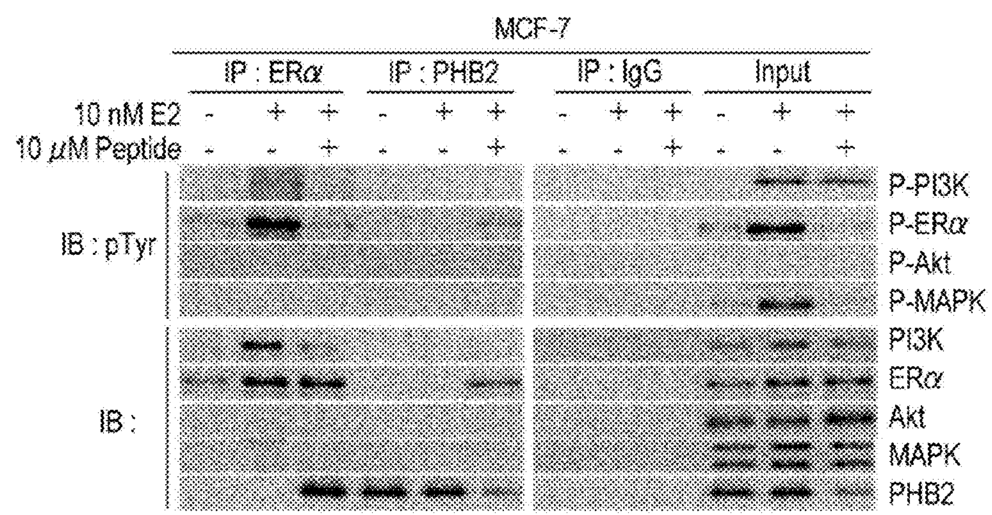
Figures 3, 10:
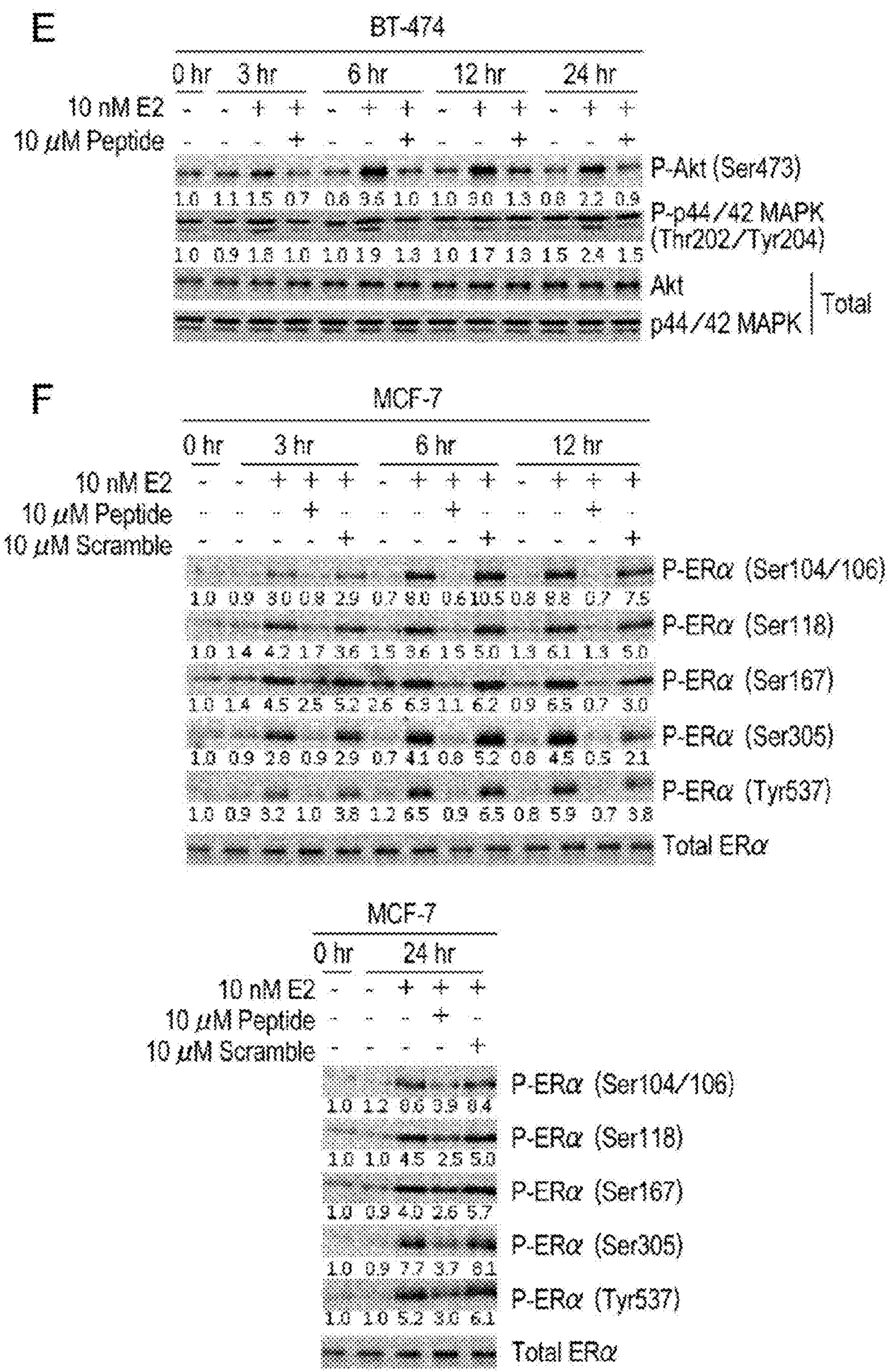

First, the influences of the ERAP1-peptide on the interaction of IGF-1Rβ and ERα via an adapter molecule reported so fir, i.e., Shc protein (Song R X, et al., Proc Natl Acad Sci USA. 2004; 101: 2076-81.) and on the interaction of PI3K protein and ERα, were examined, respectively. MCF-7 cells were recognized to have expressions of IGF-1Rβ and PI3K protein (FIG. 9A), and thus these cells were added with the ERAP1-peptide. After 24 hours, the cytoplasm fraction comprising the cell membrane fraction was extracted, and immunoprecipitation was performed respectively with anti-ERα antibody. As a result, it was found that when the ERAP1-peptide was administered, PHB2/REA bound to ERα, and inhibited the binding of ERα and Shc and the binding of ERα and IGF-1Rβ, respectively, and as a result, phosphorylation of the tyrosine residues of IGF-1Rβ and Shc, which is important for cell proliferation signal, was suppressed (FIG. 10A).

In addition, the influence of the ERAP1-peptide on the interaction between ERα and PI3K, which is another E2-dependent no-genomic activation route via membrane type ERα, was investigated. It was found that when the ERAP1-peptide was added to MCF-7 cells, PHB2/REA bound to ERα, whereby to inhibit the binding of ERα and PI3K (FIG. 10B). Subsequently, the influences on phosphorylations of Akt and MAPK, which are downstream signal molecules of IGF-1Rβ and PI3K, were also examined. As a result, phosphorylation of Ser473 of Akt and phosphorylation of MAPK were inhibited respectively within 3 hours after addition of the ERAP1-peptide, and the suppression was maintained even after 24 hours (FIG. 10C). On the other hand, direct binding of PHB2/REA dissociated from ERAP1 by addition of the ERAP1-peptide to each of Akt and MAPK was not recognized (FIG. 10B). From those described above, it was found that the ERAP1-peptide dissociated PHB2/REA from ERAP1, and the dissociated PHB2/REA directly inhibited E2-dependent binding of IGF-1Rβ and ERα and the binding of PI3K and ERα, whereby to inhibit activation thereof by the phosphorylation, and as a result, suppressed activation of downstream signal routes thereof, i.e., AKt and MAPK routes. It was recognized that the binding of ERα and Shc and the binding of ERα and IGF-1Rβ were inhibited (FIG. 9B) and activations of AKT and MAPK were suppressed also in KPL-3C cells in which IGF-1Rβ and PI3K proteins were recognized to be expressed (FIG. 9C).

Furthermore, using ERα-positive breast cancer cells BT474, in which all of Her2, EGFR, iGF-1Rβ and PI3K were recognized to be expressed (FIG. 9A), similar tests were performed. As a result, it was recognized that all of the bindings of ERα to Her2, EGFR, IGF1-Rβ and PI3K were inhibited, respectively (FIG. 10D), and activations of downstream signal routes thereof, i.e. AKt and MAPK routes, were suppressed by the ERAP1-peptide (FIG. 10E). From the results above, it was suggested that the ERAP1-peptide dissociated PHB2/REA from ERAP1 and directly conjoined cell membrane ERβ and PHB2/REA in E2-dependent manner, whereby to inhibit the binding of ERα to IGF-1Rβ, HER2 or EGFR, and suppress the "non-genomic signal activity route", and finally induce inhibition of the cell proliferation.

Influence of ERAP1-Peptide on ERα Phosphorylation

It has been considered in recent years that post-translational modification, particularly phosphorylation of ERα is a regulatory factor important for various signaling routes in cell proliferation (Lannigan D A. Steroids. 2002; 68: 1-9.; Barone I, et al., Clin Cancer Res. 2010; 16: 2702-08); Murphy L C, et al., Endocrine-Related Cancer. 2011; 18: R1-14.). It was reported so far that ERα is phosphorylated on many sites in E2-dependent manner. However, it is known that phosphorylation of six amino acid residues (Ser104, Ser 106, Ser118, Ser67, Ser357 and TyrS37) is particularly important for the transcriptional activity of ERα and the binding to E2 (Lannigan D A. Steroids. 2002; 68: 1-9.; Barone I, et al., Clin Cancer Res. 2010; 16: 2702-08; Murphy L C, et al. Endocrine-Related Cancer. 2011; 18: R1-14.). Accordingly, the influence of the ERAP1-peptide on ERα phosphorylation after addition of E2 in MCF-7 cells was examined. Potentiation of the phosphorylation was confirmed in all of the six sites of ERα (Ser104, Ser106, Ser118, Ser167, Ser357 and Tr537) continuously from 3 hours to 24 hours after addition of E2, and when the ERAP1-peptide was administered, the phosphorylations in all of them were suppressed to the same degree as that of no administration of E2 (FIG. 10F). However, the suppression effect was not recognized with the ERAP1-scramble peptide (FIG. 10F).

As described above, it was suggested that PHB2/REA nuclear-translocated by the ERAP1-peptide suppressed E2-dependent phosphorylation of ERβ whereby to decrease the transcriptional activation ability of ERα and the binding ability to E2, and thus to inactivate ERα. Furthermore, the present inventors performed similar experiments also for other ER-positive breast cancer cells, i.e., KPL-3C (FIG. 9D) and BT-474 (FIG. 9E) cells. As a result, it was found that also in these cells, E2-dependent phosphorylation in all of the sites was suppressed by administration of the ERAP1-peptide. These are the results obtained by performing triplicate experiments three times independently.

Investigation for In Vivo Antitumor Effect of ERAP1-Peptide

Figures 1, 11:
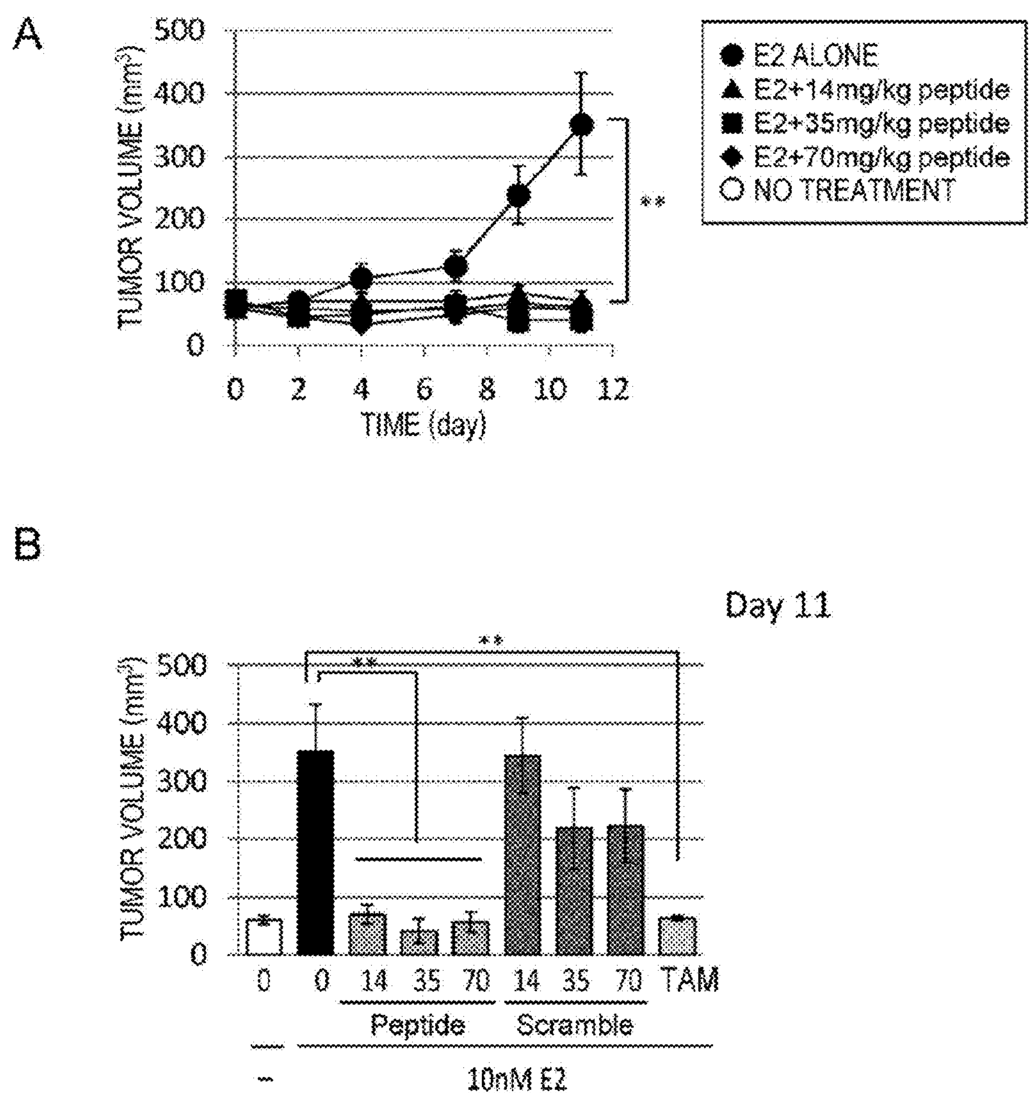
Figure 11:
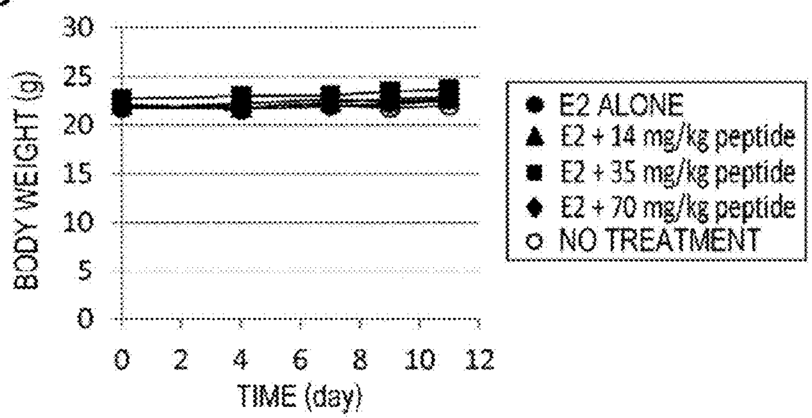
Figure 3:
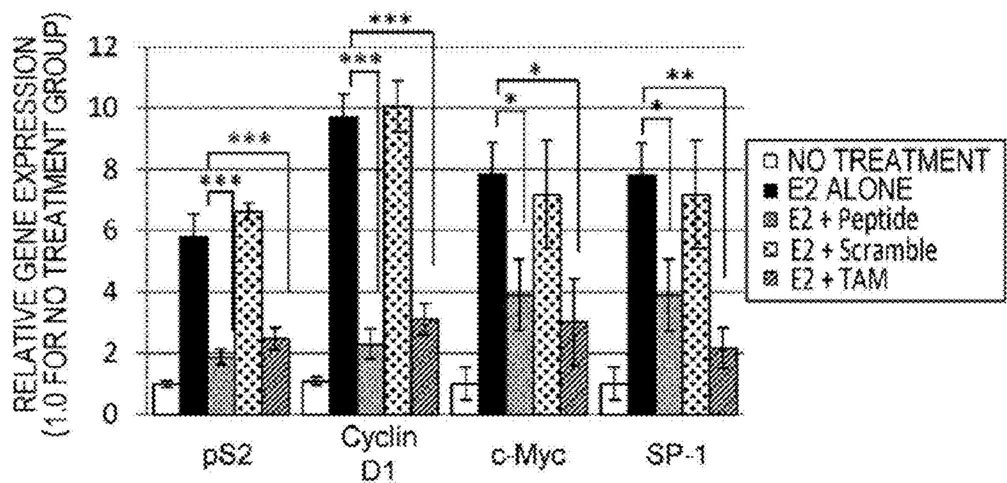
Figures 4, 11:
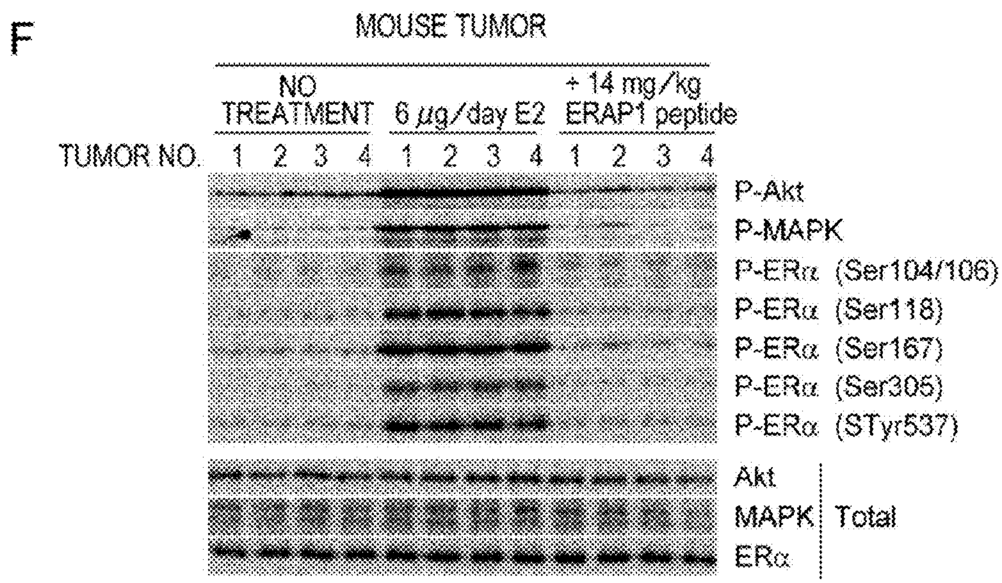
Figure 12:
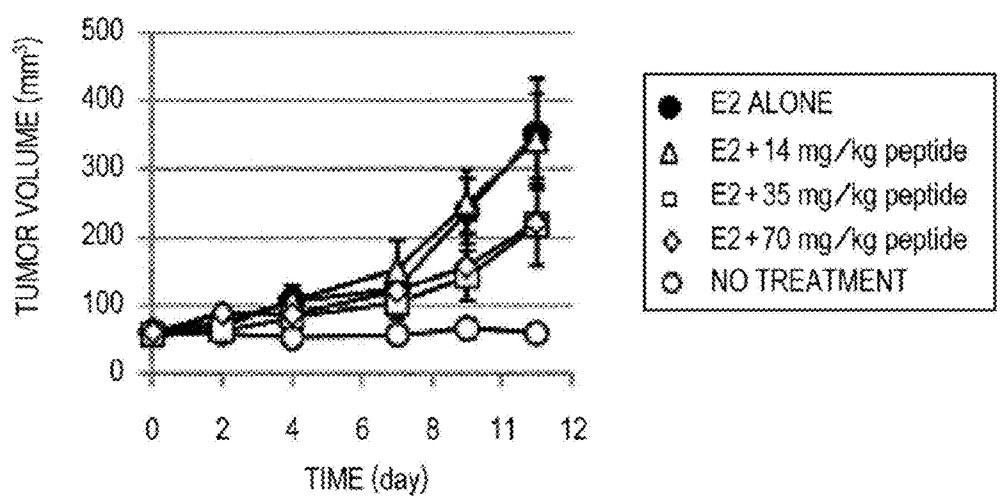
FIG. 12 is a diagram illustrating the influence of the ERAP1-scramble peptide on the tumor volume. The ERAP1-scramble peptide (14, 35 and 70 mg/kg) was administered every day by intraperitoneal injection to a cancerous mouse orthotopically transplanted with KPL-3C tumor.

Next, in vivo antitumor effect by the ERAP1-peptide was investigated. The ER-positive breast cancer KPL-3C cells were orthotopically transplanted to the mammary gland of a nude mouse. When the tumor reached about 701 $mm^3$, E2 was subcutaneously administered and also the ERAP1-peptide, the ERAP1-scramble peptide or tamoxifen (TAM) was intraperitoneally administered, respectively, and the antitumor effect was examined. As a result, the antitumor effect was recognized in the tumor of the mouse to which the ERAP1-peptide was administered to the same degree as that in E2-non-administration mouse, and in the same degree as that of TAM administration, in all of the doses (FIGS. 11A, 11B and 11C). In addition, change of the body weight was not recognized (FIG. 11D). On the contrary, significant tumor suppression effect was not recognized in any of the doses in the mouse to which the ERAP1-scramble peptide was administered (FIGS. 11B and 11C, and FIG. 12).

Next, the activation state of the target gene of ERα was examined in the tumor of a mouse to which these peptides were administered. As a result, the expressions of target genes of ERα, i.e., PS2, cyclin D1, C-Myc and SP-1 were completely suppressed in the tumor to which the ERAP1-peptide was administered, whereas suppression for the expression was not recognized in the tumor to which the ERAP1-scramble peptide was administered (FIG. 1E). Furthermore, suppression for the phosphorylations of the non-genomic activation signal routes, i.e., Akt and MAPK, was also confirmed in the tumor to which the ERAP1-peptide was administered (FIG. 11F). As described above, it was suggested that the ERAP1-peptide inhibited the binding of ERAP1 and PHB2/REA also in vivo like in vitro, to induce the binding of PHB2/REA and ERα, and as a result, suppressed the routes of the "genomic activation" and the "non-genomic activation" of ERα and thus exhibited the antitumor effect.

Acceleration of Expression by Positive Feedback Mechanism of ERAP1

Figure 13:
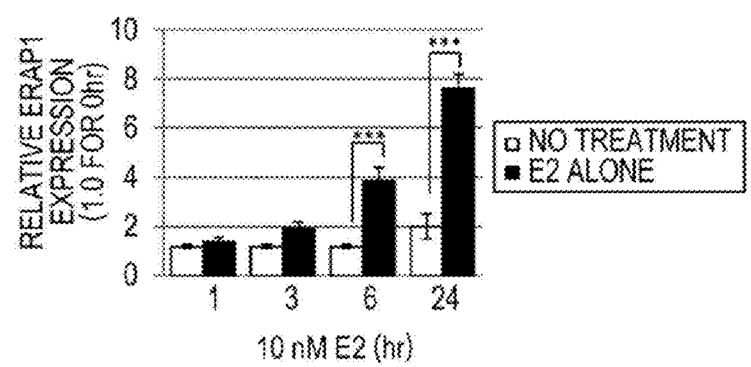
Figure 1:
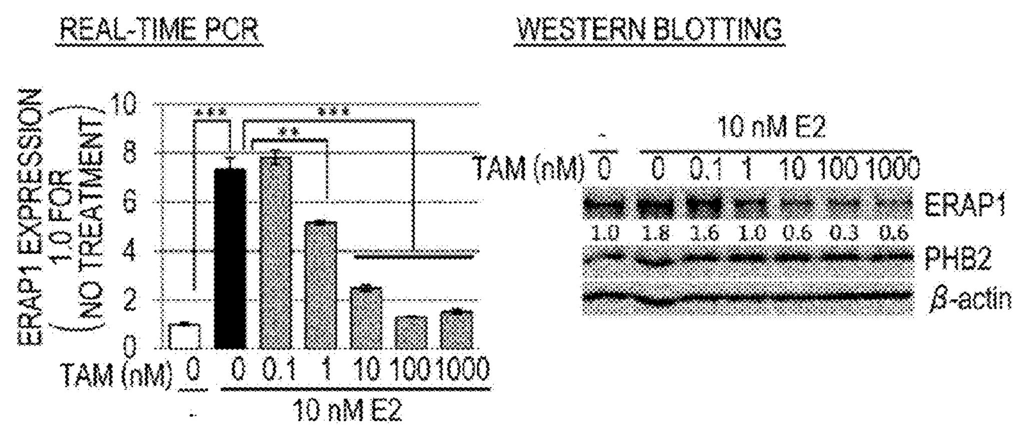

The present inventors have found so far that expression of ERAP1 is accelerated by E2 stimulation (Kim J W, et al., Cancer Sci. 2009; 100: 1468-78.). From this, the present inventors built a hypothesis that ERAP1 was one of the target genes of ERα, and performed the experiments described below. The expression of ERAP1 at the mRNA level after E2 administration in MCF-7 cells was examined with quantitative RT-PCR method. As a result, it was recognized that the expression was accelerated time-dependently up to 24 hours after E2 administration (FIG. 13A). Then, the expression of ERAP1 when the cells were treated with an anti-E2 agent tamoxifen (TAM), was also examined with quantitative RT-PCR method and Western method. As a result, it was recognized that the expression of ERAP1 was suppressed depending on the concentration of TAM at both of the mRNA level and the protein level (FIG. 13B). As described above, it was found that ERAP1 received E2-dependent expression regulation in ERα-positive breast cancer cells.

Next, it was searched with computer estimation whether ERE (estrogen responsible element, E2 responsive sequence: AGGTCAnnnTGACCT (SEQ ID NO: 25)) is present on the ERAP1 gene. As a result, conserved ERE sequence of TCCAGTTGCATTGACCT (SEQ ID NO: 26) was confirmed on the intron 1 of 5626 bp to 5644 bp downstream from the transcription initiation point (FIG. 13C). Expression vector constructs consisting of a region comprising this estimated ERE sequence (ERE in ERAP1), only the upstream sequence not containing ERE sequence (UP−) or only the downstream sequence not containing ERE sequence (Down−) were manufactured, respectively, and the luciferase reporter activity was examined. As a result, acceleration of the reporter activity after E2 stimulation was confirmed only in the cells to which a construct comprising ERE sequence on the ERAP1 gene was introduced. Subsequently, whether or not ERα directly binds to this estimated ERE sequence, was examined with the chromatin immunoprecipitation method (ChIP method) using ERα and PHB2/REA and antibodies for HDAC and NcoR that were proved to form a complex with them. As a result, ERAP1 was recognized to be bound to the DNA sequence with addition of the ERAP1-peptide in any immunoprecipitate using the antibodies for any of the proteins (FIG. 13D). However, when a transcriptional activator SRC-1 antibody was used in the immunoprecipitate, the binding decreased (FIG. 13D).

As described above, it was suggested that ERAP1 was one of the target genes of ERα, and was regulated by positive feedback mechanism where if activation of ERα was induced in E2-dependent manner, the expression thereof was accelerated. Then, the influence of the ERAP1-peptide on the expression of ERAP1 itself was examined. As shown in FIG. 13A, ERAP1 was recognized to be expression-accelerated in E2-dependent manner, but the expression thereof was temporally suppressed by administration of the ERAP1-peptide. From those described above, it was found that the ERAP1-peptide inhibited positive feedback mechanism of ERAP1 in E2-dependent ERα-positive breast cancer cells, and as a result, induced dissociation of PHB2/REA, and inhibited every ERα activation mechanism, and thus induced cell proliferation suppression effect.

[Example 2] Suppression Effect of ERAP1-Peptide on Tamoxifen-Resistant MCF-7 Cells 1. Materials and Methods Tamoxifen-Resistant MCF-7 Cells As the tamoxifen-resistant MCF-7 cell lines, those provided from Dr. Satoshi Inoue (Saitama Medical University Research Center for Genomic Medicine) under Material transfer agreement were offered for the experiment described below. The culture of tamoxifen-resistant MCF-7 cell was performed under the conditions recommended by the depositor. The tamoxifen-resistant MCF-7 cells were cultured in DMEM (Invitrogen, Carlsbad, Calif., USA) reinforced with 10% FBS (Nichirei Biosciences, Tokyo, Japan), 1% penicillin/streptomycin (Nacalai tesque, Kyoto, Japan), 1 μM tamoxifen (Sigma, St. Louis. Mo., USA).

Proliferation Suppression Effect of ERAP1 Peptide on Tamoxifen-Resistant MCF-7 Cells Cell proliferation assay was evaluated using Cell-Counting Kit-8 (CCK-8, manufactured by Dojindo Company). First, tamoxifen-resistant MCF-7 cells were seeded in $2\times10^4$/well on a 48-well plate in DMEM/F12 culture medium containing phenol red and stood in a $CO_2$ incubator for 24 hours. Then, the culture medium was exchanged with DMEM/F12 culture medium containing 10% FBS, 1% penicillin/streptomycin and 1 μM tamoxifen and not containing phenol red, and the cells were further pre-cultured for 24 hours. The supernatant was removed, and then 180 μl of the ERAP1-peptide in each concentration was added, and subsequently 20 μl of 100 nM E2 was added (final concentration: 10 nM), and the mixture was reacted for 24 hours. The reaction solution was removed, and then 125 μl portion of 10 fold-diluted CCK-8 solution was added to each well, and the coloration reaction was performed for 1 hour in a $CO_2$ incubator. Then, 100 μl was moved to a 96-well plate from each well, and the absorbance at 450 nm was measured with a microplate reader.

Investigation for Suppression Effect of the ERAP1-Peptide on Phosphorylation of Ak, MAPK and ERα in Tamoxifen-Resistant MCF-7 Cells MCF-7 cells and tamoxifen-resistant MCF-7 cells were seeded in $1\times10^5$/well in DMEM/F12 culture medium containing phenol red on a 24-well plate and stood in a $CO_2$ incubator for 24 hours. Then, the culture medium was exchanged with DMEM/F12 culture medium containing 10% FBS, 1% penicillin/streptomycin and 1 μM tamoxifen, and not containing phenol red, and the cells were further pre-cultured for 24 hours. The supernatant was removed, and then 180 μl of 100 μM ERAP1-peptide was added (final concentration: 10 μM), and subsequently 20 μl of 100 nM E2 was added (final concentration: 10 nM), and the mixture was reacted for 24 hours. The reaction solution was removed, and then 100 μl of SDS-sample buffer was added and the cells were lysed. The cells were subjected to boiling treatment at 95° C. for 5 minutes, and subjected to polyacrylic amide electrophoresis. Phosphorylations of Akt and MAPK were detected with anti-phosphorylation Akt (Ser473) (587F11) and anti-phosphorylation p44/42 MAP Kinase (Thr202/Tyr204) antibodies, and phosphorylation of ERα was detected with anti-phosphorylation ERα (Ser104/106), anti-phosphorylation ERα (Ser118), anti-phosphorylation ERα (Ser167), anti-phosphorylation ERα (Ser305) and anti-phosphorylation ERα (Tyr537) antibodies.

2. Results

Figure 14:
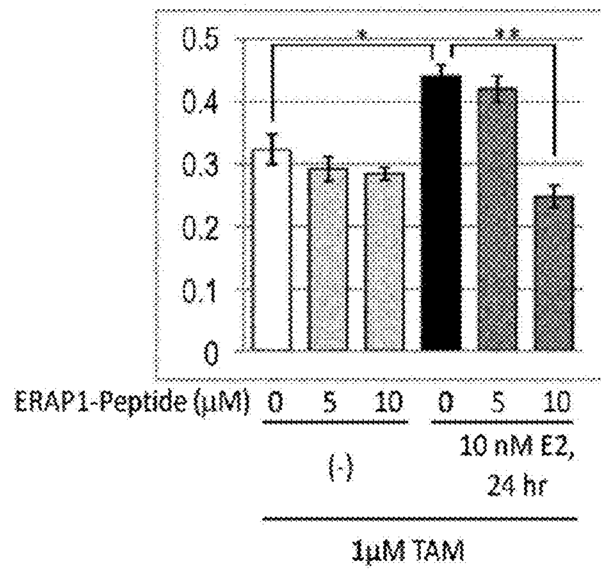
FIG. 14 is a diagram illustrating the suppression effect of the ERAP1-peptide on tamoxifen-resistant MCF-7 cells. (A) shows the results of MT T assay by which the inhibition effect of the ERAP1-peptide on proliferation of tamoxifen-resistant MCF-7 cells was evaluated. The tamoxifen-resistant MCF-7 cells were treated with the ERAP1-peptide in each concentration (0, 5 and 10 μM). Then, immediately, the cells were stimulated with 10 nM E2 for 24 hours. The data show the mean±SE of three independent experiments. *P<0.05; **P<0.01. (B) shows the results of Western blotting in which the inhibition effect of the ERAP1-peptide was evaluated on phosphorylations of Aki and MAPK (upper panel), and ERα (S104/106, S118, S167, S305 and Y537) (lower panel) in tamoxifen-resistant MCF-7 cells (Tam-R MCF7) and MCF-7 cells (MCF-7WT), which are the original cells, in the presence and in the absence of E2.
Figure 14:
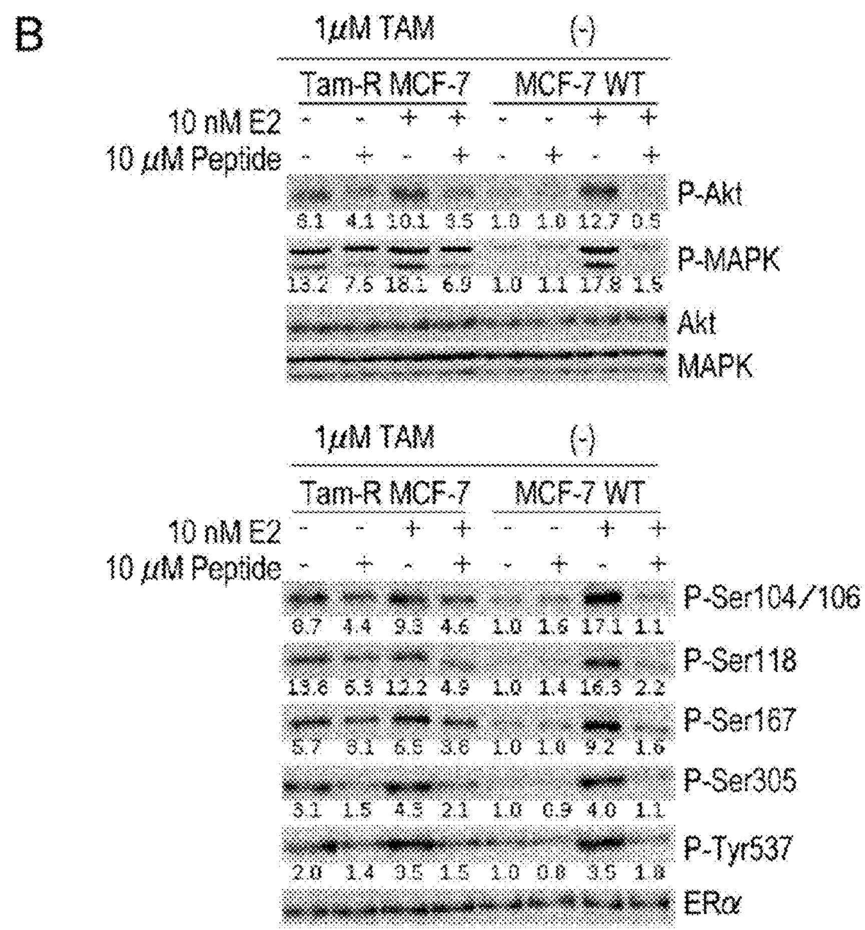

The influence of the ERAP1-peptide on cell proliferation in tamoxifen-resistant MCF7-cells (Tam-R MCF-7) was investigated. After 24 hours from administration of the ERAP1-peptide, it was recognized that the ERAP1-peptide remarkably suppressed the cell proliferation in dose-dependent manner in the presence of E2 and tamoxifen (FIG. 14A). Then, the influences of "activation of the non-genomic route of tamoxifen (Akt and MAPK phosphorylations)" and "phosphorylation of ERα by tamoxifen" on activation of ERα were investigated, which had been considered so far to be one of the causes for the tamoxifen resistance. When Tam-R MCF-7 cells were subjected to a treatment of tamoxifen alone or concomitant treatment of tamoxifen and E2, it was recognized that each of them accelerated phosphorylations of Akt and MAPK (FIG. 14B, the upper panel). On the contrary, when Tam-R MCF-7 cells were subjected to a treatment of the ERAP1-peptide in each condition, it was recognized that phosphorylations of Akt and MAPK were remarkably decreased similarly in MCF-7 wild type cell line (MCF-7WT). Furthermore, it was found that all phosphorylation of ERα was also decreased (FIG. 14B, the lower panel). From those described above, it was suggested that the ERAP1-peptide also inhibited activation of the non-genomic route and ERα phosphorylation, which were one of the causes for tamoxifen-resistant breast cancer, in the tamoxifen-resistant breast cancer, and thus could induce cell proliferation suppression.

[Example 3] Investigation for Effects of the ERAP1-Peptide on E2-Independent Cell Proliferation 1. Materials and Methods Investigation for Effects of the ERAP1-Peptide on E2-Independent Cell Proliferation MCF-7 cells or ZR-75-1 cells were seeded in $2\times10^4$/well, and KPL-3C cells were seeded in $1\times10^4$/well on a 48-well plate, and stood in a $CO_2$ incubator for 24 hours. Then, for MCF-7 cells, the culture medium was exchanged with DMEM/F12 culture medium containing 10% FBS (Nichirei Biosciences, Tokyo, Japan), 1% antibiotic/antimycotic solution (Invitrogen), 0.1 mM NEAA48 (invitrogen), 1 mM sodium pyruvate and 10 μg/ml insulin (Sigma, St. Louis, Mo., USA) and not containing phenol red, and the cells were further pre-cultured for 24 hours. On the other hand, for ZR-75-1 cells and KPL-3C cells, the culture media were exchanged with RPMI culture media containing 10% FBS and 1% antibiotic/antimycotic solution and not containing phenol red, and the cells were further pre-cultured for 24 hours. The supernatant was removed, and then 200 μl of the ERAP1-peptide in each concentration or tamoxifen as a positive control was added, respectively and the mixture was reacted for 24 hours. The reaction solution was removed, and then 125 μl portion of 10 fold-diluted CCK-8 solution was added to each well, and the coloration reaction was performed for 1 hour in a $CO_2$ incubator. Then, 100 μl from each well was moved to a 96-well plate, and the absorbance at 450 nm was measured with a microplate reader.

Investigation for Influence of the ERAP1-Peptide on Non-Genomic Activation Route via IGF-1Rβ

MCF-7 cells were subjected to a treatment of 10 μM ERAP1-peptide alone, stimulation with 10 nM E2 alone, and co-stimulation with the ERAP1 peptide and E2, respectively, and after 24 hours, the cytoplasm fraction was isolated from the cells of each treatment. The cytoplasm fraction was precleaned using normal IgG and rec-Protein G Sepharose 4B (Zymed, San Francisco, Calif., USA) at 4° C. for 3 hours, and centrifuged, and then the supernatant was incubated in the presence of anti-ERα antibody at 4° C. for 6 hours. Then, the supernatant was added with rec-Protein G Sepharose 4B and incubated at 4° C. for 1 hour whereby to precipitate an antigen-antibody complex. The immunoprecipitated protein complex was washed with a lysis buffer three times, and separated by SDS-PAGE. Then, anti-IGF-1Rβ, anti-ERα anti-She and anti-PHB2 antibodies were used in detection of each complete protein, and anti-phosphorylation tyrosine antibody was used in detection of tyrosine phosphorylation of each protein by Western blotting.

2. Results

Figure 15:
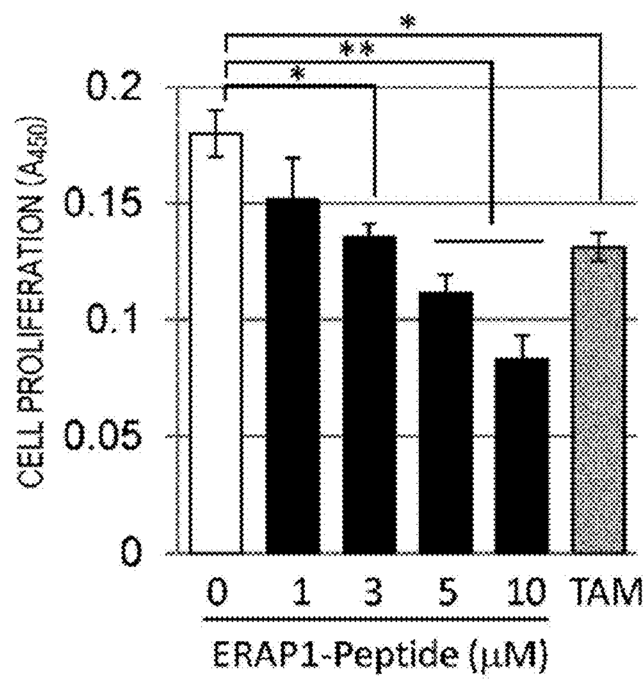
FIG. 15 is a diagram illustrating the effects of the ERAP1-peptide on E2-independent cell functions. (A) shows the results of MTT assay by which the inhibition effect of the ERAP1-peptide on proliferation of MCF-7 cells was evaluated. MCF-7 cells were treated with the ERAP1-peptide in each concentration (1, 3, 5 and 10 μM) or 10 nM tamoxifen as a positive control for 24 hours. The data show the mean±SE of three independent experiments. *P<0.05; **P<0.01. (B) shows the results of immunoblotting analysis by which the effects of the ERAP1-peptide on the interaction between ERα and IGF-1Rβ or Shc were evaluated. MCF-7 cells were stimulated with 10 μM ERAP1-peptide treatment only, 10 nM E2 treatment only, or 10 μM ERAP1-peptide treatment and immediately 10 nM E2 for 24 hours, and the cytoplasm fraction was isolated from each of the treated cells. Then, the cytoplasm fraction was immunoprecipitated with anti-ERα antibody. Furthermore, with respect to the obtained sample, Western blotting analysis was performed using the antibodies shown in the figure.
Figure 15:
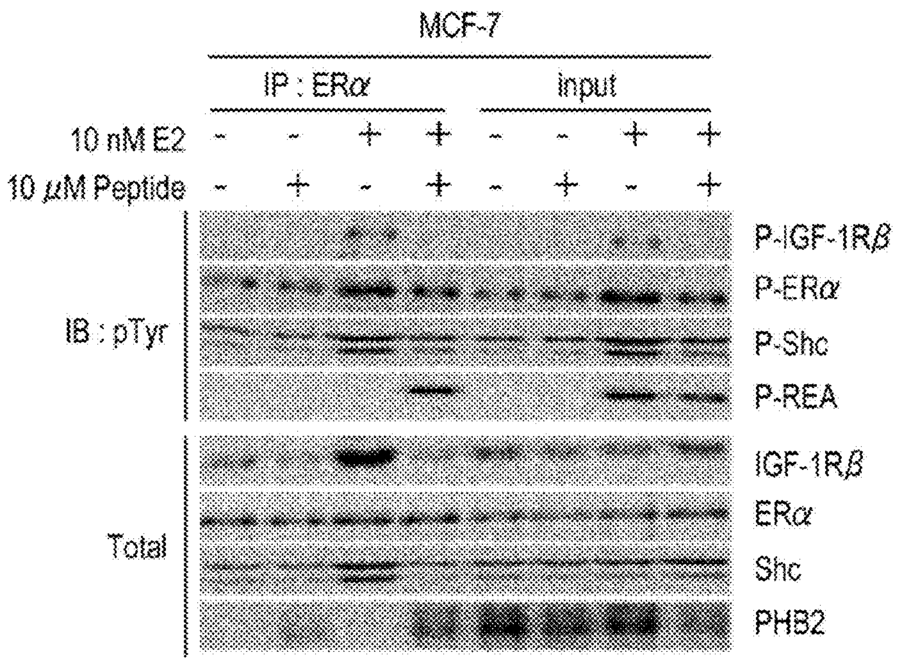

The influence of treatment of the ERAP1 peptide in the absence of E2 on cell proliferation was examined with MTT assay. Namely, MCF-7 cells were treated with the ERAP1-peptide in each concentration (1, 3, 5 and 10 μM) or TAM as a positive control for 24 hours. As a result, dose-dependent cell proliferation suppression effect of the ERAP1-peptide was recognized (FIG. 15A).

Then, the molecular mechanism for the effect was investigated. The influence on estrogen-independent activation of the non-genomic route of ER was examined in the same way as the estrogen-dependent activation of the non-genomic route. The binding of ERα to PHB2 in the cytoplasm was recognized with ERAP1-peptide treatment, while each interaction of IGF-1Rβ and Shc, and ERα was inhibited. As a result, it was found that tyrosine phosphorylation of IGF-1R and Shc important for the signal cascade was also suppressed (FIG. 15B). From those described above, it was suggested that E2-independent proliferation was also inhibited in ER-positive MCF7 cells.

Figure 16:
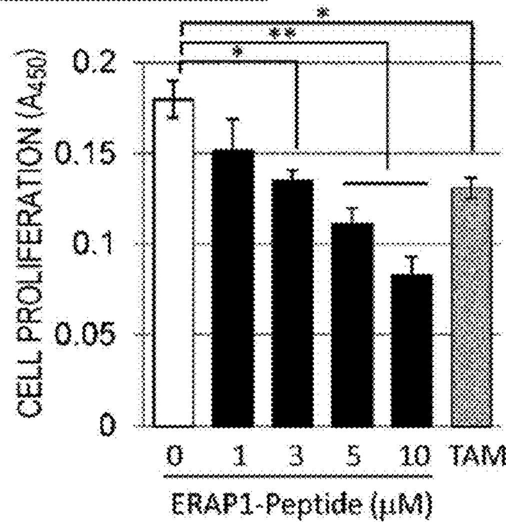
FIG. 16 is a diagram illustrating the influence of the ERAP1-peptide on proliferation of E2-independent breast cancer cells.
Figure 16:
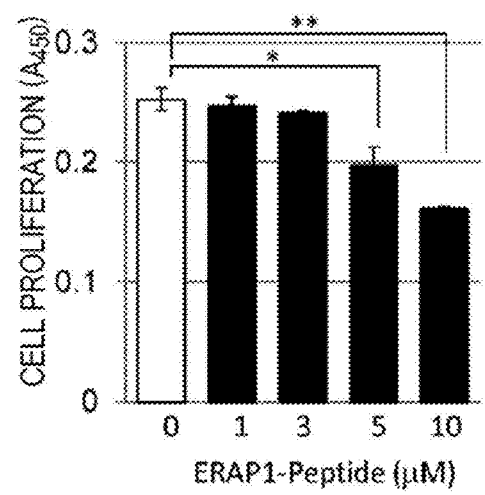
Figure 16:
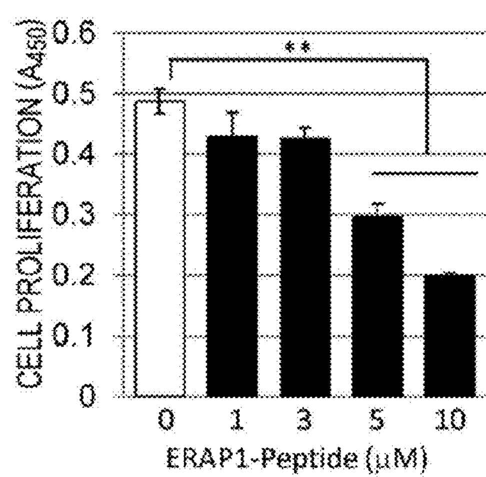
Figure 16:
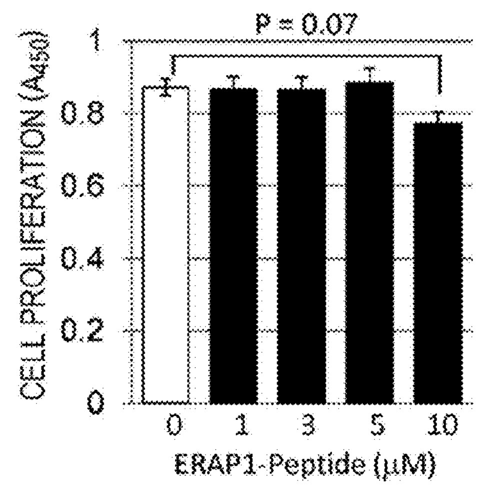

Furthermore, in order to verify these results, the proliferation suppression effect was examined using other ER-positive breast cancer cell lines. Administration of 10 μM ERAP1-peptide was performed every 24 hours. Thus, significant cell proliferation suppression effect was confirmed at 48 hours in KPL3 cells, and at 96 hours in ZR75-1 cells (FIG. 16). From those described above, it was found that the ERAP-1 peptide inhibited the binding of ERAP1-PHB2 to cause the suppression effect for the E2-independent ER-positive breast cancer cell proliferation.

[Example 4] Investigation for Effect of Concomitant Use of ERAP1-Peptide and Tamoxifen 1. Materials and Methods Knockdown of ERAP1 in Breast Cancer Cells The inhibition effect of tamoxifen when ERAP1 was knocked down by siRNA method was evaluated with MTT assay. The sequences of si-ERAP1, and si-control (si-EGFP) and the method for the experiment were in accordance with the report of Kim et, al. (Cancer Science, 2009, 100; 1468-78) MCF-7 cells were seeded in 2×10/well on a 48-well plate, and stimulated with 1 μM E2, and after 24 hours, treated with si-ERAP1 or si-control. After 24 hours, the cells were treated with 10 μM tamoxifen and the number of living cells was evaluated with MTT assay after 96 hours.

In addition, the inhibition effect of tamoxifen when ERAP1 was knocked down by siRNA method was evaluated with ERE-luciferase assay. MCF-7 cells were seeded in $2\times10^4$/well on a 96-well plate, and were temporarily transfected with ERE-luciferase reporter. Then, the cells were stimulated with 1 μM E2, and after 24 hours, treated with si-ERAP1 or si-control. After 24 hours, the cells were treated with 10 μM tamoxifen and after 96 hours, ERE luciferase activity was measured.

Test for In Vivo Inhibition of Tumor Proliferation

KPL-3 cells were subcutaneously transplanted into the breast fat body of a BALB/c nude mouse. When the volume of the tumor reached about 50-80 $mm^3$ in the absence of E2, the treatment test (5 individuals/group) was initiated (day 0). KPL-3C tumor heterotransplant-carrying mouse was administered with the ERAP1-peptide alone (3.5, 7 and 14 mg/kg), the scramble peptide alone (14 mg/kg), tamoxifen alone (4 mg/kg) or a combination of the ERAP1-peptide (14 mg/kg) and tamoxifen (4 mg/kg) every day by intraperitoneal injection.

Cell Cycle Analysis

MCF-7 cells were treated with 10 μM ERAP1-peptide and/or 10 nM tamoxifen. Then, immediately, the cells were stimulated with 10 nM E2 for 24 hours. After the immobilization, the cells were stained with propidium iodide, and analyzed by flow cytometry.

2. Results

Figure 17:
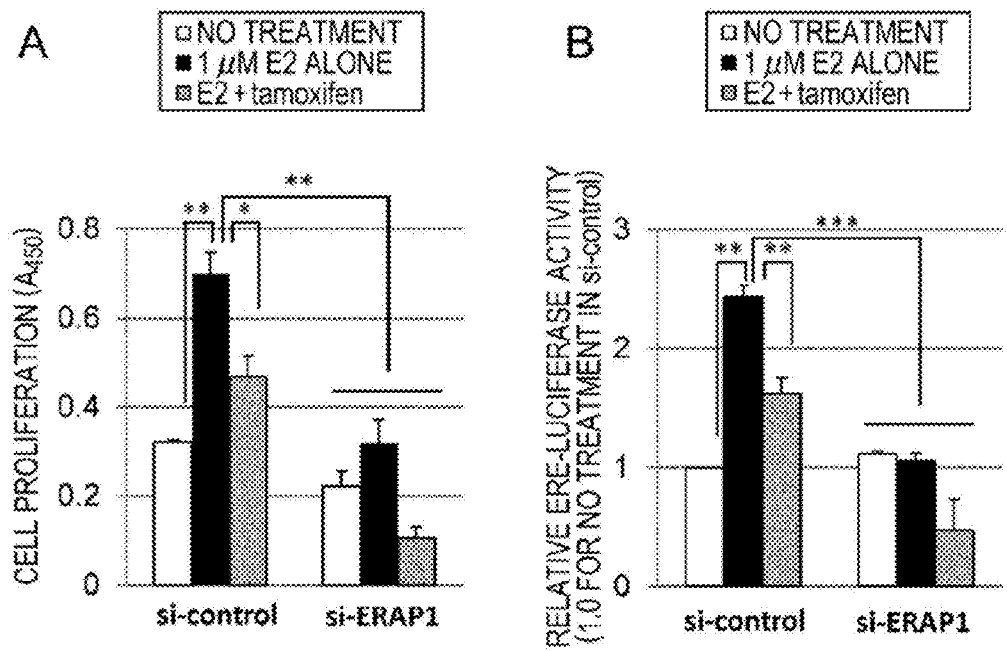
FIG. 17 is a diagram illustrating the influence of ERAP1 knockdown on the suppression effect on proliferation of breast cancer cells by tamoxifen. (A) shows the results of MTT assay by which the inhibition effect of tamoxifen when ERAP1 was knocked down by siRNA method was evaluated. The data show the mean±SE of three independent experiments. *P<0.05; **P<0.01. (B) shows the results of the ERE luciferase assay by which the inhibition effect of tamoxifen when ERAP1 was knocked down by siRNA method was evaluated. The data show the ratio when the value of the si-control for non-treated cells was designated as 1, and show the mean±SE of three independent experiments.

Influence of Knockdown of ERAP1 on Suppression Effect of Breast Cancer Cell Proliferation by Tamoxifen The inhibition effect of tamoxifen when expression of ERAP1 was suppressed in MCF-7 cells by siRNA method was investigated. It was confirmed that the cell proliferation was suppressed more in the case where the cells transfected with siERAP1 were treated with tamoxifen than in the case where the cells transfected with Si-control were treated with tamoxifen (FIG. 17A). In addition, ERE reporter activity was examined at the time. Thus, it was confirmed similarly that the reporter activity was suppressed more in the case where the cells transfected with siERAP1 were treated with tamoxifen (FIG. 17B). From those described above, it was suggested that synergistic cell proliferation suppression effect could be induced by suppression for the expression of ERAP1 and concomitant use of the ERAP1 peptide and tamoxifen.

Figure 18:
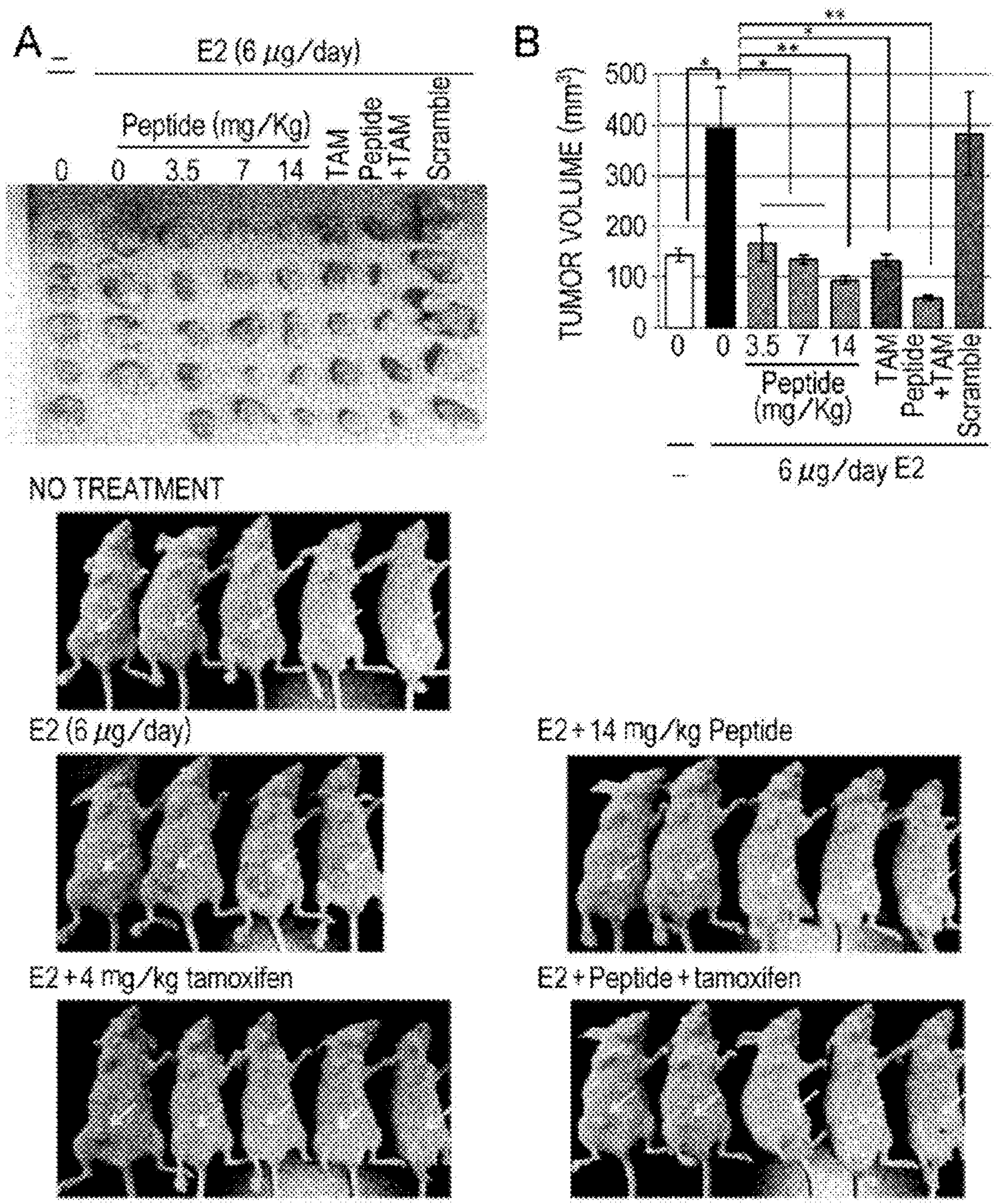
FIG. 18 is a diagram illustrating the influence of concomitant use of the ERAP1-peptide and tamoxifen on tumor proliferation in a human breast cancer-transplanted mouse. KPL-3 cells were subcutaneously transplanted into the breast fat body of a BALB/c nude mouse. The treatment test individuals/group) was initiated (day 0) when the volume of the tumor reached about 50-80 $mm^3$ in the absence E2. (A) shows representative examples of KPL-3C orthotopically transplanted tumor (upper panel) and mouse (lower panel) at day 14 after the test initiation. (B) shows the average tumor volume at day 14 after the test initiation.

Investigation for Antitumor Effect by Concomitant Use of ERAP1-Peptide and Tamoxifen The antitumor effect by concomitant use of the ERAP1-peptide and tamoxifen was investigated using a BALB/c nude mouse model to which KPL-3 cells were orthotopically transplanted to the mammary gland. With respect to the proliferation of estrogen-dependent breast cancer, administration of the ERAP1-peptide alone was recognized to have dose-dependent (3.5, 7 and 14 mg/kg) antitumor effect, but in the case of administration of scramble-peptide alone (14 mg/kg), the effect was not recognized (FIG. 18). It was recognized that concomitant use of the ERAP1-peptide (14 mg/kg) and tamoxifen (4 mg/kg) had further remarkable antitumor effect (FIG. 18). Change of the body weight was not recognized in any of the administration methods. From those described above, it was found that the ERAP1-peptide inhibited the estrogen signal of ER, and thus also exhibited remarkable antitumor effect in vivo, and the effect was further enhanced by concomitant use with tamoxifen.

Influence of Concomitant Use of ERAP1-Peptide and Tamoxifen on the Cell Cycle

Figure 19:
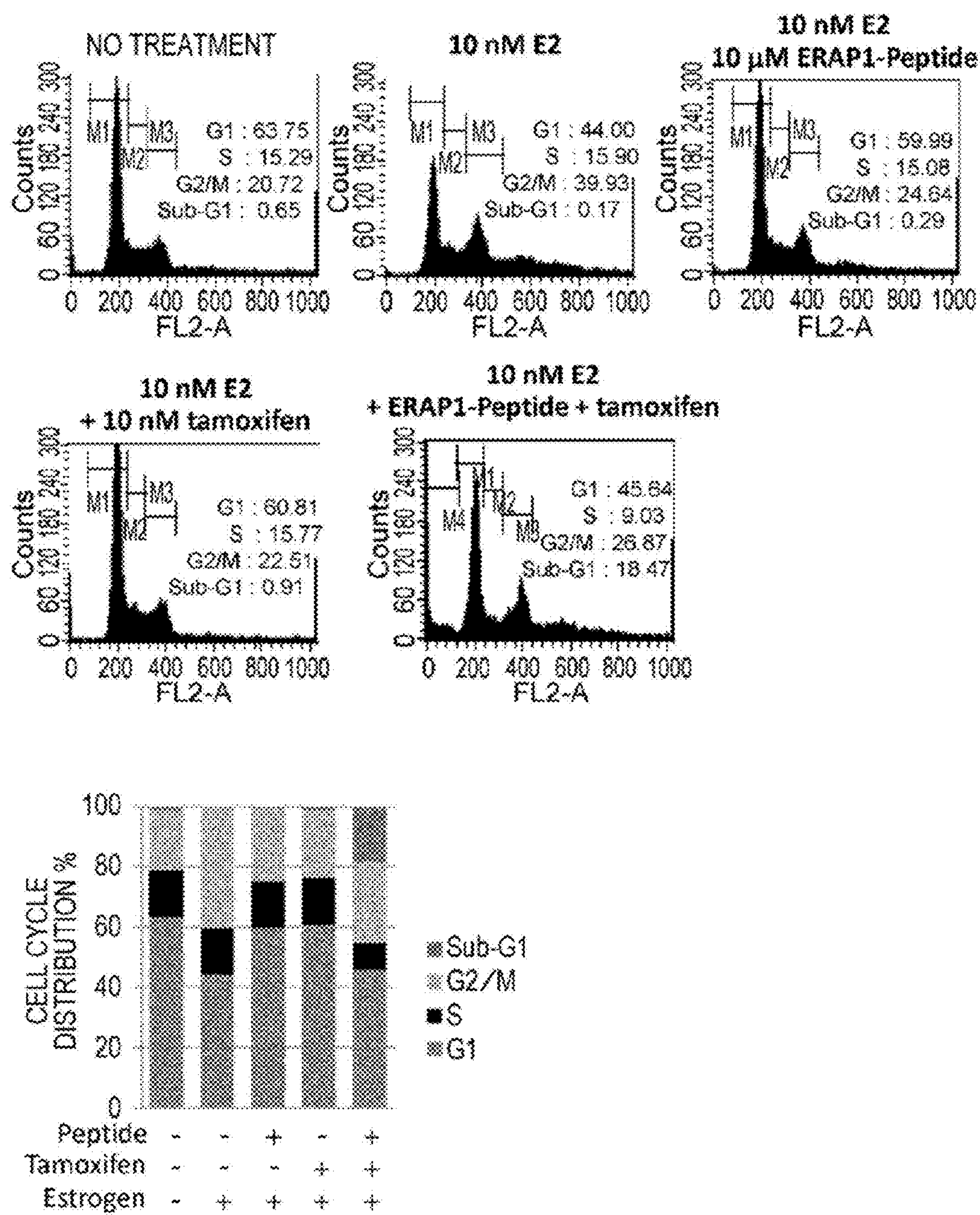
FIG. 19 is a diagram illustrating the results of FACS analysis showing the effects of concomitant use of the ERAP1-peptide and tamoxifen on the cell cycle.

The influence of concomitant use of the ERAP1-peptide and tamoxifen on the cell cycle was examined by FACS analysis. When MCF-7 cells were treated with 10 μM ERAP1-peptide alone or 10 nM tamoxifen alone, increase of cells having stopped in the G1 phase was confirmed. However, when 10 μM ERAP1-peptide and 10 nM tamoxifen were used concomitantly cells in the subG1 phase remarkably increased, and cell death was recognized (FIG. 19). From those described above, it was found that concomitant use of the ERAP1-peptide and tamoxifen having different action mechanism remarkably promoted the antitumor effect in vitro and in vivo as well.

Figure 20:
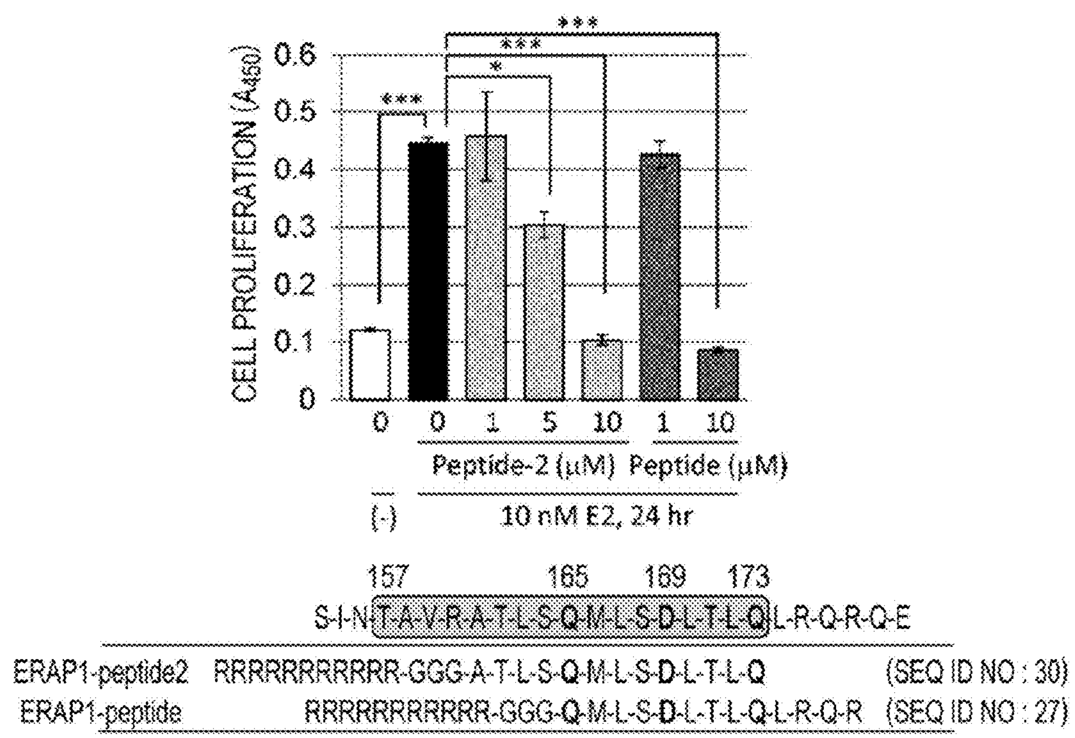
FIG. 20 is a diagram illustrating the results of evaluations for the influence of the difference of the sequence on E2-dependent cell proliferation suppression effect. The upper panel shows the results of MTT assay by which the inhibition effect of 2 kinds of the peptides (the ERAP-peptide and the ERAP1-peptide-2) on proliferation of E2-dependent MCF-7 cells was evaluated. MCF-7 cells were treated with the ERAP1-peptide or ERAP1-peptide-2 in the concentrations shown in the figure. Then, immediately, the cells were stimulated with E2 for 24 hours. The data show the mean±SE of three independent experiments. *P<0.05; ***P<0.001. The lower panel shows the sequences of the ERAP1-peptide and the ERAP1-peptide-2. The enclosed sequence shows the region for the interaction with PHB2 that is estimated by the PISVER software.

[Example 5] Investigation for Breast Cancer Cell Proliferation Suppression Effects of Peptides Having Different Sequence 1. Materials and Methods In order to confirm whether or not a peptide having a different sequence from the ERAP1-peptide used in Examples above would provide similar effects, ERAP1-peptide-2 (161-173 amino acid residue; ATLSQMLSDLTLQ (SEQ ID NO: 30)) was constructed, which had a different sequence from the ERAP1-peptide and comprised the 3 amino acid residues estimated as the binding site to PHB2/REA (FIG. 20, the lower panel). The cell proliferation assay was evaluated using Cell-Counting Kit-8 (CCK-8, Dojindo, Kumamoto, Japan). First, MCF-7 cells were seeded in $2\times10^4$/well in DMEM/F12 culture medium containing 10% FBS and 1% antibiotic/antimycotic solution and not containing phenol red on a 48-well plate, and stood in a $CO_2$ incubator. Then, 1801 μl of the ERAP1-peptide (165-177 amino acid residues) or the ERAP1-peptide-2 (pep-1: 161-173 amino acid residues) in each concentration was added, and subsequently 20 μl of 100 nM E2 was added (final concentration: 10 nM), and the mixture was reacted for 24 hours. The reaction solution was removed, and then 125 μl portion of 10 fold-diluted CCK-8 solution was added to each well, and the coloration reaction was performed for 1 hour in a $CO_2$ incubator. Then, 100 μl from each well was moved to a 96-well plate, and the absorbance at 450 nm was measured with a microplate reader.

2. Results

It was recognized that in the same way as the ERAP1-peptide, the ERAP1-peptide-2 administration also suppressed the E2-dependent cell proliferation in dose-dependent manner tip to 24 hours (FIG. 20, the upper panel). From this, it was suggested that the ERAP1-peptide-2 also caused suppression for cell proliferation of breast cancer cells by the mechanism similar to that of the ERAP1-peptide analyzed in Examples above. In addition, it was suggested that a sequence of 165-173 amino acid residues (QMLSDIJTLQ (SEQ ID NO: 3)), which was the overlapping sequence of the ERAP1-peptide and the ERAP1-peptide-2, was involved in suppression for cell proliferation of breast cancer cells.

[Example 6] Investigation for PHB2 Phosphorylation in ERα-Positive/ERAP1-Negative Breast Cancer Cell Lines 1. Materials and Methods Fractionation of Nucleus/Cytoplasm In order to evaluate the locality of PHB2, ERα-positive/ERAP1-negative breast cancer cell line HCC1395 cells were treated with the ERAP1-peptide and/or E2. Then, the extracts of the cytoplasm and the nucleus of HCC1395 cells were prepared using NE-PER nuclear and cytoplasmic extraction reagent (Thermo Fisher Scientific).

Effects of ERAP1-Peptide on ERα-Positive/ERAP1-Negative Breast Cancer Cell Line HCC1395 Cells The proliferation assay of HCC1395 cells was evaluated using Cell-Counting Kit-8 (CCK-8, Dojindo, Kumamoto, Japan). First, HCC1395 cells were seeded in $2\times10^4$/well in RPMI culture medium containing 10% FBS and 1% antibiotic/antimycotic solution and not containing phenol red on a 48-well plate, and stood in a $CO_2$ incubator. Then, 180 μl of the ERAP1-peptide in each concentration was added, and subsequently 20 μl of 100 nM E2 was added (final concentration: 10 nM), and the mixture was reacted for 96 hours. The reaction solution was removed, and then 125 μl portion of 10 fold-diluted CCK-8 solution was added to each well, and the coloration reaction was performed for 1 hour in a $CO_2$ incubator. Then, 100 μl from each well was moved to a 96-well plate, and the absorbance at 450 nm was measured with a microplate reader.

Phosphorylation of PHB2 by ERAP1-Peptide Treatment

MCF-7 cells and HCC1395 cells were treated with 5 μM ERAP1-peptide. Then, immediately the cells were stimulated with 1 μM E2 for 24 hours. Then, the nuclear fraction was isolated from the cells of each treatment. The nuclear fraction was precleaned at 4° C. for 3 hours using Normal IgG and rec-Protein G Sepharose 4B (Zymed, San Francisco, Calif., USA), and centrifuged, and then the supernatant was incubated in the presence of an anti-ERα antibody at 4° C. for 6 hours. Then, the supernatant was added with rec-Protein G Sepharose 4B and incubated at 4° C. for 1 hour to precipitate a antigen-antibody complex. The immunoprecipitated protein complex was washed with a lysis buffer three times, and separated by SDS-PAGE. Then, anti-ERα antibody and anti-PHB2 antibody were used in detection of each complete protein by Western blotting, and an anti-phosphorylation tyrosine antibody, an anti-phosphorylation serine antibody, and an anti-phosphorylation threonine antibody were used in detection of the phosphoric acid of PHB2.

Influence of the Serine Residue at Position 39 of PHB2 on ERα Transcriptional Activity Using expression vector constructs in which the serine residue at position 39 of PHB2 was mutated to alamine and glutamic acid, the influence of E2 stimulation on ERE activity was investigated. COS-7 cells were transfected with PHB2 (or PHB2 mutation vector), ERα, ERE-luciferase vector and each plasmid of pRL-TK as an internal standard by FuGENE6 transfection reagent. After 6 hours, the cells were stimulated with 1 μM E2 for 48 hours. The cells were harvested, and the activities of luciferase and *Renilla*-luciferase were evaluated using Promega dual luciferase reporter assay (Tokyo, Japan). In consideration of the transfection efficiency, all of the data were standardized with the activity of *Renilla*-luciferase.

2. Results

Figure 21:
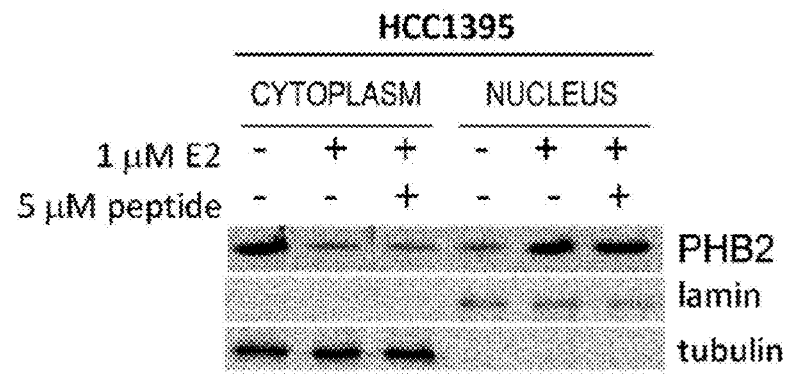
FIG. 21 is a diagram illustrating that PHB32 was translocated into the nucleus by E2 stimulation in ERAP1-negative breast cancer cell lines, HCC1395 cells. (A) shows the results of immunoblotting analysis by which the locality of PHB112 was detected HCC1395 cells were treated with 5 μM ERAP11-peptide. Then, immediately, the cells were stimulated with 1 μM E2 for 24 hours. The cells were fractionated into cytoplasm and nuclear fractions by specific gravity centrifugation. Then, each fraction was subjected to immunoblotting analysis using an anti-PHB2 antibody. Lamin and Tubulin are markers for cytoplasm and nuclear fractions, respectively. (B) shows the results of immunoblotting analysis by which reconstitution of ERα-centered chromatin complex was examined. HCC1395 cells were treated with 5 μM ERAP1-peptide. Then, immediately, the cells were stimulated with 1 μM E2 for 24 hours. Then, the nuclear fraction was immunoprecipitated with anti-ERα antibody. Furthermore, with respect to the obtained sample, the immunoprecipitate was subjected to immunoblotting analysis with the antibodies shown in the figure. (C) shows the results of MTT assay by which the effects of the ERAP1-peptide on proliferation of ERAP1-negative breast cancer cell lines HCC1395 cells were evaluated. HCC1395 cells were treated with the ERAP1-peptide in the concentrations shown in the figure. Then, immediately the cells were stimulated with 10 nM E2 for 96 hours. The data show the mean±SE of three independent experiments. *P<0.05; NS, no significance.
Figure 21:
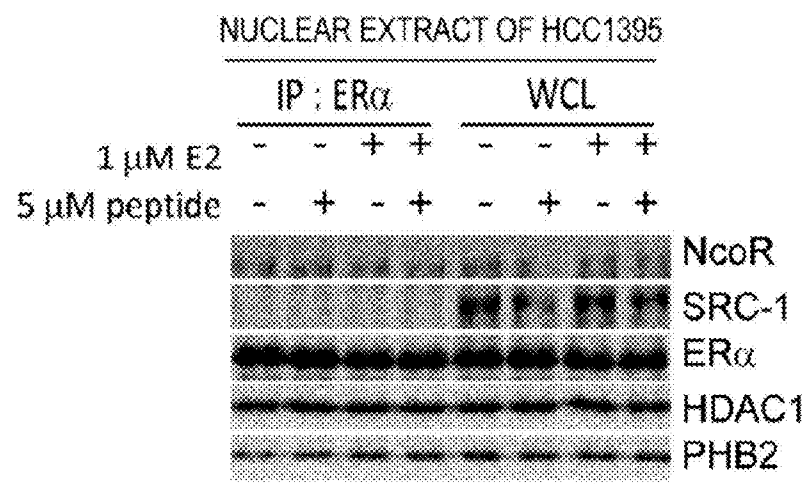
Figure 21:
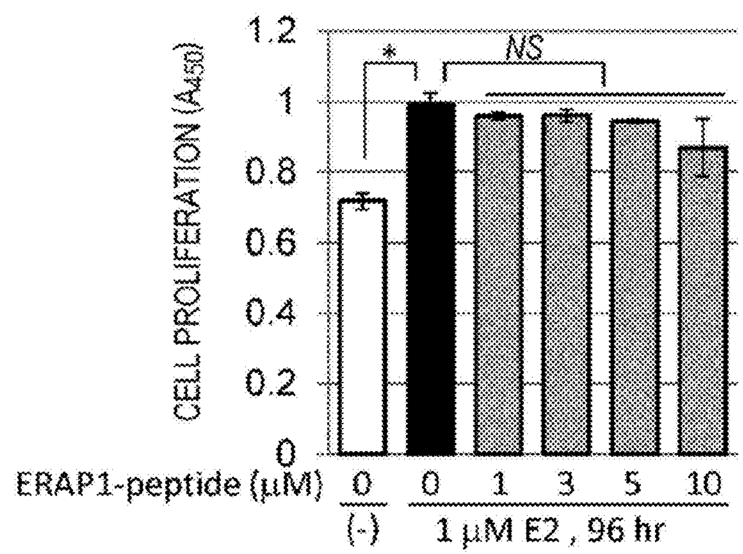

From the results so far, there was shown a possibility that ERAP1 is one of the target genes of ERα, and is regulated by positive feedback mechanism where if activation of ERα was induced in E2-dependent manner, the expression thereof was accelerated. Furthermore, it was confirmed that the ERAP1-peptide induced dissociation of PHB2, REA from ERAP1 in ERα-positive breast cancer cells, and as a result, inhibited the positive feedback mechanism of ERAP1, and inhibited every ERαc activation mechanism, to induce cell proliferation suppression effect. However, ERAP1-negative ER-positive breast cancer cells are also present, and the mechanism for accelerated expression of the ER target gene in such cells has not been found. In addition, REA/PHB2 directly binds to ER to have a function of suppressing the activation thereof as described above. Prom this, the role of PHB2/REA as an ER suppression factor in ERAP1-negative and ER-positive breast cancer cells is not clear. Accordingly, nuclear translocation of PHB2 using ERAP1-negative and ER-positive breast cancer cell line HCC1395 cells, was investigated first (FIG. 21).

In HCC1395 cells, nuclear translocation of PHB2/REA only with E2 treatment was recognized (FIG. 21A), and further the binding to ERα in the nucleus was confirmed by immunoprecipitation method (FIG. 21B). The recruit of each coupling factor of ERα at the time was investigated. As a result, quantitative changes of a coupling suppression factor NcoR and a deacetylation enzyme HDAC1, were not recognized by the presence or absence of E2 treatment, but the binding to ERα was recognized. However, the binding of ERα with a coupling activation factor SRC-1 was not recognized in any of the conditions.

From the results above, it was found that PHB2 was translocated into the nucleus in E2-dependent manner and directly bound to the nuclear ERα, and recruited a coupling suppression factor NcoR and a deacetylation enzyme HDAC1 in HCC1395 cells that were ERAP1-negative and ER-positive breast cancer cells. In addition, the influence of the ERAP1-peptide on cell proliferation was not recognized (FIG. 21C). However, this HCC1395 cell line was recognized for E2-dependent cell proliferation (FIG. 21C). From this, the inventors focused on post-translational-modification, particularly phosphorylation of PHB2/REA with respect to the mechanism for PHB2/REA to lead ERα to inactivation, and considered a hypothesis that suppression for ERα activity was regulated by the presence or absence of the phosphorylation of PHB2/REA.

It has been reported so far that regions important for suppression for ERα activity by PHB2/REA are 19-49 amino acids and 150-174 amino acids (PNAS, 1999, 96, 6947-6952). In addition, it has been reported that PHB2/REA is phosphorylated at residues of serine at position 39, and threonine at position 42 in comprehensive phosphorylation analysis (JBC, 283, 4699-4713, 2008). As described above, the inventors focused on these phosphorylations of 39s and 42T, and performed the experiment described below.

Figure 22:
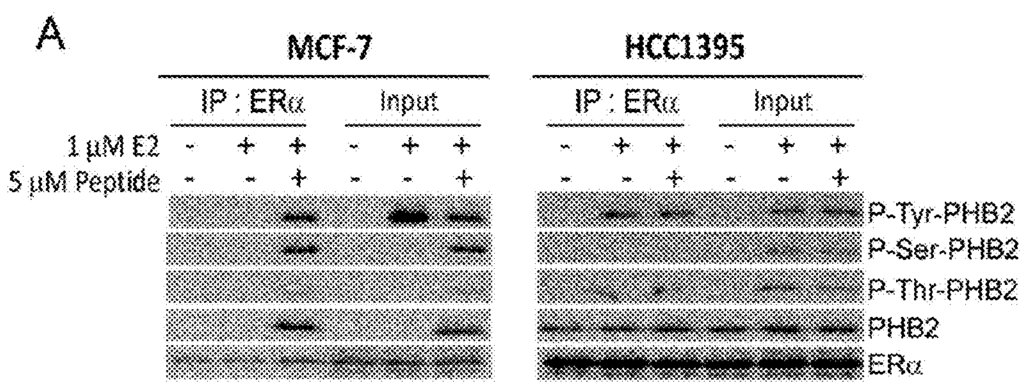
FIG. 22 is a diagram illustrating that phosphorylation of PHB2 serine regulates the transcriptional activity of ERα. (A) shows the results of immunoblotting analysis by which the influence of ERAP1-peptide treatment on phosphorylation of PHB2 bound to ERα was evaluated. MCF-7 cells and HCC1395 cells were treated with 5 μM ERAP1-peptide. Then, immediately, the cells were stimulated with 1 μM E2 for 24 hours. Then, the nuclear fraction of each cell was immunoprecipitated with anti-ERα antibody. Furthermore, with respect to the obtained sample, immunoblotting analysis was performed using the antibodies shown in the figure and the phosphorylation antibody. (B) shows the results of the luciferase assay by which regulation of ERα transcriptional activation by the serine residue at position 39 of PHB2 was evaluated. COS-7 cells temporarily transfected with PHB2 (or PHB2 mutation vectors, S39A and S39G), ERα, ERE-luciferase vector, and each plasmid of pRL-TK as an internal standard were stimulated with 1 μM E2 for 48 hours. The data show the mean±SE of three independent experiments. **P<0.01.
Figure 22:
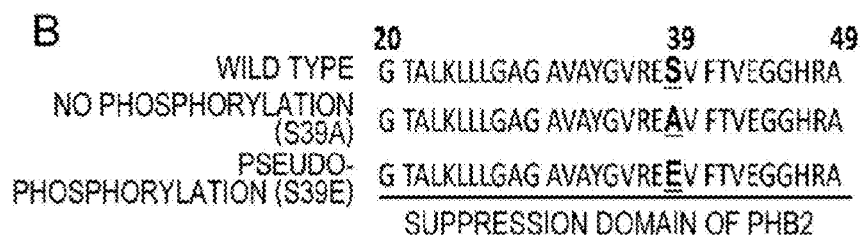
Figure 22:
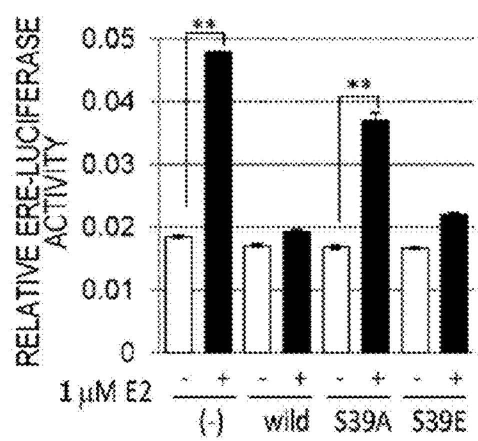

In ER-positive/ERAP1-positive breast cancer cell line MCF-7 cells, binding of PHB2 to ERα in the nucleus with administration of the ERAP1-peptide in the presence of E2 was recognized, and further phosphorylations of the tyrosine and serine residues in the binding-recognized PHB2/REA were recognized, whereas phosphorylation in the threonine residue was not nearly recognized. On the other hand, in HCC1395 cells, PHB2/REA was nuclear-translocated by E2 treatment, and bound to ERα, and in such PHB2/REA, phosphorylation of the tyrosine residue was recognized, while phosphorylation of the serine residue was not confirmed. These results suggested that 39S in the region important for suppression for the activity by PHB2/REA described above was a candidate site for the phosphorylation. Then, COS-7 cells were temporarily transfected with normal type PHB2/REA, an expression vector construct (S39A) in which 39S of PHB2/REA was substituted with alanine, or an expression vector construct (S39E) in which 39S of PHB2/REA was substituted with a glutamic acid residue that could make constitutively the state similar to the phosphorylation state, together with ERα, ERE-luciferase vector, and each vector of pRL-TK as an internal standard. Then, the cells were treated with E2, and ERE reporter activity was examined. As a result, the activity of ERα was suppressed in the cells to which normal type PHB2/REA was introduced. On the other hand, suppression of the activity of ERα was not recognized in the cells to which the mutation construct of S39A was introduced. In addition, also in S39E construct, suppression for the activity of ERα was recognized (FIG. 22B). From those described above, it was suggested that the phosphorylation of the serine residue at position 39 was important in suppression for the activity of ERα by PHB2/REA, and in the ER-positive breast cancer cells having no expression of ERAP1, the phosphorylation was suppressed and thus PHB2/REA became an inactive type.

[Example 7] Expression of ERAP1 and PHB2 in Human Breast Cancer Cell Line and Human Breast Cancer-Resected Specimens I. Materials and Methods Analysis for Expression of ERAP1 in Breast Cancer Cell Lines The cell lysates of human ER-positive breast cancer cell lines (KPL-3L, BT-474, ZR-75-1, YMB-1, T47D, HBC4, and KPL-1) and mammary epithelial cells (MCF-10A) were immunoblotted using anti-ERAP1 antibody, anti-PHB2 antibody and anti-ERα antibody.

Analysis for Expression of ERAP1 and PHB2 in Human Breast Cancer-Reselected Specimens Expressions of ERAP1 and PHB2/REA were evaluated with immune tissue staining using anti-ERAP1 antibody (diluted by 75 times, 7 hours, 4° C.) and anti-PHB2 antibody (diluted by 300 times, 12 hours, 4° C.) for 103 cases of paraffin-embedded breast cancer-resected specimens. Determination for the stainability of the cancer part by the immunostaining was performed such that a case where the cancer tissue was not stained at all was determined negative, and a case where the cytoplasm was lightly stained was determined weak positive, and a case where the cancer tissue was almost uniformly strongly stained was determined strong positive. The results of this immune tissue staining were confirmed by pathologists, and the staining intensity of each case was evaluated independently by three researchers. For the correlation between the ERAP1 expression and the relapse-free survival period of the respective case, a curve of the relapse-free survival was prepared with Kaplan-Meier method using Statview 3-5.0, and was evaluated with Logrank test.

2. Results

Expression of ERAP1 in Breast Cancer Cell Lines

Figure 23:
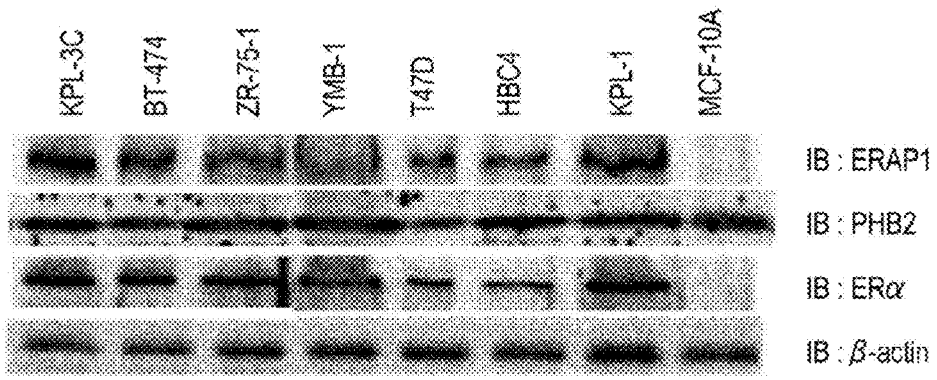
FIG. 23 is a diagram illustrating the results of immunoblotting analysis showing expressions of ERAP1, PHB2, and ERα in human breast cancer cell lines. The cell lysates of the human breast cancer cell lines and mammary epithelial cells (MCF-10A) shown in the figure were subjected to immunoblotting analysis with the antibodies shown in the figure.

The expressions of ERAP1, PHB2 and ERα of human ER-positive breast cancer cell lines were investigated. In the ER-positive breast cancers, all cell lines except for HCC1395 were confirmed for the expression of ERAP1 (FIG. 23 and Cancer Science, 2009; 100: 1468-78).

Expressions of ERAP1 and P1HB132 in Human Breast Cancer-Resected Specimens

Figure 24:
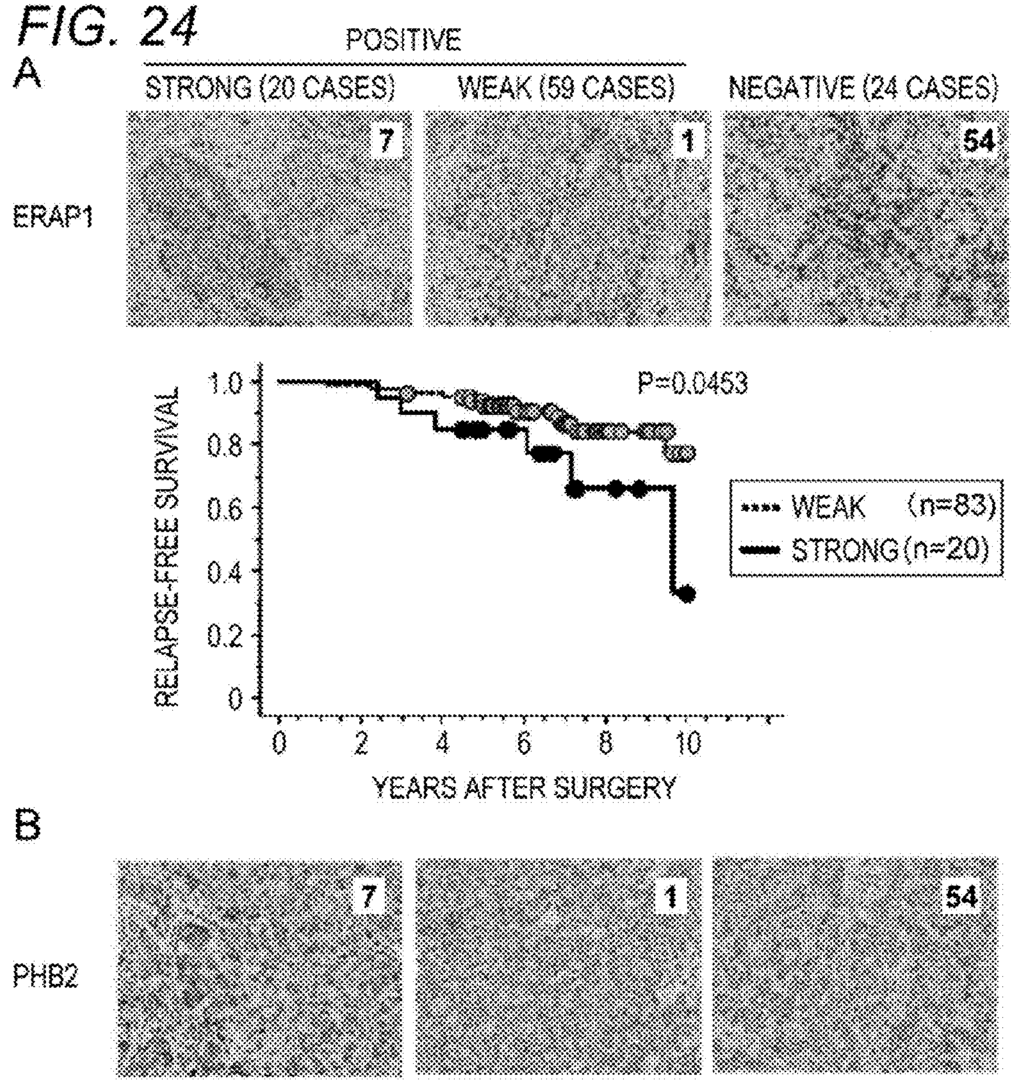
FIG. 24 is a diagram illustrating the expressions of ERAP1 in human breast cancer-resected specimens. (A) shows the results of immune tissue staining in which the expression of ERAP1 for the breast cancer-resected specimens was evaluated. The upper panel illustrates representative images of the stained immune tissues in paraffin-embedded breast cancer-resected specimens showing the expression of ERAP1. Judgment for the stainability of the cancer part by the immunostaining was performed such that a case where the cancer tissue was not stained at all was determined negative (Negative: 24 cases, 23%) a case where the cytoplasm was lightly stained was determined weak positive (Weak: 59 cases, 57%), and a case where the cancer tissue was almost uniformly strongly stained was determined strong positive (Strong: 20 cases, 19%). The lower panel is a curve of the relapse-free survival constructed for the correlation between the ERAP1 expression and the relapse-free survival period with Kaplan-Meier method when the respective cases were classified to Weak (negative cases and weak positive cases) and Strong (strong positive cases). (B) shows representative staining images of the immune tissues in which the expression of PHB2 for the breast cancer-resected specimens was evaluated.

The expression of ERAP1 was evaluated by immune tissue staining in breast cancer-resected specimens. Among the 103 cases evaluated, Negative where the cancer tissue was not stained at all, was 24 cases (23%). Weak where the cytoplasm was lightly stained, was 59 cases (57%), and Strong where the cancer tissue was almost uniformly strongly stained, was 20 cases (19%) (FIG. 24A, the upper panel). Furthermore, the respective cases were classified into Weak (negative cases and weak positive cases) and Strong (strong positive), and evaluated with a curve of the relapse-free survival constructed for the correlation between the ERAP1 expression and the relapse-free survival period with Kaplan-Meier method. As a result, it was recognized that the expression of ERAP1 significantly correlated with the relapse-free survival period (FIG. 24A, the lower panel).

In addition, the expression of PHB2 was similarly evaluated with immune tissue staining. As a result, almost all cases of the investigated breast cancer-resected specimens were strong positive (Strong) (FIG. 24B).

[Example 8] Investigation for Action Mechanism of ERAP1 Peptide in Human Breast Cancer Cells 1. Materials and Methods Cell Lines Human breast cancer cell lines (MCF-7, ZR-75-1, BT-474, T47D, and HCC1395) were purchased from American Type Culture Collection (ATCC, Rockville, Md., USA). KPL-3C was provided from Dr. Junichi Kurebayashi (Kawasaki Medical School, Okayama, Japan) under Material transfer agreement. HEK293T was purchased from RIKEN (Ibaraki, Japan). All of the cell lines were cultured under the conditions recommended by each depositor.

Treatment of Cell

MCF-7 cells were suspended in MEM (Invitrogen, Carlsbad, Calif., USA) reinforced with 10% FBS (Nichirei Biosciences. Tokyo, Japan), 1% antibiotic/antimycotic solution (Invitrogen), 0.1 mM NEAA (Invitrogen), mM sodium pyruvate and 10 μg/ml insulin (Sigma, St. Louis, Mo., USA). Then, the obtained suspension was seeded on a 4-well plate (1 & $10^5$ cells/1 ml), a 6-well plate ($5\times10^5$ cells/2 ml) or 10 cm dish ($2\times10^6$ cells/10 ml). The cells were maintained in humidified atmosphere containing 5% carbon dioxide at 37° C. On the next day of the seeding, the culture medium was exchanged to phenol red-free DMEM/F12 (Invitrogen) rein forced with FBS, an anti bioticiantimycotic solution, NEAA, sodium pyruvate and insulin. After 24 hours, the cells were treated with 10 nM 17β estradiol (E2, Sigma), In the inhibition test, the ERAP1-peptide was added just before the E2 stimulation.

Luciferase Reporter Assay

HEK293T cells were transfected with a commercially available ERE reporter (SABiosciences, Frederick, Md., USA) and ERE reporter of the PP1α gene (tandem sequence consisting of the 5' upstream ERE motif and ERE motif of the 5' upstream and intron 2) and pRL-TK as an internal standard. After 16 hours from the transfection, the culture medium was exchanged to an assay culture medium (Opti-MEM, 10% FBS). After 24 hours from the transfection, the cells were treated with 10 nM E2 for 24 hours. The cells were harvested and the activities of luciferase and *Renilla*-luciferase were evaluated with Promega dual luciferase reporter assay (Tokyo, Japan). In consideration of the transfection efficiency, all of the data were standardized with the activity of *Renilla*-luciferase.

Western Blotting Analysis

The cells were lysed with a lysis buffer (50 mM Tris-HCl: pH 8.0, 150 mM NaCl, 0.1% NP-40, 0.5% CHAPS) containing 0.1% protease inhibitor cocktail III (Calbiochem, San Diego, Calif., USA). The cell lysate was subjected to electrophoresis, and blotted on a nitrocellulose membrane, and blocked with a 4% BlockAce solution (Dainippon Pharmaceutical, Osaka, Japan) for 1 hour. The membrane was incubated in the presence of the antibodies described below for 1 hour:

Anti-β-actin (AC-15) antibody (Sigma);

Anti-ERAP1 purified antibody (anti-hA7322 (His13)) (Sigma);

Anti-FLAG-tag M2 antibody (Sigma):

Anti-HA-tag antibody (Roche, Mannheim, Germany);

Anti-PHB2/REA antibody (Abcarm, Cambridge, UK);

Anti-ERα (AER314) antibody (Thermo Fisher Scientific, Fremont, Calif., USA);

Ainti-α/β-tubulin antibody (Cell Signaling Technology, Danvers, Mass., USA);

Anti-Akt (PKB) antibody (Cell Signaling Technology, Danvers, Mass., USA);

Anti-phosphorylation Akt antibody (Ser473) (587F11) (Cell Signaling Technology, Danvers, Mass., USA);

Anti-p44/42 Map Kinase antibody (Cell Signaling Technology, Danvers, Mass., USA);

Anti-phosphorylation p44/42 Map Kinase antibody (Thr202/Tyr204) (Cell Signaling Technology Danvers, Mass., USA);

Anti-PP2A A subunit antibody (81G5) (Cell Signaling Technology, Danvers, Mass., USA);

Anti-Lamin B antibody (Santa Cruz Biotechnology, Santa Cruz, Calif., USA);

Anti-PKA IIα reg antibody (C-20) (Santa Cruz Biotechnology, Santa Cruz, Calif., USA); or Anti-PP1 antibody (FL-18) (Santa Cruz Biotechnology, Santa. Cruz, Calif., USA).

Alternatively, the membrane was incubated overnight in the presence of the antibodies described below:

Anti-phosphorylation PHB2/REA purified antibody (Ser39) (Scrum, Tokyo, Japan);

Anti-phosphorylation tyrosine antibody (Zymed, San Francisco, Calif., USA);

Anti-phosphorylation serine antibody (Zymed, San Francisco, Calif., USA); or

Anti-phosphorylation threonine antibody (Zymed, San Francisco, Calif., USA).

The membrane was incubated in the presence of HRP-binding secondary antibody (Santa Cruz Biotechnology) for 1 hour. Then, the membrane was developed with enhanced chemiluminescence system (GE Healthcare, Buckinghamshire, UK). The blotting was scanned using Image Reader LAS-3000 mini (Fujifilm, Tokyo, Japan).

Immunoprecipitation

As described in the item of "Western blotting analysis", the cells were lysed with 0.1% NP-40 lysis buffer. The cell lysate was precleaned using Normal IgG and rec-Protein G Sepharose 4B (Zymed, San Francisco, Calif., USA) at 4° C. for 3 hours. The cell lysate was centrifuged, and then the supernatant was incubated in the presence of an anti-ERAP1 purified antibody a an anti-PHB2/REA antibody, an anti-ERα antibody and an anti-FLAG-tag M2 antibody at 4° C. for 6 hours. Then, the supernatant was incubated in the presence of rec-Protein G Sepharose 4B at 4° C. for 1 hour to precipitate an antigen-antibody complex. The immunoprecipitated protein complex was washed with a lysis buffer three times, and separated by SDS-PAGE. Then, Western blotting analysis was performed.

Fractionation of the Nucleus and the Cytoplasm

In order to evaluate the locality and the phosphorylation of PHB2/REA, immunoprecipitation was performed using an anti-PHB2/REA antibody in the presence of rec-protein G sepharose using the nucleus and cytoplasm extracts of MCF-7 cells. The nucleus and cytoplasm extracts were prepared using NE-PER nuclear and cytoplasmic extraction reagent (Thermo Fisher Scientific).

Immune Cell Chemical Staining

MCF-7 cells were seeded in an 8-well chamber (Laboratory-Tek II Chamber Slide System, Nalgen Nunc International, Naperville, Ill., USA) in $5\times10^4$ cells/well, and cultured under estrogen-free condition for 24 hours. MCF-7 cells were exposed to 10 nM E2 with the ERAP1-peptide and λ-phosphatase. After 24 hours, the cells were treated with 4% paraformaldehyde at 4° C. for 30 minutes to be fixed, and treated with 0.1% Triton X-100 for 2 minutes to be made permeable. Then, the cells were coated with 3% BSA to block non-specific hybridization. Then, the cells were incubated further for 1 hour in the presence of anti-PHB2/REA antibody and anti-phosphorylation PHB2/REA antibody (Ser39). The cells were washed with PBS, and then incubated for 1 hour in the presence of Alexa 594 and Alexa 488 binding anti-rabbit antibody (Molecular Probe, Eugene, Oreg., USA) to be stained. The nucleus was counter-stained with 4,6-diamidine-2'-phenylindole dihydrochloride (DAPI, Vectashield, Vector Laboratories, Burlingame, Calif., USA). The fluorescence image was obtained under Olympus IX71 microscope (Tokyo, Japan).

In Vivo Inhibition of Tumor Proliferation

KPL-3C cell suspension ($1\times10^7$ cells/mouse) was mixed with an equal amount of Matrigel (BD), and was injected into the breast fat body of 6 weeks old female BALB/c nude mice (CLEA Japan, Tokyo, Japan). The mice were kept in a sterile isolated facility with a cycle of 12 hour light period/12 hour dark period, and freely fed with rodent food and water. The tumor was grown over 1 week until the size thereof reached 50 to 80 $mm^3$ (calculated as ½×(width×length$^2$)). Then, the mice were randomly divided into nine treatment groups (5 individuals/group): no treatment group, 6 μg/day E2 treatment group, E2+0.28 mg/day ERAP1-peptide treatment group, E2+0.7 mg/day ERAP1-peptide treatment group, E2+1.4 mg/day ERAP1-peptide treatment group, E2+0.28 mg/day ERAP1-scramble peptide treatment group, E2+0.7 mg/day ERAP1-scramble peptide treatment group, E2+1.4 mg/day ERAP1-scramble peptide treatment group and E2+83 μg/day tamoxifen treatment group. The mice were treated every day with 6 μg/day E2 solution (100 μl: $2.2\times10^4$ M) on the neck skin. The ERAP1-peptide or the ERAP1-scramble peptide was administered to the mice every day by intraperitoneal injection in 0.28, 0.7, or 1.4 mg/day (14, 35 and 70 mg/kg). Tamoxifen was also intraperitoneally administered to the mice every day in a dose of 4 mg/kg. The tumor volume was measured over 2 weeks using calipers. When the test was completed, the animals were euthanatized, and the tumor was removed in order to evaluate the serine phosphorylation of PHB2/REA, and crushed under liquid nitrogen and was subjected to Western blotting. All of the tests were performed in accordance with the guideline of the animal facility of The University of Tokushima.

PP1α Phosphatase Activity

The phosphatase activity of PP1α was measured using Protein Phosphaase Assay Kit (AnaSpec, Fremont, Calif., USA). MCF-7 cells were treated with E2 and the ERAP1-peptide for 24 hours. Then, the cell lysate solution was immunoprecipitated with anti-PP1α antibody. Subsequently, the immunoprecipitated cell extract was incubated with a substrate (p-Nitrophenyl phosphate) at room temperature for 60 minutes. Then, the reaction was stopped, and the absorbance at 405 nm was measured. The PP1α activity (μmole/min) was defined as an enzymatic amount catalyzing 1 μmole of the substrate per 1 minute.

Real Time PCR

PP1α expression was evaluated with real time PCR. Complete RNA was extracted from the E2-treated cells using RNeasy Mini purification kit (Qiagen), and reverse-transcribed into cDNA using Superscript II reverse transcriptase (Invitrogen), oligo dT primer (Invitrogen) and 25 mM dNTP Mixture (Invitrogen). cDNA was analyzed with real time PCR in 500 Real Time PCR System (Applied Biosystems) using SYBR (registered trademark) Premix Ex Taq (Takara Bio, Shiga, Japan). Each sample was standardized with the mRNA content of β2-MG. The primers used for the amplification are as described below: PP1α: 5'-ACTATGTGGACAGGGGCAAG-3' (SEQ ID NO: 58) and 5'-CAGGCAGTTGAAGCAGTCAG-3Y (SEQ ID NO: 59), β2-MG: 5'-AACTTAGAGGTGGGGAGGCAG-3' (SEQ ID NO: 21) and 5'-CACAACCATGCCTTACTTTATC-3' (SEQ ID NO: 22).

ChIP Assay

ChIP analysis was performed using EZ-ChIP (Millipore, Billerica, Mass., USA). MCF-7 cells were treated with 10 nM E2 for 24 hours, and then fixed with 37% formaldehyde, and resuspended in a lysis buffer. Subsequently, the cells were crushed with ultrasonic waves in 10 seconds×10 with Microson XL-2000 (Misonix, Farmingdale, N.Y. USA). The supernatant was precleared with protein G agarose beads, and 1% input was collected. Immunoprecipitation (for each $1\times10^6$ cells) was performed (overnight, 4° C.) using anti-ER antibody and mouse IgG, and the DNA-protein complex was pulled-down with protein G agarose beads (1 hour, 4° C.), and was washed, and then, the immunoprecipitate was resuspended in an elution buffer. Then, the obtained suspension was incubated at 65° C. for 5 hours to release the cross-linking. Then, the immunoprecipitate was purified using accessory purification column. The DNA fragment was detected with 28 cycles of PCR. As the primers for ERE region of PP1α genome, used were −726/−704: 5'-TCAAAAGCTAATTATGGGGC-3' (SEQ ID NO: 60) and 5'-TCAAGCGATTCTCCTGCCTCA-3' (SEQ ID NO: 61), +1851/+1873: 5'-GAGATCCGCGGTCTGTGCCTG-3' (SEQ ID NO: 62) and 5'-CAGGACTGCGCTCAAGGGAGG-3' (SEQ ID NO: 63), and +1936/+1959: 5'-CACTGGACCCCACAGAGTTCC-3' (SEQ ID NO: 64) and 5'-TAGTTGCTCTCGGGAGGGAAA-3' (SEQ ID NO: 65).

2DICAL

MCF-7 cells were treated with 10 μM ERAP1-peptide and ERAP1-scramble peptide. Then, immediately, the cells were stimulated with 10 nM E2. Then, the cells were fixed with methanol. The cells were dried under reduced pressure, and then treated with trypsin in the presence of 2% sodium deoxycholate and 5 M urea at 37° C. for 20 hours. The protein was extracted with ethyl acetate. Subsequently, the extracts were dried under reduced pressure, and then subjected to 2DICAL (2 Dimensional Image Converted Analysis of LCMS), 2DICAL is a proteome analysis method in which temporally obtained spectrum with ultra low speed liquid chromatography and mass analysis is digitalized, and depicted to a plane having two axes of the mass charge ratio (m/z) and the retention time. The data were calculated as a ratio to the value at 0 hour.

Microarray

MCF-7 cells were treated with 10 μM ERAP1-peptide. Then, immediately the cells were stimulated with 10 nM E2. Then, RNA extraction was performed. Cy3 labeled cRNA was synthesized with Low Input Quick Amp Labeling Kit (Agilent Technologies, Loveland, Colo., USA) and hybridized with a custom microarray at 65° C. for 17 hours. The microarray was washed. Then, the product hybridized was measured with a microarray scanner (Agilent). The results thereof were digitized with Future Extraction software (Agilent). The data were statistically analyzed with GeneSpring software (Agilent), and the ratio to the value at 0 hour was calculated.

Biacore

In order to evaluate the binding of PHB2/REA and the ERAP1-peptide, 6×His-tagged recombinant PHB2/REA protein was immobilized on a sensor chip (CM5) by amine coupling. Then, the chip was set with Biacore 3000 (GE Healthcare, Tokyo, Japan), and an HA-tagged ERAP1-peptide in each concentration was injected. The dissociation rate constant was calculated with BIAevaluation software (GE Healthcare).

Fluorescence Correlation Spectroscopy Method

In order to evaluate the binding of PHB2/REA and the ERAP1-peptide, 10 mM. FITC-tagged ERAP1-peptide and FITC-tagged ERAP1-scramble peptide, and 6×His-tagged recombinant PHB2/REA protein were reacted for 1 hour. Then, FITC fluorescence was measured using FlucDeux device (MBL, Tokyo, Japan), and the ratio of the ERAP1-peptide bound to PHB2/REA protein was calculated.

Purification of Anti-ERAP1 Monoclonal Antibody

A rat (WKY/Izm, 10 weeks old, female) was sensitized with a human ERAP1 partial sequence (residues 459-572 aa). After 2 weeks, the lymphocytes were collected from the iliac lymph node, and cell-fused with myeloma of SP2 mouse, and the hybridoma was cultured. Antibodies produced by the hybridoma and screened were collected from the mouse ascites, and purified with cation exchange chromatography (HiTrap SP HPcolumn).

Purification of Anti-Phosphorylation PHB2/REA (S39) Antibody

In order to prepare Ser39-specific anti-phosphorylation antibody of human PHB2/REA, a peptide antigen (C+(PEG Spacer)+YGVRE pS VFTVE) was synthesized, and conjugated with KLH, and used to sensitize a rabbit five times every 2 weeks. After 2 months, the whole blood was collected, and anti-serum was prepared, and anti-phosphorylation. PHB2/REA (S39) antibody was purified with phosphorylation affinity.

Cell Proliferation Assay

Cell proliferation assay was performed using Cell-Counting Kit-8 (CCK-8, Dojindo, Kumaamoto, Japan). The cells were harvested, and plated in $2\times10^4$ cells/well on a 48-well plate, and maintained in a humidified incubator (37° C.). 10 fold-diluted CCK-8 solution was added at indicated time points and the cells were incubated for 1 hour. Then, the absorbance at 450 nm was measured and the number of living cells was calculated.

Statistical Analysis

For determining the statistical significance of the difference between the test groups, Student's t-test was used. P value<0.05 was regarded as significant.

2. Results

Figure 25:
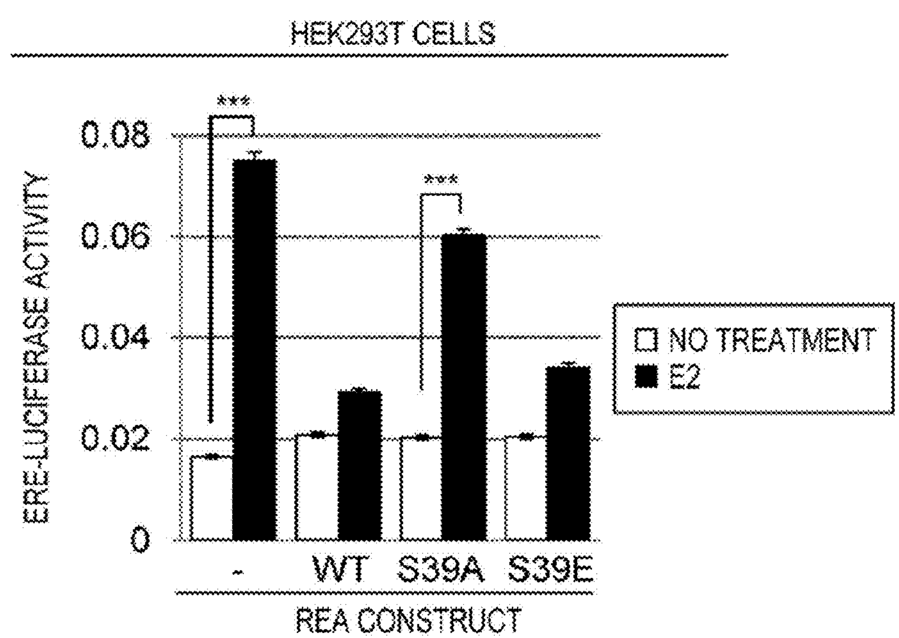
FIG. 25 is a diagram illustrating the results of evaluations for the influence of phosphorylation of Ser39 of PHB2/REA on the ERα transcriptional activity. (A) shows the results of the luciferase assay by which the inhibition effect of PHB2/REA (Ser39) for the phosphorylation in the ERα transcriptional activity was evaluated. HEK293T cells were temporarily transfected with full-length REA (WT) and a construct in which Ser at position 39 was mutated to Ala or Gin (S39A and S39E), together with an ERE-luciferase reporter vector and an ERα construct. The cells were stimulated with 10 nM E2 for 24 hours. The data show the mean±SE of three independent experiments. **P<0.01. (B) shows the results of immunoblotting analysis for phosphorylation of Ser39 of PHB2/REA. HEK293T cells were transfected with a PHB2/REA construct (WT, S39A and S39E). After 48 hours, the cells were stimulated with 10 nM E2 for 24 hours. Then, the cells were lysed. Then, the HA-tagged PHB2/REA was immunoprecipitated from the cell lysate with anti-HA antibody. Furthermore, with respect to the obtained sample, the immunoprecipitated protein was subjected to immunoblotting analysis with the antibodies shown in the figure. The data are representative examples of two independent experiments. (C) shows that Ser39 of PHB2/REA suppressed the non-genomic activation route. HEK293T cells were transfected with a PHB2/REA construct (WT S39A and S39E). After 48 hours, the cells were stimulated with 10 nM E2 for 24 hours. Then, the cell lysate was subjected to immunoblotting analysis with the antibodies shown in the figure. The data are representative examples of two independent experiments.
Figure 25:
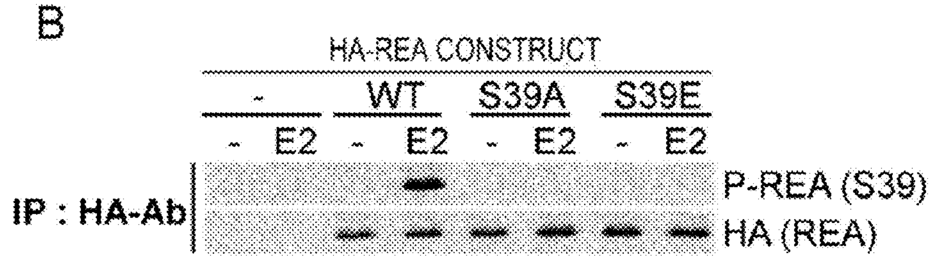
Figure 25:
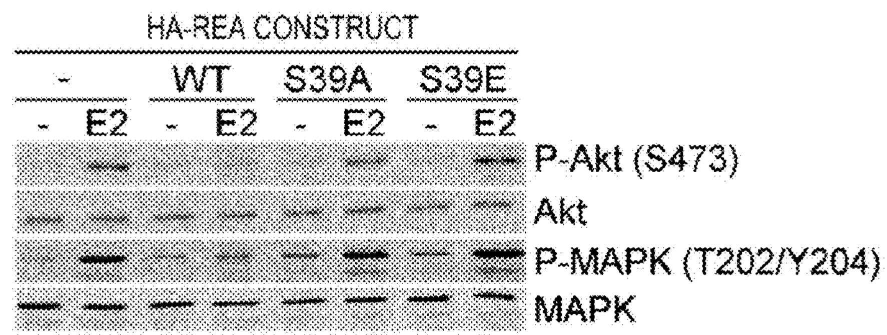

Suppression of ERα Transcriptional Activity by Phosphorylation of Ser39 of PHB2/REA The fact that the phosphorylation of the serine residue at position 39 (Ser39) was important for suppressing the activity of ERα by PHB2/REA (FIG. 22), was verified using anti-PHB2/REA-Ser39-specific polyclonal phosphorylation antibody manufactured above. HEK293T cells were temporarily transfected with a mutation type expression vector construct (S39A) in which 39S of normal type PHB2/REA was substituted with alanine (Ala), or an expression vector construct (S39E) in which the 39S was substituted with a glutamic acid residue that can make constitutively the state similar to the phosphorylation state, together with ERα, ERE-luciferase vector and each vector of pRL-TK as an internal standard. Then, the cells were treated with E2, and ERE reporter activity was examined. As a result, in the same way as FIG. 22, in the cells into which normal type PHB2/REA was introduced, the activity of ERα was suppressed (WT), whereas suppression for the activity of ERα was not recognized in the cells into which the mutation construct of S39A was introduced (S39A). In addition, also with S39E construct, suppression for the activity of ERα was recognized (FIG. 25A). Subsequently, the phosphorylation state of PHB2/REA was examined using the anti-PHB2/REA-Ser39 phosphorylation antibody. As a result, phosphorylation of Ser39 of PHB2/REA was recognized only in the cells into which normal type PHB2/REA was introduced, but not recognized in the cells into which other constructs were introduced (FIG. 25B). In addition, suppressions for Ser39 phosphorylation of PHB2/REA and E2-dependent non-genomic ER activation route were examined. Thus, decrease of the phosphorylations of Akt and MAPK (T201/Y204) in E2-dependent manner was recognized only in the cells into which normal type PHB2/REA was introduced, but not recognized in the cells into which other constructs were introduced (FIG. 25C). From the results above, it was revealed that Ser39 phosphorylation of PHB2/REA was important for suppression activity of E2-dependent genomic and non-genomic ER activation routes of PHB2/REA.

Investigation for Ser39 Phosphorylation of Nuclear-Translocated PHB2/REA

Figure 26:
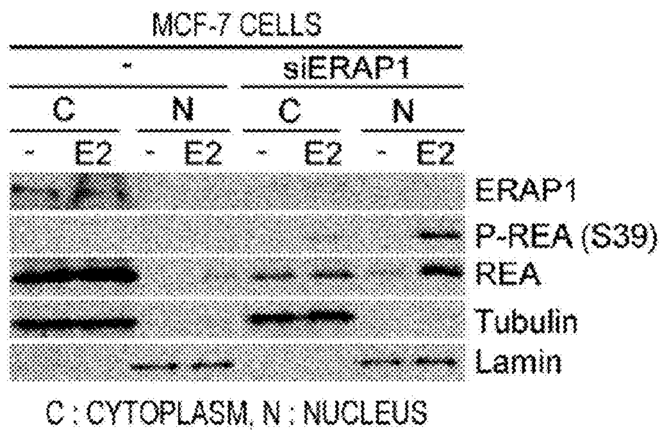
Figure 2:
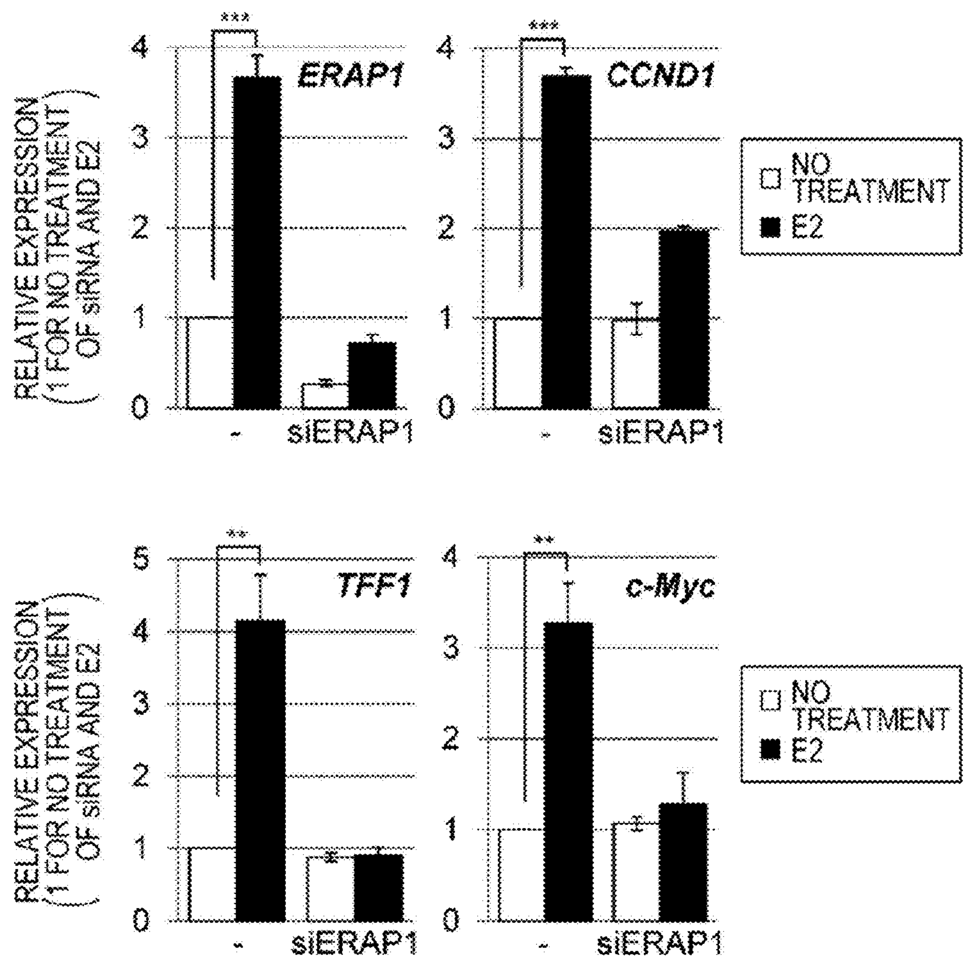

Next, MCF-7 cells were treated with E2 and the ERAP1-peptide, and then cytoplasm and nuclear fractions were collected, and the phosphorylation state of PHB2/REA there was examined. As a result, PHB2/REA translocated to the nucleus by the ERAP1-peptide was recognized for the phosphorylation of Ser39, and further similarly PHB2/REA remaining in the cytoplasm was also confirmed for the phosphorylation of Ser39 (FIG. 26A). Subsequently, the successive change of the phosphorylation of the serine residue of inherent PHB2/REA released by ERAP1-peptide treatment was examined. As a result, E2-dependent Ser phosphorylation of PHB2/REA was recognized continuously from 1 hour to 24 hours after the ERAP1-peptide administration (FIG. 26B). Furthermore, the locality of the phosphorylated inherent PHB2/REA was also examined by immune cell staining. Thus, prompt nuclear translocation of inherent PHB2/REA was recognized after the ERAP1-peptide administration to MCF-7 cells, and the phosphorylation of Ser39 was recognized (FIG. 26C). In addition, it was similarly detected with anti-Ser39 phosphorylation antibody by administration of the ERAP1-peptide also in the cytoplasm PHB2/REA. This fluorescence signal disappeared by λ phosphatase treatment, indicating that PHB2/REA localized in the nucleus and the cytoplasm dissociated from ERAP1 by the ERAP1-peptide were phosphorylated. Subsequently, phosphorylation of PHB2/REA when ERAP1 was knocked down by ERAP1-specific siRNA was examined. As a result, phosphorylation of Ser39 of PHB2/REA in the nucleus and the cytoplasm by suppression for ERAP1 expression was recognized (FIG. 26D). In addition, it was found that E2-dependent acceleration of the expression of ERα target genes CCND1, TFF1 and c-Myc, was significantly suppressed at the time (FIG. 26E). From those described above, it was revealed that Ser39 of PHB2/REA released from ERAP1 was phosphorylated in the nucleus and the cytoplasm.

Investigation for Ser39 Phosphorylation of PHB2/REA In Vivo by ERAP1-Peptide

Figure 27:
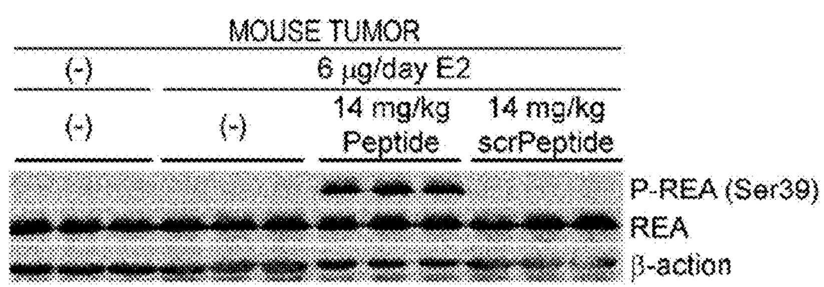
FIG. 27 is a diagram illustrating the inhibition effect of the ERAP1-peptide on tumor proliferation in a mouse orthotopically transplanted with human breast cancer. (A) shows the results of immunoblotting analysis by which phosphorylation of PHB2/REA (Ser39) was evaluated in the transplanted tumor of a mouse orthotopically transplanted with human breast cancer to which the ERAP1-peptide was administered. KPL-3 cells were subcutaneously transplanted into the breast fat body of a BALB/c nude mouse. The treatment test (5 individuals/group) was initiated (day 0) when the volume of the tumor reached about 50-80 $mm^3$ in the absence of E2. To a cancerous mouse orthotopically transplanted with KPL-3C tumor, the ERAP1-peptide (Peptide: 14 mg/kg) or the ERAP1-scramble peptide (scrPeptide: 14 mg/kg) was administered every day by intraperitoneal injection. At the same time, E2 (6 μg/day) was administered subcutaneously every day. On day 14, the mouse was euthanatized, and the tumor was removed, and phosphorylation of PHB2/REA (S39) in each tumor was evaluated with immunoblotting analysis. (B) shows the results of the evaluations for the tumor volume in a tamoxifen-resistant breast cancer-transplanted mouse to which the ERAP1-peptide was administered. The tamoxifen-resistant MCF7-cells (Tam-R MCF-7) were subcutaneously transplanted into the breast fat body of a BALB/c nude mouse, and the treatment test (5 individuals/group) was initiated (day 0) when the volume of the tumor reached about 50-80 $mm^3$ in the presence of tamoxifen (37 ng/day, 1.85 μg/kg). To a cancerous mouse orthotopically transplanted with Tam-R MCF-7 tumor, the ERAP1-peptide (Peptide: 3.5, 7 and 14 mg/kg) or the ERAP1-scramble peptide (scrPeptide: 14 mg/kg) was administered every day by intraperitoneal injection. At the same time, E2 (6 μg/day) was administered subcutaneously every day: Tam-R MCF-7 heterotransplanted tumor at day 21 and the mean tumor volume±SE (n=5) are shown. *P<0.05, P<0.01, *P<0.001.
Figure 27:
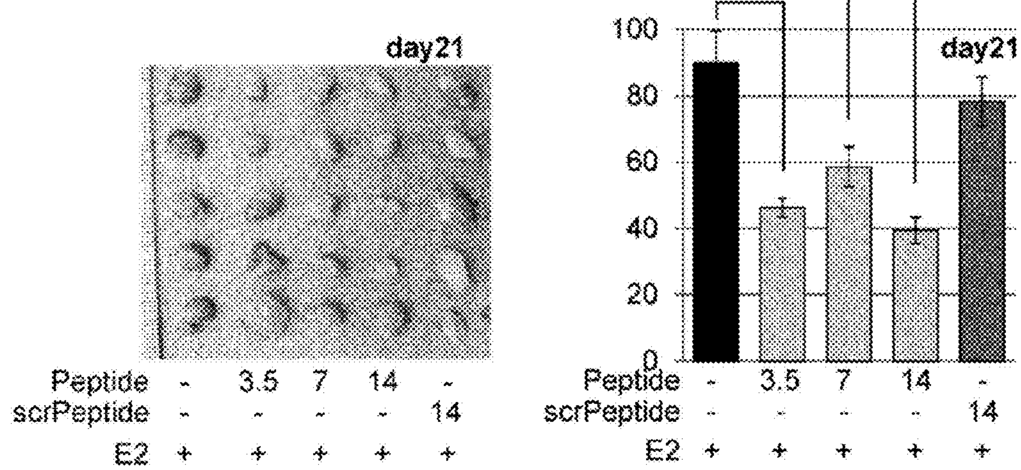

Using tumors of a mouse to which the ERAP1-peptide was administered, Ser39 phosphorylation state of PHB2/REA was examined in the tumors. As a result, phosphorylation of Ser39 of PHB21/REA was confirmed in the tumor to which the ERAP1-peptide was administered. On the other hand, in the tumor to which the ERAP1-scramble peptide was administered, the phosphorylation of PHB2/REA was not recognized like the tumor to which E2 only was administered (FIG. 27A). From those described above, it was found that Ser39 phosphorylation of PHB2/REA was also important in tumor suppression in vivo.

Investigation for Antitumor Effect In Vivo of ERAP1-Peptide in Tamoxifen-Resistant Breast Cancer Subsequently, using a model of a BALB/c nude mouse in which the tamoxifen-resistant breast cancer cell lines (Tam-R MCF-7) were orthotopically transplanted to the mammary gland, the antitumor effect by the ERAP1-peptide was investigated. The antitumor effect was recognized with administration of the ERAP1-peptide (3.5, 7 and 14 mg/kg) on the proliferation of the E2-dependent breast cancer, but was not recognized with the ERAP1-scramble-peptide (14 mg/kg) (FIG. 27B). From those described above, it was found that the ERAP1-peptide also exhibited remarkable antitumor effect in vivo in the tamoxifen-resistant breast cancer.

Investigation for Interaction of ERAP1 and PP1α

Figure 28:
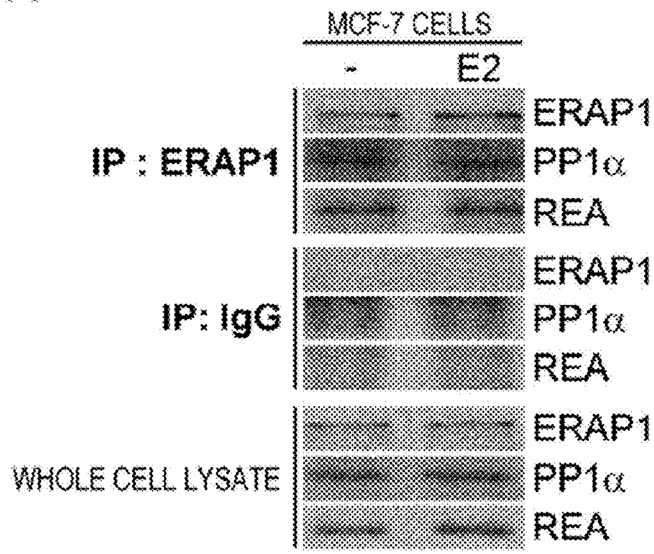
Figure 1:
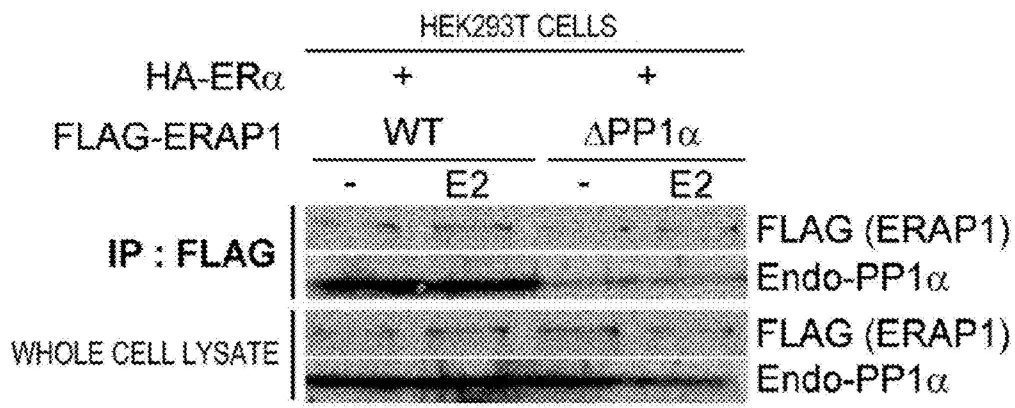
Figures 2, 28:
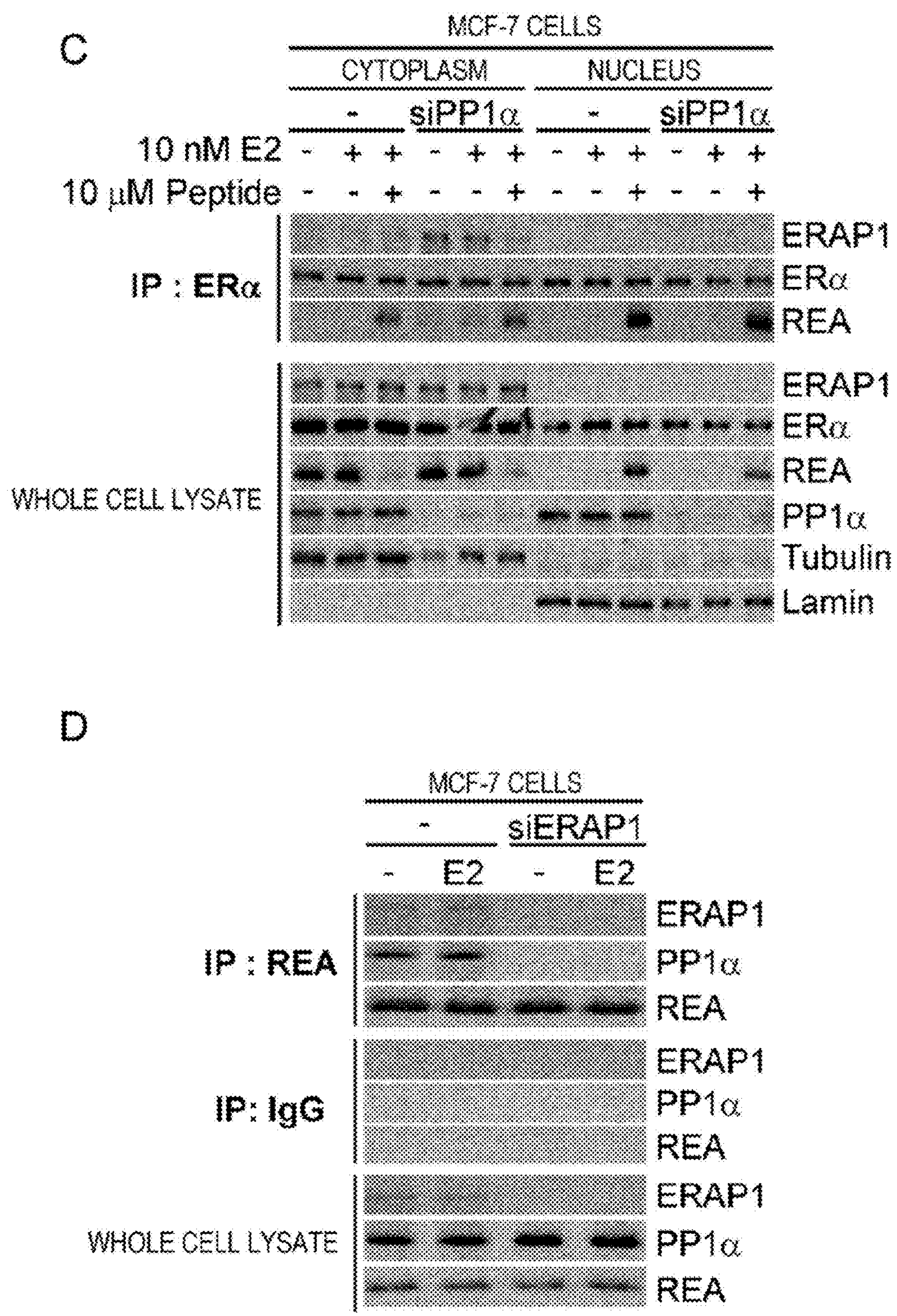

It was reported from exploratory research for binding protein of dephosphorylation enzyme, PP1α (protein phosphatase 1α) with in vitro GST-pull down assay method that PP1α bound to a partial length of KIAA1244 (another name of ERAP1) and the binding motif of PP1α (KAVSF) was conserved in 1228-1232 amino acid residues of ERAP1 (Chem. Biol., 16, 365, 2009). From this, first, interaction of inherent PP1α and ERAP1 in breast cancer cells MCF-7 was verified. As a result, binding of inherent of ERAP1 and inherent PP1α was confirmed, and further binding of PHB2/REA was also recognized regardless of the presence or absence of E2 (FIG. 28A), Then, an ERAP1 construct which was deficit of the PP1α binding motif (FLAG-ERAP1-ΔPP1α) was manufactured, and the binding to PP1α was investigated. As a result, binding of WT-ERAP1 construct and inherent PP1α was confirmed, but the binding was not recognized in the ERAP1 construct (ΔPP1α) in which 1228-1232 aa (KAVSF) were deleted (FIG. 28B). Then, the influence of suppression for inherent PP1α expression using siRNA on respective interaction of ERAP1, PHB2/REA and ERα in MCF-7 cells was examined. As a result, interestingly, in the cytoplasm fraction of MCF-7 cells in which PP1α expression was suppressed, binding of ERAP1 and ERα was recognized, but when the cytoplasm fraction was treated with the ERAP1-peptide, binding of ERα and PHB2/REA was confirmed (FIG. 28C). On the other hand, in the nuclear fraction, binding of ERα and PHB2/REA was confirmed only when the nuclear fraction was treated with the ERAP1-peptide as reported so far (FIG. 28C). Subsequently, the interactions when the expression of ERAP1 was suppressed by siRNA were also investigated. As a result, interaction of PHB2/REA and PP1α could not be confirmed (FIG. 28D). As described above, it was found that ERAP1 directly bound to PP1α and PHB2/REA, respectively, but PHB2/REA indirectly bound to PP1α through ERAP1.

Influence of Inhibition of Binding of ERAP1 and PP1α on Phosphorylation of PHB2/REA (S39)

Figure 29:
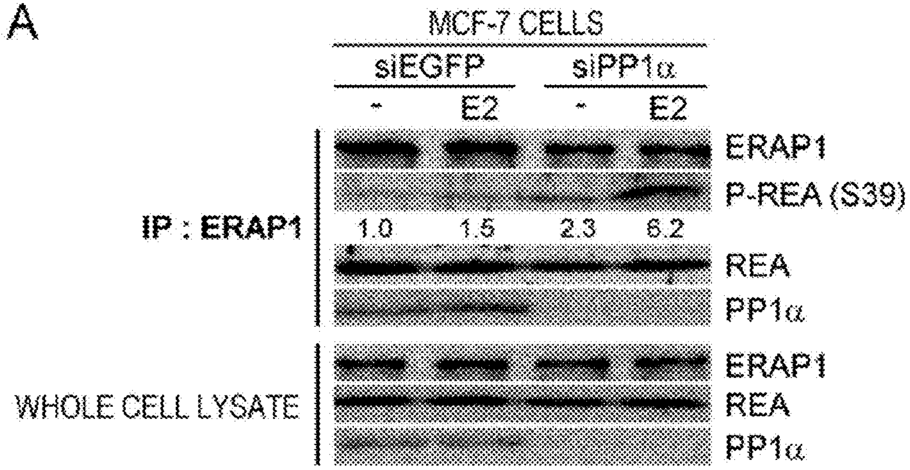
FIG. 29 is a diagram illustrating that inhibition of binding of ERAP1 to PP1α induces phosphorylation of PHB2/REA (S39). (A) shows the results of immunoblotting analysis by which the influence of suppression for PP1α expression on phosphorylation of PHB2/REA (Ser39) was evaluated. MCF-7 cells in which PP1α expression was suppressed by siRNA method were stimulated with 10 nM E2 for 24 hours. Then, the cells were lysed. Then, ERAP1 was immunoprecipitated from the cell lysate with anti-ERAP1 antibody. Furthermore, the obtained sample was subjected to immunoblotting analysis with the antibodies shown in the figure. The data are representative examples of three independent experiments. (B) shows the results of immunoblotting analysis by which phosphorylation of PHB2/REA (Ser39) in ERAP1-treated cells in which the PP1α binding region is deleted, was evaluated. HEK293T cells were transfected with the PP1α binding motif (1228-1232 aa)-deleted ERAP1 construct (ΔPP1α), and an ERα construct. After 48 hours, the cells were stimulated with 10 nM E2 for 24 hours. The cells were lysed, and then PHB2/REA was immunoprecipitated from the cell lysate with anti-PHB2/REA antibody. Furthermore, the obtained sample was subjected to immunoblotting analysis with the antibodies shown in the figure. The data are representative examples of two independent experiments. (C) shows the results of immunoblotting analysis by which phosphorylation of PHB2/REA (Ser39) was evaluated in cells treated with ERAP1-PP1α binding inhibition peptide. MCF-7 cells were treated with 50 and 100 μM of the inhibition peptide. Then, immediately, the cells were stimulated with 10 nM E2 for 24 hours. These cell lysates were immunoprecipitated with anti-ERAP1 antibody. Furthermore, the obtained sample was subjected to immunoblotting analysis with the antibodies shown in the figure.
Figure 29:
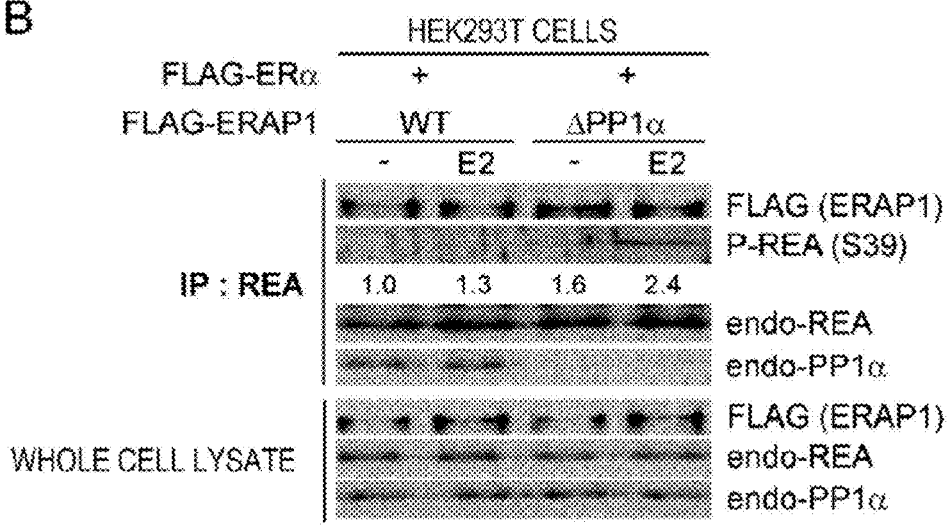
Figure 29:
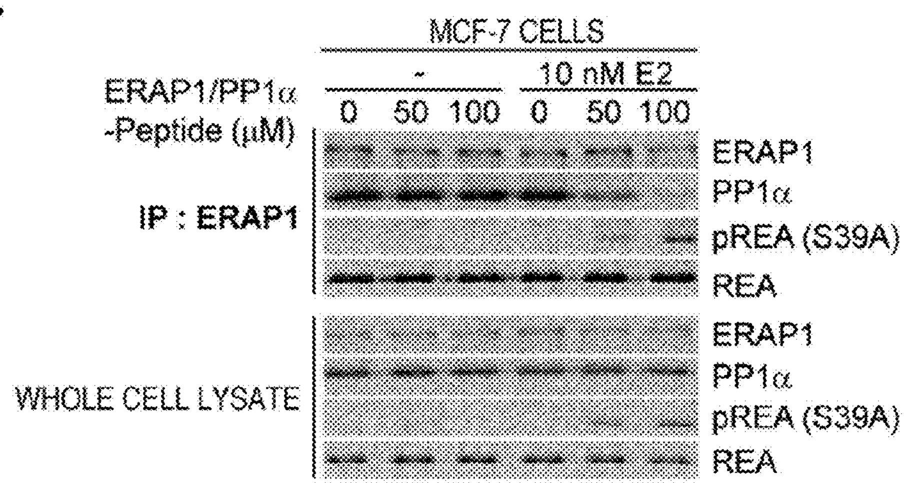

Next, the influence of suppression for PP1α expression on phosphorylation of PHB2/REA (S39) was examined. As a result, it was recognized that E2-dependent phosphorylation of PHB2/REA (Ser39) was remarkably accelerated in cells treated with siPP1α in comparison to cells treated with siEGFP as a control (FIG. 29A). Then, the influence of the expression of the ERAP1 construct (ΔPP1) in which the PP1α binding region was deleted on phosphorylation of PHB2/REA (Ser39) was also investigated. It was recognized that E2-dependent phosphorylation of inherent PHB2/REA (Ser39) was clearly accelerated in cells into which ΔPP1α construct was introduced in comparison to cells into which WT-ERAP1 construct was introduced (FIG. 29B). Subsequently, cell membrane-permeable ERAP1 dominant negative peptide (ERAP1/PP1α-Peptide) having the PP1α binding motif was synthesized, and the influences on ERAP1-PP1α interaction when introduced into MCF-7 cells and phosphorylation of inherent PHB2/REA (Ser39) were examined. As a result, E2 dependent inhibition of ERAP1-PP1α binding by administration of the cell membrane-permeable ERAP1 dominant negative peptide was confirmed, and further remarkable phosphorylation of inherent PHB2/REA (Ser3) when this dominant negative peptide was introduced, was recognized (FIG. 29C). From the results above, it was revealed that inhibition of the binding of ERAP1 to PP1α induced E2-dependent phosphorylation of inherent PHB2/REA (S39).

Influence of ERAP1 Phosphorylation on PP1α Phosphatase Activity

Next, the relationship between ERAP1 and the phosphatase activity of PP1α was investigated. The phosphatase activity was examined when the expression of ERAP1 or PP1α was suppressed by siRNA method, respectively in MCF-7 cells. Thus, it was confirmed that the phosphatase activity remarkably increased in the cells in which the ERAP1 expression was suppressed (FIG. 30A). Subsequently, in order to verify this inhibition effect of the phosphatase activity of PP1α by ERAP1, the influence of excessive expression of ERAP1 on the PP1α phosphatase activity was examined. HEK293T cells were transfected with the ERAP1 construct (0.5, 1.0, 2.0 μg) and the ERAP1 construct (ΔPP1α: 2.0 μg) in which the PP1α binding region was deleted. Then, after immunoprecipitating with anti-PP1α antibody, the phosphatase activity of the cells was examined. As a result, it was confirmed that as the expression amount of ERAP1 increased, the PP1α activity decreased (FIG. 30B). Then, the influence of estrogen stimulation on the PP1α activity was investigated. MCF-7 cells were stimulated with 10 nM E2 for 6, 12 and 24 hours, and then the phosphatase activity was examined. Thus, it was confirmed that the PP1α phosphatase activity was accelerated with E2 treatment for 6 hours (FIG. 30C).

From the results above, it was revealed that 1) ERAP1 was a negative regulator that suppressed the phosphatase activity of PP1α by binding to PP1α, and 2) PHB2/REA dephosphorylated the phosphorylation of Ser39 by binding to ERAP1 that was a regulation unit of PP1α. However, these results are opposite to each other. Thus, in order to resolve this question, the present inventors built a hypothesis that the inhibition activity of ERAP1 to the phosphatase activity of PP1α was inhibited by E2 stimulation. Namely, the present inventors first focused on phosphorylation of ERAP1 by E2 stimulation. MCF-7 cells, which were cell lines highly expressing ERAP1, were stimulated with 110 nM E2 for 24 hours, and then immunoblotting analysis was performed using each anti-phosphorylation antibody. As a result, it was found that ERAP1 was phosphorylated in serine, threonine and tyrosine residues in E2-dependent manner (FIG. 30D). As described above, a possibility was suggested that ERAP1 might be phosphorylated by E2 stimulation, and as a result, the function of PP1α suppressing the phosphatase activity might be suppressed, to accelerate the phosphatase activity of PP1α.

Investigation for Regulation of Phosphorylation of PHB2 REA (S39) by ERAP1 Phosphorylation by PKA and PKB Via PP1α Activity Subsequently, kinase phosphorylating ERAP1 was investigated. It was reported that family molecules of ERAP1, i.e., BIG1 and BIG2 formed a complex with PKA and protein phosphatase, to function as one of the AKAP proteins (Proc Natl Acad Sci USA. 2003 Feb. 1; 100 (4): 1627-32. Proc Natl Acad Sci USA. 2006 Feb. 21; 1.03 (8): 2683-8. Genes to Cells 11, 949-959, 2006: Journal of Biological chemistry 283, 25364-25371; Proc Natl Acad Sci USA. 2007 Feb. 27; 104 (9): 3201-6; Proc Natl Acad Sci USA. 2009 Apr. 14; 106(15): 6158-63). From this fact, a possibility was considered that ERAP1 might also function similarly as an AKAP-like protein. Accordingly, the binding of ERAP1 and PKA was investigated. MCF-7 cells were stimulated with 10 nM E2 for 24 hours. Then, the binding was examined with immunoprecipitation using anti-ERAP1 antibody. As a result, the binding of inherent ERAP1 and inherent PKA was recognized (FIG. 30E). In addition, PKB, which has been identified for binding in many AKAP proteins, was similarly investigated. As a result, binding of inherent ERAP1 and inherent PKB was also confirmed (FIG. 30E). Then, the influence on PP1α phosphatase activity when expressions of PKA and PKB were suppressed, respectively by siRNA method was examined. Thus, it was confirmed that acceleration of E2-dependent phosphatase activity was significantly suppressed (FIG. 31A). Subsequently, the phosphorylation state of ERAP1 and PHB2/REA was investigated. In cells transfected with siEGFP as a control, phosphorylation of serine and threonine residues of ERAP1 by E2 treatment was recognized. Furthermore, in cells treated with the ERAP1-peptide, phosphorylation of Ser39 of PHB2/REA was recognized. On the other hand, in cells suppressed for expression of PKA, it was recognized that phosphorylation of the serine residue of ERAP1 disappeared regardless of the presence or absence of ERAP1-peptide treatment. Furthermore, phosphorylation of ser39 of PHB2/REA after E2 treatment was also confirmed (FIG. 31B). In addition, in cells suppressed for expression of PKB, change for phosphorylation of the serine residue of ERAP1 was not recognized. On the other hand, for the threonine residue, remarkable decrease of the phosphorylation was recognized. On the other hand, phosphorylation of Ser39 of PHB2/REA was showed to be recovered by E2 treatment, whereas phosphorylations of the serine and threonine residues of ERAP1 were not nearly influenced (FIG. 31B). Then, the influence of inhibition of PKA activity by PKA inhibitor H-89 compound on phosphorylation of ERAP1 and PHB2/REA was also investigated. MCF-7 cells were treated with H-89, and then phosphorylation of ERAP1 and PHB2/REA was examined. As a result, it was recognized that phosphorylations of the serine and tyrosine residues of ERAP1 remarkably decreased at 0.5 μM, and that the phosphorylation of the threonine residue also decreased in dose-dependent manner (FIG. 31C). On the contrary, in cells of no H-89 treatment, phosphorylation of Ser39 of PHB2/REA was recognized only when the cells were treated with the ERAP1-peptide. On the other hand, remarkable recovery was recognized in cells that were stimulated by E2 and treated with H-89 (FIG. 31C). Very interestingly, it was recognized that when the binding of ERAP1 and PHB2/REA was inhibited by administration of the ERAP-peptide, phosphorylation of Ser39 decreased depending on the dose of H-89, and particularly the phosphorylation completely disappeared in 20 μM H-89-treated cells (FIG. 31C). This result shows the possibility of non-specific phosphorylation inhibition of H-89.

Next, in order to investigate specificity of PKA inhibition, comparison between the influences of suppression for specific expression of PKA by siRNA and H-89 treatment on serine phosphorylation of ERAP1 and phosphorylation of PHB2/REA (S39) was done. MCF-7 cells suppressed for expression of PKA by siRNA method, and MCF-7 cells treated with H-89, were used in the investigation. As a result, phosphorylation of the serine residue of ERAP1 was not recognized at all in the cells transfected with siPKA, regardless of the presence or absence of E2 stimulation. On the other hand, in the H-89-treated cells, recovery of phosphorylation of ERAP1 after E2 treatment in the low concentration was detected, whereas as the dose of H-89 increased, disappearance of the phosphorylation was confirmed (FIG. 31D). In addition, it was recognized in siPKA-treated cells that phosphorylation of PHB2/REA was recovered when the cells were treated with E2. On the contrary, in H-89-treated cells, recovery of the phosphorylation was confirmed like the siPKA treated cells when the concentration of H-89 was low, but as the dose of H-89 increased, Ser39 phosphorylation of PHB2/REA also decreased (FIG. 31D). It has been reported so far that H-89 also acts on other kinases than PKA (Science signaling 1, re4, 2008), and these results also suggested a possibility by non-specific inhibition of kinases than PKA. Then, the influences of treatment of PP1α inhibitor, okadaic acid on phosphorylation of PHB2/REA and phosphorylation of Akt and MAPK were examined. With respect to Ser39 phosphorylation of PHB2/REA in MCF-7 cells, E2-dependent PHB2/REA phosphorylation was recognized to be recovered when the cells were treated with IC50 value of PP1α, i.e. 20 nM of okadaic acid, but the phosphorylation was confirmed to decrease with 40 μM (FIG. 31E). This phenomenon also suggests a possibility that okadaic acid might non-specifically inhibit the activity besides PP1α.

Then, identification of a kinase phosphorylating PHB2/REA was tried. The experiment described below was performed using PKCα as a candidate as a kinase phosphorylating PHB2/REA from the results described above that disappearance of PHB2/REA phosphorylation by 40 nM okadaic acid treatment was confirmed; and okadaic acid was reported to inhibit PKC activity; further the sequence in the vicinity of Ser39 of PHB2/REA was highly conserved also for PKA and PKCα; and PKCα is highly expressed in breast cancer. MCF-7 cells suppressed for expression of PKCα by siRNA method were treated with E2 and the ERAP1-peptide, and then fractionated into cytoplasm and nuclear fractions. Then, immunoblotting analysis of each fraction was performed. As a result, it was recognized that phosphorylation of Ser39 of PHB2/REA remarkably decreased in the nucleus and the cytoplasm of cells treated with E2 and the ERAP1-peptide (FIG. 31F). From those described above, a possibility was suggested that PKCα might phosphorylate REA (S39). From the results above, it was suggested that PKA phosphorylated the serine residue of ERAP1, and as a result, the phosphatase activity of PP1α was accelerated, and thus Ser39 of PHB2/REA binding to PP1α-ERAP1 complex was dephosphorylated.

Investigation for Whether PP1α is a Target Gene of ERα or not

Figure 32:
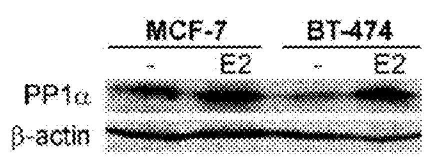
FIG. 32 is a diagram illustrating that PP1α is a target gene of ERα. (A) shows the results of immunoblotting analysis by which up-regulation of PP1α by E2 stimulation was evaluated. MCF-7 cells and BT-474 cells were stimulated with 10 nM E2 for 24 hours, and the protein level of PP1α was evaluated by Western blotting analysis. The data were standardized with β-actin. (B) shows the results of real time PCR by which up-regulation of PP1α by E2 stimulation was evaluated. MCF-7 cells, ZR-75-1 cells, T47D cells and BT-474 cells were stimulated with 10 nM E2 for 24 hours, and the mRNA level of PP1α was obtained with real time PCR. The data are standardized with the β2-MG content, and show the mean±SE of three independent experiments. P<0.01, P<0.001. (C) shows ERE-conserved motif located in the 5' upstream and intron 2 of the PP1α gene estimated by Genomatix software (Genomatix Software, Munchen, Germany). (D) shows the results of ChIP assay by which trans-activation of PP1α via the ERE sequence of 5' upstream and intron 2 was evaluated. MCF-7 cells were stimulated with 10 nM E2 for 24 hours, and then chromatin was prepared, and immunoprecipitated with the antibodies shown in the figure. Chromatin immunoprecipitation analysis was performed using primers specific for the ERE region of 5' upstream and intron 2 of PP1α. (E) shows the results of the luciferase assay by which trans-activation of PP1α via the ERE sequence in PP1α gene was evaluated. HEK293T cells were transfected with a luciferase reporter vector consisting of a construct comprising ERE-conserved motif located in the 5' upstream and intron 2 of the PP1α gene (the lower panel: 5'-ERE and 5'- and intron 2-ERE). Then, the cells were stimulated with 10 nM E2 for 24 hours, and the luciferase activity was measured. The data show the mean±SE of three independent experiments. ***P<0.001.
Figure 32:
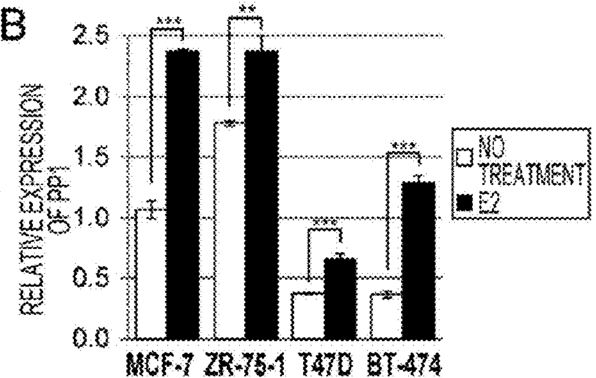
Figure 32:
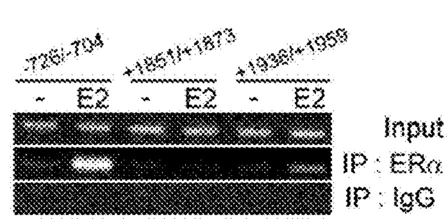
Figure 32:
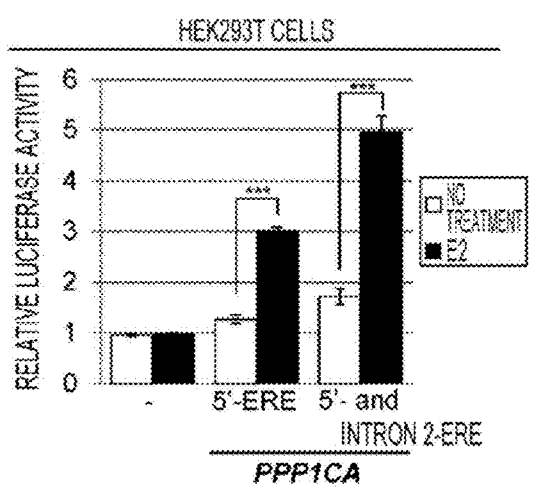
Figure 32:
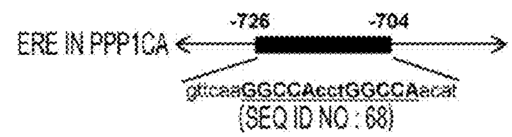
Figure 32:
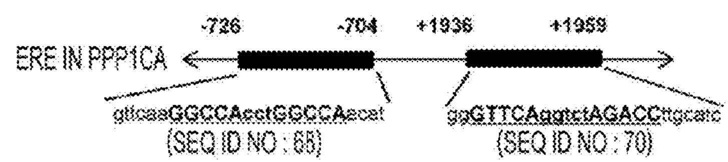

Based on the fact that PP1α has functions as a catalyst unit of ERAP1, the present inventors built a hypothesis that PP1α might be also one of the ERα target genes like ERAP1 in breast cancer cells, and performed the experiment described below. ER-positive cell lines, i.e., MCF-7 cells, ZR-75-1 cells, T47D cells and BT-474 cells were stimulated with E2 for 24 hours, and then the protein level and the mRNA expression level of PP1α were examined with Western blotting and real time PCR (FIGS. 32A, B). As a result, it was recognized that expression of PP1α was accelerated in E2-dependent manner in all of the cell lines in both of the protein level (FIG. 32A) and the mRNA level (FIG. 32B). Then, whether or not ERE (estrogen responsible element, E2 responsible sequence: AGGTCAnnnTGACCT) was present on PP1α gene (PPPICA), was searched by Genomatix software (Genomatix Software, Munchen, Germany). As a result, conserved ERE sequences were confirmed at 3 spots (FIG. 32C). Then, whether or not ERα directly bound to this estimated ERE sequence was examined with chromatin immunoprecipitation method (ChIP method) using ERα antibody. As a result, the binding was recognized in a region comprising from the translation initiation point (−726) to −704 and a region comprising from +1936 to +1959 (FIG. 32D), but the binding was not recognized in a region from +1851 to −1873 (FIG. 32D). 5'-ERE construct comprising this estimated region comprising from −726 to −704, and an expression vector construct consisting of 5'-ERE and tandem of the region of +1936 to +1959 (5'-ERE and intron 2 ERE) were manufactured, respectively, and the luciferase reporter activity was examined (FIG. 32E). As a result, in the cells into which 5'-ERE construct was introduced, the luciferase reporter activity was recognized to be accelerated by 3 times in comparison to a control, and further in 5'-ERE and intron 2 ERE construct, the luciferase reporter activity was recognized to be accelerated by 5 times. From those described above, it was suggested that PP1α might be one of the target genes of ERα like ERAP1, and be regulated by positive feedback mechanism where if activation of ERα was induced in E2-dependent manner, the expression thereof was accelerated.

Figure 33:
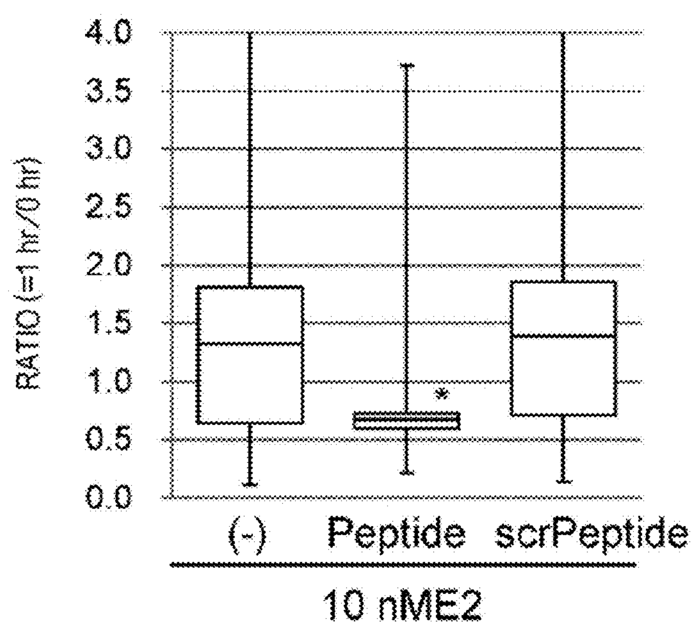
FIG. 33 is a diagram illustrating that ERAP1-peptide treatment suppressed acceleration of protein and gene expressions by estrogen stimulation. (A) shows the results of statistical analysis of proteomes in ERAP1-peptide treated cells. MCF-7 cells were treated with 10 μM ERAP1-peptide (Peptide) and the ERAP1-scramble peptide (scrPeptide). Then, immediately, the cells were stimulated with 10 nM E2 for 1 hour. Subsequently, the obtained cell lysate solution was digested with trypsin and subjected to 2DICAL. The data were calculated as the ratio to the value at 0 hour, and each proteome was statistically analyzed with the box plot. *P<0.05, (B) shows the results of statistical analysis of the transcriptome in ERAP1-peptide treated cells. MCF-7 cells were treated with 10 μM ERAP1-peptide. Then, immediately, the cells were stimulated with 10 nM E2 for 5, 10 and 15 hours. Then, RNA extraction and then Cy3-cRNA synthesis were performed, and the Cy3-cRNA was subjected to the microarray. The data were statistically analyzed by GeneSpring software, and the ratio to the value at 0 hour was calculated. **P<0.01.
Figure 33:
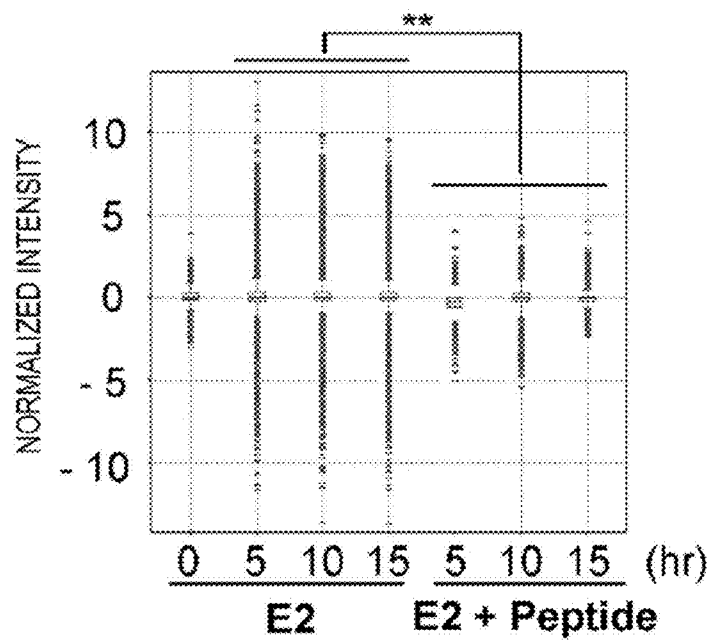

Influence of ERAP1-Peptide Treatment on Acceleration of Protein and Gene Expression by Estrogen Stimulation From the results so far, it was proved that the ERAP1-peptide suppressed E2-dependent ER genomic activation route and the non-genomic activation route in ER-positive cell. However, only the influence on known ER activation route has been focused so far, but it was not clear whether which gene or protein expression was influenced genome-widely. Accordingly, mRNA and protein expressions in MCF-7 cells after being administered with E2 and the ERAP1-peptide were examined with microarray/proteome analysis. MCF-7 cells were treated with the ERAP1-peptide or ERAP1-scramble-peptide (scrPeptide), and the cells were collected after 1 hour of the treatment, and offered to the experiment. As a result, interestingly, it was recognized that many proteins (FIG. 33A) and mRNAs (FIG. 33B) decreased significantly and genome-widely by administration of ERAP1-peptide, in comparison to change of the expressions when E2 or E2+ ERAP1-scramble-peptide was administered. Furthermore, as shown in Table 1, it was found that expressions of many genes not reported so far including known estrogen responsive genes and ER target genes were suppressed merely at 1 hour after ERAP1-peptide treatment, and the functions of these genes were wide-ranging (Tables 1 and 2). From the results above, it was found that ERAP1-peptide administration that could induce suppression function of PHB2/REA, suppressed unknown E2 signal routes in addition to known E2 signal route.

TABLE 1

Estrogen-dependent gene of which expression is suppressed by ERAP1-peptide treatment

| Ref. seq | Gene symbol | Fold change |
|---|---|---|
| NM_020169 | LXN | 11.09 |
| NM_020311 | CXCR7 | 10.15 |
| NM_000067 | CA2 | 9.87 |
| XM_003119804 | LOC100508679 | 9.85 |
| NM_000101 | CYBA | 9.51 |
| NM_033512 | TSPYL5 | 9.50 |
| NM_006806 | BTG3 | 9.06 |
| NM_173551 | ANKS6 | 9.00 |
| NM_002402 | MEST | 8.84 |
| NM_007231 | SLC6A14 | 8.73 |
| NM_015916 | CALHM2 | 8.63 |
| NM_018655 | DDX43 | 8.53 |
| NR_001564 | XIST | 8.53 |
| NM_144584 | C1orf59 | 8.43 |
| NM_001719 | BMP7 | 8.40 |
| NM_001008539 | SLC7A2 | 8.32 |
| NM_002239 | KCNJ3 | 8.31 |
| NM_144947 | KLK11 | 8.08 |
| NM_006317 | BASP1 | 8.01 |
| NM_145168 | SDR42E1 | 8.01 |
| NM_001017372 | SLC27A6 | 8.00 |
| NM_000853 | GSTT1 | 7.93 |
| NM_207308 | NUP210L | 7.84 |
| NM_004586 | RP86KA3 | 7.84 |
| NM_004734 | DCLK1 | 7.84 |
| NM_001353 | AKR1C1 | 7.79 |
| NM_018479 | ECHDC1 | 7.73 |
| NM_021073 | BMP5 | 7.72 |
| NM_207355 | POTEB | 7.70 |
| NM_032756 | HPDL | 7.68 |
| NM_003290 | TPM4 | 7.60 |
| NM_001080506 | TMEM150C | 7.57 |
| NM_003506 | FZD6 | 7.54 |
| NM_031935 | HMCN1 | 7.54 |
| NM_001039966 | GPER | 7.51 |
| NM_015976 | SNX7 | 7.48 |
| NM_001753 | CAV1 | 7.44 |
| NM_138711 | PPARG | 7.30 |
| NR_026869 | NCRNA00052 | 7.27 |
| NM_005856 | RAMP3 | 7.25 |
| NM_015668 | RGS22 | 7.22 |
| NM_001145077 | LRRC10B | 7.17 |
| NM_017770 | ELOVL2 | 7.14 |
| NM_004321 | KIF1A | 7.12 |
| NR_003245 | HAR1B | 7.11 |
| AK092688 | LOC732272 | 7.09 |
| NM_144967 | ARHGAP36 | 7.08 |
| NM_144601 | CMTM3 | 7.06 |
| NM_005668 | ST8SIA4 | 6.99 |
| NM_002356 | MARCKS | 6.99 |
| NM_002395 | ME1 | 6.91 |
| NM_004363 | CEACAM5 | 6.84 |
| NM_001332 | CTNND2 | 6.83 |
| NM_006528 | TFPI2 | 6.82 |
| NM_174981 | POTED | 6.82 |
| NM_030801 | MAGED4B | 6.80 |

TABLE 1-continued

Estrogen-dependent gene of which expression is suppressed by ERAP1-peptide treatment

| Ref. seq | Gene symbol | Fold change |
|---|---|---|
| NM_173556 | CCDC83 | 6.76 |
| NM_003881 | WISP2 | 6.73 |
| NM_020672 | S100A14 | 6.73 |
| NR_015377 | LOC654433 | 6.72 |
| NM_013453 | SPANXA1 | 6.68 |
| NM_144586 | LYPD1 | 6.66 |
| NM_178505 | TMEM26 | 6.66 |
| NM_001233 | CAV2 | 6.63 |
| NM_019076 | UGT1A8 | 6.60 |
| NM_020436 | SALL4 | 6.60 |
| NR_002728 | KCNQ1OT1 | 6.60 |
| NM_001080507 | OOEP | 6.57 |
| NM_001010853 | PM20D2 | 6.56 |
| NM_145664 | SPANXB2 | 6.55 |
| NR_024418 | LOC389332 | 6.52 |
| NM_005634 | SOX3 | 6.52 |
| NM_001008495 | TMEM64 | 6.46 |
| NM_004982 | KCNJ8 | 6.44 |
| NM_017422 | CALML5 | 6.39 |
| NM_133374 | ZNF618 | 6.39 |
| NM_001444 | FABP5 | 6.38 |
| NM_003739 | AKR1C3 | 6.37 |
| NM_004816 | FAM189A2 | 6.33 |
| NM_032883 | TOX2 | 6.29 |
| NM_014646 | LPIN2 | 6.27 |
| NM_173515 | CNKSR3 | 6.27 |
| NM_058173 | MUCL1 | 6.13 |
| NM_001740 | CALB2 | 6.05 |
| NM_005434 | MALL | 6.05 |
| NM_001818 | AKR1C4 | 6.00 |
| NM_001012964 | KLK6 | 5.98 |
| NM_000361 | THBD | 5.97 |
| NM_138441 | C6orf150 | 5.95 |
| NM_000304 | PMP22 | 5.93 |
| NM_021116 | ADCY1 | 5.92 |
| NM_017679 | BCAS3 | 5.92 |
| NM_000624 | SERPINA5 | 5.87 |
| NM_005855 | RAMP1 | 5.82 |
| NM_025113 | C13orf18 | 5.79 |
| NM_001072 | UGT1A6 | 5.78 |
| NM_020815 | PCDH10 | 5.78 |
| NM_006207 | PDGFRL | 5.77 |
| NM_020134 | DPYSL5 | 5.76 |
| NM_003264 | TLR2 | 5.74 |

Fold change: Gene expression level with E2 stimulation alone/Gene expression level with E2 stimulation + peptide treatment Table 1 shows estrogen-dependent genes of which the expression was suppressed by ERAP1-peptide treatment. Top 100 genes are listed of which expression was strongly accelerated by estrogen stimulation in comparison to those at 0 hours, and was suppressed by the ERAP1-peptide.

TABLE 2

GO analysis of estrogen-dependent gene of which expression is suppressed by ERAP1-peptide treatment

| GO term | P value |
|---|---|
| Response to estrogen stimulus | 0.001 |
| Response to harmone stimulus | 0.002 |
| Response to organic substance | 0.002 |
| Lipid homeostasis | 0.002 |
| Regulation of G-protein coupled receptor protein signaling pathway | 0.002 |
| Response to steroid hormone stimulus | 0.002 |
| Response to endogenous stimulus | 0.003 |
| Response to nutrient | 0.004 |
| Carboxylic acid transport | 0.005 |
| Organic acid transport | 0.005 |
| Negative regulation of cell proliferation | 0.007 |
| Membrane raft formation | 0.008 |

TABLE 2-continued

GO analysis of estrogen-dependent gene of which expression is suppressed by ERAP1-peptide treatment

| GO term | P value |
|---|---|
| Blood circulation | 0.011 |
| Circulatory system process | 0.011 |
| Response to nutrient levels | 0.013 |
| Sterol homeostasis | 0.013 |
| Response to drug | 0.013 |
| Response to extracellular stimulus | 0.018 |
| Monocarboxylic acid transport | 0.019 |
| Regulation of blood vessel size | 0.023 |
| Regulation of tube size | 0.025 |
| Response to abiotic stimulus | 0.025 |
| Vascular process in circulatory system | 0.028 |
| Lipid transport | 0.030 |
| Membrane raft organization | 0.030 |
| Microtubule polymerization | 0.032 |
| Lipid localization | 0.037 |
| Response to vitamin | 0.037 |
| Cellular protein complex assembly | 0.038 |
| Bile acid and bile salt transport | 0.040 |
| Positive regulation of G-protein coupled receptor protein signaling pathway | 0.048 |

Table 2 shows GO analysis of estrogen-dependent gene of which the expression was suppressed by ERAP1-peptide treatment. The gene of which expression was strongly accelerated by estrogen stimulation in comparison to those at 0 hour, and suppressed by the ERAP1-peptide, was subjected to GO analysis. The data were statistically treated with Fisher's exact test.

Investigation for Specific Binding of the ERAP1-Peptide to PHB2/REA

Figure 34:
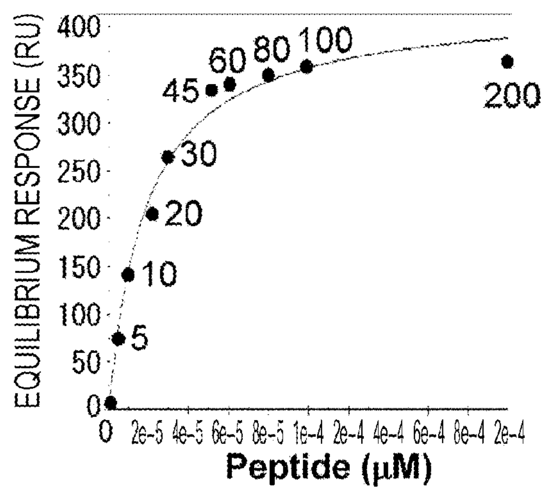
FIG. 34 is a diagram illustrating that the ERAP1-peptide specifically binds to PHB2/REA. (A) shows the results of evaluations for binding of the ERAP1-peptide to PHB2/REA by Biacore. 6×His-tagged recombinant PHB2/REA protein was immobilized on a sensor chip, and then reacted with an HA-tagged ERAP1-peptide in the concentrations shown in the figure, and the dissociation rate constant (Kd) was calculated from the curve of Sensorgram. (B) shows the results of evaluations for binding of PHB2/REA to the ERAP1-peptide by fluorescence correlation spectroscopy method. 10 nM FITC-tagged ERAP1-peptide (Peptide), FITC-tagged ERAP1-scramble peptide (scrPeptide) and 6×His-tagged recombinant PHB2/REA protein in the various concentrations shown in the figure were reacted for 1 hour. Then, FITC fluorescence of the sample was measured.
Figure 34:
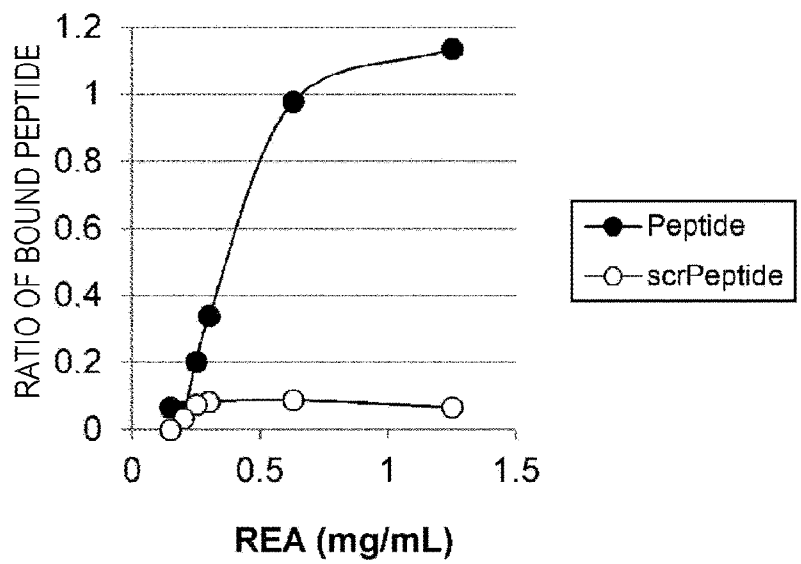

It was proved in Example 1 that the ERAP1-peptide specifically binds to PHB2/REA, and in this Example, Kd (the dissociation rate constant) value as a biochemical index for the interaction of the two was obtained. First, the binding of ERAP1-peptide and PHB2/REA by Biacore was examined. 6×His-tagged recombinant PHB2/REA protein was immobilized on a sensor chip. Then, HA-tagged ERAP1-peptide in the concentrations shown in FIG. 34A was reacted, and then Kd value was calculated from the curve of Sensorgram. As a result, Kd value of the ERAP1-peptide was 18.9 μM (FIG. 34A). Then, Kd value of PHB2/REA was measured in fluorescence correlation spectroscopy method. 10 nM FITC-tagged ERAP1-peptide, FITC-tagged ERAP1-scramble peptide (scrPeptide), and 6×His-tagged recombinant PHB2/REA protein were reacted for 1 hour, and then FITC fluorescence was measured. As a result, Kd value of PHB2/REA recombinant protein was 14.4 μM (FIG. 34B).

Manufacture of Anti-ERAP1 Monoclonal Antibody

Figure 35:
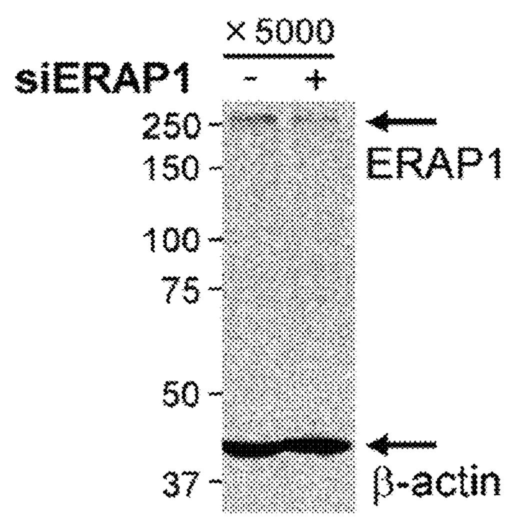
FIG. 35 is a diagram illustrating the results of immunoblotting analysis with an anti-ERAP1 monoclonal antibody. (A) shows the results of immunoblotting analysis showing that ERAP1 was specifically detected with anti-ERAP1 purified antibody. MCF-7 cells suppressed for expression of ERAP1 by siRNA method were lysed. Then, the obtained sample was subjected to immunoblotting analysis with a monoclonal antibody against an antigen of human ERAP1 (459-572 aa). (B) shows the results of immunoblotting analysis by which coprecipitation of PHB2/REA by anti-ERAP1 purified antibody was evaluated. The lysates of MCF-7 cells (M) and T47D cells (T) were immunoprecipitated with anti-ERAP1 purified antibody. Furthermore, the obtained sample was subjected to immunoblotting an analysis with the antibodies shown in the figure.
Figure 35:
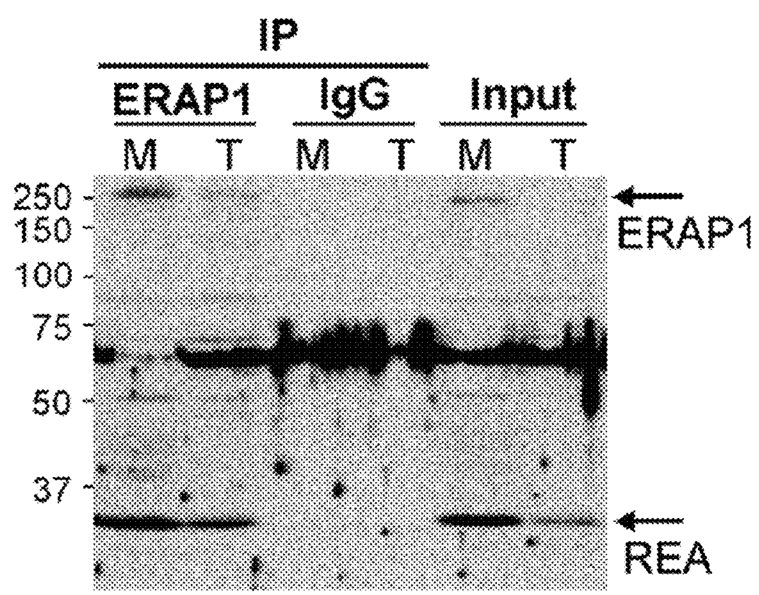

Manufacture of anti-ERAP1 monoclonal antibody was performed. First, confirmation for the specificity of anti-ERAP1 purified monoclonal antibody was performed. With use of MCF-7 cells suppressed for expression of ERAP1 by siRNA method, immunoblotting analysis with anti-ERAP1 purified antibody was performed. As a result, the anti-ERAP1 purified antibody was not recognized for non-specific band, and ERAP1-specific band was detected (FIG. 35A). Subsequently, whether the anti-ERAP1 purified antibody could be immunoprecipitated or not was examined. The lysates of MCF-7 cells (M) and T47D cells (T) were immunoprecipitated with anti-ERAP1 purified antibody, and coprecipitation of the binding protein PHB2/REA was recognized (FIG. 35B). From those described above, it was found that an anti-ERAP1 monoclonal antibody established this time could recognize ERAP1 specifically, and be immunoprecipitated.

Construct of Anti-Phosphorylation PHB2/REA (S39) Antibody

Figure 36:
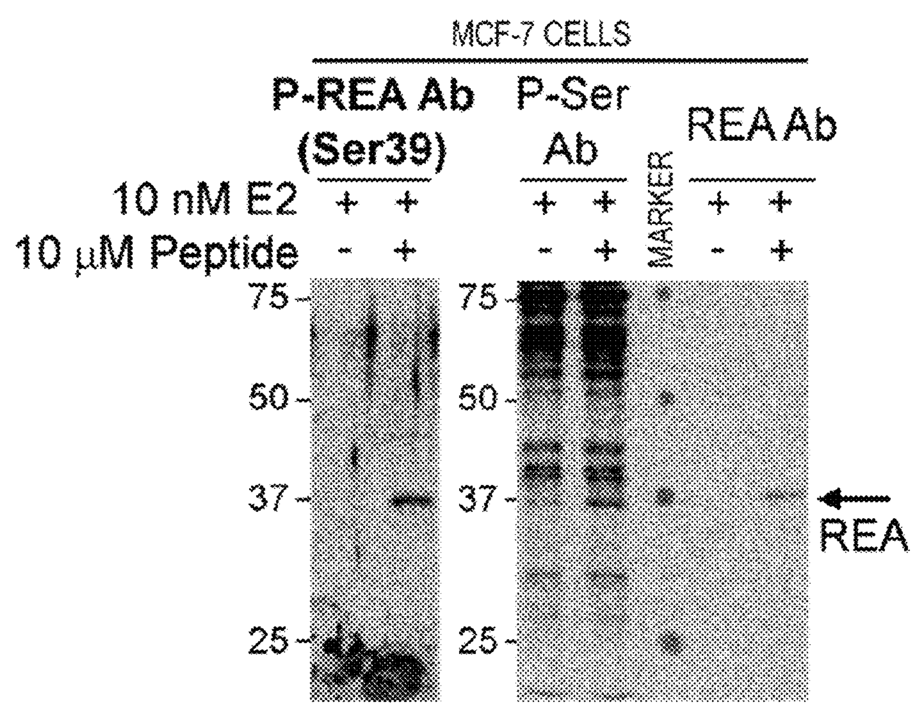
FIG. 36 is a diagram illustrating the results of immunoblotting analysis showing that an anti-phosphorylation PHB2/REA (S39) antibody specifically detected phosphorylation of Ser39 of PHB/REA. MCF-7 cells were treated with 10 μM ERAP1-peptide. Then, immediately, the cells were stimulated with 10 nM E2 for 24 hours. The obtained cell lysate was subjected to immunoblotting analysis with an anti-phosphorylation PHB2/REA (S39) antibody, an anti-phosphorylation serine antibody and an anti-PHB/REA antibody.

Manufacture of polyclonal antibody specifically recognizing Ser39 of PHB2/REA was performed. ER-positive breast cancer cell line MCF-7 was treated with E2, and then phosphorylation of Ser39 of PHB2/REA only when the ERAP1-peptide was administered, was detected by the manufactured anti-phosphorylation PHB2/REA (S39) antibody (FIG. 36). From the results above, it was suggested that the phosphorylation of Ser39 of PHB2/REA was dephosphorylated when PHB2/REA bound to ERAP1, and the binding of PHB2/REA and ERAP1 was inhibited by the ERAP1-peptide, and when PHB2/REA was released from ERAP1, PHB2/REA was phosphorylated at Ser39.

The Stability of ERAP1-Peptide and its Influence on Cellular E2

Figure 37:
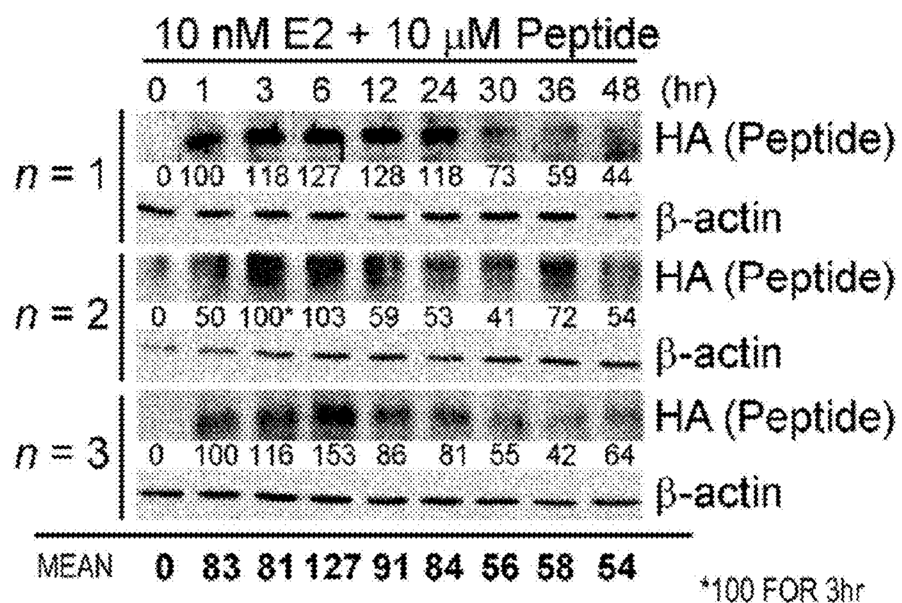
FIG. 37 is a diagram illustrating the results of evaluations for the stability of the ERAP1-peptide and the influence of the ERAP1-peptide on cellular E2. (A) shows the results of immunoblotting analysis by which the stability of the ERAP1-peptide was evaluated. MCF-7 cells were treated with 10 μM HA-tagged ERAP1-peptide. Then, immediately, the cells were temporally stimulated with 10 nM E2. Then, the cell lysate was subjected to immunoblotting analysis with the antibodies shown in the figure. The data are standardized with β-actin, and show the ratio when the value at 1 hour (n=1, 3) or at 3 hours (n=2) is designated as 100. (B) shows the results of evaluations for the influence of the ERAP1-peptide on the concentration of cellular E2. MCF-7 cells were treated with 10 μM ERAP1-peptide. Then, immediately, the cells were temporally stimulated with 10 nM E2. The cell lysate was centrifuged, and then the supernatant and a precipitate lysed with methanol were mixed (final concentration of methanol: 10%), and the cellular E2 concentration was measured with a commercially available kit (17β-estradiol ELISA kit, Wako Pure Chemical Industries, Ltd.). The data show the mean±SE of three independent experiments.
Figure 37:
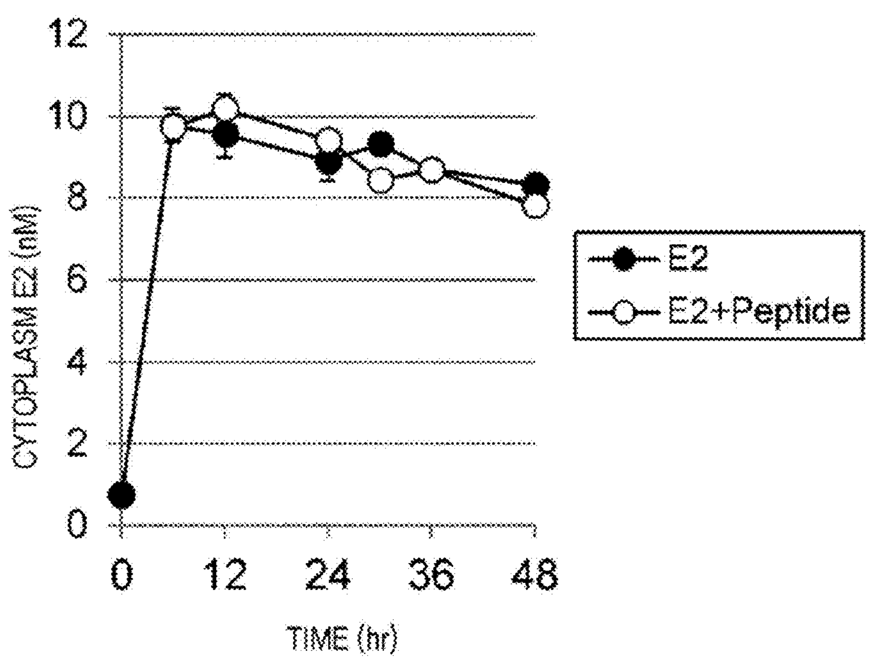

The stability of ERAP1-peptide and its influences on the cellular E2 were investigated. First, MCF-7 cells were treated with E2 and an HA-tagged ERAP-peptide, and then immunoblotting analysis was performed. As a result, it was found that the residual percentage of the ERAP1-peptide was 84% on average 24 hours after the administration, and 56%, 58% and 54% after 30, 36 and 48 hours, respectively, and the half-life of the ERAP1-peptide was generally about 30 hours (FIG. 37A). Then, the influence of the ERAP1-peptide on the cellular E2 concentration was investigated. MCF-7 cells were treated with 10 nM E2 and 10 μM ERAP1-peptide, and then the cell lysate was collected temporally, and the cellular E2 concentration was measured. As a result, a maximum value of about 10 nM was shown at 6 hours after the administration, which decreased to about 80% after 48 hours (FIG. 37B).

Participation of Particular Amino Acid of ERAP1 in Binding to PHB2/REA

Figure 38:
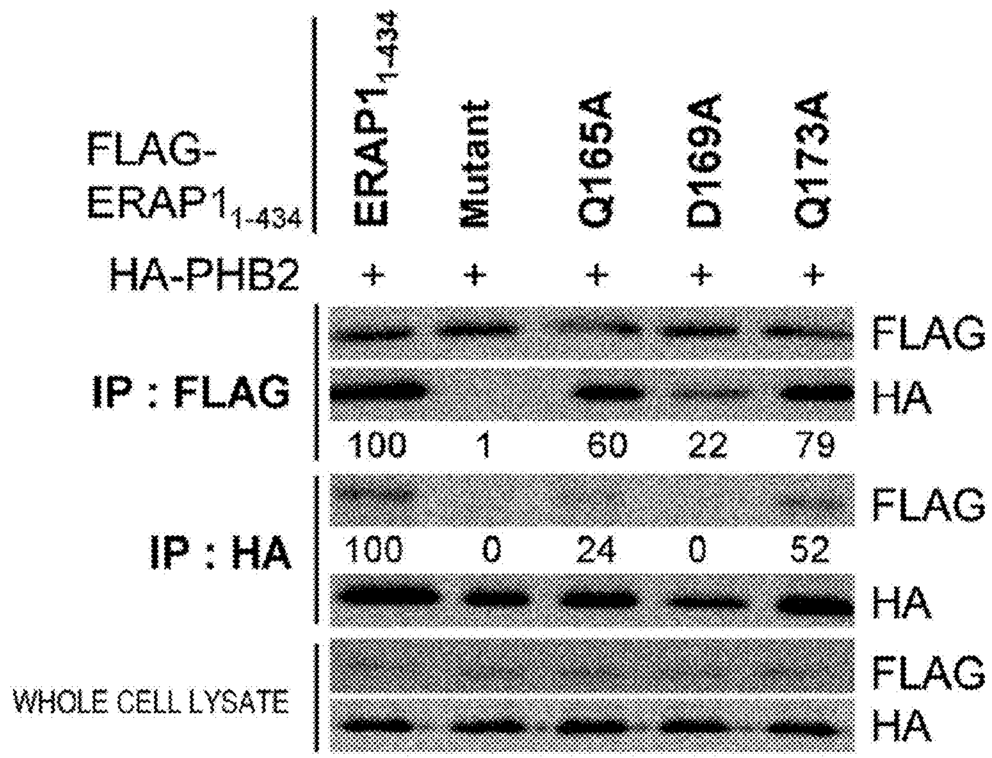
FIG. 38 is a diagram illustrating the results of immunoblotting analysis by which an amino acid in ERAP1 that binds to PHB was identified. COS-7 cells were transfected with the PHB2 construct together with any one of ERAP1 (1-434 an), an alanine mutant of Q165, D169 and Q173, an alanine mutant of Q165 (Q165A), an alanine mutant of D169 (D169A), an alanine mutant of Q173 (Q173A) or an alanine mutant of Q165 and D169 (Q165A, D169A). The cells were lysed after 48 hours from the transfection. Then, the cells were immunoprecipitated with anti-FLAG antibody and an anti-HA antibody. The immunoprecipitated protein and the cell lysate were subjected to immunoblotting analysis with the antibodies shown in the figure. The data show the ratio when the coprecipitation band with ERAP1 (1-434 aa) is designated as 100.
Figure 38:
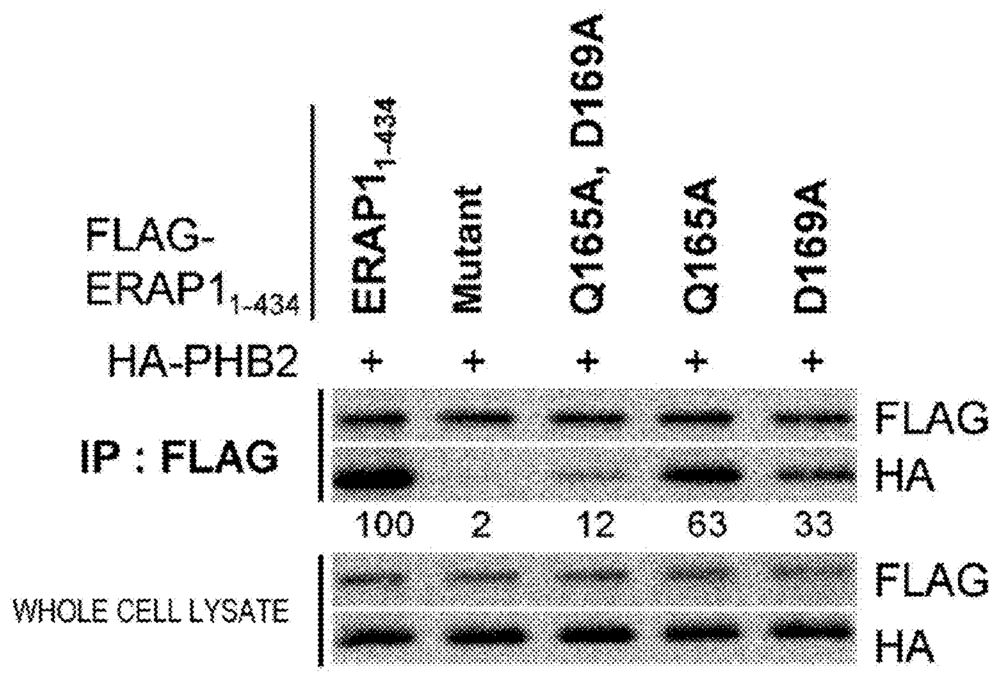

It was shown in Example 1 that three amino acids, i.e., Q165, D169 and Q173 of ERAP1 were important for the binding to PHB2/REA. Thus, which amino acid among these three amino acids is s the most important for the binding, was investigated. COS-7 cells were transfected with any one of a PHB2/REA construct and ERAP1-WT normal type (1-434 an), an alanine mutant of Q165, D169 and Q173 (Mutant), an alanine mutant of Q165 (Q165A), an alanine mutant of D169 (D169A), an alanine mutant of Q173 (Q173A), and an alanine mutant of Q165 and D169 (Q165A, D169A). Then, after 48 hours, the cells were collected, and immunoprecipitation and immunoblotting analysis were performed. As a result, the highest inhibition of the binding to PHB2/REA was recognized in the experiment using the D169 mutant construct (22% with IP of anti-FLAG antibody, and 0% with IP of anti-HA antibody). In addition, the next highest inhibition of the binding was recognized when Q165 mutant construct was used (60% with IP of anti-FLAG antibody, 24% with IP of anti-HA antibody) (FIG. 38A). Subsequently, in order to verify these results, similar experiment was performed using the alanine mutant of Q165 and D169 (Q165A, D169A). Thus, equivalent degree of the inhibition of the binding was confirmed in comparison to the case where a construct in which all amino acids were mutated with Ala, was used (Mutant: Q165A, D169A=2%: 12%) (FIG. 38B). From those described above, it was bound that the rank of the amino acids that were important for the binding to PHB2/REA among these 3 amino acids was D169>Q165>Q173, and D169 and Q165 occupied 90% of this binding.

Influence of Phosphorylation of ERAP1 by PKA and PKB on Phosphorylation of PHB2/REA (S39) through regulation of PP1α Activity (KPL-3C Cells)

Figure 39:
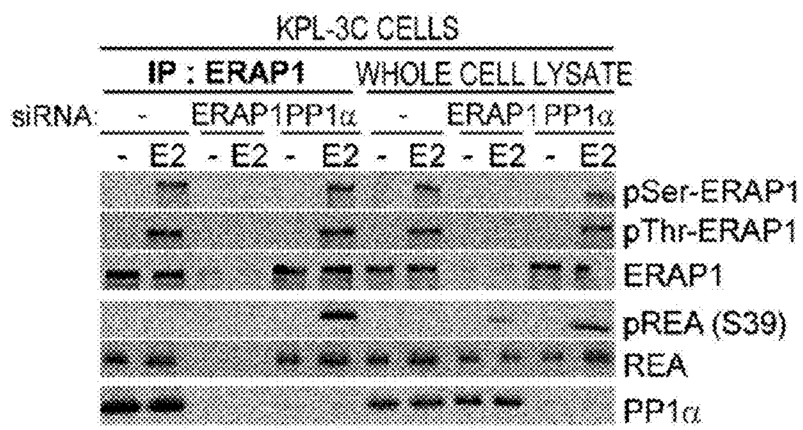
FIG. 39 is a diagram illustrating that phosphorylation of ERAP1 by PKA and PKB regulates phosphorylation of PHB2/REA (S39) through the PP1α activity in KPL-3C cells. (A) shows the results of immunoblotting analysis showing that PP1α regulates the serine phosphorylation of PHB2/REA. KPL-3C cells suppressed for the expression of ERAP1 and PP1α by siRNA method were stimulated with 10 nM. E2 for 24 hours. Then, the cells were lysed. ERAP1 was immunoprecipitated from the cell lysate with anti-ERAP1 antibody. Furthermore, the obtained sample was subjected to immunoblotting analysis with the antibodies shown in the figure. (B) shows the results of immunoblotting analysis showing that PKA and PKB cause phosphorylation of ERAP1. KPL-3C cells suppressed for expression of PKA and PKB by siRNA method were stimulated with 10 nM E2 for 24 hours. Then, the cells were lysed. Then, ERAP1 was immunoprecipitated from the cell lysate with anti-ERAP1 antibody. Furthermore, the obtained sample was subjected to immunoblotting analysis with the antibodies shown in the figure. (C) shows the results of the phosphatase assay showing that PKA and PKB cause the PP1α activity. KPL-3C cells suppressed for expression of ERAP1, PP1α, PKA and PKB by siRNA method were stimulated with 10 nM E2 for 24 hours. Then, the cell lysate was immunoprecipitated with anti-ERAP1 antibody. Furthermore, with respect to the obtained sample, the phosphatase activity was calculated. The data show the mean±SE of three independent experiments.
Figure 39:
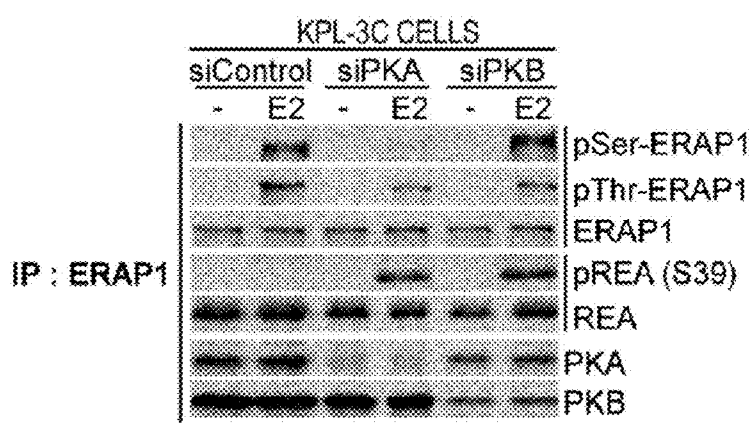
Figure 39:
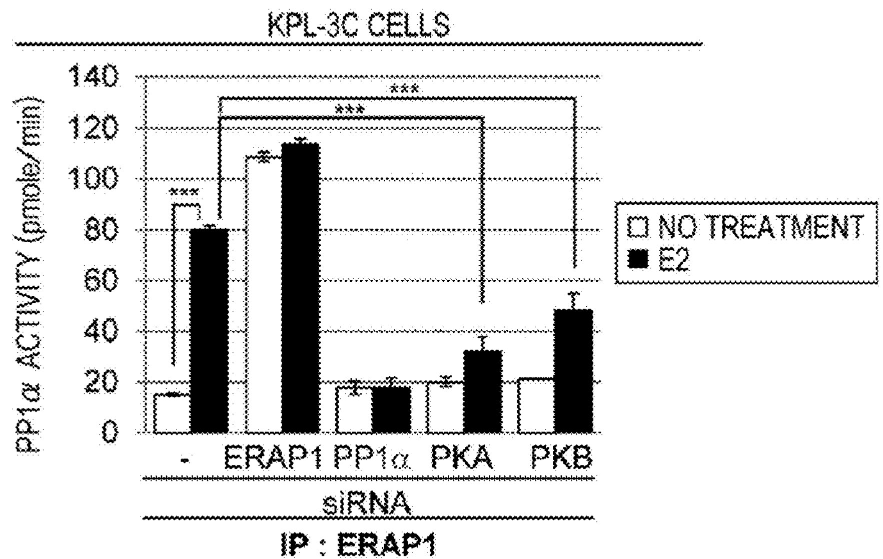

Next, in the same way as MCF-7 cells described above, the phosphorylation states of ERAP1 and PHB2/REA were investigated in ERα-positive breast cancer cell line KPL-3C. First, KPL-3C cells in which expression of ERAP1 or PP1α was suppressed by siRNA, were stimulated with E2 for 24 hours, and then ERAP1 and PHB2/REA were immunoprecipitated with anti-ERAP1 antibody or anti-PHB2/REA antibody. Furthermore, with respect to the obtained sample, immunoblotting analysis was performed. In the cells transfected with control siRNA, phosphorylation of the serine and threonine residues of ERAP1 by E2 treatment, and dephosphorylation of Ser39 of PHB2/REA were recognized. However, in the cells suppressed for PP1α expression, ERAP1 had no influence on phosphorylation of the serine and the threonine residues, but recovery of phosphorylation of Ser39 of PHB2/REA was confirmed after E2 treatment (FIG. 39A). Then, with KPL-3C cells suppressed for expression of PKA with siRNA, disappearance of the phosphorylation of the serine residue of ERAP1 was recognized, but recovery of the phosphorylation of the serine residue of Ser39 of PHB2/REA was recognized (FIG. 39B). On the other hand, when expression of PKB was suppressed, the influence on phosphorylation of the serine residue or the threonine residue of ERAP1 was not recognized. On the other hand, recovery of the phosphorylation of Ser39 of PHB2/REA was recognized in the same way as suppression for the expression of PKA (FIG. 39B). Subsequently, in KPL-3C cells, the influence of suppression for the expression of PP1α, PKA, PKB or ERAP1 by siRNA on the phosphatase activity of PP1α was also investigated. As a result, it was confirmed that if the expression of ERAP1 was suppressed, the phosphatase activity of PP1α was accelerated regardless of the presence or absence of E2. On the other hand, it was recognized that if expressions of PP1α, PKA and PKB were suppressed, respectively, the phosphatase activity of PP1α decreased. From the results above, it was suggested that also in the ER-positive breast cancer cell line KPL-3C, ERAP1 promoted acceleration of the phosphatase activity of PP1α through phosphorylation of the serine residue by PKA in the same way as MCF-7 cells, and as a result, caused dephosphorylation of Ser39 of PHB2/REA.

Proliferation Suppression for ERα Negative Breast Cancer Cell Lines by ERAP1-Peptide Proliferation suppression effect of the ERAP1-peptide in ERα negative breast cancer cell lines was investigated. ERα negative breast cancer cell lines, SK-BR-3 cells were treated with the ERAP1-peptide or the ERAP1-scramble peptide (scrPeptide). At 24 hours and 48 hours after the treatment, the influence on the cell proliferation was examined. As a result, it was recognized that the ERAP1-peptide had suppression effect on the cell proliferation in dose-dependent manner both at 24 hours and 48 hours after the treatment although the degree of the effect was lower in comparison to the suppression effect of the ERAP1-peptide in ER-positive cell lines (FIG. 40). From those described above, it was recognized that ERAP1-peptide had proliferation suppression effect also on ER negative and ERAP1-positive breast cancer.

Investigation for ROS Production in the Mitochondria Induced by E2 Stimulation Through ERAP1

Figures 1, 41:
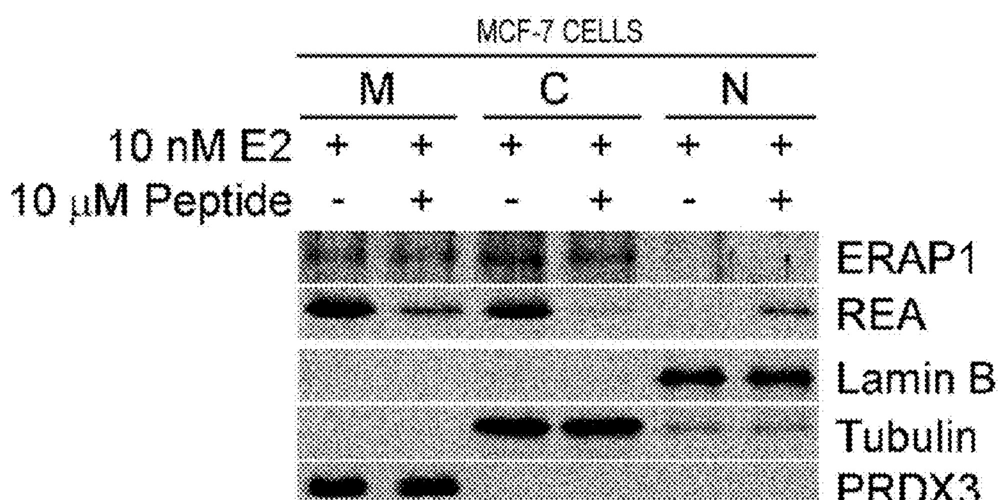
Figures 2, 41:
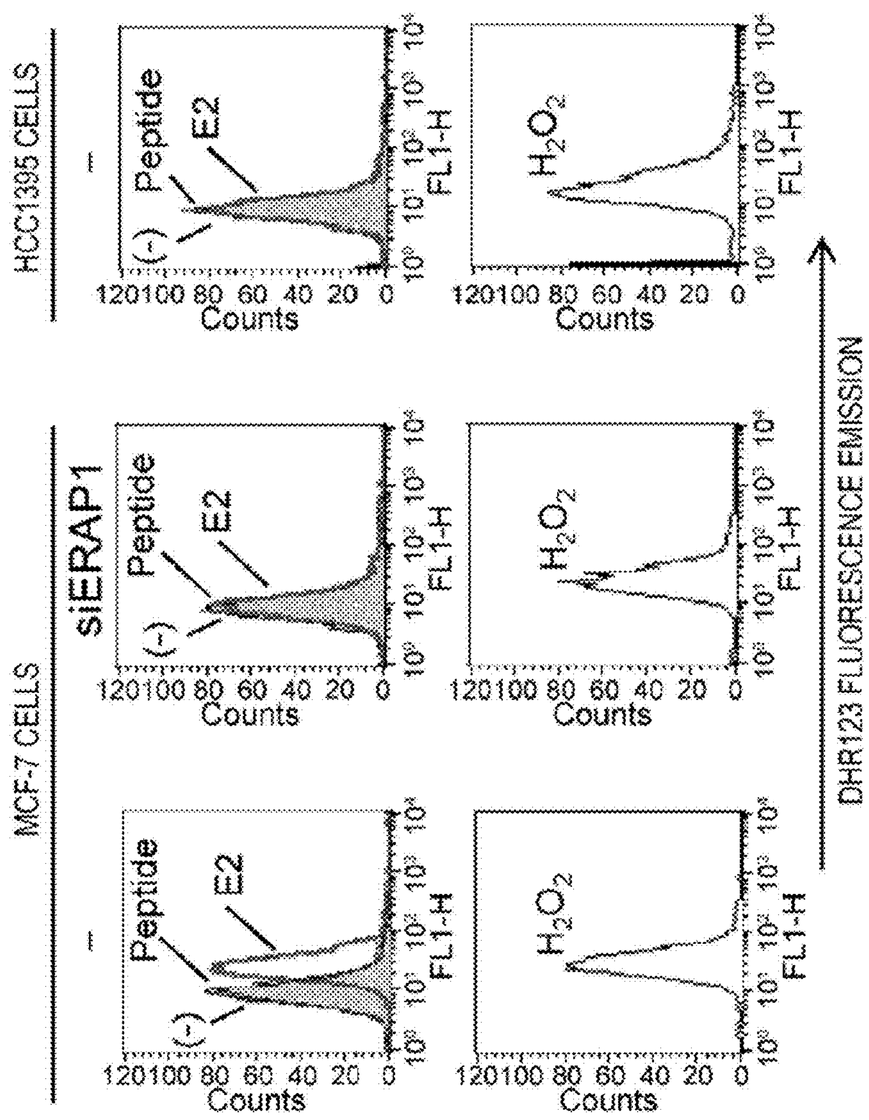

Investigation for the locality of ERAP1 in the ER-positive breast cancer cell lines MCF-7 cells was performed. In Example 1, inherent ERAP1 in breast cancer cells was shown to be localized mainly in the cytoplasm but the locality in the mitochondria was also recognized. In addition, PHB2/REA, which is the binding protein of ERAP1, is also recognized to be localized in the mitochondria. Thus, the present inventors focused on the functions of ERAP1 in the mitochondria. First, the localities of ERAP1 and PHB2/REA were investigated. MCF-7 cells were treated with E2 and the ERAP1-peptide. Then, the cells were centrifuged by specific-gravity to fractionate into the mitochondria fraction (M), the cytoplasm fraction (C) and the nuclear fraction (N). Then, immunoblotting analysis of each fraction was performed. As a result, high locality of ERAP1 in the cytoplasm and the mitochondria fractions was recognized. On the other hand, it was found that PHB2/REA was also localized similarly in the mitochondria, and translocated to the nucleus when the ERAP1-peptide was administered (FIG. 41A). Subsequently, in consideration of the roles of ERAP1 and PHB2/REA in the mitochondria, production of ROS (reactive oxygen species) in the mitochondria via ERAP1 was investigated. MCF-7 cells, MCF-7 cells in which expression of ERAP1 was suppressed, and HCC1395 cells were treated with DHR123 for 15 minutes, and then stimulated with 10 μM ERAP1-peptide and E2 for 24 hours, and analyzed by flow cytometry. As a result, it was observed in MCF-7 cells that generation of ROS was remarkably suppressed by administration of the ERAP1-peptide in the cells transfected with control siRNA. However, it was recognized in the cells in which expression of ERAP1 was suppressed that administration of the ERAP1-peptide had no influence on the generation of ROS. In addition, observation was performed using ER-positive/ERAP1-negative breast cancer cell lines (HCC1395 cells) as a positive control. However, there was no significant detection (FIG. 41B). As described above, it was suggested that ROS production in the mitochondria by E2 stimulation in the mitochondria of breast cancer cells was induced through ERAP1, and suppressed by the ERAP1 peptide.

INDUSTRIAL APPLICABILITY

The ERAP1 peptide provided by the present invention is useful for treatment of cancer. More specifically the peptide of tire present invention can be expected to have therapeutic effects by new mechanism in cancer which is estrogen receptor-positive, and in which the ERAP1 polypeptide is expressed. The ERAP1 peptide of the present invention particularly targets ERAP1, which is a protein that is highly expressed specifically in estrogen receptor-positive cancer. Thus, the peptide of the present invention is expected to have low side effects. In addition, the peptide of the present invention is expected to have therapeutic effects also on tamoxifen-resistant breast cancer. In addition, the ERAP1 peptide of the present invention itself suppresses proliferation of cancer cells, and in addition, has actions of potentiating the therapeutic effects of a hormone therapy agent or a chemotherapy agent. Thus, the ERAP1 peptide of the present invention can be used in combination with other hormone therapy agents or chemotherapy agents, and thus expected to have more effective cancer treatment. The present invention can also provide a screening method for a drug candidate for treating and/or preventing cancer, which uses inhibition of the binding of the ERAP1 polypeptide to PP1-polypeptide, PKA polypeptide, or PKB polypeptide as an index, to contribute to development of a novel cancer treatment strategy.

The invention claimed is:

1. A peptide that inhibits binding of Estrogen Receptor Activity-regulated Protein 1 (ERAP1) polypeptide to prohibitin2 (PHB2) polypeptide, consisting of an amino acid sequence selected from a group consisting of:

an amino acid sequence as set forth in SEQ ID NO: 31;

an amino acid sequence of variant of SEQ ID NO: 31 in which one or two amino acid residues other than glutamine at position 1, aspartic acid at position 5, and glutamine at position 9 of SEQ ID NO: 31 are substituted with other amino acid residues as long as the ability of inhibiting the binding of the ERAP1 polypeptide to the PHB2 polypeptide is maintained;

an amino acid sequence as set forth in SEQ ID NO: 27;

an amino acid sequence of variant of SEQ ID NO: 27 in which one or two amino acid residues other than glutamine at position 1, aspartic acid at position 5 and glutamine at position 9 of SEQ ID NO: 27 are substituted with other amino acid residues as long as the ability of inhibiting the binding of the ERAP1 polypeptide to the PHB2 polypeptide is maintained;

an amino acid sequence as set forth in SEQ ID NO: 30; and an amino acid sequence of variant of SEQ ID NO: 30 in which one or two amino acid residues other than glutamine at position 5, aspartic acid at position 9 and glutamine at position 13 of SEQ ID NO: 30 are substituted with other amino acid residues as long as the ability of inhibiting the binding of the ERAP1 polypeptide to the PHB2 polypeptide is maintained.

2. The peptide according to claim 1, wherein the peptide is modified by a cell membrane-permeable substance.

3. The peptide according to claim 1, having one or both of properties (i) and (ii) described below:

(i) property of promoting nuclear translocation of PHB2 polypeptide in estrogen receptor-positive cells expressing ERAP1 polypeptide; and (ii) property of promoting binding of estrogen receptors present in the nucleus and/or on the cell membrane to PHB2 polypeptide in estrogen receptor-positive cells expressing ERAP1 polypeptide.

* * * * *